US008921361B2

(12) United States Patent
Cmiljanovic et al.

(10) Patent No.: US 8,921,361 B2
(45) Date of Patent: Dec. 30, 2014

(54) TRIAZINE, PYRIMIDINE AND PYRIDINE ANALOGS AND THEIR USE AS THERAPEUTIC AGENTS AND DIAGNOSTIC PROBES

(75) Inventors: Vladimir Cmiljanovic, Basel (CH); Natasa Cmiljanovic, Basel (CH); Bernd Giese, Fribourg (CH); Matthias Wymann, Bern (CH)

(73) Assignee: University of Basel, Basel (CH)

( * ) Notice: Subject to any disclaimer, the term of this patent is extended or adjusted under 35 U.S.C. 154(b) by 60 days.

(21) Appl. No.: 13/128,436

(22) PCT Filed: Nov. 10, 2009

(86) PCT No.: PCT/IB2009/007404
§ 371 (c)(1),
(2), (4) Date: Jul. 1, 2011

(87) PCT Pub. No.: WO2010/052569
PCT Pub. Date: May 14, 2010

(65) Prior Publication Data
US 2011/0275762 A1    Nov. 10, 2011

(30) Foreign Application Priority Data

Nov. 10, 2008 (GB) .................. 0821219.3

(51) Int. Cl.
| | |
|---|---|
| C07D 401/04 | (2006.01) |
| C07D 403/04 | (2006.01) |
| A61K 31/5375 | (2006.01) |
| C07D 251/18 | (2006.01) |
| C07D 401/12 | (2006.01) |
| C07D 403/12 | (2006.01) |
| C07D 403/14 | (2006.01) |
| C07D 405/04 | (2006.01) |
| C07D 405/14 | (2006.01) |
| C07D 409/04 | (2006.01) |
| C07D 413/04 | (2006.01) |
| C07D 413/14 | (2006.01) |
| C07D 417/04 | (2006.01) |
| C07D 417/14 | (2006.01) |
| C07D 491/048 | (2006.01) |
| C07D 491/147 | (2006.01) |
| C07D 495/04 | (2006.01) |
| C07D 495/14 | (2006.01) |
| C07D 498/04 | (2006.01) |
| C07D 513/04 | (2006.01) |
| C07D 519/00 | (2006.01) |

(52) U.S. Cl.
CPC ............ *C07D 401/04* (2013.01); *C07D 251/18* (2013.01); *C07D 401/12* (2013.01); *C07D 403/04* (2013.01); *C07D 403/12* (2013.01); *C07D 403/14* (2013.01); *C07D 405/04* (2013.01); *C07D 405/14* (2013.01); *C07D 409/04* (2013.01); *C07D 413/04* (2013.01); *C07D 413/14* (2013.01); *C07D 417/04* (2013.01); *C07D 417/14* (2013.01); *C07D 491/048* (2013.01); *C07D 491/147* (2013.01); *C07D 495/04* (2013.01); *C07D 495/14* (2013.01); *C07D 498/04* (2013.01); *C07D 513/04* (2013.01); *C07D 519/00* (2013.01)
USPC .......................................... 514/232.2; 544/83

(58) Field of Classification Search
None
See application file for complete search history.

(56) References Cited

U.S. PATENT DOCUMENTS

| | | | |
|---|---|---|---|
| 5,489,591 A * | 2/1996 | Kobayashi et al. ........... 514/245 |
| 7,173,029 B2 | 2/2007 | Hayakawa et al. | |
| 8,217,036 B2 * | 7/2012 | Venkatesan et al. ....... 514/232.2 |
| 2010/0069629 A1 | 3/2010 | Shimma et al. | |

FOREIGN PATENT DOCUMENTS

| | | |
|---|---|---|
| EP | 1 864 665 A1 | 12/2007 |
| WO | 2005/028444 A1 | 3/2005 |
| WO | 2007/127175 A2 | 11/2007 |
| WO | 2008/018426 A1 | 2/2008 |
| WO | 2009/093981 A1 | 7/2009 |
| WO | 2009/143313 A1 | 11/2009 |
| WO | 2009/143317 A1 | 11/2009 |

OTHER PUBLICATIONS

Menicagli R. et al: "2-Alkyl-4,6-dialkylamino-1,3,5-triazines via Grignard Alkylation of Cyanuric Chloride: An Aged Reaction Revisited" in: Tetrahedron, Elsevier Science Publishers, vol. 56, No. 49, Dec. 1, 2000, pp. 9705-9711.
Matsuno T et al: "Synthesis and Antitumor Activity of Benzimidazolyl-1,3,5-Triazine and Benzimidazolylpyrimidine Derivatives" in: Chemical and Pharmaceutical Bulletin, Pharmaceutical Society of Japan, vol. 48, No. 11, Nov. 1, 2000, pp. 1778-1781.

* cited by examiner

*Primary Examiner* — Alicia L Otton
(74) *Attorney, Agent, or Firm* — Joyce von Natzmer; Agris & von Natzmer LLP

(57) ABSTRACT

The invention relates to novel therapeutic agents and diagnostic probes. The invention also relates to phosphoinositide 3-kinase (PI3K) and mammalian target of rapamycin (mTOR) inhibitor triazine-, pyrimidine- and pyridine-based compounds^ Formula (I), their stereoisomers, geometric isomers, tautomers, solvates, metabolites, N-oxide derivatives, pharmaceutically acceptable salts, and prodrugs thereof compositions of the new compounds; either alone or in combination with at least one additional therapeutic agent, with a pharmaceutically acceptable carrier; and uses of the new compounds, either alone or in combination with at least one additional therapeutic agent, for treating disorders mediated by lipid kinases. •Methods of using compounds of Formula (I) for in vitro, in situ, and in vivo diagnosis, prevention or treatment of such disorders in mammalian cells, or associated pathological conditions, are disclosed. (Formula I)

16 Claims, No Drawings

TRIAZINE, PYRIMIDINE AND PYRIDINE ANALOGS AND THEIR USE AS THERAPEUTIC AGENTS AND DIAGNOSTIC PROBES

This is the U.S. national stage of International application PCT/IB2009/007404, filed Nov. 10, 2009 designating the United States and claims priority to GB 0821219.3, filed Nov. 10, 2008.

FIELD OF THE INVENTION

The invention relates to new therapeutic agents and diagnostic probes, including pharmaceutically acceptable salts, prodrugs and metabolites thereof, which are useful for modulating protein or enzyme activity for modulating cellular activities such as signal transduction, proliferation, differentiation, programmed cell death, migration and cytokine secretion. More specifically the invention provides compounds which inhibit, regulate, detect and/or modulate kinase activity, in particular phosphoinositide 3-kinase (PI3K), mammalian target of rapamycin (mTOR), DNA-PK and ATM kinase inhibitor compounds, their pharmaceutically acceptable salts, and prodrugs thereof; compositions of the new compounds, either alone or in combination with at least one additional therapeutic agent, with a pharmaceutically acceptable carrier; and uses of the new compounds, either alone or in combination with at least one additional therapeutic agent, in the prophylaxis or treatment of a number of diseases, in particular, those characterized by the abnormal activity of serine/threonine kinases, receptor tyrosine kinases and lipid kinases. The invention also relates to methods of using the compounds for in vitro, in situ, and in vivo diagnosis, assay development or treatment of mammalian cells, or associated pathological conditions.

BACKGROUND OF THE INVENTION

Protein kinases participate in the signaling events which control the activation, growth, differentiation, survival and migration of cells in response to extracellular mediators or stimuli including growth factors, cytokines or chemokines. In general, these kinases are classified in two groups, those that preferentially phosphorylate tyrosine residues and those that preferentially phosphorylate serine and/or threonine residues. The tyrosine kinases include membrane-spanning growth factor receptors, for example the epidermal growth factor receptor (EGFR) and cytosolic non-receptor kinases including Src family kinases, the Syk family kinases and the Tec family kinases.

Inappropriately high protein kinase activity is involved in many diseases including cancer, metabolic diseases, immunological diseases and inflammatory disorders. This can be caused either directly or indirectly by the failure of control mechanisms due to mutation, overexpression or inappropriate activation of the enzyme.

Protein tyrosine kinases—both receptor tyrosine kinases and non-receptor kinases—are essential for the activation and proliferation of cells of the immune system. Among the earliest detectable events upon the immunoreceptor activation in mast cells, T cells and B cells is the stimulation of non-receptor tyrosine kinases.

Phosphoinositide 3-kinases (PI3Ks) were early on identified as lipid kinases associated with viral oncogens [Whitman et al., Nature 315:239-242 (1985); Sugimoto et al., Proc. Natl. Acad. Sci. 81:2117-2121 (1984); Macara et al., Proc. Natl. Acad. Sci. 81:2728-2732 (1984)], and for the last 20 years, the connection between cancer and PI3K has been further substantiated [Cully et al., Nat. Rev., Cancer 6:184-192 (2006); Wymann et al., Curr. Opin. Cell Biol. 17:141-149 (2005); Vivanco et al., Nat. Rev., Cancer 2:489-501 (2002)]. PI3Ks have since been recognized to modulate a wide range of cellular activities, and to be central to the growth and metabolic control. Genetically modified mice targeting the PI3K pathway, and the elucidation of human hereditary disease like Cowden's syndrome, tuberous sclerosis, ataxia telangiectasia, X-linked myotubular myopathy and Charcot-Marie-Tooth neuropathy, have provided further insight in the cellular and systemic role of phosphoinositide signaling. Deregulation of phosphoinositide levels, and in particular the product of class I PI3Ks, PtdIns (3,4,5)P3, is involved in the pathogenesis of cancer, chronic inflammation, allergy, metabolic disease, diabetes and cardiovascular problems.

PI3Ks are a family of enzymes, which phosphorylate the 3'-OH position of the inositol ring of phosphoinositides. They have been divided into three classes on the basis of structural features and in vitro lipid substrate specificity [(Marone et al, Biochimica et Biophysica Acta 1784:159-185 (2008)]. Class I PI3Ks form heterodimers, which consist of one of the four closely related ~110 kDa catalytic subunits, and an associated regulatory subunit belonging to two distinct families. In vitro they are capable to convert PtdIns to PtdIns-3-P, PtdIns-4-P to PtdIns(3,4)P2, and PtdIns(4,5)P2 to PtdIns(3,4,5)P3, but the in vivo substrate is PtdIns(4,5)P2 [Cantley et al., Science 296:1655-1657 (2002)]. Class I PI3Ks are activated by a large variety of cell-surface receptors, comprising growth factor receptors as well as G protein-coupled receptors.

Class II PI3Ks are capable to phosphorylate PtdIns and PtdIns-4-P in vitro, but their relevant in vivo substrates are still under investigation. This class of large (170-200 kDa) enzymes has three members, all characterized by a C-terminal C2 homology domain. No adaptor molecules for class II PI3Ks have been identified so far. Class III PI3Ks are solely able to phosphorylate PtdIns, and thus generate only PtdIns-3-P. The single member of this class is Vps34, of which the S. cerevisiae Vps34p (vacuolar protein sorting mutant 34 protein) is the prototype, and has been shown to play an essential role in trafficking of newly synthesized proteins from the Golgi to the yeast vacuole, an organelle equivalent to lysosomes in mammals [Schu et al., Science 260:88-91 (1993)].

Phosphoinositide 4-kinases (PI4Ks) phosphorylate the 4'-OH position of the inositol ring of PtdIns, and thereby generate PtdIns-4-P. This lipid can then be further phosphorylated by PtdIns-4-P 5-kinases to generate PtdIns (4,5)P2, which is the main source for phospholipase C and PI3K signaling at the plasma membrane. Four PI4Ks isoforms are known: PI4KIIα and β, and PI4KIIIα and β. The PI4KIIIs are most closely related to PI3Ks.

The class of PI3K-related proteins, referred to as class IV PI3Ks, consists of high molecular weight enzymes with a catalytic core similar to PI3Ks and PI4Ks and include the target of rapamycin (mTOR, also known as FRAP), DNA-dependent protein kinase (DNA-PKcs), the ataxia telangiectasia mutated gene product (ATM), ataxia telangiectasiarelated (ATR), SMG-1 and transformation/transcription domain-associated protein (TRRAP). The first five members are active protein serine-threonine kinases that are involved in cell growth control and genome/transcriptome surveillance [(Marone et al., Biochimica et Biophysica Acta 1784:159-185 (2008)]. DNA-PKcs, ATM, ATR and SMG-1 are involved in DNA-damage responses. The only active kinase not involved in DNA-damage is mTOR, which is regulated by growth factors and nutrient availability, and coordinates protein synthesis, cell growth and proliferation. Target of rapamycin (mTOR) complexes 1 and integrate growth factor signaling (via PI3K/PKB and the Ras/MAPK cascade), energy status (LKB1 and AMPK) and nutrient detection. TOR is positively regulated by PKB/Akt, which phosphorylates the negative regulator TSC2 in the tuberous sclerosis complex (TSC), resulting in activation of the GTPase Rheb and mTOR [(Marone et al., *Biochimica et Biophysica Acta* 1784:159-185 (2008)]. In parallel, mTOR stimulates translation of ribosomal proteins and therefore ribosome biogenesis via the activation of $p70^{S6K}$ [Wullschleger et al., *Cell* 124:471 (2006)]. Rapamycin, and its derivatives RAD001 and CCI-779, bind to FKBP12, and the complex blocks mTOR complex 1 (mTORC1) activity very selectively. Various clinical trials were initiated using Rapamycin and derivatives, mostly in patients with tumors displaying elevated PI3K signaling and hyperactive mTOR. Promising results were obtained in mantle cell lymphoma, endometrial cancer and renal cell carcinoma [Guertin et al., *Cancer Cell* 12:9 (2007)]. Rapamycin and its derivatives possess anti-angiogenic activity because they counteract VEGF action [Guba et al., *Nat. Med.* 8:128 (2002)]. This opens avenues for combinatorial treatments with conventional chemotherapy [Beuvink et al., *Cell* 120:747 (2005)].

The PI3K pathway is a key signaling transduction cascade controlling the regulation of cell growth, proliferation, survival as well as cell migration. PI3Ks are activated by a wide variety of different stimuli including growth factors, inflammatory mediators, hormones, neurotransmitters, and immunoglobulins and antigens [Wymann et al., *Trends Pharmacol. Sci.* 24:366-376 (2003)]. The class IA PI3K isoforms PI3Kα, β and δ, are all bound to one of the p85/p55/p50 regulatory subunits, which all harbor two SH2 domains that bind with high affinity to phosphorylated Tyr-X-X-Met motifs. These motifs are present in activated growth factor receptors, their substrates and numerous adaptor proteins. As described above, activation of the PI3K/PKB signaling cascade has a positive effect on cell growth, survival and proliferation. Constitutive up-regulation of PI3K signaling can have a deleterious effect on cells leading to uncontrolled proliferation, enhanced migration and adhesion-independent growth. These events favor not only the formation of malignant tumors, but also the development of inflammatory and autoimmune disease.

The PI3 kinase/Akt/PTEN pathway is an attractive target for cancer drug development since such agents would be expected to inhibit proliferation, reverse the repression of apoptosis and surmount resistance to cytotoxic agente in cancer cells. PI3 kinase inhibitors have been reported [see notably Marone et al., *Biochimica et Biophysica Acta* 1784:159-185 (2008); Yaguchi et al. (2006) Jour. Of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 6,703,414; WO9715658; WO2006046031; WO2006046035; WO2006046040; WO2007042806; WO2007042810; WO2004017950; US2004092561; WO2004007491; WO2004006916; WO2003037886; US2003149074; WO2003035618; WO2003034997; WO2007084786; WO2007095588; WO2008098058; US2003158212; EP1417976; US2004053946; JP2001247477; JP08175990; JP08176070].

1,3,5-triazine and pyrimidine derivatives as pharmaceuticals have been made with respect to antitumor, anti-inflammatory, analgesic and antispasmodic activities. Especially, hexamethylmelamine or altretamin (HMM or $N^2,N^2,N^4,N^4,N^6,N^6$-hexamethyl-1,3,5-triazine-2,4,6-triamine) is well-known, which has been developed as analogue of antitumor agent triethylenemelamine (TEM); HMM acts as a prodrug of hydroxymethylpentamethylmelamine (HMPMM: metabolically active type of HMM) [Johnson et al., Cancer, 42:2157-2161 (1978)]. HMM has been marketed in Europe under the indications for the treatment of ovarian and small cell lung cancers.

Certain triazine compounds are known to have PI3 kinase inhibitor activity and inhibit the growth of cancer cells [WO02088112 (EP1389617), "HETEROCYCLIC COMPOUNDS AND ANTITUMOR AGENT CONTAINING THE SAME AS ACTIVE INGREDIENT", Kawashima et al., Filing date: 26 Apr. 2002; WO05095389 (EP1741714), "HETEROCYCLIC COMPOUND AND ANTI-MALIGNANT-TUMOR AGENT CONTAINING THE SAME AS ACTIVE INGREDIENT", Kawashima et al., Filing date: 30 Mar. 2005; WO06095906 (EP1864665), "IMMUNOSUPPRESSIVE AGENT AND ANTI-TUMOR AGENT COMPRISING HETEROCYCLIC COMPOUND AS ACTIVE INGREDIENTS", Haruta et al., Filing date: 11 Mar. 2005; WO09905138 (EP1020462), HETEROCYCLIC COMPOUNDS AND ANTITUMOR AGENT CONTAINING THE SAME AS ACTIVE INGREDIENT, Kawashima et al., Filing date: 24 Jul. 1998;]. The triazine compound ZSTK474, developed in research laboratories of Zenyaku Kogyo is the first orally administered triazine compound highly active against PI3Ks that displayed potent antitumor activity against human cancer xenografts in mice, without evidence of critical toxicity [Yaguchi et al., Journal of the National Cancer Institute, 98:545-556, (2006)]. ZSTK474 is an ATP-competitive inhibitor of class I phosphatidylinositol 3-kinase isoforms [Kong et al., Cancer Sci, 98:1638-1642 (2007)].

Certain pyrimidine compounds are known to have p110 alpha binding, PI3 kinase inhibitor activity and inhibit the growth of cancer cells [IP of AstraZeneca: WO07066103, WO07080382, WO08023159, WO08023180, WO08032027, WO08032033, WO08032036, WO08032041, WO08032072, WO08032077, WO08032086, WO08032089, WO08032091; IP of Genentech/Piramed/Roche: US2007009880, WO07127183, WO08073785, WO07042810, WO07122410, WO07127175, WO07129161, WO08070740, WO2006046031, WO2006046040, WO2007042806, WO2007122410; IP of Novartis: WO07084786, WO08098058].

In order to expand antitumor spectrum of and increase antitumor activities of such compounds, active against PI3Ks and/or mTOR, the inventors carried out intensive studies on triazine-, pyrimidine- and pyridine-based derivatives. They thus prepared new heterocyclic compounds represented by the formula (I) and formulas (Ia) to (Ii) which exhibit strong biological activity against lipid kinases.

In comparison with the PI3K inhibitors disclosed by Zenyaku Kogyo [WO02088112 (EP1389617), WO2005095389 (EP 1741714), WO2006095906 (EP1864665), WO09905138 (EP1020462)], AstraZeneca (WO07066103, WO07080382, WO08023159, WO08023180, WO08032027, WO08032033, WO08032036, WO08032041, WO08032072, WO08032077, WO08032086, WO08032089, WO08032091), Piramed/Genentech (US2007009880, WO07127183, WO08073785, WO07042810, WO07122410, WO07127175, WO08070740, WO2006046031, WO2006046040, WO2007122410), Yamanouchi/Piramed (WO01083456) and Novartis (WO07084786, WO08098058), the inhibitors of the invention differ in the insertion of a N atom in the basic heterocyclic ring that makes better biological activity to the target enzyme, and/or in the insertion of a novel molecular fragment making the whole molecule more active or more selective to the appropriate enzyme.

SUMMARY OF THE INVENTION

The invention relates generally to new triazine-, pyrimidine- and pyridine-based derivatives and their use as therapeutic agents and diagnostic probes.

The invention also relates to kinase inhibitors and kinase diagnostic probes.

The invention also relates to phosphoinositide 3-kinase (PI3K) and mammalian target of rapamycin (mTOR) inhibitor compounds with anti-cancer activity, pharmaceutical formulations thereof, which are potentially useful in treatment of disease, conditions and/or disorders modulated by PI3K and mTOR kinases. The compounds may inhibit tumor growth in mammals and may be useful for treating human cancer patients.

The invention also relates to methods of using the compounds for in vitro, in situ, and in vivo diagnosis or treatment of mammalian cells, organisms, or associated pathological conditions.

Specifically, one aspect of the invention provides compounds of formula W.

More specifically, one aspect of the invention provides triazine compounds of formulas (Ia) to (Id), pyrimidine compounds of formulas (If) to (Ii) and pyridine compounds of formulas (Ie) and (If) to (Ii):

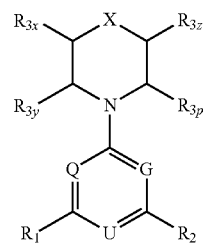

(I)

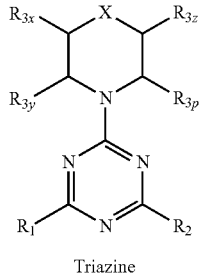

(Ia)

Triazine

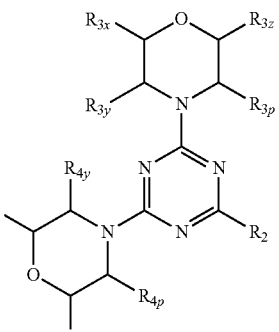

(Ib)

Triazine

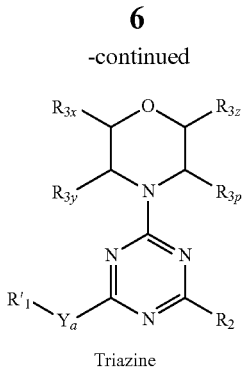

(Ic)

Triazine

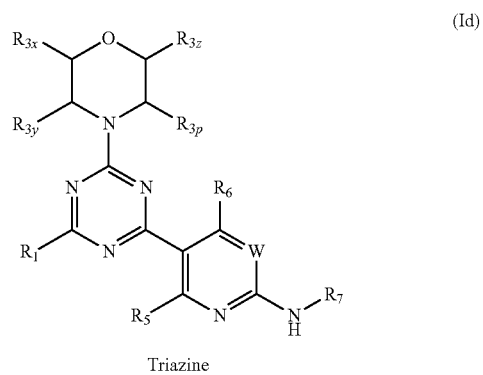

(Id)

Triazine

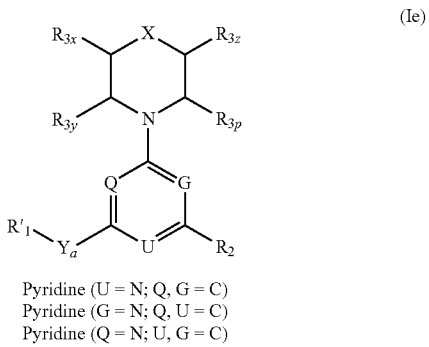

(Ie)

Pyridine (U = N; Q, G = C)
Pyridine (G = N; Q, U = C)
Pyridine (Q = N; U, G = C)

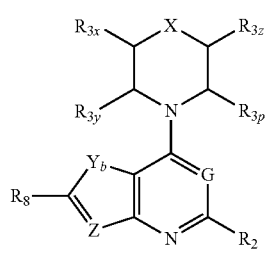

(If)

Fused Pyrimidine (G = N)
Fused Pyridine (G = C)

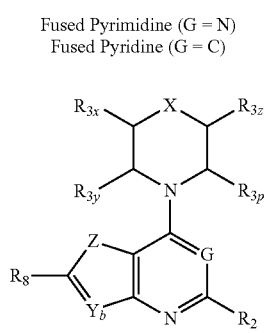

(Ig)

Fused Pyrimidine (G = N)
Fused Pyridine (G = C)

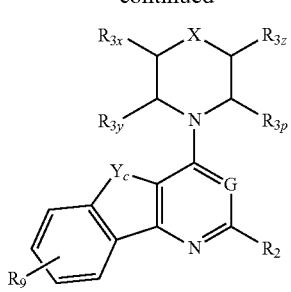

Fused Pyrimidine (G = N)
Fused Pyridine (G = C)

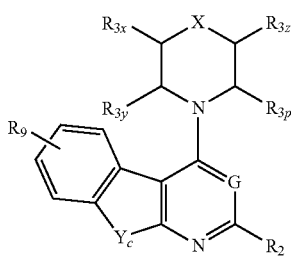

Fused Pyrimidine (G = N)
Fused Pyridine (G = C)

and stereoisomers, geometric isomers, tautomers, solvates, metabolites, N-oxide derivatives and pharmaceutically acceptable salts thereof.

Another aspect of the invention provides a pharmaceutical composition comprising a triazine or a pyrimidine or a pyridine compound of formula (I) or one of formulas (Ia) to (Ii) and a pharmaceutically acceptable carrier. The pharmaceutical composition may further comprise one or more additional therapeutic agents selected from anti-proliferative agents, anti-inflammatory agents, immunomodulatory agents, neurotropic factors, agents for treating blood disorders, agents for treating diabetes, and agents for treating immunodeficiency disorders.

Another aspect of the invention provides methods of inhibiting PI3 kinase activity, comprising contacting a PI3 kinase with an effective inhibitory amount of a compound of formula (I) or one of formulas (Ia) to (Ii), or a stereoisomer, geometric isomer, tautomer, solvate, metabolite, N-oxide derivative or pharmaceutically acceptable salt or prodrug thereof.

Another aspect of the invention provides methods of preventing or treating a disease or disorder modulated by PI3 kinases, comprising administering to a mammal in need of such treatment an effective amount of a compound of formula (I) or one of formulas (Ia) to (Ii), or a stereoisomer, geometric isomer, tautomer, solvate, metabolite, N-oxide derivative or pharmaceutically acceptable salt or prodrug thereof. Examples of such diseases, conditions and disorders include, but are not limited to, hyperproliferative disorders (e.g., cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, autoimmune diseases, atherosclerosis, restenosis, psoriasis, allergis disorders, inflammation, neurological disorders, hormone-related diseases, conditions associated with organ transplantation, immunodeficiency disorders, destructive bone disorders, hyperproliferative disorders, infectious diseases, conditions associated with cell death, thrombin-induced platelet aggregation, chronic myelogenous leukaemia (CML), liver disease, pathologic immune conditions involving T cell activation, and CNS disorders.

Another aspect of the invention provides methods of preventing or treating a hyperproliferative disorder, comprising administering to a mammal in need of such treatment an effective amount of a compound of formula (I) or one of formulas (Ia) to (Ii), or a stereoisomer, geometric isomer, tautomer, solvate, metabolite, N-oxide derivative or pharmaceutically acceptable salt or prodrug thereof, alone or in combination with one or more additional compounds having anti-hyperproliferative properties.

In a further aspect the present invention provides a method of using a compound of this invention to treat a disease or condition modulated by PI3 kinase and/or mTOR in a mammal.

An additional aspect of the invention is the use of a compound of this invention in the preparation of a medicament for the treatment or prevention of a disease or condition modulated by PI3 kinase in a mammal.

Another aspect of the invention includes kits comprising a compound of formula (I) or one of formulas (Ia) to (Ii), or a stereoisomer, geometric isomer, tautomer, solvate, metabolite, N-oxide derivative or pharmaceutically acceptable salt or prodrug thereof, a container, and optionally a package insert or label indicating a treatment.

Another aspect of the invention includes methods of preparing, methods of separating, and methods of purifying compounds of formula (I) or one of formulas (Ia) to (Ii).

Another aspect of the invention includes novel intermediates useful for preparing formula (I) or one of formulas (Ia) to (Ii).

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar to equivalent to those described herein, which could be used in the practice of the present invention. The present invention is in no way limited to the methods and materials herein described.

In the event that one or more of the literature, patents, and similar materials referred to differs from or contradicts the present application, as regards including but not limited to defined terms, term usage, described techniques, or the like, only the teaching of the present application will be taken into consideration.

DEFINITIONS

The term "alkyl" as used herein refers to a saturated linear or branched-chain monovalent hydrocarbon radical of one to twelve carbon atoms (C1-C12), wherein the alkyl radical may be optionally substituted independently with one or more substituents described below. In another embodiment, an alkyl radical is one to eight carbon atoms (C1-C8), or one to six carbon atoms (C1-C6). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$) CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—CH(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$) C(CH$_3$)$_3$, 1-heptyl, 1-octyl, and the like.

The term "alkenyl" refers to linear or branched-chain monovalent hydrocarbon radical of two to eight carbon atoms (C2-C8) with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkynyl" refers to a linear or branched monovalent hydrocarbon radical of two to eight carbon atoms (C2-C8) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "halogen" (or halo) preferably represents chloro or fluoro, but may also be bromo or iodo.

The terms "carbocycle", "carbocyclyl", "carbocyclic ring" and "cycloalkyl" refer to a monovalent non-aromatic, saturated or partially unsaturated ring having 3 to 12 carbon atoms (C3-C12) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicycle[5,6] or [6,6] system, or as bridged systems such as bicyclo[2.2.1]heptane, bicycle [2.2.2]octane and bicycle[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms (C6-C20) derived by the removal of one hydrogen atom from a single carbon atom of a parent aromatic ring system. Some aryl groups are represented by the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene(phenyl), substituted benzenes, naphthalene, anthracene, biphenyl, indenyl, indanyl, 1,2-dihydronapthalene, 1,2,3,4-tetrahydronaphthyl, and the like. Aryl groups are optionally substituted independently with one or more substituents described herein.

The terms "heterocycle", "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorus and sulphur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicycle[4, 5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo [3.1.0]hexanyl, 3-azabicyclo[4.1.0]heptanyl, azabicyclo [2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulphur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzooxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "monocyclic heteroaryl" refers to a five- or six-membered, unsubstituted or substituted, monocyclic heteroaryl radical which contains 1, 2, 3 or 4 ring heteroatoms independently selected from N, O and S. The monocyclic heteroaryl may be attached to the C-2 position of the pyrimidine ring according to formula Ia-Ii at any carbon (carbon-linked), or nitrogen (nitrogen-linked) atom of the monocyclic heteroaryl R3 group. Monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Monocyclic heteroaryl are optionally substituted independently with one or more substituents described herein.

The term "treat" and "treatment" refer to both therapeutic treatment and prophylactic or preventative measures, wherein the object is to prevent or slow down (lessen) an undesired pathological change or disorder, such as the development or spread of cancer. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may be reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukaemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatome, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of known chemotherapeutic agents include trastuzumab, pertuzumab, erlotinib (TARCEVA®, Genetech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafarnib (SCH 66336), sorafenib (NEXAVAR, Bayer Labs), and gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins; a camptothecin (including the synthetic analog topotecan); bryostatin; callystatin; CC-1065 (including its adozelesin, carzelesin and bizelesin synthetic analogs); cryptophycins; dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A; biphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophillin, chromomycinis, dactinomycin, daunorubicin, detorubicin, 6-diazol-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex; razoxane; rhizoxin; sizofiran; spirogermanium; tenuazonic acid; triaziquone; trichothecenes; urethane; vindesine; dacarbazine; mannomustine; mitobronitol; mitolactol; pipobroman; gacytosine; arabinoside; taxoids, e.g., TAXOL® (paclitaxel; Bristol-Myers Squibb), ABRAXANE™ (Cremophor-free), albumin-engineered nanoparticle formulations of paclitaxel, and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide; ifosfamide; mitoxantrone; vincristine; NAVELBINE® (vinorelbine); novantrone; teniposide; edatrexate; daunomycin; aminopterin; capecitabine (XELODA®); ibandronate; CP-11; topoisomerase inhibitor RFS 2000; difluoromethylornithine (DMFO); retinoids such as retinoic acid; and pharmaceutically acceptable salts; acids and derivatives of any of the above.

Also included in the definition of "chemotherapeutic agent" are: (i) anti-hormonal agents that act to regulate or inhibit hormone action on tumors such as anti-estrogens and selective receptor modulators (SERMs), including, for example, tamoxifen (including NOLVADEX®; tamoxifen citrate), raloxifene, droloxifene, and FARESTON® (toremifine citrate); (ii) aromatase inhibitors that inhibit the enzyme aromatase, which regulates estrogen production in the adrenal glands, such as, for example, 4(5)-imidazoles, MEGASE® (megestrol acetate); AROMASIN® (exemestane; Pfizer), formestanie, fadrazole, RIVISOR® (vorozole), FEMARA® (letrozole; Novartis), and ARIMIDEX® (anastrozole; AstraZeneca); (iii) anti-androgens such as flutamide, nilutamide; (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Rafl and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECANE®; ABARELIX® rmRH; (ix) anti-angiogenic agents such as bevacizumab (AVASTIN®, Genentech); and (x) pharmaceutically acceptable salts, acids and derivatives of any of the above.

The term "prodrug" as used in this application refers to a precursor or derivative form of a compound of the invention that may be less cytotoxic to cells compared to the parent compound or drug and is capable of being enzymatically or hydrolytically activated or converted into the more active parent form. The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant, which is useful for delivery of a drug (such as the PI3K and mTOR kinase inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules, which have the property of non-superimposability of the mirror image partner, while the term "achiral" refers to molecules, which are superimposable on their mirror image partner.

The term "stereoisomers" refers to compounds, which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diasteremers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McRaw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate.

The term "tautomer" or "tautomeric form" refers to structural isomers of different energies, which are interconvertible via a low energy barrier. For example, proton tautomers include interconversions via migration of a proton, such as keto-enol and imin-enamine isomerizations.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxyl acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine, an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminium and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl and 9-fluorenylmethylenoxycarbonyl (Fmoc). For a general description of protecting groups and their use, see T. W. Greene, Protective Groups I Organic Synthesis, John Wiley & Sons, New York, 1991.

The terms "compound of this invention" and "compounds of the present invention" and "compounds of formula (I) or one of formulas (Ia) to (Ii)" include compounds of formula (I) or one of formulas (Ia) to (Ii) and stereoisomers, geometric isomers, tautomers, solvates, metabolites, N-oxide derivatives and pharmaceutically acceptable salts and prodrugs thereof.

The term "mammal" includes, but is not limited to, humans, mice, rats, guinea, pigs, monkeys, dogs, cats, horses, cows, pigs, and sheep.

Triazine, Pyrimidine and Pyridine Analogs and their Use as Therapeutic Agents and Diagnostic Probes The present invention provides triazine, pyrimidine and pyridine compounds, and pharmaceutical formulations thereof, which are useful as therapeutic agents and novel diagnostic probes. Moreover, these compounds are potentially useful in the treatment of diseases, conditions and/or disorders modulated by protein kinases and lipid kinases.

More specifically, the present invention provides compounds of formula I,

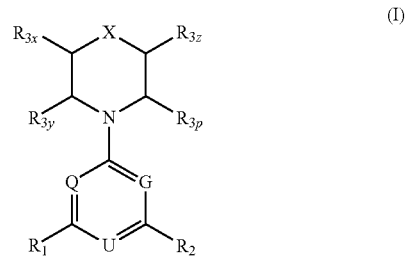

and stereoisomers, geometric isomers, tautomers, solvates, metabolites, N-oxide derivatives and pharmaceutically acceptable salts thereof, wherein:

Q=N, G=N, U=N (triazine-based compounds of formulas (Ia) to (Id));

Q=C, G=C, U=N (pyridine-based compounds of formula (Ie));

Q=C, U=C, G=N (pyridine-based compounds of formula (Ie);

U=C, G=C, Q=N (pyridine-based compounds of formula (Ie));

Q=$CR_z$, G=N, U=N (fused-pyrimidine-based compounds of formulas (If) to (Ii)); or Q=$CR_z$, G=C, U=N (fused pyridine-based compounds of formulas (If) to (Ii));

wherein $R_z$ is selected from the group consisting of:
(1) hydrogen, (2) cyano, (3) halogen, (4) methyl, (5) trifluoromethyl, (6) sulfonamido, (7) sulfon, (8) linker moiety (hydrophobic linkers, hydrophilic linkers (pegylated linkers), photo-cleaveable linkers, redox reaction-cleaveable linkers), (9) linker moiety with covalently bonded TAG-molecules (a TAG could be a fluorophor, biotin, different polymer beads and different reactive groups), (10) F, Cl, Br, I, —$C(C_1$-$C_6$-alkyl$)_2NR_{10}R_{11}$, —$(CR_{14}R_{15})_tR_{10}R_{11}$, —$C(R_{14}R_{15})_nNR_{12}C(=Y)R_{10}$, —$(CR_{14}R_{15})_nNR_{12}S(O)_2R_{10}$, —$CH(OR_{10})R_{10}$, —$(CR_{14}R_{15})_nOR_{10}$, —$(CR_{14}R_{15})_nS(O)_2R_{10}$, —$(CR_{14}R_{15})_nS(O)_2NR_{10}R_{11}$, —$C(=Y)R_{10}$, —$C(=Y)OR_{10}$, —$C(=Y)NR_{10}R_{11}$, —$C(=Y)NR_{12}OR_{10}$, —$C(=O)NR_{12}S(O)_2R_{10}$, —$C(=O)NR_{12}(CR_{14}R_{15})_mNR_{10}R_{11}$, —$NO_2$, —$NHR_{12}$, —$NR_{12}C(=Y)R_{11}$, —$NR_{12}C(=Y)OR_{11}$, —$NR_{12}C(=Y)NR_{10}R_{11}$, —$NR_{12}S(O)_2R_{10}$, —$NR_{12}SO_2NR_{10}R_{11}$, —$S(O)_2R_{10}$, —$S(O)_2NR_{10}R_{11}$, —$SC(=Y)R_{10}$, —$SC(=Y)OR_{10}$, C1-C12 alkyl, C2-C8 alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl; or $C_3$-$C_{12}$ carbocyclyl, $C_2$-$C_{20}$ heterocyclyl, $C_6$-$C_{20}$ aryl, or $C_1$-$C_{20}$ heteroaryl;

where said alkyl, alkenyl, alkynyl, carbocyclyl, heterocyclyl, aryl and heteroaryl are optionally substituted with one or more groups independently selected from F, Cl, Br, I, —CN, $CF_3$, —$NO_2$, oxo, —$C(=Y)R_{10}$, —$C(=Y)OR_{10}$, —$C(=Y)NR_{10}R_{11}$, —$(CR_{14}R_{15})_nNR_{10}R_{11}$, —$(CR_{14}R_{15})_nC(=Y)NR_{10}R_{11}$, —$(CR_{14}R_{15})_nC(=Y)OR_{10}$, —$(CR_{14}R_{15})_nNR_{12}SO_2R_{10}$, —$(CR_{14}R_{15})_nOR_{10}$, —$(CR_{14}R_{15})_nR_{10}$, —$(CR_{14}R_{15})_nSO_2R_{10}$, —$NR_{10}R_{11}$, —$NR_{12}C(=Y)R_{10}$, —$NR_{12}C(=Y)OR_{11}$, —$NR_{12}C(=Y)NR_{10}R_{11}$, —$NR_{12}SO_2R_{10}$, =$NR_{12}$, $OR_{10}$, —$OC(=Y)R_{10}$, —$OC(=Y)OR_{10}$, —$OC(=Y)NR_{10}R_{11}$, —$OS(O)_2(OR_{10})$, —$OP(=Y)(OR_{10})(OR_{11})$, —$OP(OR_{10})(OR_{11})$, $SR_{10}$, —$S(O)R_{10}$, —$S(O)_2R_{10}$, —$S(O)_2NR_{10}R_{11}$, —$S(O)(OR_{10})$, —$S(O)_2(OR_{10})$, —$SC(=Y)R_{10}$, —$SC(=Y)OR_{10}$, —$SC(=Y)NR_{10}R_{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

X is $CR_x$ or O, S, $NR_y$, wherein $R_x$ and $R_y$ are independently selected from the group consisting of:
(1) hydrogen, (2) cyano, (3) halogen, (4) methyl, (5) trifluoromethyl, (6) sulfonamido, (7) sulfon, (8) linker moiety (hydrophobic, hydrophilic, photo-cleavable, redox reaction-cleavable linkers), (9) linker moiety with covalently bonded TAG-molecules (a TAG could be a fluorophor, biotin, different polymer beads and different reactive groups);

the linker moiety being selected from the group consisting of:
optionally substituted $C_1$-$C_{20}$ alkyl, optionally substituted halo-substituted $C_1$-$C_{20}$ alkyl, optionally substituted $C_1$-$C_{20}$ alkoxy, optionally substituted halo-substituted $C_1$-$C_{20}$ alkoxy, optionally substituted $C_1$-$C_{20}$ pegylated alkyl;

the tag molecule being selected from the group consisting of:
dye molecules, fluorophore dyes (for example bodipy, or rhodamine derivatives), biotine, a polymer resin or a reactive group (for example acrylamid, iodoacetamid, fluoroacetamid, chloroacetamid, bromoacetamid, photo-reactive chemical groups, oxirane carboxamide, redox-reaction reactive chemical groups);

$R_{3x}$, $R_{3y}$, $R_{3z}$ and $R_{3p}$ are independently selected from the group consisting of: hydrogen, F, Cl, Br, I, —$C(C_1$-$C_8$ alkyl$)_2NR_{10}R_{11}$, —$(CR_{14}R_{15})_tNR_{10}R_{11}$, —$C(R_{14}R_{15})_nNR_{12}C(=Y)R_{10}$, —$(CR_{14}R_{15})_nNR_{12}S(O)_2R_{10}$, —$CH(OR_{10})R_{10}$, —$(CR_{14}R_{15})_nOR_{10}$, —$(CR_{14}R_{15})_nS(O)_2R_{10}$, —$(CR_{14}R_{15})_nS(O)_2NR_{10}R_{11}$, —$C(=Y)R_{10}$, —$C(=Y)OR_{10}$, —$C(=Y)NR_{10}R_{11}$, —$C(=Y)NR_{12}OR_{10}$, —$C(=O)NR_{12}S(O)_2R_{10}$, —$C(=O)NR_{12}(CR_{14}R_{15})_mNR_{10}R_{11}$, —$NO_2$, —$NHR_{12}$, —$NR_{12}C(=Y)R_{11}$, —$NR_{12}C(=Y)OR_{11}$, —$NR_{12}C(=Y)NR_{10}R_{11}$, —$NR_{12}S(O)_2R_{10}$, —$NR_{12}SO_2NR_{10}R_{11}$, —$S(O)_2R_{10}$, —$S(O)_2NR_{10}R_{11}$, —$SC(=Y)R_{10}$, —$SC(=Y)OR_{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl; or where the $C_3$-$C_{12}$ carbocyclyl, $C_2$-$C_{20}$ heterocyclyl, $C_6$-$C_{20}$ aryl, or $C_1$-$C_{20}$ heteroaryl is substituted at vicinal carbon atoms of the morpholine and forms a fused bicyclic morpholinyl;

where said alkyl, alkenyl, alkynyl, carbocyclyl, heterocyclyl, aryl and heteroaryl are optionally substituted with one or more groups independently selected from F, Cl, Br, I, —CN, $CF_3$, —$NO_2$, oxo, —$C(=Y)R_{10}$, —$C(=Y)OR_{10}$, —$C(=Y)NR_{10}R_{11}$, —$(CR_{14}R_{15})_nNR_{10}R_{11}$, —$(CR_{14}R_{15})_nNR_{10}R_{11}$, —$(C_{14}R_{15})_nC(=Y)OR_{10}$, —$(CR_{14}R_{15})_nNR_{12}SO_2R_{10}$, —$(CR_{14}R_{15})_nOR_{10}$, —$(CR_{14}R_{15})_nR_{10}$, —$(CR_{14}1R_{15})_nSO_2R_{10}$, —$NR_{10}R_{11}$, —$NR_{12}C(=Y)R_{10}$, —$NR_{12}C(=Y)OR_{10}$, —$NR_{12}C(=Y)NR_{10}R_{11}$, —$NR_{12}SO_2R_{10}$, =$NR_{12}$, $OR_{10}$, —$OC(=Y)R_{10}$, —$OC(=Y)OR_{10}$, —$OC(=Y)NR_{10}R_{11}$, —$OS(O)_2(OR_{10})$, —$OP(=Y)(OR_{10})(OR_{11})$, —$OP(OR_{10})(OR_{11})$, $SR_{10}$, —$S(O)R_{10}$, —$S(O)_2R_{10}$, —$S(O)_2NR_{10}R_{11}$, —$S(O)(OR_{10})$, —$S(O)_2(OR_{10})$, —$SC(=Y)R_{10}$, —$SC(=Y)OR_{10}$, —$SC(=Y)NR_{10}R_{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

$R_1$ is selected from the group consisting of:
(1) H, F, Cl, Br, I, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$C(C_1$-$C_6$ alkyl$)_2NR_{10}R_{11}$, —$(CR_{14}R_{15})_tNR_{10}R_{11}$, —$C(R_{14}R_{15})_nNR_{12}C(=Y)R_{10}$, —$(CR_{14}R_{15})_nNR_{12}S(O)_2R_{10}$, —$CH(OR_{10})R_{10}$, —$(CR_{14}R_{15})_nOR_{10}$, —$(CR_{14}R_{15})_nS(O)_2R_{10}$, —$(CR_{14}1R_{15})_nS(O)_2NR_{10}R_{11}$, —$C(=Y)R_{10}$, —$C(=Y)OR_{10}$, —$C(=Y)NR_{10}R_{11}$, —$C(=Y)NR_{12}OR_{10}$, —$C(=O)NR_{12}S(O)_2R_{10}$, —$C(=O)NR_{12}(CR_{14}R_{15})_mNR_{10}R_{11}$, —$NO_2$, —$NHR_{12}$, —$NR_{12}C(=Y)R_{11}$, —$NR_{12}C(=Y)OR_{11}$, —$NR_{12}C(=Y)NR_{10}R_{11}$, —$NR_{12}S(O)_2R_{10}$, —$NR_{12}SO_2NR_{10}R_{11}$, —$S(O)_2R_{10}$, —$S(O)_2NR_{10}R_{11}$, —$SC(=Y)R_{10}$, —$SC(=Y)OR_{10}$, $C_1$-$C_{12}$ alkyl, $C_2$-$C_6$ alkenyl, $C_2$-$C_8$ alkynyl, $C_3$-$C_{12}$ carbocyclyl, $C_2$-$C_{20}$ heterocyclyl, $C_6$-$C_{20}$ aryl or $C_1$-$C_{20}$ heteroaryl;

$R_2$ is selected from the group consisting of:
(1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$COR_{2a}$, (13) —$CO_2R_{2a}$, (14) —$CONR_{2a}R_{2b}$, (15) —$NR_{2a}R_{2b}$, (16) —$NR_{2a}COR_{2b}$, (17) —$NR_{2a}SO_2R_{2b}$, (18) —$OCOR_{2a}$, (19)

—OR$_{2a}$, (20) —SR$_{2a}$, (21) —SOR$_{2a}$, (22) —SO$_2$R$_{2a}$, and (23) —SO$_2$NR$_{2a}$R$_{2b}$, (24) linker moiety (hydrophobic linkers, hydrophilic linkers, photo-cleavable linkers, redox reaction-cleavable linkers), (25) linker moiety with covalently bonded TAG-molecules (a TAG could be a fluorophor, biotin, different polymer beads and different reactive groups);

wherein R$_{2a}$ and R$_{2b}$ are independently selected from the group consisting of (a) hydrogen, (b) substituted or unsubstituted alkyl, (c) substituted or unsubstituted aryl, (d) substituted or unsubstituted heteroaryl, (e) substituted or unsubstituted heterocyclyl, and (f) substituted or unsubstituted cycloalkyl, wherein R$_{10}$, R$_{11}$ and R$_{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$_{10}$, R$_{11}$ together with the nitrogen to which they are attached optionally form a C$_3$-C$_{20}$ heterocyclic ring optionally containing one or more additional ring atoms selected from N, O or S, wherein said heterocyclic ring is optionally substituted with one or more groups independently selected from oxo, CF$_3$, F, Cl, Br, I, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

wherein R$_{14}$ and R$_{15}$ are independently selected from H, C$_1$-C$_{12}$ alkyl, or —(CH$_2$)$_n$-aryl, or R$_{14}$ and R$_{15}$ together with the atoms to which they are attached form a saturated or partially unsaturated C$_3$-C$_{12}$ carbocyclic ring wherein Y is O, S, or NR$_{12}$;

m is 0, 1, 2, 3, 4, 5 or 6;

n is 1, 2, 3, 4, 5, or 6; and t is 2, 3, 4, 5 or 6.

Preferably,

X is O (the ring containing X being morpholine) and/or

R$_{3x}$, R$_{3y}$, R$_{3z}$, R$_{3p}$ are independently selected from the structures:

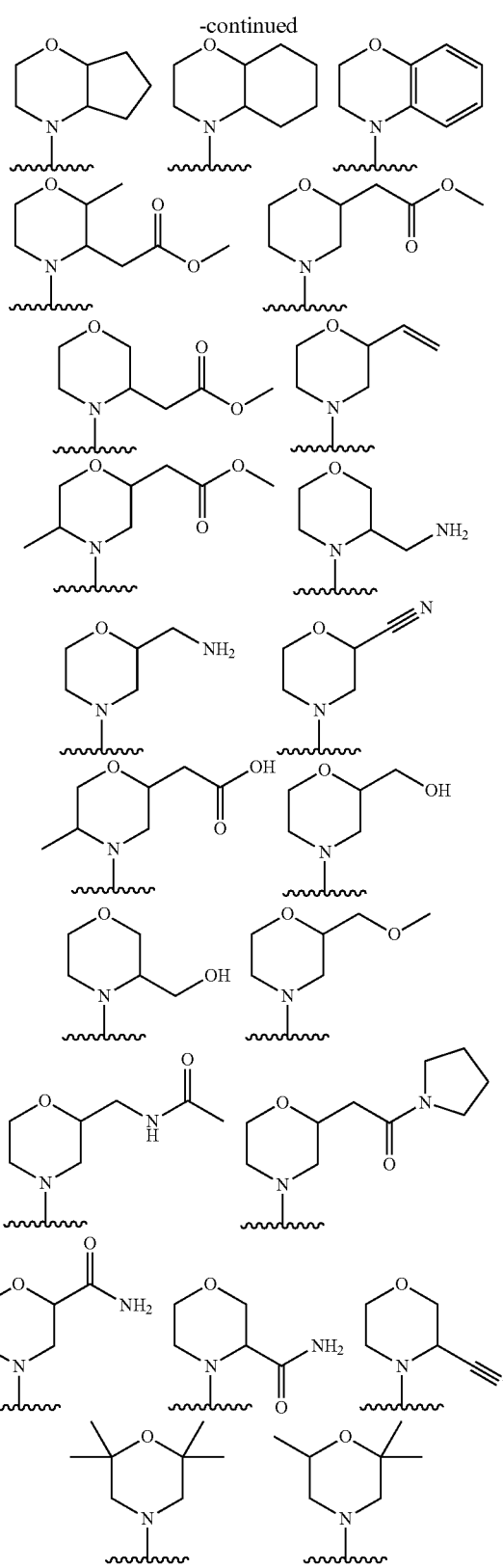

where the wavy line indicates the attachment to the 4-position of the core ring (triazine or pyrimidine or pyridine ring).

In another aspect of the invention, R$_1$ is substituted or unsubstituted heterocyclyl, or substituted or unsubstituted —O-heterocyclyl. In another aspect, $R_1$ is substituted or unsubstituted morpholinyl; more particularly, $R_1$ is unsubstituted N-linked morpholinyl.

In another aspect, $R_1$ comprises substituted or unsubstituted heterocyclylalkyl, or substituted or unsubstituted heteroarylalkyl.

In another aspect, $R_1$ is substituted or unsubstituted tetrahydropyran or substituted or unsubstituted tetrahydropyranyloxy. More particularly, $R_1$ is unsubstituted 4-tetrahydropyranyloxy.

In another aspect, $R_1$ comprises substituted or unsubstituted tetrahydropyran. In a more particular aspect, tetrahydropyran comprises 4-tetrahydropyranyloxy.

In another aspect, $R_1$ is substituted or unsubstituted tetrahydrofuran or substituted or unsubstituted tetrahydrofuranyloxy. More particularly, $R_1$ is unsubstituted 3-tetrahydrofuranyloxy.

In another aspect, $R_1$ is phenyl, wherein phenyl is unsubstituted or substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-(dimethylamino)acetamide, amino, acetylamino, carboxamide, (4-methylsulfonylpiperazino)-1-methyl, (4-methylpiperazino)-1-methyl, hydroxymethyl, and methoxy.

In certain embodiments, $R_1$ is pyridyl, thiazolyl, isoxazolyl, oxadiazolyl, or pyrimidyl, which heterocycyl group is unsubstituted or substituted with one or more groups selected from N-methylcarboxamide, isopropylsulfonylamino, methylsulfonyl, 2-hydroxy-2-methylpropanamide, 2-hydroxypropanamide, 2-meth oxyacetamide, (propan-2-ol)sulfonyl, 2-amino-2-methylpropanamide, 2-aminoacetamide, 2-hydroxyacetamide, methylsulfonylamino, 2-(dimethylamino)acetamide, amino, acetylamino, carboxamide, (4-methylsulfonylpiperazino)-1-methyl, (4-methylpiperazino)-1-methyl, hydroxymethyl, and methoxy.

In another aspect of the invention, $R_2$ is substituted or unsubstituted heterocyclyl, or substituted or unsubstituted —O-heterocyclyl.

In another aspect, $R_2$ comprises substituted or unsubstituted heterocyclylalkyl, or substituted or unsubstituted heteroarylalkyl.

In another aspect $R_2$ is a monocyclic heteroaryl group selected from pyridyl, isoxazolyl, imidazolyl, pyrazolyl, pyrrolyl, thiazolyl, pyridazinyl, pyrimidinyl, pyrazinyl, oxazolyl, furanyl, thienyl, triazolyl, tetrazolyl, where the monocyclic heteroaryl group is optionally substituted with one or more groups selected from F, Cl, Br, I, —CN, —$NR_{10}R_{11}$, —$OR_{10}$, —$C(O)R_{10}$, —$NR_{10}C(O)R_{11}$, —$N(C(O)R_{11})_2$, —$NR_{10}C(O)NR_{10}R_{11}$, —$C(=O)OR_{10}$, —$C(=O)NR_{10}R_{11}$, C1-C12 alkyl and (C1-C12 alkyl)-$OR_{10}$;

In a particular embodiment, $R_2$ is selected from the structures:

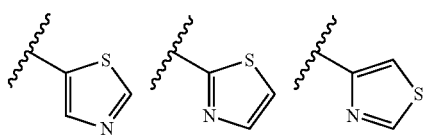

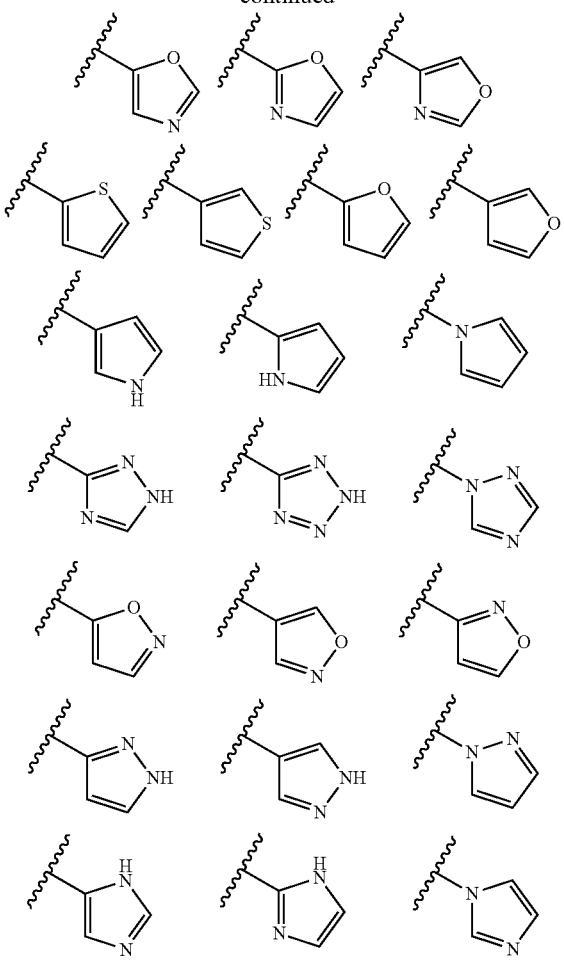

where the wavy line indicates the attachment to the 4-position of the core ring (triazine or pyrimidine or pyridine ring), and where the monocyclic heteroaryl group is optionally substituted with one or more groups selected from F, Cl, Br, I, —$NR_{10}R_{11}$, —$OR_{10}$, —$C(O)R_{10}$, —$NR_{10}C(O)R_{11}$, —$N(C(O)R_{11})_2$, —$NR_{10}C(O)NR_{10}R_{11}$, —$C(=O)OR_{10}$, —$C(=O)NR_{10}R_{11}$, and $C_1$-$C_{12}$ alkyl.

In certain embodiments, $R_2$ is selected from the structures:

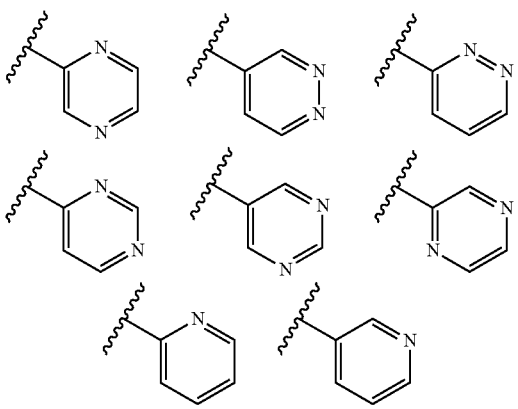

-continued

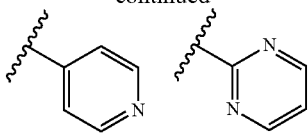

where the wavy line indicates the attachment to the 4-position of the core ring (triazine or pyrimidine or pyridine ring), and where the monocyclic heteroaryl group is optionally substituted with one or more groups selected from F, Cl, Br, I, —NR$_{10}$R$_{11}$, —OR$_{10}$, —C(O)R$_{10}$, —NR$_{10}$C(O)R$_{11}$, —N(C(O)R$_{11}$)$_2$, —NR$_{10}$C(O)NR$_{10}$R$_{11}$, —C(=O)OR$_{10}$, —C(=O)NR$_{10}$R$_{11}$, and C$_1$-C$_{12}$ alkyl.

In certain embodiments, R$_2$ is a monocyclic or bicyclic heteroraryl group selected from the following structures:

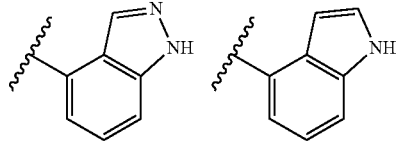
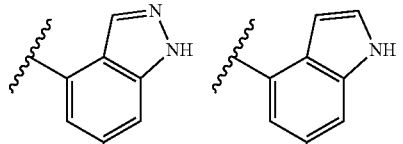
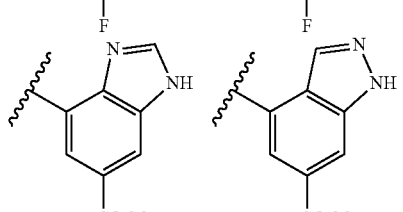
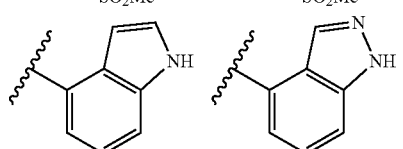
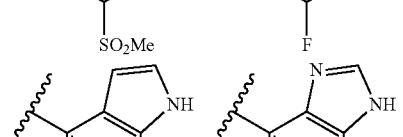
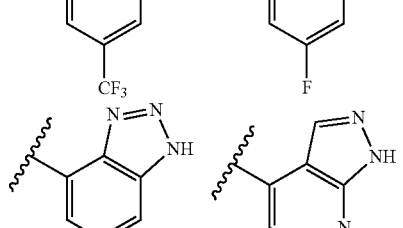
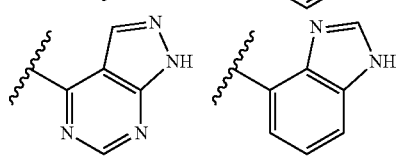

-continued

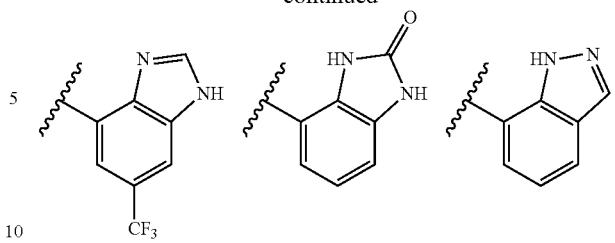
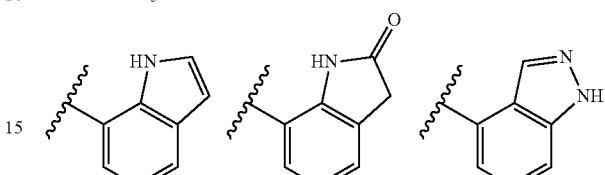
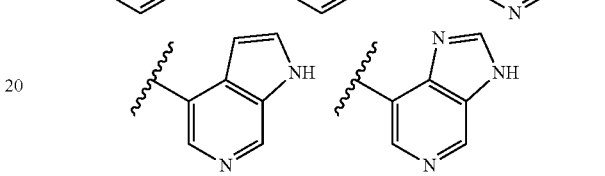
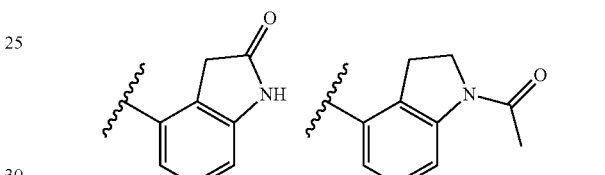
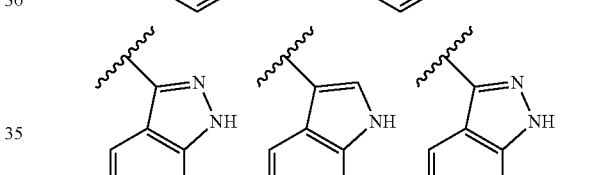
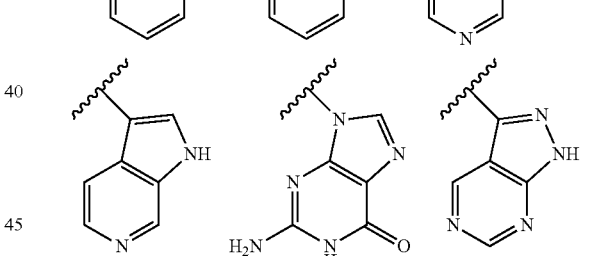
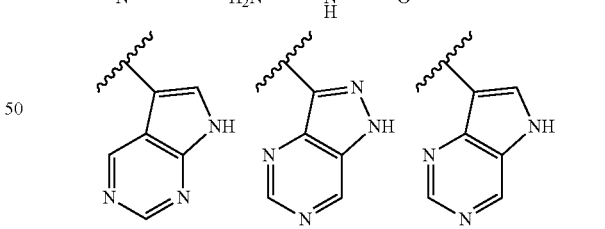
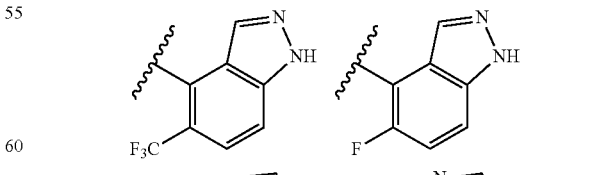
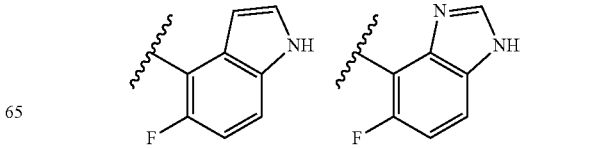

25
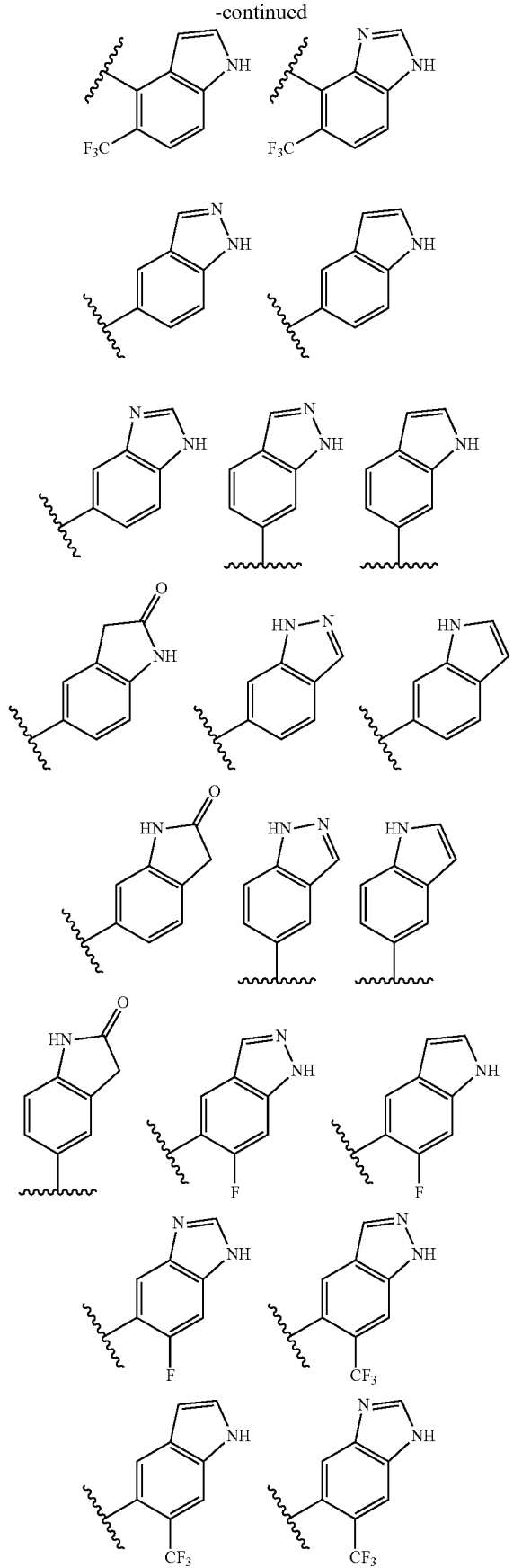
-continued
26
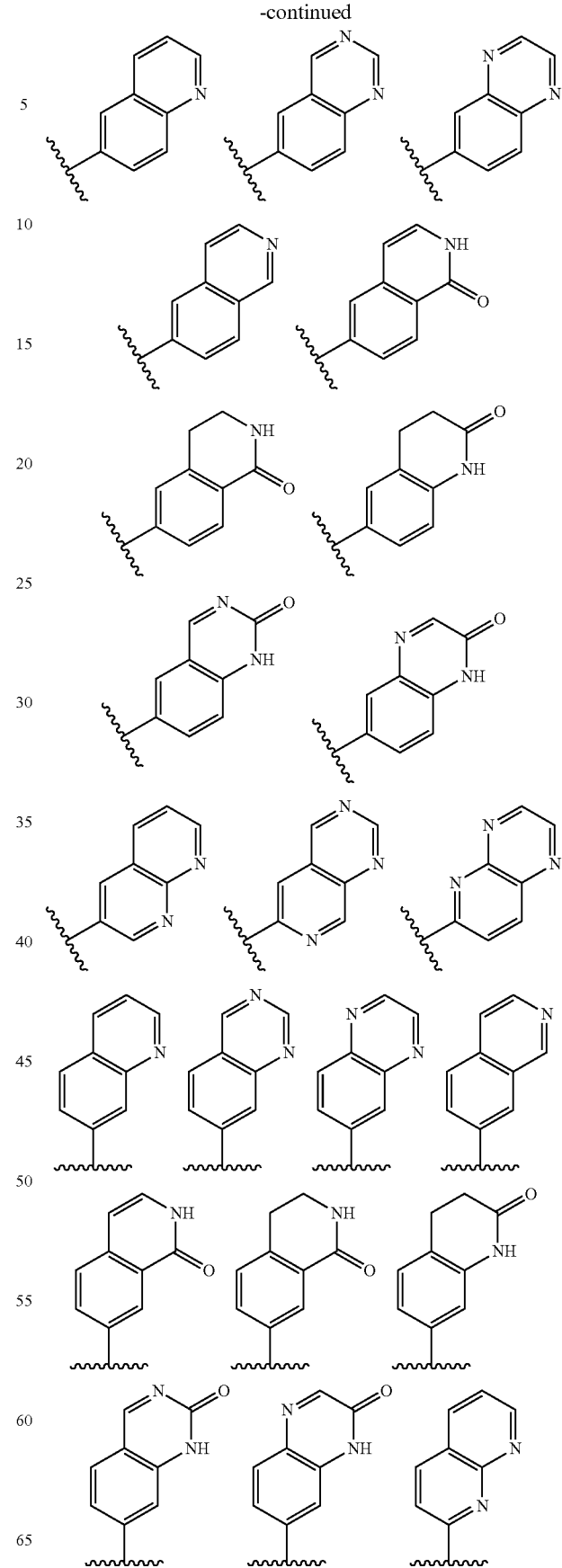
-continued

27
-continued
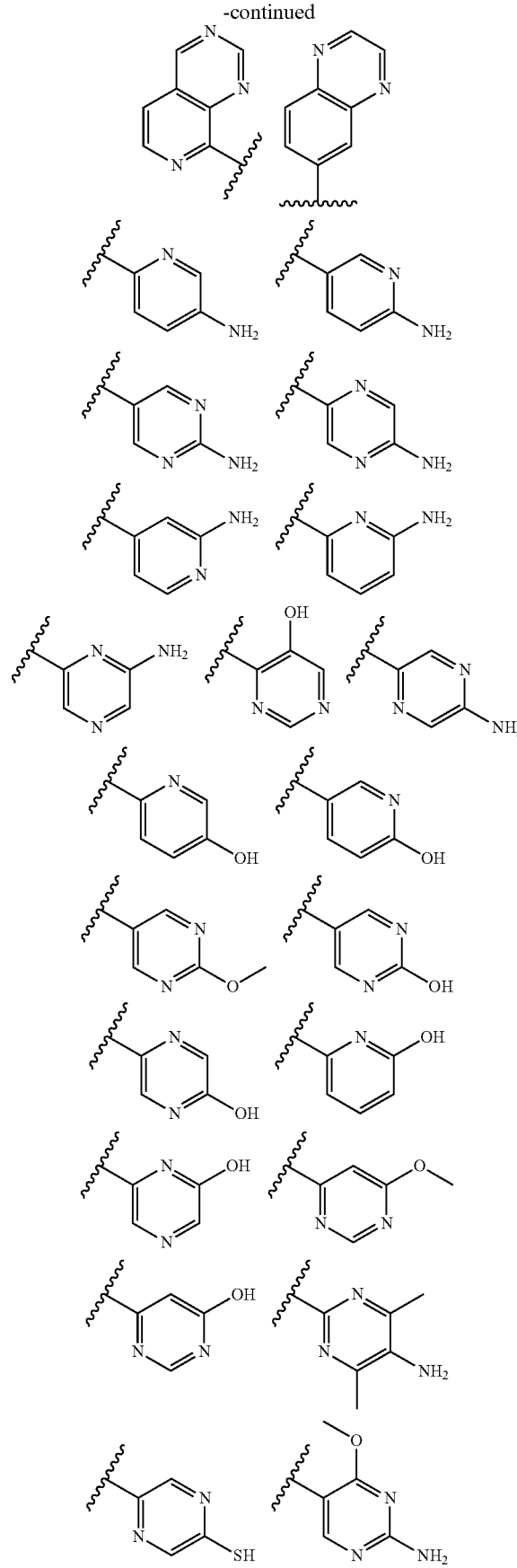
28
-continued
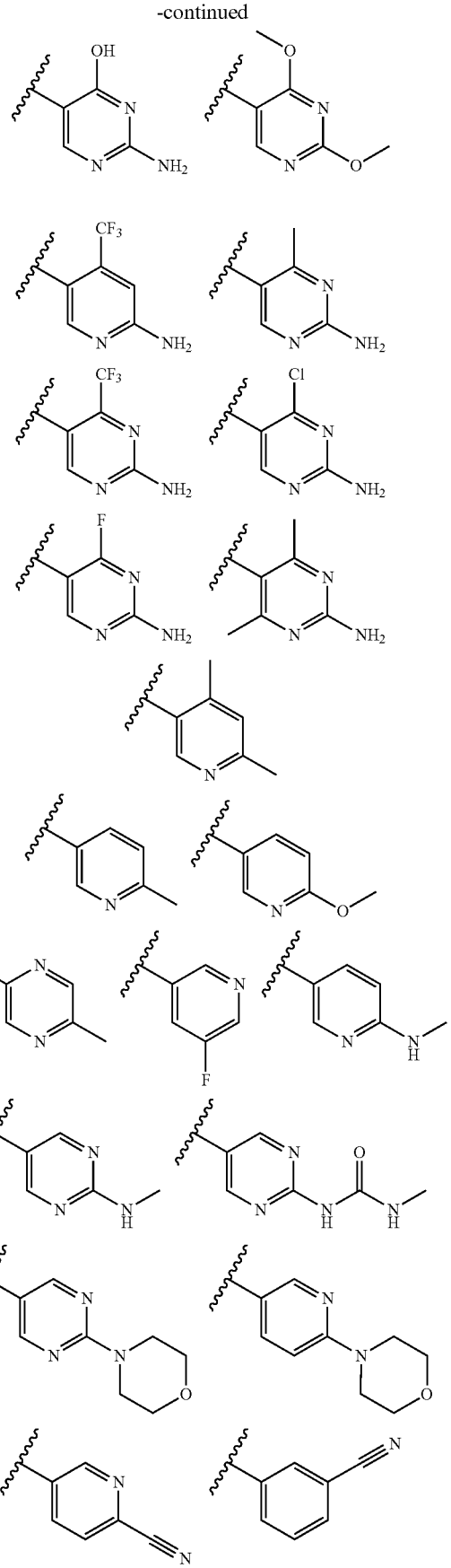

-continued

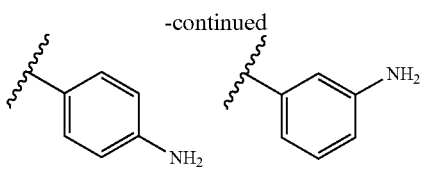

where the wavy line indicates the site of attachment,

In certain embodiments, the monocyclic or bicyclic heteroaryl group is substituted with one or more groups selected from F, —$NH_2$, —$NHCH_3$, —$N(CH_3)_2$, —OH, —$OCH_3$, —$C(O)CH_3$, —$NHC(O)CH_3$, —$N(C(O)CH_3)_2$, —$NHC(O)NH_2$, —$CO_2H$, —CHO, —$CH_2OH$, —$C(=O)NHCH_3$, —$C(=O)NH_2$, and —$CH_3$.

One aspect of the invention provides compounds having general formula (Ia):

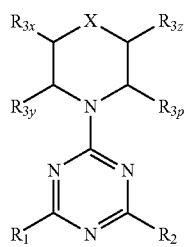

and stereoisomers, geometric isomers, tautomers, solvates, metabolites, N-oxide derivatives and pharmaceutically acceptable salts thereof, wherein X, $R_{3x}$, $R_{3y}$, $R_{3z}$, $R_{3p}$, $R_1$ and $R_2$ are as defined above for formula (I).

The preferences, particular aspects and embodiments set forth above for X, $R_{3x}$, $R_{3y}$, $R_{3z}$, $R_{3p}$. $R_1$ and $R_2$ in formula (I) apply to these substituents in formula (Ia).

Another aspect of the invention provides a compound having general formula (Ib):

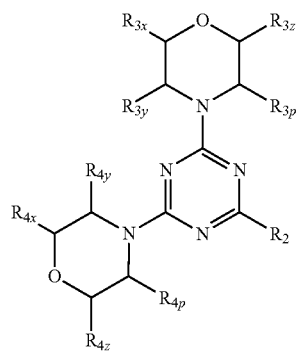

and stereoisomers, geometric isomers, tautomers, solvates, metabolites, N-oxid derivatives and pharmaceutically acceptable salts thereof, wherein $R_{3x}$, $R_{3y}$, $R_{3z}$, $R_{3p}$ and $R_2$ are as defined above for formula (I), $R_{4x}$, $R_{3y}$, $R_{4z}$ and $R_{4p}$ are independently from each other and selected from the group consisting of:

F, Cl, Br, I, —$C(C_1$-$C_8$ alkyl$)_2NR_{10}R_{11}$, —$(CR_{14}R_{15})_c$ $NR_{10}R_{11}$, —$C(CR_{14}R_{15})_nNR_{12}C(=Y)R_{10}$, —$(CR_{14}R_{15})_n$ $NR_{12}S(O)_2R_{10}$, —$CH(OR_{10})R_{10}$, —$(CR_{14}R_{15})_nOR_{10}$, —$(CR_{14}R_{15})_nS(O)_2R_{10}$, —$(CR_{14}R_{15})_nS(O)_2NR_{10}R_{11}$, —$C(=Y)R_{10}$, —$C(=Y)OR_{10}$, —$C(=Y)NR_{10}R_{11}$, —$C(=Y)NR_{12}OR_{10}$, —$C(=O)NR_{12}S(O)_2R_{10}$, —$C(=O)$ $NR_{12}(CR_{14}R_{15})_mNR_{10}R_{11}$, —$NO_2$, —$NHR_{12}$, —$NR_{12}C(=Y)R_{11}$, —$NR_{12}C(=Y)OR_{11}$, —$NR_{12}C(=Y)NR_{10}R_{11}$, —$NR_{12}S(O)_2R_{10}$, —$NR_{12}SO_2NR_{10}R_{11}$, —$S(O)_2R_{10}$, —$S(O)_2NR_{10}R_{11}$, —$SC(=Y)R_{10}$, —$SC(=Y)OR_{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl; or where the $C_3$-$C_{12}$ carbocyclyl, $C_2$-$C_{20}$ heterocyclyl, $C_6$-$C_{20}$ aryl, or $C_1$-$C_{20}$ heteroaryl is substituted at vicinal carbon atoms of the morpholine and forms a fused bicyclic morpholinyl;

where said alkyl, alkenyl, alkynyl, carbocyclyl, heterocyclyl, aryl and heteroaryl are optionally substituted with one or more groups independently selected from F, Cl, Br, I, —CN, $CF_3$, —$NO_2$, oxo, —$C(=Y)R_{10}$, —$C(=Y)OR_{10}$, —$C(=Y)NR_{10}R_{11}$, —$(CR_{14}R_{15})_nNR_{10}R_{11}$, —$(CR_{14}R_{15})_nC(=Y)NR_{10}R_{11}$, —$(CR_{14}R_{15})(—C(=Y)OR_{10}$, $(CR_{14}R_{15})_n$ $NR_{12}SO_2R_{10}$, —$(CR_{14}R_{15})_nOR_{10}$, —$(CR_{14}R_{15})_nR_{10}$, —$(CR_{14}R_{15})_nSO_2R_{10}$, —$NR_{10}R_{11}$, —$NR_{12}C(=Y)R_{10}$, —$R_{12}C(=Y)OR_{11}$, —$NR_{12}C(=Y)NR_{10}R_{11}$, —$NR_{12}SO_2R_{10}$, =$NR_{12}$, $OR_{10}$, —$OC(=Y)R_{10}$, —$C(=Y)OR_{10}$, —$OC(=Y)NR_{10}R_{11}$, —$OS(O)_2(OR_{10})$, —$OP(=Y)(OR_{10})(OR_{11})$, —$OP(OR_{10})(OR_{11})$, $SR_{10}$, —$S(O)R_{10}$, —$S(O)_2R_{10}$, —$S(O)_2NR_{10}R_{11}$, —$S(O)(OR_{10})$, —$S(O)_2(OR_{10})$, —$SC(=Y)R_{10}$, —$C(=Y)OR_{10}$, —$SC(=Y)NR_{10}R_{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

wherein $R_{10}$, $R_{11}$ and $R_{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ hetero-aryl, or $R_{10}$, $R_{11}$ together with the nitrogen to which they are attached optionally form a $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR_{10}$, $(CH_2)_mNR_{10}R_{11}$, $CF_3$, F, Cl, Br, I, $SO_2R_{10}$, $C(=O)R_{10}$, $NR_{12}C(=Y)R_{11}$, $C(=Y)NR_{10}R_{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

wherein $R_{14}$ and $R_{15}$ are independently selected from H, $C_1$-$C_{12}$ alkyl, or —$(CH_2)_n$-aryl, or $R_{14}$ and $R_{15}$ together with the atoms to which they are attached form a saturated or partially unsaturated $C_3$-$C_{12}$ carbocyclic ring wherein Y is O, S, or $NR_{12}$;

m is 0, 1, 2, 3, 4, 5 or 6;

n is 1, 2, 3, 4, 5, or 6 and t is 2, 3, 4, 5 or 6.

The preferences, particular aspects and embodiments set forth above for $R_{3x}$, $R_{3y}$, $R_{3z}$, $R_{3p}$. $R_1$ and $R_2$ in formula (I) apply to these substituents in formula (Ib).

Another aspect of the invention provides a compound having general formula (IC):

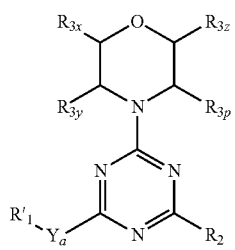

and stereoisomers, geometric isomers, tautomers, solvates, metabolites, N-oxide derivatives and pharmaceutically acceptable salts thereof, wherein $R_{3x}$, $R_{3y}$, $R_{3z}$, $R_{3p}$ and $R_2$ are as defined above for formula (I), $Y_a$ is O, S, NH, or a direct bond, $R'_1$ is selected from the group consisting of:
(1) H, F, Cl, Br, I, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —C($C_1$-$C_6$ alkyl)$_2$$NR_{10}R_{11}$, —$(CR_{14}R_{15})_t$$NR_{10}R_{11}$, —C($R_{14}R_{15})_n$$NR_{12}$C(=Y)$R_{10}$, —$(CR_{14}R_{15})_n$$NR_{12}$S(O)$_2$$R_{10}$, —CH(O$R_{10}$)$R_{10}$, —$(CR_{14}R_{15})_n$O$R_{10}$, —$(CR_{14}R_{15})_n$S(O)$_2$$R_{10}$, —$(CR_{14}R_{15})_n$S(O)$_2$$NR_{10}R_{11}$, —C(=Y)$R_{10}$, —C(=Y)O$R_{10}$, —C(=Y)$NR_{10}R_{11}$, —C(=Y)$NR_{12}$O$R_{10}$, —C(=O)$NR_{12}$S(O)$_2$$R_{10}$, —C(=O)$NR_{12}$(C$R_{14}R_{15})_m$$NR_{10}R_{11}$, —NO$_2$, —NH$R_{12}$, —$NR_{12}$C(=Y)$R_{11}$, —$NR_{12}$C(=Y)O$R_{11}$, —$NR_{12}$C(=Y)$NR_{10}R_{11}$, —$NR_{12}$S(O)$_2$$R_{10}$, —$NR_{12}$SO$_2$$NR_{10}R_{11}$, —S(O)$_2$$R_{10}$, —S(O)$_2$$NR_{10}R_{11}$, —SC(=Y)$R_{10}$, —SC(=Y)O$R_{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_5$-$C_{20}$ aryl or $C_1$-$C_{20}$ heteroaryl, (13) linker moiety (hydrophobic linkers, hydrophilic linkers, photo-cleavable linkers, redox reaction-cleavable linkers), (14) linker moiety with covalently bonded TAG-molecules (a TAG could be a fluorophor, biotin, different polymer beads and different reactive groups) wherein $R_{10}$, $R_{11}$, $R_{12}$, $R_{14}$, $R_{15}$, Y, m, n and t are as defined above for formula (I).

The preferences, particular aspects and embodiments set forth above for $R_{3x}$, $R_{3y}$, $R_{3z}$, $R_{3p}$ and $R_2$ in formula (I) apply to these substituents in formula (Ic).

In another aspect of the invention $R'_1$ is substituted or unsubstituted heterocyclyl, or substituted or unsubstituted —O-heterocyclyl. In another aspect, $R'_1$ is substituted or unsubstituted morpholinyl; more particularly, $R'_1$ is unsubstituted N-linked morpholinyl; more particularly, X is a direct link. In another more particular embodiment, $R_1$ is 4-tetrahydropyranyl; more particularly, X is O. In another embodiment, $R_1$ is 3-tetrahydrofuranyl; more particularly, X is O.

In another aspect thereof, $R'_1$ comprises substituted or unsubstituted heterocyclylalkyl, or substituted or unsubstituted heteroarylalkyl.

In another aspect, $R'_1$ is substituted or unsubstituted tetrahydropyran or substituted or unsubstituted tetrahydropyranyloxy. More particularly, $R'_1$ is unsubstituted 4-tetrahydropyranyloxy.

In another aspect thereof, $R'_1$ comprises substituted or unsubstituted tetrahydropyran. In a more particular aspect, tetrahydropyran comprises 4-tetrahydropyranyloxy.

In another aspect, $R'_1$ is substituted or unsubstituted tetrahydrofuran or substituted or unsubstituted tetrahydrofuranyloxy. More particularly, $R'_1$ is unsubstituted 3-tetrahydrofuranyloxy.

In another aspect, $R'_1$ is phenyl, wherein phenyl is unsubstituted or substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-(dimethylamino)acetamide, amino, acetylamino, carboxamide, (4-methylsulfonylpiperazino)-1-methyl, (4-methylpiperazino)-1-methyl, hydroxymethyl, and methoxy.

In certain embodiments, $R'_1$ is pyridyl, thiazolyl, isoxazolyl, oxadiazolyl, or pyrimidyl, which heterocycyl group is unsubstituted or substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-(dimethylamino) acetamide, amino, acetylamino, carboxamide, (4-methylsulfonylpiperazino)-1-methyl, (4-methylpiperazino)-1-methyl, hydroxymethyl, and methoxy.

In another embodiment, $R'_1$ is selected from the group consisting of: (1) substituted or unsubstituted morpholinyl, (2) substituted or unsubstituted tetrahydropyranyl, and (3) substituted or unsubstituted tetrahydrofuranyl.

In a more particular embodiment thereof, $R'_1$ is N-linked morpholinyl. In another more particular embodiment, $R'_1$ is 4-tetrahydropyranyl. In another embodiment, $R'_1$ is 3-tetrahydrofuranyl.

Another aspect of the invention provides a compound having general formula (Id):

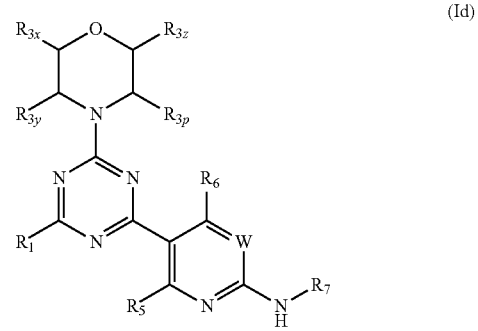

and stereoisomers, geometric isomers, tautomers, solvates, metabolites, N-oxide derivatives and pharmaceutically acceptable salts thereof, wherein $R_{3x}$, $R_{3y}$, $R_{3z}$, $R_{3p}$ and $R_1$ are as defined above for formula (I), W is $CR_w$ or N, wherein Rw is selected from the group consisting of:
(1) hydrogen, (2) cyano, (3) halogen, (4) methyl, (5) trifluoromethyl, (6) sulfonamido;

$R_5$ is selected from the group consisting of:
(1) hydrogen, and (2) halogen, $R_6$ is selected from the group consisting of:
(1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —COR$_{3a}$, (13) —NR$_{3a}$R$_{3b}$, (14) —NR$_{3a}$COR$_{3b}$, (15) —NR$_{3a}$SO$_2$R$_{3b}$, (16) —OR$_{3a}$, (17) —SR$_{3a}$, (18) —SOR$_{3a}$, (19) —SO$_2$R$_{3a}$, and

(20) —SO$_2$NR$_{3a}$R$_{3b}$, wherein R$_{3a}$, and R$_{3b}$ are independently selected from the group consisting of: (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalky, and R$_7$ is selected from the group consisting of:
(1) hydrogen, (2) substituted and unsubstituted alkyl, and (3) substituted and unsubstituted cycloalkyl, (4) methyl, (5) ethyl, (6) trifluoromethyl, (7) sulfonamid, (8) acetate, (9) linker moiety (hydrophobic linkers, hydrophilic linkers, photo-cleavable linkers, redox reaction-cleavable linkers), (10) linker moiety with covalently bonded TAG-molecules (a TAG could be a fluorophor, biotin, different polymer beads and different reactive groups).

The preferences, particular aspects and embodiments set forth above for R$_{3x}$, R$_{3y}$, R$_{3z}$, R$_{3p}$, and R$_1$ in formula (I) apply to these substituents in formula (Id).

In a more particular embodiment, W is CH.

In another embodiment, W is N. In a more particular embodiment thereof, R$_6$ is =O.

In another embodiment, R$_6$ is selected from the group consisting of:
(1) cyano, (2) nitro, (3) halogen, (4) hydroxyl, (5) amino, and (6) trifluoromethyl. In another embodiment, R$_6$ is trifluoromethyl. In another embodiment, R$_6$ is cyano.

Another aspect of the invention provides a compound having general formula (Ie):

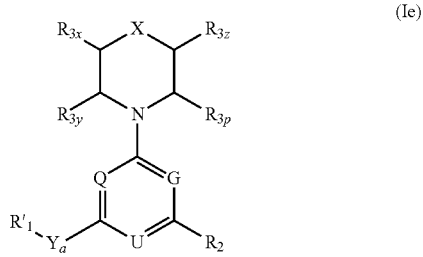

(Ie)

and stereoisomers, geometric isomers, tautomers, solvates, metabolites, N-oxide derivatives and pharmaceutically acceptable salts thereof, wherein
Q=C, G=C, U=N;
Q=C, U=C, G=N; or
U=C, G=C, Q=N;
X, R$_{3x}$, R$_{3y}$, R$_{3z}$, R$_{3p}$ and R$_2$ are as defined above for formula (I),
Y$_a$ is O, S, NH, or a direct bond,
R'$_1$ is selected from the group consisting of:
(1) H, F, Cl, Br, I, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —C(C$_1$-C$_6$ alkyl)$_2$NR$_{10}$R$_{11}$, —(CR$_{14}$R$_{15}$)$_n$NR$_{10}$R$_{11}$, —C(R$_{14}$R$_{15}$)$_n$NR$_{12}$C(=Y)R$_{10}$, —(CR$_{14}$R$_{15}$)$_n$NR$_{12}$S(O)$_2$R$_{10}$, —CH(OR$_{10}$)R$_{10}$, —(CR$_{14}$R$_{15}$)$_n$OR$_{10}$, —(CR$_{14}$R$_{15}$)$_n$S(O)$_2$R$_{10}$, —(CR$_{14}$R$_{15}$)$_n$S(O)$_2$NR$_{10}$R$_{11}$, —C(=Y)R$_{10}$, —C(=Y)OR$_{10}$, —C(=Y)NR$_{10}$R$_{11}$, —C(=Y)NR$_{12}$OR$_{10}$, —C(=O)NR$_{12}$S(O)$_2$R$_{10}$, —C(=O)NR$_{12}$(CR$_{14}$R$_{15}$)$_m$NR$_{10}$R$_{11}$, —NO$_2$, —NHR$_{12}$, —NR$_{12}$C(=Y)R$_{11}$, —NR$_{12}$C(=Y)OR$_{11}$, —NR$_{12}$C(=Y)NR$_{10}$R$_{11}$, —NR$_{12}$S(O)$_2$R$_{10}$, —NR$_{12}$SO$_2$NR$_{10}$R$_{11}$, —S(O)$_2$R$_{10}$, —S(O)$_2$NR$_{10}$R$_{11}$, —SC(=Y)R$_{10}$, —SC(=Y)OR$_{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl or C$_1$-C$_{20}$ heteroaryl, (13) linker moiety (hydrophobic linkers, hydrophilic linkers, photo-cleavable linkers, redox reaction-cleavable linkers), (14) linker moiety with covalently bonded TAG-molecules (a TAG could be a fluorophor, biotin, different polymer beads and different reactive groups) wherein R$_{10}$, R$_{11}$, R$_{12}$, R$_{14}$, R$_{15}$, Y, m, n and t are as defined above for formula (I).

The preferences, particular aspects and embodiments set forth above for X, R$_{3x}$, R$_{3y}$, R$_{3z}$, R$_{3p}$ and R$_2$ in formula (I) apply to these substituents in formula (Ie).

In another aspect of the invention R'$_1$ is substituted or unsubstituted heterocyclyl, or substituted or unsubstituted —O-heterocyclyl. In another aspect, R'$_1$ is substituted or unsubstituted morpholinyl; more particularly, R'$_1$ is unsubstituted N-linked morpholinyl; more particular still, X is a direct link. In another more particular embodiment, R$_1$ is 4-tetrahydropyranyl; more particularly, X is O. In another embodiment, R$_1$ is 3-tetrahydrofuranyl; more particularly, X is O.

In another aspect thereof, R'$_1$ comprises substituted or unsubstituted heterocyclylalkyl, or substituted or unsubstituted heteroarylalkyl.

In another aspect, R'$_1$ is substituted or unsubstituted tetrahydropyran or substituted or unsubstituted tetrahydropyranyloxy. More particularly, R'$_1$ is unsubstituted 4-tetrahydropyranyloxy.

In another aspect thereof, R'$_1$ comprises substituted or unsubstituted tetrahydropyran. In a more particular aspect, tetrahydropyran comprises 4-tetrahydropyranyloxy.

In another aspect, R'$_1$ is substituted or unsubstituted tetrahydrofuran or substituted or unsubstituted tetrahydrofuranyloxy. More particularly, R'$_1$ is unsubstituted 3-tetrahydrofuranyloxy.

In another aspect, R'$_1$ is phenyl, wherein phenyl is unsubstituted or substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-(dimethylamino)acetamide, amino, acetylamino, carboxamide, (4-methylsulfonylpiperazino)-1-methyl, (4-methylpiperazino)-1-methyl, hydroxymethyl, and methoxy.

In certain embodiments, R'$_1$ is pyridyl, thiazolyl, isoxazolyl, oxadiazolyl, or pyrimidyl, which heterocycyl group is unsubstituted or substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-(dimethylamino)acetamide, amino, acetylamino, carboxamide, (4-methylsulfonylpiperazino)-1-methyl, (4-methylpiperazino)-1-methyl, hydroxymethyl, and methoxy.

In another embodiment, R'$_1$ is selected from the group consisting of: (1) substituted or unsubstituted morpholinyl, (2) substituted or unsubstituted tetrahydropyranyl, and (3) substituted or unsubstituted tetrahydrofuranyl.

In a more particular embodiment thereof, R'$_1$ is N-linked morpholinyl. In another more particular embodiment, R'$_1$ is 4-tetrahydropyranyl. In another embodiment, R'$_1$ is 3-tetrahydrofuranyl.

Another aspect of the invention provides compounds having one of general formulas (If) and (Ig):

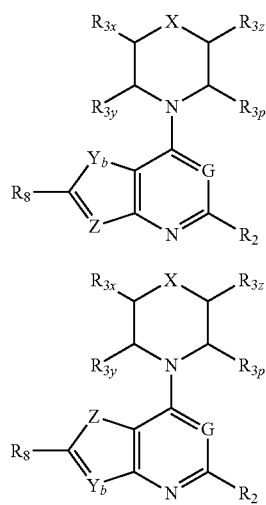

and stereoisomers, geometric isomers, tautomers, solvates, metabolites, N-oxide derivatives and pharmaceutically acceptable salts thereof, wherein G is N or G is C, X, $R_{3x}$, $R_{3y}$, $R_{3z}$, $R_{3p}$ and $R_2$ are as defined above for formula (I), $Y_b$ is O, S or $SO_2$, Z is N or $CR_q$, wherein $R_q$ is selected from the group consisting of:
(1) linker moiety (hydrophobic linkers, hydrophilic linkers, photo-cleavable linkers, redox reaction-cleavable linkers),
(2) linker moiety with covalently bonded TAG-molecules (a TAG could be a fluorophor, biotin, different polymer beads and different reactive groups), $R_8$ is selected from the group consisting of:
(1) H, F, Cl, Br, I, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —C($C_1$-$C_8$ alkyl)$_2$$NR_{10}R_{11}$, —$(CR_{14}R_{15})_n NR_{10}R_{11}$, —C($R_{14}R_{15})_n NR_{12}$C(=Y)$R_{10}$, —$(CR_{14}R_{15})_n NR_{12}$S(O)$_2$$R_{10}$, —CH(O$R_{10}$)$R_{10}$, —$(CR_{14}R_{15})_n OR_{10}$, —$(CR_{14}R_{15})_n$S(O)$_2$$R_{10}$, —$(CR_{14}R_{15})_n$S(O)$_2$$NR_{10}R_{11}$, —C(=Y)$R_{10}$, —C(=Y)O$R_{10}$, —C(=Y)$NR_{10}R_{11}$, —C(=Y)$NR_{12}OR_{10}$, —C(=O)$NR_{12}$S(O)$_2$$R_{10}$, —C(=O)$NR_{12}(CR_{14}R_{15})_m NR_{10}R_{11}$, —$NO_2$, —$NHR_{12}$, —$NR_{12}$C(=Y)$R_{11}$, —$NR_{12}$C(=Y)O$R_{11}$, —$NR_{12}$C(=Y)$NR_{10}R_{11}$, —$NR_{12}$S(O)$_2$$R_{10}$, —$NR_{12}$SO$_2$$NR_{10}R_{11}$, —S(O)$_2$$R_{10}$, —S(O)$_2$$NR_{10}R_{11}$, —SC(=Y)$R_{10}$, —SC(=Y)O$R_{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl or $C_1$-$C_{20}$ heteroaryl, (13) linker moiety (hydrophobic linkers, hydrophilic linkers, photo-cleavable linkers, redox reaction-cleavable linkers), (14) linker moiety with covalently bonded TAG-molecules (a TAG could be a fluorophor, biotin, different polymer beads and different reactive groups), wherein, $R_{11}$ and $R_{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, $R_{10}$ is selected from the group consisting of:
(1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$COR_{2a}$, (13) —$CO_2R_{2a}$, (14) —$CONR_{2a}R_{2b}$, (15) —$NR_{2a}R_{2b}$, (16) —$NR_{2a}COR_{2b}$, (17) —$NR_{2a}SO_2R_{2b}$, (18) —$OCOR_{2a}$, (19) —$OR_{2a}$, (20) —$SR_{2a}$, (21) —$SOR_{2a}$, (22) —$SO_2R_{2a}$, and (23) —$SO_2NR_{2a}R_{2b}$, (24) linker moiety (hydrophobic linkers, hydrophilic linkers, photo-cleavable linkers, redox reaction-cleavable linkers), (25) linker moiety with covalently bonded TAG-molecules (a TAG could be a fluorophor, biotin, different polymer beads and different reactive groups);

wherein $R_{2a}$ and $R_{2b}$ are independently selected from the group consisting of (a) hydrogen, (b) substituted or unsubstituted alkyl, (c) substituted or unsubstituted aryl, (d) substituted or unsubstituted heteroaryl, (e) substituted or unsubstituted heterocyclyl, and (f) substituted or unsubstituted cycloalkyl, or $R_{10}$, $R_{11}$ together with the nitrogen to which they are attached optionally form a $C_3$-$C_{20}$ heterocyclic ring optionally containing one or more additional ring atoms selected from N, O or S, wherein said heterocyclic ring is optionally substituted with one or more groups independently selected from oxo, $CF_3$, F, Cl, Br, I, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

wherein $R_{14}$ and $R_{15}$ are independently selected from H, $C_1$-$C_{12}$ alkyl, or —$(CH_2)_n$-aryl, or $R_{14}$ and $R_{15}$ together with the atoms to which they are attached form a saturated or partially unsaturated $C_3$-$C_{12}$ carbocyclic ring wherein Y is O, S, or $NR_{12}$;

m is 0, 1, 2, 3, 4, 5 or 6;

n is 1, 2, 3, 4, 5, or 6; and t is 2, 3, 4, 5 or 6.

The preferences, particular aspects and embodiments set forth above for X, $R_{3x}$, $R_{3y}$, $R_{3z}$, $R_{3p}$ and $R_2$ in formula (I) apply to these substituents in formulas (If) and (Ig).

In particular aspect of the invention, $R_8$ is substituted or unsubstituted heterocyclyl, or substituted or unsubstituted —O-heterocyclyl. In another aspect, $R_8$ is substituted or unsubstituted morpholinyl; more particularly, $R_8$ is unsubstituted N-linked morpholinyl.

In another aspect, $R_8$ comprises substituted or unsubstituted heterocyclylalkyl, or substituted or unsubstituted heteroarylalkyl.

In another aspect, $R_8$ is substituted or unsubstituted tetrahydropyran or substituted or unsubstituted tetrahydropyranyloxy. More particularly, $R_8$ is unsubstituted 4-tetrahydropyranyloxy.

In another aspect thereof, $R_8$ comprises substituted or unsubstituted tetrahydropyran. In a more particular aspect, tetrahydropyran comprises 4-tetrahydropyranyloxy.

In another aspect, $R_8$ is substituted or unsubstituted tetrahydrofuran or substituted or unsubstituted tetrahydrofuranyloxy. More particularly, $R_8$ is unsubstituted 3-tetrahydrofuranyloxy.

In another aspect, $R_8$ is optionally substituted phenyl, wherein phenyl is substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-(dimethylamino)acetamide, amino, acetylamino, carboxamide, (4-methylsulfonylpiperazino)-1-methyl, (4-methylpiperazino)-1-methyl, hydroxymethyl, and methoxy.

In certain embodiments, $R_8$ is optionally substituted pyridyl, optionally substituted thiazolyl, optionally substituted isoxazolyl, optionally substituted oxadiazolyl, or optionally substituted pyrimidyl.

In another embodiment, $R_8$ is selected from the group consisting of: (1) substituted or unsubstituted morpholinyl, (2) substituted or unsubstituted tetrahydropyranyl, and (3) substituted or unsubstituted tetrahydrofuranyl.

In a more particular embodiment thereof, $R_8$ is N-linked morpholinyl. In another more particular embodiment, $R_8$ is 4-tetrahydropyranyl; in another embodiment, $R_8$ is 3-tetrahydrofuranyl.

For the use of $R_{10}$, see general reaction scheme 45.

Another aspect of the invention provides compounds having general formulas (Ih) and (Ii):

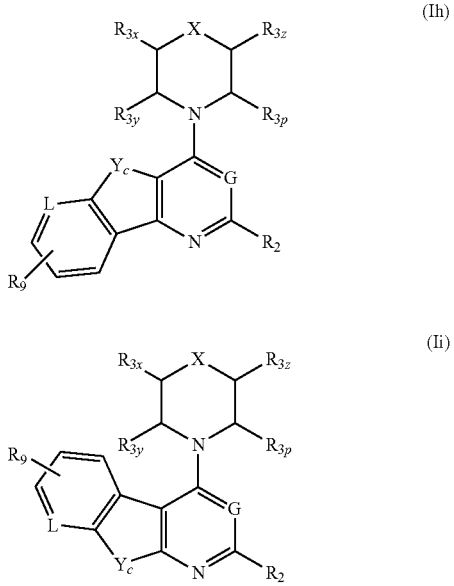

and stereoisomers, geometric isomers, tautomers, solvates, metabolites, N-oxide derivatives and pharmaceutically acceptable salts thereof, wherein G is N or G is C, X, $R_{3x}$, $R_{3y}$, $R_{3z}$, $R_{3p}$ and $R_2$ are as defined above for formula (I), $Y_c$ is O, S, $SO_2$, NH, or a direct bond, L is C, N or N-oxide, $R_9$ is selected from the group consisting of:
(1) H, F, Cl, Br, I, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —C($C_1$-$C_6$ alkyl)$_2$N$R_{10}R_{11}$, —(C$R_{14}R_{15}$)$_t$N$R_{10}R_{11}$, —C(R$_{14}R_{15}$)$_n$N$R_{12}$C(=Y)$R_{10}$, —(C$R_{14}R_{15}$)$_n$N$R_{12}$S(O)$_2$R$_{10}$, —CH(O$R_{10}$)$R_{10}$, —(C$R_{14}R_{15}$)$_n$O$R_{10}$, —(C$R_{14}R_{15}$)$_n$S(O)$_2R_{10}$, —(C$R_{14}R_{15}$)$_n$S(O)$_2$N$R_{10}R_{11}$, —C(=Y)$R_{10}$, —C(=Y)O$R_{10}$, —C(=Y)N$R_{10}R_{11}$, —C(=Y)N$R_{12}$O$R_{10}$, —C(=O)N$R_{12}$S(O)$_2R_{10}$, —C(=O)N$R_{12}$(C$R_{14}R_{15}$)$_m$N$R_{10}R_{11}$, —NO$_2$, —NHR$_{12}$, —N$R_{12}$C(=Y)$R_{11}$, —N$R_{12}$C(=Y)O$R_{11}$, —N$R_{12}$C(=Y)N$R_{10}R_{11}$, —N$R_{12}$S(O)$_2R_{10}$, —N$R_{12}$SO$_2$N$R_{10}R_{11}$, —S(O)$_2R_{10}$, —S(O)$_2$N$R_{10}R_{11}$, —SC(=Y)$R_{10}$, —SC(=Y)O$R_{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl or $C_1$-$C_{20}$ heteroaryl, (13) linker moiety (hydrophobic linkers, hydrophilic linkers, photo-cleavable linkers, redox reaction-cleavable linkers), (14) linker moiety with covalently bonded TAG-molecules (a TAG could be a fluorophor, biotin, different polymer beads and different reactive groups), wherein $R_{10}$, $R_{11}$, $R_{12}$, $R_{14}$, $R_{15}$, Y, m, n and t are as defined above for formula (I).

In another aspect of the invention, $R_9$ is substituted or unsubstituted heterocyclyl, or substituted or unsubstituted —O-heterocyclyl. In another aspect, $R_9$ is substituted or unsubstituted morpholinyl; more particularly, $R_9$ is unsubstituted N-linked morpholinyl.

In another aspect, $R_9$ comprises substituted or unsubstituted heterocyclylalkyl, or substituted or unsubstituted heteroarylalkyl.

In another aspect, $R_9$ is substituted or unsubstituted tetrahydropyran or substituted or unsubstituted tetrahydropyranyloxy. More particularly, $R_9$ is unsubstituted 4-tetrahydropyranyloxy.

In another aspect thereof, $R_9$ comprises substituted or unsubstituted tetrahydropyran. In a more particular aspect, tetrahydropyran comprises 4-tetrahydropyranyloxy.

In another aspect, $R_9$ is substituted or unsubstituted tetrahydrofuran or substituted or unsubstituted tetrahydrofuranyloxy. More particularly, $R_9$ is unsubstituted 3-tetrahydrofuranyloxy.

In another aspect, $R_9$ is optionally substituted phenyl, wherein phenyl is substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol) sulfonyl, 2-amino-2-methylpropanamide, 2-aminoacetamide, 2-hydroxyacetamide, methylsulfonylamino, 2-(dimethylamino)acetamide, amino, acetylamino, carboxamide, (4-methylsulfonylpiperazino)-1-methyl, (4-methylpiperazino)-1-methyl, hydroxymethyl, and methoxy.

In certain embodiments, $R_9$ is optionally substituted pyridyl, optionally substituted thiazolyl, optionally substituted isoxazolyl, optionally substituted oxadiazolyl, or optionally substituted pyrimidyl.

In another embodiment, $R_9$ is selected from the group consisting of: (1) substituted or unsubstituted morpholinyl, (2) substituted or unsubstituted tetrahydropyranyl, and (3) substituted or unsubstituted tetrahydrofuranyl.

In a more particular embodiment thereof, $R_9$ is N-linked morpholinyl. In another more particular embodiment, $R_9$ is 4-tetrahydropyranyl; in another embodiment, $R_9$ is 3-tetrahydrofuranyl.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a compound of the invention incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embraces both solvated and unsolvated forms.

The compounds of the invention may also exist in different tautomeric forms (tautomers), and all such forms are embraced with the scope of the invention.

The present invention also embrace a isotopically-labelled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulphur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labelled compounds of the present invention (e.g., those labelled with $^{3}H$ and $^{14}C$) are useful in compound and/or substrate tissue distribution assays. Tritiated (3H) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labelled compounds of the present invention can generally be prepared by following procedures analogous to those disclosed in the Schemes and/or in the Examples herein below, by substituting an isotopically labelled reagent for a non-isotopically labeled reagent.

Preparation of Compounds of the Invention

The compounds of the invention may be synthesized by synthetic routes that include processes analogous to those well known in the chemical arts, particularly in light of the description contained herein. The starting materials are generally available from commercial sources such as Aldrich Chemicals or are readily prepared using methods well known to those skilled in the art (e.g., prepared by methods generally described in Louis F. Fieser and Mary Fieser, Reagents for Organic Synthesis, v. 1-19, Wiley, N. Y. (1967-1999 ed.), or Beilsteins Handbuch der organischen Chemie, 4, Aufl. ed. Springer-Verlag, Berlin, including supplements (also available via the Beilstein online database).

In certain embodiments, the compounds of the invention may be readily prepared using procedures well-known to prepare triazines and other heterocycles, which are described in: Comprehensive Heterocyclic Chemistry, Editors Katritzky and Rees, Pergamon Press, 1984.

Compounds of the invention may be prepared singly or as compound libraries comprising at least 2, for example 5 to 1,000 compounds, or 10 to 100 compounds. Libraries of compounds of the invention may be prepared by a combinatorial 'split and mix' approach or by multiple parallel syntheses using either solution phase or solid phase chemistry, by procedures well known to those skilled in the art. Thus according to a further aspect of the invention there is provided a compound library comprising at least 2 compounds, or pharmaceutically acceptable salts thereof.

For illustrative purposes, Schemes 1-52 show general methods for preparing the compounds of the present invention as well as key intermediates. For a more detailed description of the individual reaction steps, see the Examples hereinbelow. Those skilled in the art will appreciate that other synthetic routes may be used to synthesize the compounds of the invention. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of the invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Schemes for Preparing the Compounds of the Invention

Scheme 1

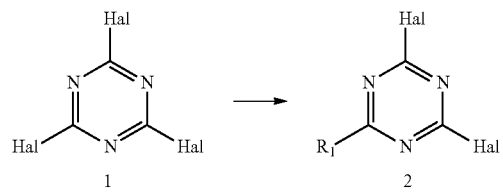

Scheme 1 shows a general method for preparation of the triazine intermediate 2 from 2,4,6-trihalo-1,3,5-triazine reagent (1), wherein Hal is Cl, Br, or I; and $R_1$ is as defined for formula Ia-d compounds, or precursors or prodrugs thereto.

Scheme 2

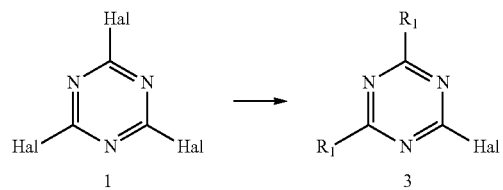

Scheme 2 shows a general method for preparation of the triazine intermediate 3 from 2,4,6-trihalo-1,3,5-triazine reagent (1), wherein Hal is Cl, Br, or I; and $R_1$ is as defined for formula Ia-d compounds, or precursors or prodrugs thereto.

Scheme 3

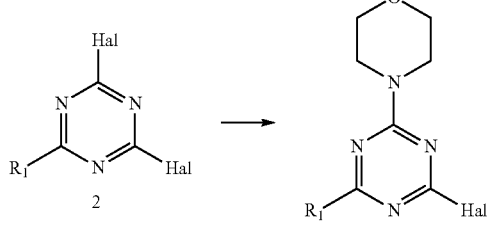

Scheme 3 shows a general method for selectively displacing a halide from bis-halo triazine intermediate 2 with morpholine in an organic solvent to prepare morpholino triazine intermediate 4 compounds, wherein Hal is Cl, Br, or I; and $R_1$ is as defined for formula Ia-d compounds, or precursors or prodrugs thereto.

Scheme 4

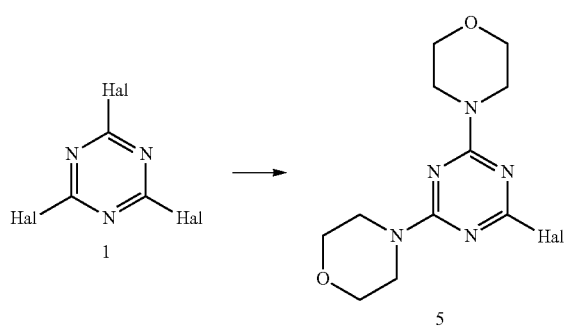

Scheme 4 shows a general method for selectively displacing two halides from tris-halo triazine 1 with morpholine in an organic solvent to prepare bis-morpholino triazine intermediate 5 compounds, wherein Hal is Cl, Br, or I.

Scheme 5

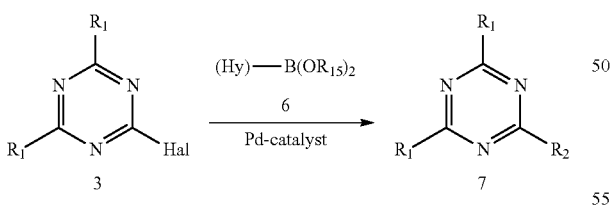

Scheme 5 shows a general method for Suzuki-type coupling of a 1-halo triazine intermediate 3 with a cyclic heteroaryl boronate acid ($R_{15}$=H) or ester ($R^{15}$=alkyl) reagent 6 to prepare the cyclic heteroaryl (Hy) compounds (7) of formulas Ia, wherein Hal is Cl, Br, or I; and $R_1$ and $R_2$ are as defined for formula Ia compounds, or precursors or prodrugs thereto. For reviews of the Suzuki reaction, see: Miyaura et al. (1995) Chem. Rev. 95:2457-2483; Suzuki, A. (1999) J. Organomet. Chem. 576:147-168; Suzuki, A. in Metal-Catalyzed Cross-Coupling Reactions, Diederich, F., Stang, P. J., Eds., VCH, Weinheim, Del. (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt—$Bu)_3$ (Owens et al. (2003) Bioorganic & Med. Chem. Letters 13:4143-4145; Molander et al. (2002) Organic Letters 4(11):1867-1870; U.S. Pat. No. 6,448,433).

Scheme 6

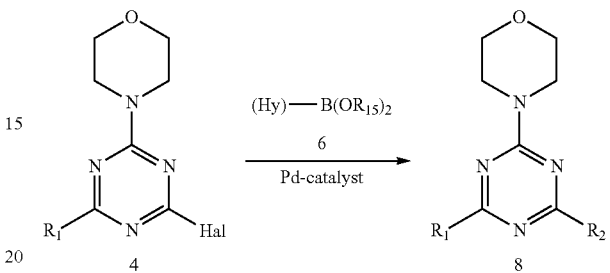

Scheme 6 shows a general method for Suzuki-type coupling of a 1-halo morpholino triazine intermediate 4 with a cyclic heteroaryl boronate acid ($R_{15}$=H) or ester ($R^{15}$=alkyl) reagent 6 to prepare the cyclic heteroaryl (Hy) compounds (8) of formulas Ia, wherein Hal is Cl, Br, or I; and $R_1$ and $R_2$ are as defined for formula Ia compounds, or precursors or prodrugs thereto.

Scheme 7

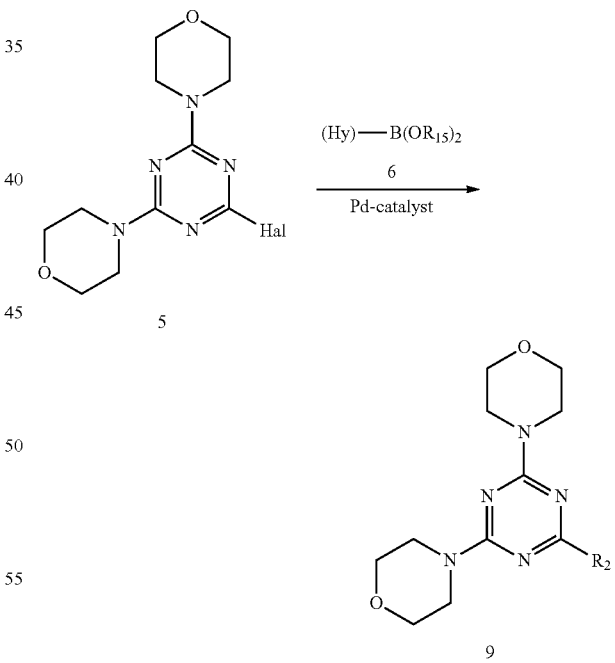

Scheme 7 shows a general method for Suzuki-type coupling of a 1-halo bis-morpholino triazine intermediate 5 with a cyclic heteroaryl boronate acid ($R_{15}$=H) or ester ($R^{15}$=alkyl) reagent 6 to prepare the cyclic heteroaryl (Hy) compounds (9) of formulas Ib, wherein Hal is Cl, Br, or I; and $R_2$ is as defined for formula Ib compounds, or precursors or prodrugs thereto.

Scheme 8

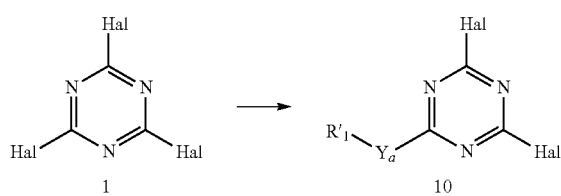

Scheme 8 shows a general method for preparation of the triazine intermediate 10 from 2,4,6-trihalo-1,3,5-triazine reagent (1), wherein Hal is Cl, Br, or I; and $R'_1$ and $Y_a$ are as defined for formula Ic compounds, or precursors or prodrugs thereto.

Scheme 9

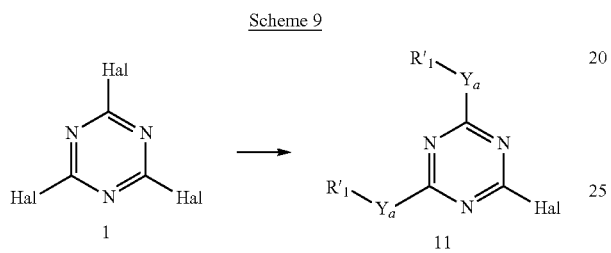

Scheme 9 shows a general method for preparation of the triazine intermediate 11 from 2,4,6-trihalo-1,3,5-triazine reagent (1), wherein Hal is Cl, Br, or I; and $R'_1$ and $Y_a$ are as defined for formula Ic compounds, or precursors or prodrugs thereto.

Scheme 10

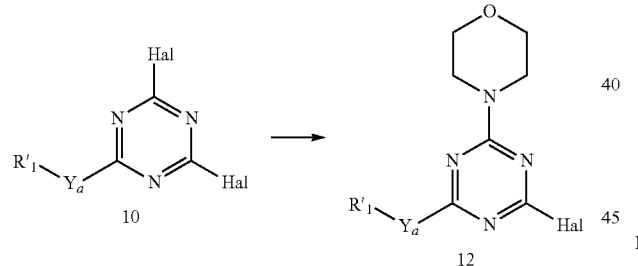

Scheme 10 shows a general method for preparation of the triazine intermediate 12 from triazine intermediate 10, wherein Hal is Cl, Br, or I; and $R'_1$ and $Y_a$ are as defined for formula Ic compounds, or precursors or prodrugs thereto.

Scheme 11

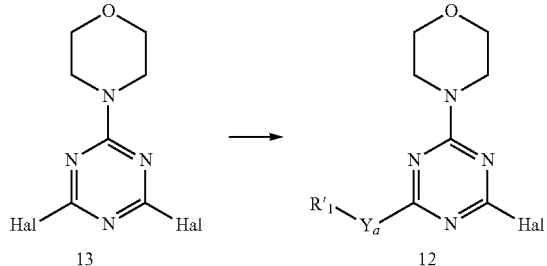

Scheme 11 shows a general method for preparation of the triazine intermediate 12 from triazine intermediate 13, wherein Hal is Cl, Br, or I; and $R'_1$ and $Y_a$ are as defined for formula Ic compounds, or precursors or prodrugs thereto.

Scheme 12

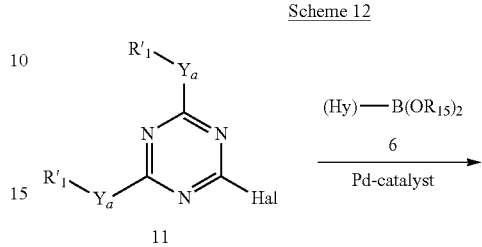

Scheme 12 shows a general method for Suzuki-type coupling of a triazine intermediate 11 with a cyclic heteroaryl boronate acid ($R_{15}$=H) or ester ($R_{15}$=alkyl) reagent 6 to prepare the cyclic heteroaryl (Hy) compounds (14), wherein Hal is Cl, Br, or I; $R'_1$ and $Y_a$ are as defined for formula Ic compounds and $R_2$ is as defined for formula I compounds, or precursors or prodrugs thereto.

Scheme 13

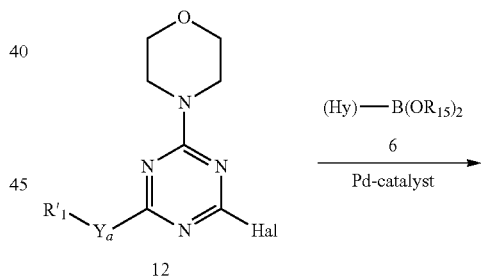

Scheme 13 shows a general method for Suzuki-type coupling of a triazine intermediate 12 with a cyclic heteroaryl boronate acid ($R_{15}$=H) or ester ($R_{15}$=alkyl) reagent 6 to prepare the cyclic heteroaryl (Hy) compounds (15), wherein Hal is Cl, Br, or I; $R'_1$ and $Y_a$ are as defined for formula Ic compounds and $R_2$ is as defined for formula I compounds, or precursors or prodrugs thereto.

Scheme 14

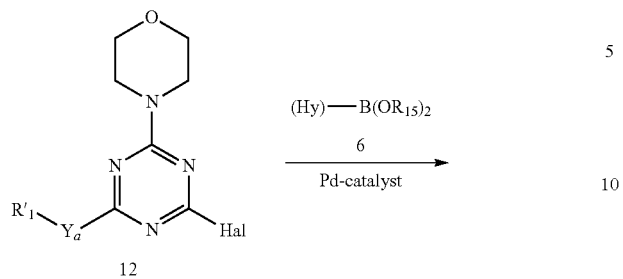

Scheme 14 shows a general method for Suzuki-type coupling of a triazine intermediate 12 with a cyclic heteroaryl boronate acid ($R_{15}$=H) or ester ($R_{15}$=alkyl) reagent 6 to prepare cyclic heteroaryl (Hy) compounds (17), wherein $R'_1$ and $Y_a$ are as defined for formula Ic compounds, $R_5$, $R_6$, $R_7$ and W are as defined for formula Id compounds, or precursors or prodrugs thereto.

Scheme 16

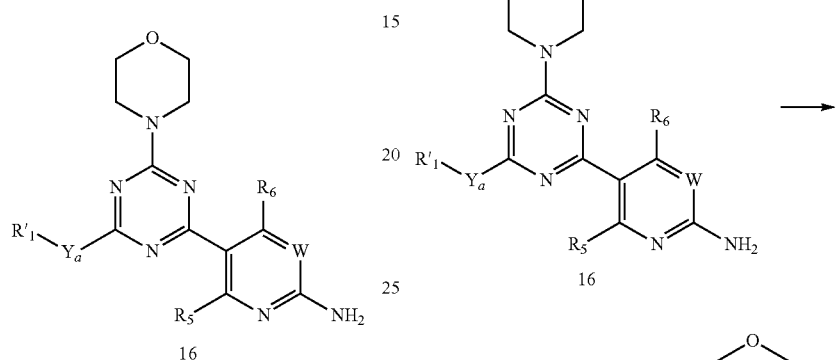

Scheme 14 shows a general method for Suzuki-type coupling of a triazine intermediate 12 with a cyclic heteroaryl boronate acid ($R_{15}$=H) or ester ($R_{15}$=alkyl) reagent 6 to prepare cyclic heteroaryl (Hy) compounds (16), wherein $R'_1$ and $Y_a$ are as defined for formula Ic compounds, $R_5$, $R_6$ and W are as defined for formula Id compounds, or precursors or prodrugs thereto.

Scheme 15

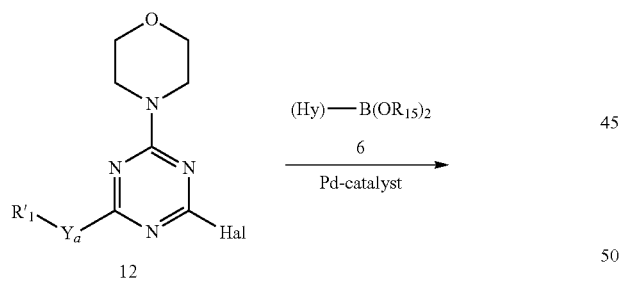

Scheme 16 shows a general method for preparation of triazine compounds 17 from triazine compounds 16, wherein $R'_1$ and $Y_a$ are as defined for formula Ic compounds, $R_5$, $R_6$, $R_7$ and W are as defined for formula Id compounds, or precursors or prodrugs thereto.

Scheme 17

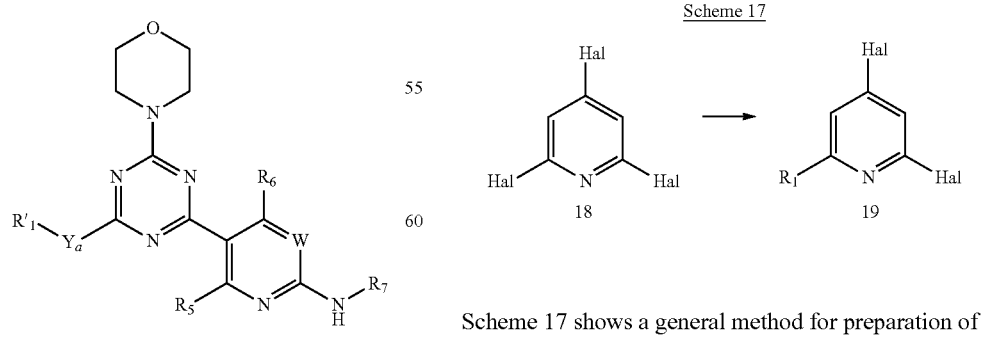

Scheme 17 shows a general method for preparation of the pyridine intermediate 19 from 2,4,6-trihalopyridine reagent (18), wherein Hal is Cl, Br, or I; and $R_1$ is as defined for formula I compounds, or precursors or prodrugs thereto.

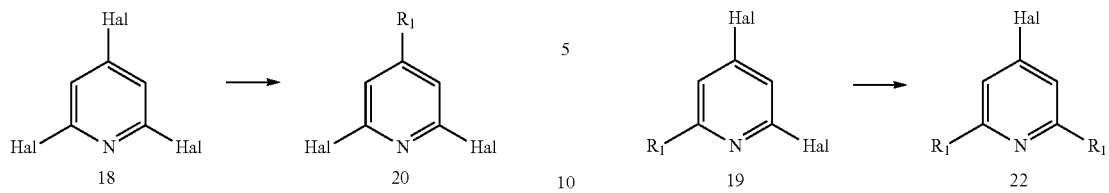

Scheme 18 shows a general method for preparation of the pyridine intermediate 20 from 2,4,6-trihalopyridine reagent (18), wherein Hal is Cl, Br, or I; and $R_1$ is as defined for formula I compounds, or precursors or prodrugs thereto.

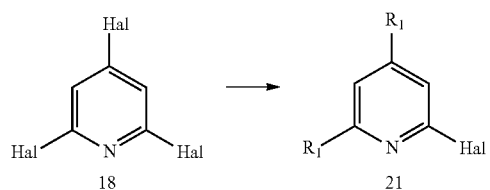

Scheme 19 shows a general method for preparation of the pyridine intermediate 21 from 2,4,6-trihalopyridine reagent (18), wherein Hal is Cl, Br, or I; and $R_1$ is as defined for formula I compounds, or precursors or prodrugs thereto.

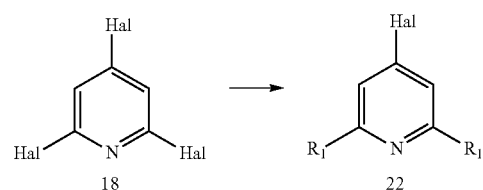

Scheme 20 shows a general method for preparation of the pyridine intermediate 22 from 2,4,6-trihalopyridine reagent (18), wherein Hal is Cl, Br, or I; and $R_1$ is as defined for formula I compounds, or precursors or prodrugs thereto.

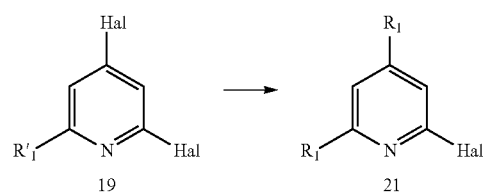

Scheme 21 shows a general method for preparation of the pyridine intermediate 21 from dihalopyridine reagent 19, wherein Hal is Cl, Br, or I; and $R_1$ is as defined for formula I compounds, or precursors or prodrugs thereto.

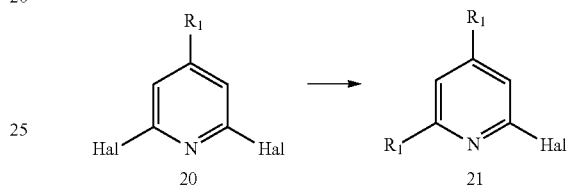

Scheme 22 shows a general method for preparation of the pyridine intermediate 22 from dihalopyridine reagent 19, wherein Hal is Cl, Br, or I; and $R_1$ is as defined for formula I compounds, or precursors or prodrugs thereto.

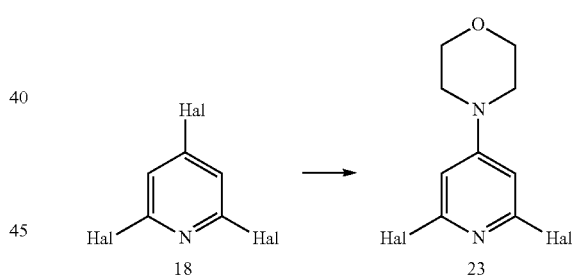

Scheme 23 shows a general method for preparation of the pyridine intermediate 21 from dihalopyridine reagent 20, wherein Hal is Cl, Br, or I; and $R_1$ is as defined for formula I compounds, or precursors or prodrugs thereto.

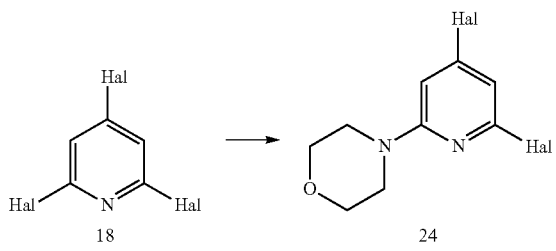

Scheme 21 shows a general method for preparation of the pyridine intermediate 23 from 2,4,6-trihalopyridine (18) and morpholine reagents, wherein Hal is Cl, Br, or I; or precursors or prodrugs thereto.

Scheme 22 shows a general method for preparation of the pyridine intermediate 24 from 2,4,6-trihalopyridine (18) and morpholine reagents, wherein Hal is Cl, Br, or I; or precursors or prodrugs thereto.

Scheme 23

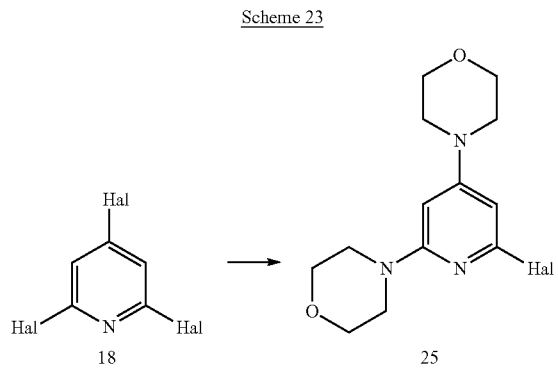

Scheme 23 shows a general method for preparation of the pyridine intermediate 25 from 2,4,6-trihalopyridine (18) and morpholine reagents, wherein Hal is Cl, Br, or I.

Scheme 24

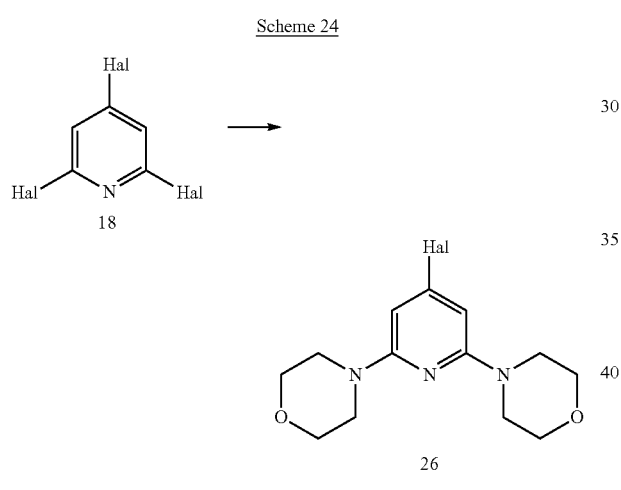

Scheme 24 shows a general method for preparation of the pyridine intermediate 26 from 2,4,6-trihalopyridine (18) and morpholine reagents, wherein Hal is Cl, Br, or I.

Scheme 25

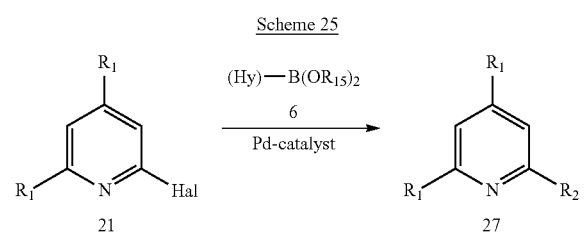

Scheme 25 shows a general method for Suzuki-type coupling of a 1-halo pyridine intermediate 21 with a cyclic heteroaryl boronate acid ($R_{15}$=H) or ester ($R_{15}$=alkyl) reagent 6 to prepare the cyclic heteroaryl (Hy) compounds (27) of formula I, wherein Hal is Cl, Br, or I; and $R_1$ and $R_2$ are as defined for formula I compounds, or precursors or prodrugs thereto.

Scheme 26

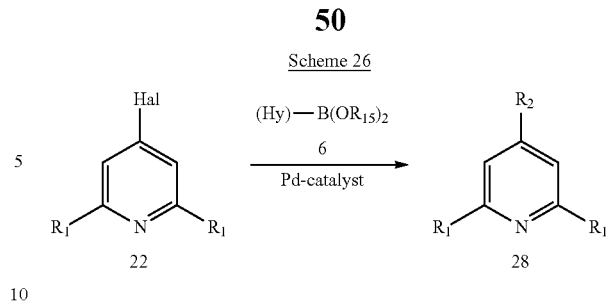

Scheme 26 shows a general method for Suzuki-type coupling of a 1-halo pyridine intermediate 22 with a cyclic heteroaryl boronate acid ($R_{15}$=H) or ester ($R_{15}$=alkyl) reagent 6 to prepare the cyclic heteroaryl (Hy) compounds (28) of formula I, wherein Hal is Cl, Br, or I; and $R_1$ and $R_2$ are as defined for formula I compounds, or precursors or prodrugs thereto.

Scheme 27

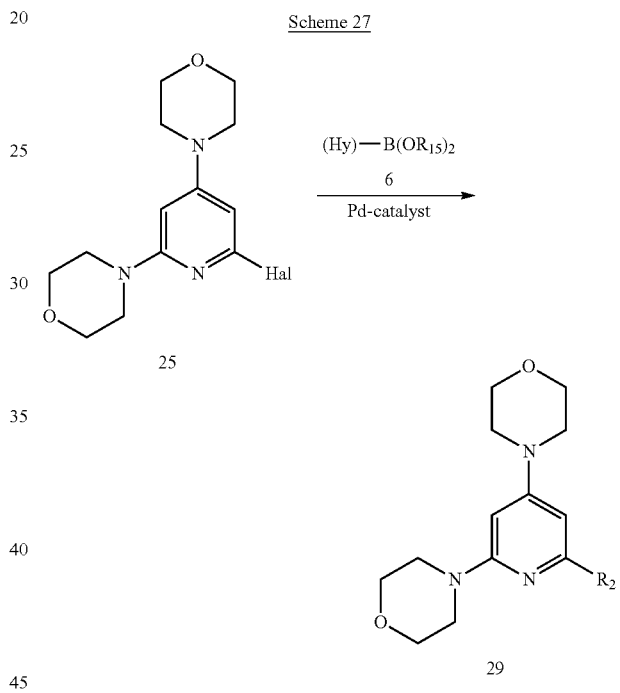

Scheme 27 shows a general method for Suzuki-type coupling of a dimorpholino pyridine intermediate 25 with a cyclic heteroaryl boronate acid ($R_{15}$=H) or ester ($R_{15}$=alkyl) reagent 6 to prepare the cyclic heteroaryl (Hy) compounds (29) of formula I, wherein Hal is Cl, Br, or I; and $R_2$ is as defined for formula I compounds, or precursors or prodrugs thereto.

Scheme 28

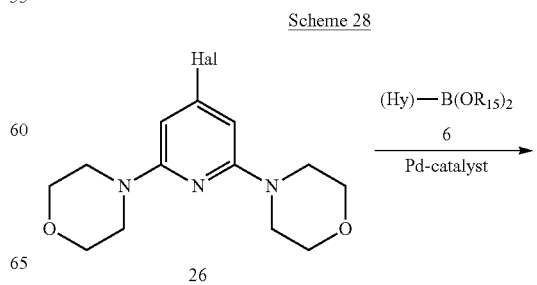

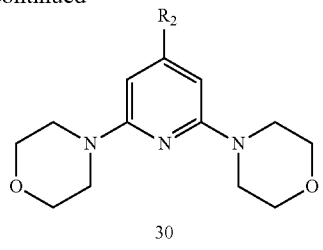

Scheme 28 shows a general method for Suzuki-type coupling of a dimorpholino pyridine intermediate 26 with a cyclic heteroaryl boronate acid ($R_{15}$=H) or ester ($R_{15}$=alkyl) reagent 6 to prepare the cyclic heteroaryl (Hy) compounds (30) of formula I, wherein Hal is Cl, Br, or I; and $R_2$ is as defined for formula I compounds, or precursors or prodrugs thereto.

Scheme 29

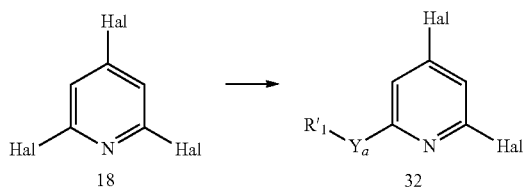

Scheme 29 shows a general method for preparation of the pyridine intermediate 32 from 2,4,6-trihalopyridine reagent (18), wherein Hal is Cl, Br, or I; and $R'_1$ and $Y_a$ are as defined for formula Ie compounds, or precursors or prodrugs thereto.

Scheme 30

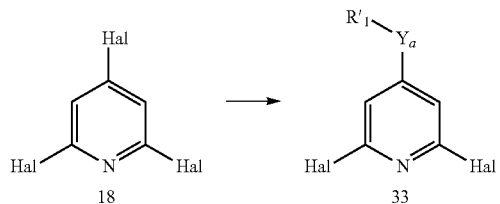

Scheme 30 shows a general method for preparation of the pyridine intermediate 33 from 2,4,6-trihalopyridine reagent (18), wherein Hal is Cl, Br, or I; and $R'_1$ and $Y_a$ are as defined for formula Ie compounds or precursors or prodrugs thereto.

Scheme 31

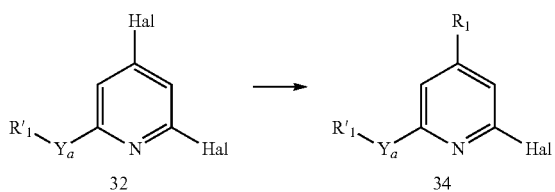

Scheme 31 shows a general method for preparation of the pyridine intermediate 34 from dihalopyridine reagent, wherein Hal is Cl, Br, or I; $R'_1$ and $Y_a$ are as defined for formula Ie compounds and $R_1$ is as defined for formula I compounds, or precursors or prodrugs thereto.

Scheme 32

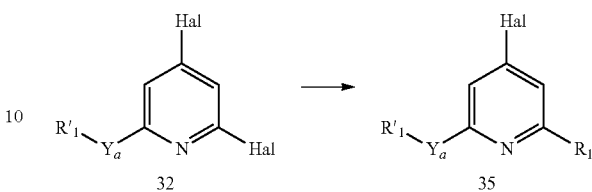

Scheme 32 shows a general method for preparation of the pyridine intermediate 35 from dihalopyridine reagent (32), wherein Hal is Cl, Br, or I; $R'_1$ and $Y_a$ are as defined for formula Ie compounds and $R_1$ is as defined for formula I compounds, or precursors or prodrugs thereto.

Scheme 33

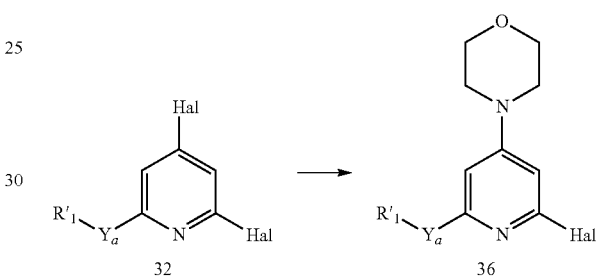

Scheme 33 shows a general method for preparation of the morpholino pyridine intermediate 36 from dihalopyridine reagent, wherein Hal is Cl, Br, or I; and $R'_1$ and $Y_a$ are as defined for formula (e compounds, or precursors or prodrugs thereto.

Scheme 34

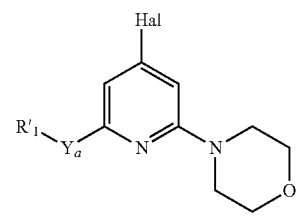

Scheme 34 shows a general method for preparation of the morpholino pyridine intermediate 37 from dihalopyridine reagent, wherein Hal is Cl, Br, or I; and $R'_1$ and $Y_a$ are as defined for formula Ie compounds, or precursors or prodrugs thereto.

Scheme 35

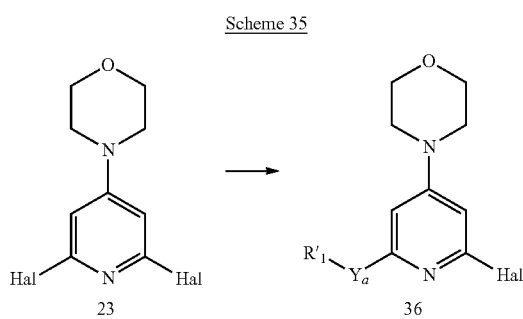

Scheme 35 shows a general method for preparation of the morpholino pyridine intermediate 36 from morpholino dihalopyridine reagent 23, wherein Hal is Cl, Br, or I; and $R'_1$ and $Y_a$ are as defined for formula Ie compounds, or precursors or prodrugs thereto.

Scheme 36

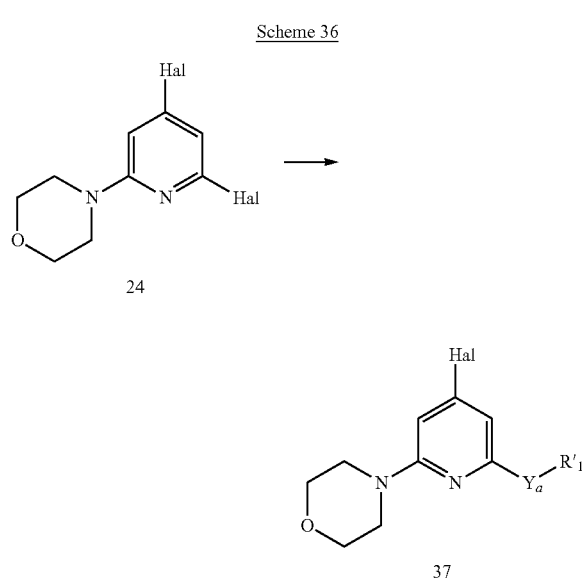

Scheme 36 shows a general method for preparation of the morpholino pyridine intermediate 37 from morpholino dihalopyridine reagent 24, wherein Hal is Cl, Br, or I; and $R'_1$ and $Y_a$ are as defined for formula Ie compounds, or precursors or prodrugs thereto.

Scheme 37

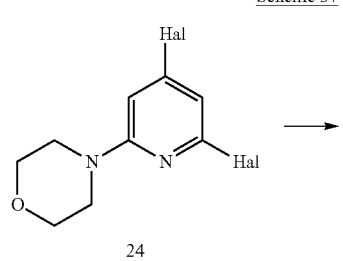

-continued

Scheme 37 shows a general method for preparation of the morpholino pyridine intermediate 38 from morpholino dihalopyridine reagent 24, wherein Hal is Cl, Br, or I; and $R'_1$ and $Y_a$ are as defined for formula Ie compounds or precursors or prodrugs thereto.

Scheme 38

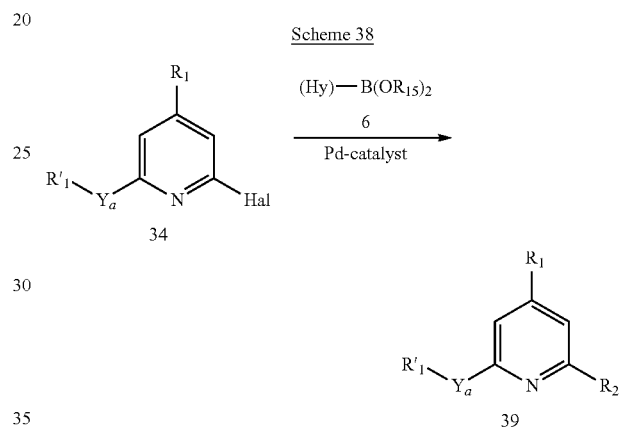

Scheme 38 shows a general method for Suzuki-type coupling of a pyridine intermediate 34 with a cyclic heteroaryl boronate acid ($R_{15}$=H) or ester ($R_{15}$=alkyl) reagent 6 to prepare the cyclic heteroaryl (Hy) compounds 39 of formula I, wherein Hal is Cl, Br, or I; $R'_1$ and $Y_a$ are as defined for formula Ie compounds and $R_1$ and $R_2$ are as defined for formula I compounds, or precursors or prodrugs thereto.

Scheme 39

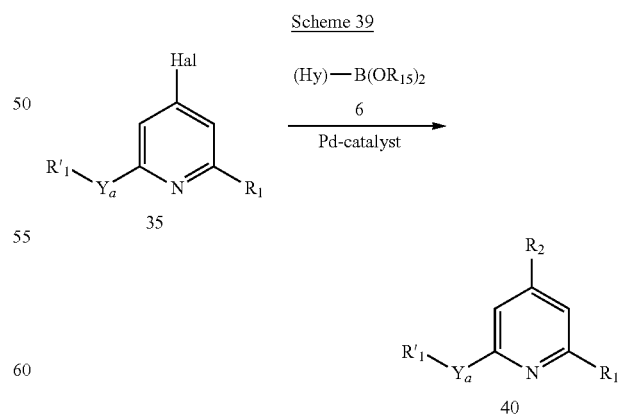

Scheme 39 shows a general method for Suzuki-type coupling of a pyridine intermediate 35 with a cyclic heteroaryl boronate acid ($R_{15}$=H) or ester ($R_{15}$=alkyl) reagent 6 to prepare the cyclic heteroaryl (Hy) compounds 40 of formula I, wherein Hal is Cl, Br, or I; $R'_1$ and $Y_a$ are as defined in formula Ie compounds and $R_1$ and $R_2$ are as defined for formula I compounds, or precursors or prodrugs thereto.

Scheme 40

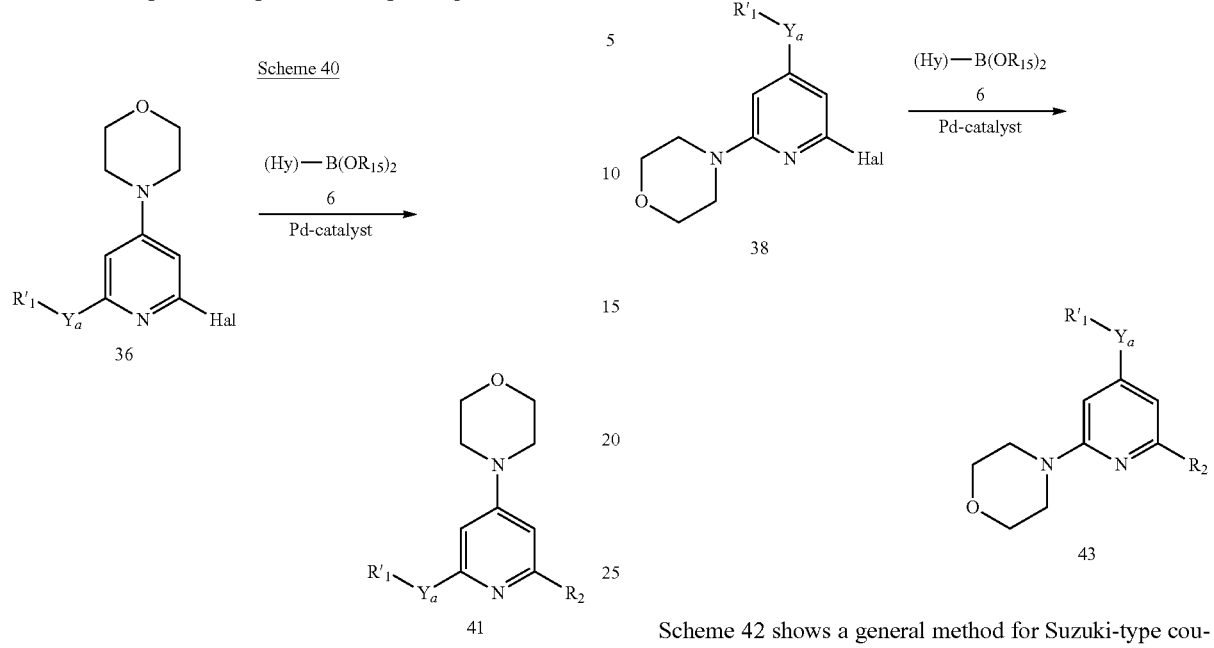

Scheme 40 shows a general method for Suzuki-type coupling of a pyridine intermediate 36 with a cyclic heteroaryl boronate acid ($R_{15}$=H) or ester ($R_{15}$=alkyl) reagent 6 to prepare the cyclic heteroaryl (Hy) compounds 41 of formula Ie, wherein Hal is Cl, Br, or I; $R'_1$ and $Y_a$ are as defined for formula Ie compounds and $R_2$ is as defined for formula I compounds, or precursors or prodrugs thereto.

Scheme 41

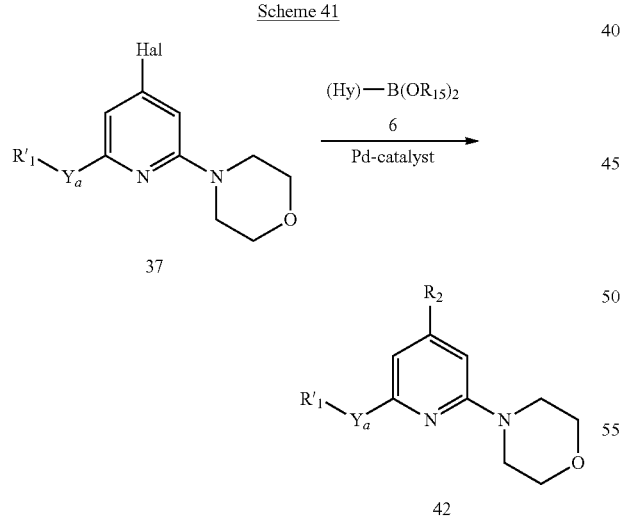

Scheme 41 shows a general method for Suzuki-type coupling of a pyridine intermediate 37 with a cyclic heteroaryl boronate acid ($R_{15}$=H) or ester ($R_{15}$=alkyl) reagent 6 to prepare the cyclic heteroaryl (Hy) compounds 42 of formula Ie, wherein Hal is Cl, Br, or I; $R'_1$ and $Y_a$ are as defined for formula Ie compounds and $R_2$ is as defined for formula I compounds, or precursors or prodrugs thereto.

Scheme 42 shows a general method for Suzuki-type coupling of a pyridine intermediate 38 with a cyclic heteroaryl boronate acid ($R_{15}$=H) or ester ($R_{15}$=alkyl) reagent 6 to prepare the cyclic heteroaryl (Hy) compounds 43 of formula Ie, wherein Hal is Cl, Br, or I; $R'_1$ and $Y_a$ are as defined for formula Ie compounds and $R_2$ is as defined for formula I compounds, or precursors or prodrugs thereto.

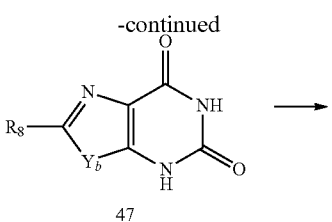

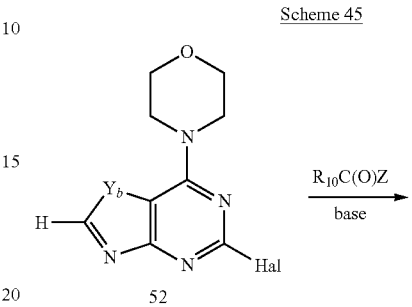

Scheme 43 shows a general method for preparation of the thiazolopyrimidine and oxazolopyrimidine intermediates 48 and 49 from 5-carboxyester, 4-aminothiazole (X=S) and oxazole (X=O), and 4-carboxyester, 5-aminothiazole (X=S) and oxazole (X=O) reagents, respectively 44 and 45, wherein $Y_b$ is O or S, Hal is Cl, Br, or I; $R_8$ and $R_{10}$ are as defined for formula If-g.

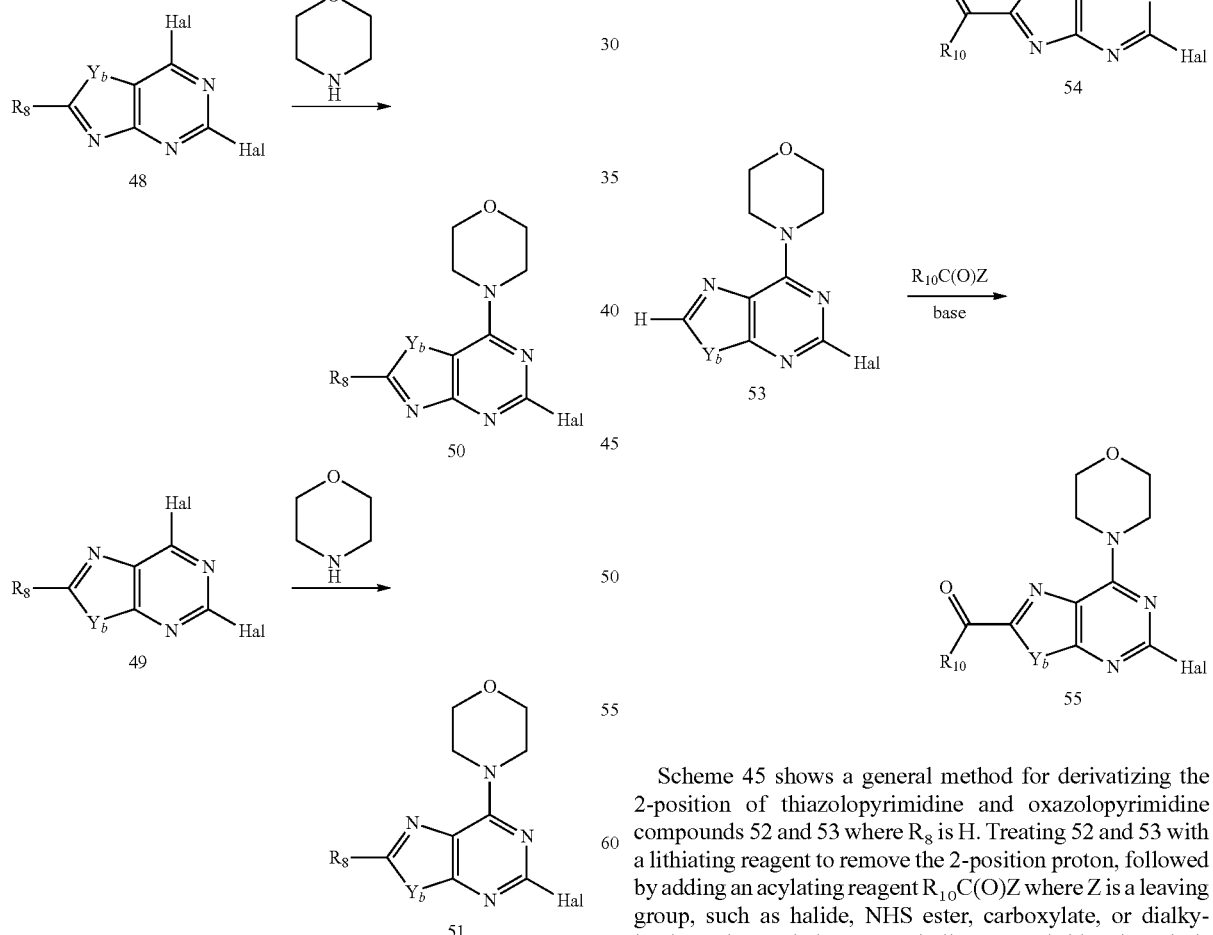

Scheme 44 shows a general method for selectively displacing a 7-halide from bis-halo thiazolopyrimidine and bis-halo oxazolopyrimidine intermediates 48 and 49 with morpholine under basic conditions in an organic solvent to prepare 5-halo, 7-morpholino thiazolo- and oxazolopyrimidine compounds 50 and 51, wherein $Y_b$ is O or S, Hal is Cl, Br, or I; and $R_8$ is as defined for formula If-g.

Scheme 45 shows a general method for derivatizing the 2-position of thiazolopyrimidine and oxazolopyrimidine compounds 52 and 53 where $R_8$ is H. Treating 52 and 53 with a lithiating reagent to remove the 2-position proton, followed by adding an acylating reagent $R_{10}C(O)Z$ where Z is a leaving group, such as halide, NHS ester, carboxylate, or dialkylamino, gives 5-halo, 7-morpholino, 2-acyl thiazolopyrimidine and oxazolopyrimidine compounds 54 and 55, wherein $Y_b$ is O or S; Hal is Cl, Br, or I; and $R_{10}$ is as defined for formula If-g.

Scheme 46

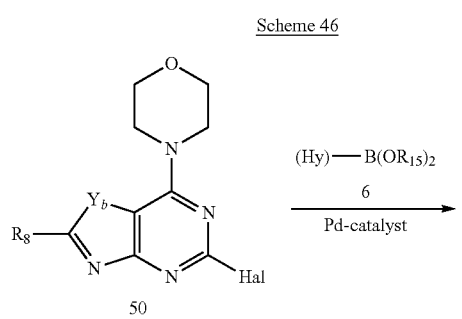

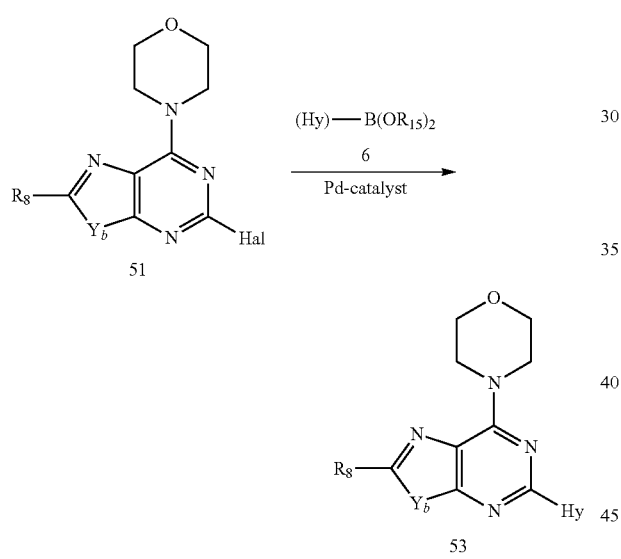

Scheme 46 shows a general method for Suzuki-type coupling of a 5-halo pyrimidine intermediate (50 and 51) with a cyclic heteroaryl boronate acid ($R_{15}$=H) or ester ($R_{15}$=alkyl) reagent 6 to prepare the 5-cyclic heteroaryl (Hy), 7-morpholino thiazolopyrimidine and oxazolopyrimidine compounds (52 and 53) of formulas If-g, wherein $Y_b$ is O or S; Hal is Cl, Br, or I; and $R_8$ is as defined for formula If-g compounds, or precursors or prodrugs thereto. For reviews of the Suzuki reaction, see: Miyaura et al. (1995) Chem. Rev. 95:2457-2483; Suzuki, A. (1999) J. Organomet. Chem. 576: 147-168; Suzuki, A. in Metal-Catalyzed Cross-Coupling Reactions, Diederich, F., Stang, P. J., Eds., VCH, Weinheim, Del. (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt—$Bu)_3$ (Owens et al. (2003) Bioorganic & Med. Chem. Letters 13:4143-4145; Molander et al. (2002) Organic Letters 4(11):1867-1870; U.S. Pat. No. 6,448,433).

Scheme 47

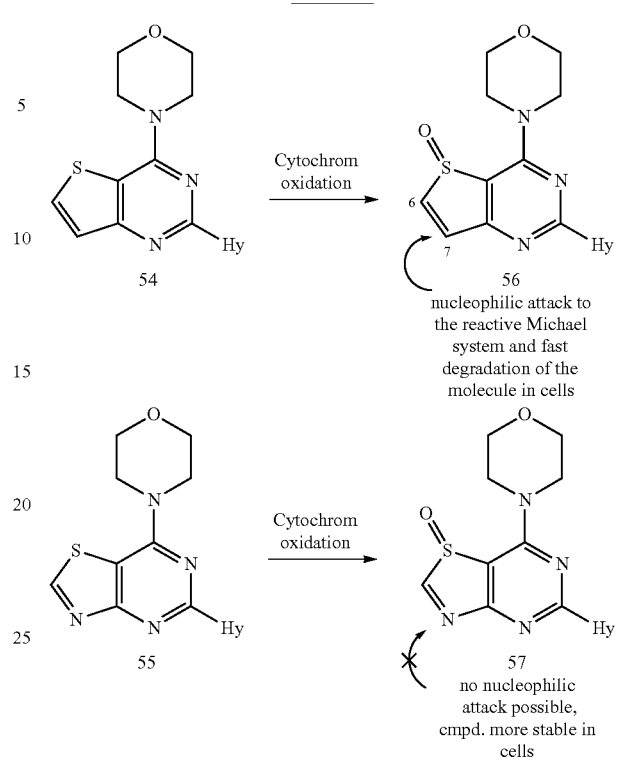

Scheme 47 shows a general method for cellular sulfur oxidation of thieno and thiazolo pyrimidine compounds 56 and 57 through the cytochroms. After sulfur oxidation of thiophene pyrimidine compounds 54 (IP of Piramed/Roche), the thiophene ring acts as an activated Michael system, where at the 7-position of the ring a nucleophilic attack is possible and therefore a fast cellular modification of thieno pyrimidine compounds 54. In comparison with thieno pyrimidines, thiazolo pyrimidine compounds 55 are chemically more stable through the N-atom at the 7-position and no possibility for a nucleophilic attack after sulfur oxidation.

Scheme 48

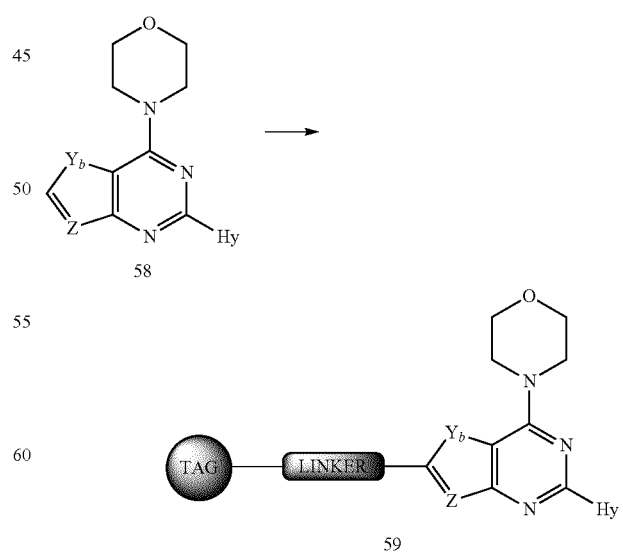

Scheme 48 shows a general method for preparation of linker-tag-modified fused pyrimidine compounds 59 from morpholino intermediate 58, wherein Hy is a cyclic heteroaryl fragment, $Y_b$ and Z are as defined for compounds of formula If-g, linker and tag are as defined for formula I compounds, or precursors or prodrugs thereto.

Scheme 49

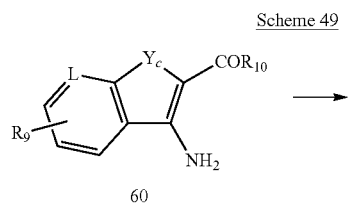

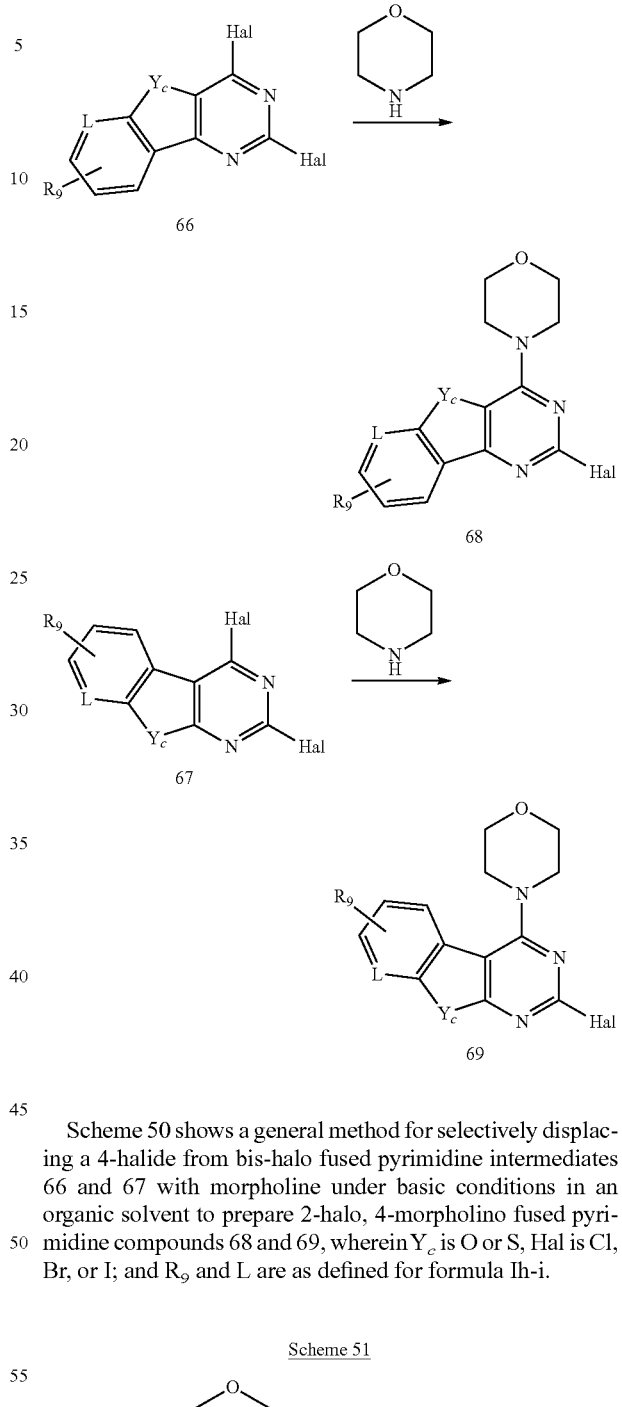

Scheme 49 shows a general method for preparation of fused pyrimidine intermediates 64 and 65 from for example 2-carboxamid, 3-aminobenzofuran and 3-aminofuropyridine (X=O, L=C) and 2-carboxamid, 3-aminobenzothiophene and 3-aminothienopyridine (X=S, L=C), respectively 60 and 61, wherein $Y_c$ is O or S, Hal is Cl, Br, or I; $R_9$ and L are as defined for formula Ih-i.

Scheme 50 shows a general method for selectively displacing a 4-halide from bis-halo fused pyrimidine intermediates 66 and 67 with morpholine under basic conditions in an organic solvent to prepare 2-halo, 4-morpholino fused pyrimidine compounds 68 and 69, wherein $Y_c$ is O or S, Hal is Cl, Br, or I; and $R_9$ and L are as defined for formula Ih-i.

Scheme 51

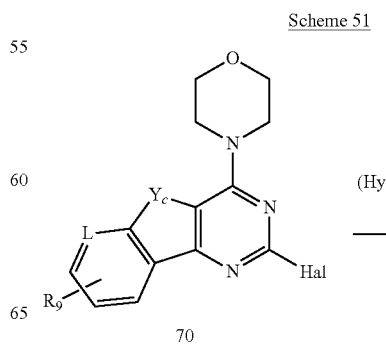

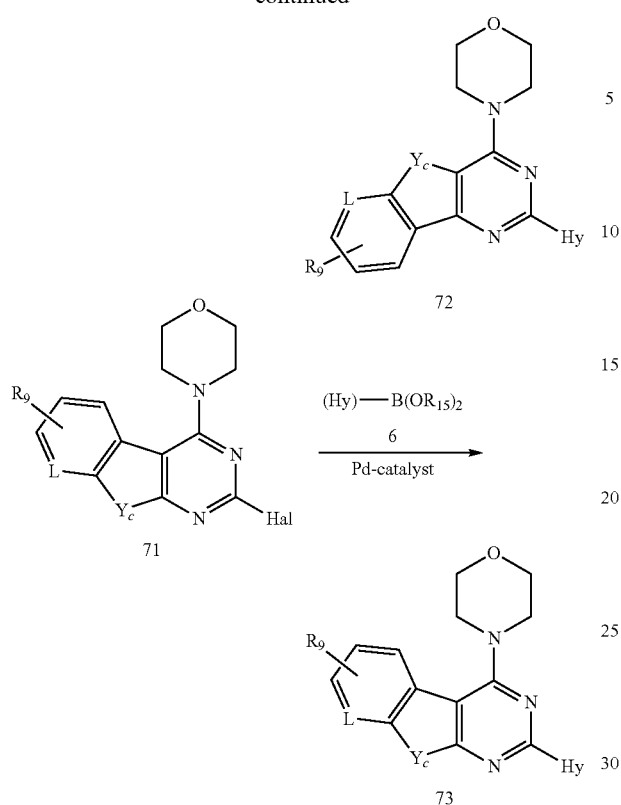

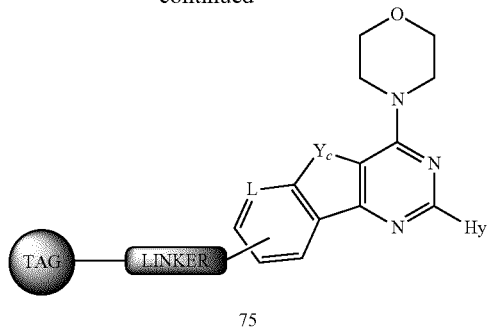

Scheme 52 shows a general method for preparation of linker-tag-modified fused pyrimidine compounds 75 from morpholino intermediate 74, wherein Hy is a cyclic heteroaryl fragment, $Y_c$ and L are as defined for formula Ih-i compounds and linker and tag are as defined for formula I compounds, or precursors or prodrugs thereto.

General Preparative Procedures
General Procedure A Triazine Substitution:

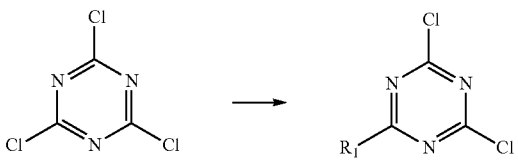

A solution of 2,4,6-trichloro-1,3,5-triazine (1.00 g, 5.42 mmol, 1.0 eq.) in dioxane (15 ml) at room temperature was treated with diisopropylethylamine (1.03 ml, 5.96 mmol, 1.1 eq.) and dropwise with aminopyridine (1.1 eq.) and stirred for 2 h. The dioxane was evaporated in vacuo, and the residue partitioned between $H_2O$ (15 ml) and $CH_2Cl_2$ (15 ml). The organic layer was separated and the aqueous layer further extracted with $CH_2Cl_2$ (2×10 ml). The combined extracts were dried ($MgSO_4$) and concentrated in vacuo. Purification by column chromatography gave the title compound.

General Procedure A-1 Triazine Substitution:

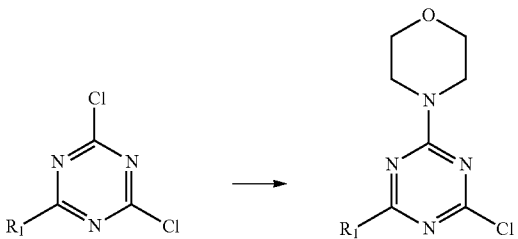

Scheme 51 shows a general method for Suzuki-type coupling of a 2-halo pyrimidine intermediate (70 and 71) with a cyclic heteroaryl boronate acid ($R_{15}$=H) or ester ($R_{15}$=alkyl) reagent 6 to prepare the 2-cyclic heteroaryl (Hy), 4-morpholino fused pyrimidine compounds (72 and 73) of formulas Ih-i, wherein $Y_c$ is O or S; Hal is Cl, Br, or I; and $R_9$ and L are as defined for formula Ih-i compounds, or precursors or prodrugs thereto. For reviews of the Suzuki reaction, see: Miyaura et al. (1995) Chem. Rev. 95:2457-2483; Suzuki, A. (1999) J. Organomet. Chem. 576:147-168; Suzuki, A. in Metal-Catalyzed Cross-Coupling Reactions, Diederich, F., Stang, P. J., Eds., VCH, Weinheim, Del. (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt—$Bu)_3$ (Owens et al. (2003) Bioorganic & Med. Chem. Letters 13:4143-4145; Molander et al. (2002) Organic Letters 4(11): 1867-1870; U.S. Pat. No. 6,448,433).

A solution of bis-chloro triazine compound (100 mg, 390 µmol, 1.0 eq.) in dioxane (1 ml) at room temperature was treated with diisopropylethylamine (0.10 ml, 590 µmol, 1.5 eq.) and morpholine (0.05 ml, 590 µmol, 1.5 eq.) and stirred at room temperature for 2 h. The dioxane was evaporated in vacuo, and the residue partitioned between $H_2O$ (5 ml) and $CH_2Cl_2$ (5 ml). The organic layer was separated and the aqueous layer further extracted with $CH_2Cl_2$ (2×2 ml). The combined extracts were dried ($MgSO_4$) and concentrated in vacuo. Purification by column chromatography gave the desired compound.

Note: for some of compounds it was necessary to add an additional amount of morpholine (0.3 eq.) after 12 h reaction time and then the reaction mixture was heated 70° C. for 8 h.

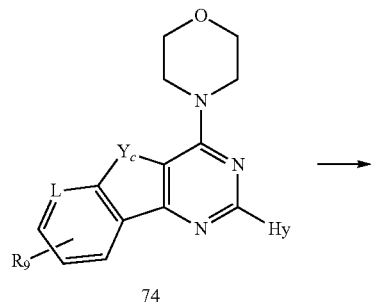

65

General Procedure A-2 Triazine Substitution:

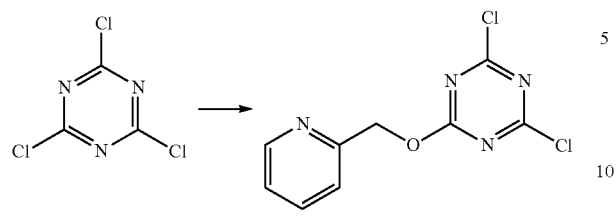

247 mg of NaH (60% in mineral oil, 10.3 mmol, 0.95 eq.) was added to a solution of 2-pyridinemethanol (940 μl, 9.76 mmol, 0.90 eq.) in THF (20 ml) at room temperature and stirred for 30 minutes. After cooling to −78° C., 2,4,6-trichloro-1,3,5-triazine (2.00 g, 10.84 mmol, 1.0 eq.) was added dropwise and the reaction allowed to warm to room temperature and stirred for 3 h. Saturated aqueous NH$_4$Cl (20 ml) was added and the mixture extracted with EtOAc (20 ml). The organic phase was dried (MgSO$_4$) and evaporated in vacuo. Column chromatography gave desired product.

General Procedure B Suzuki Coupling:

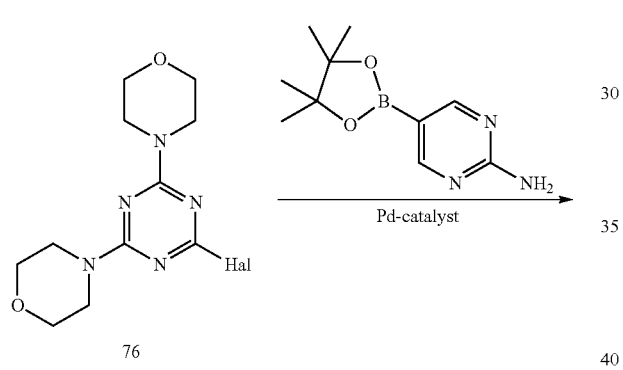

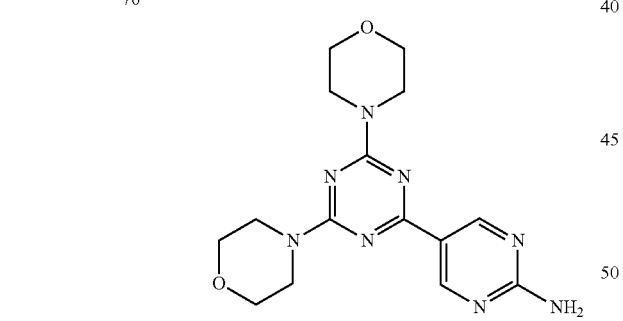

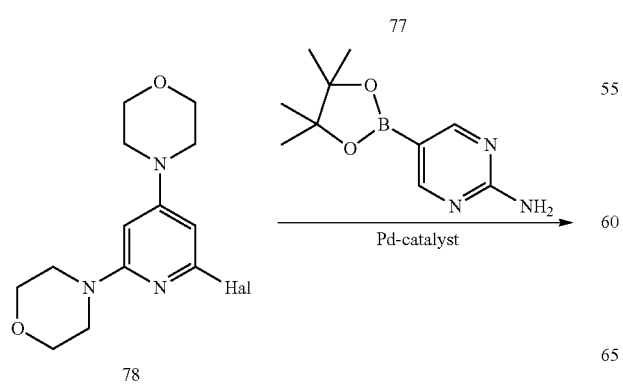

66

-continued

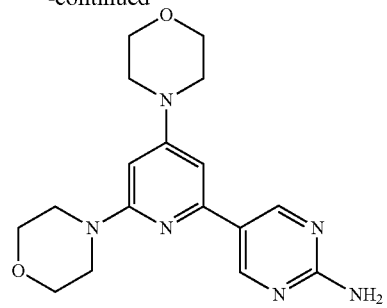

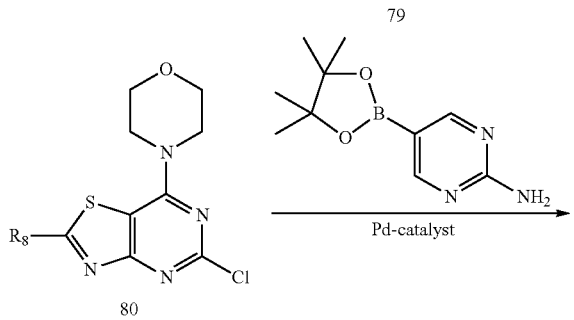

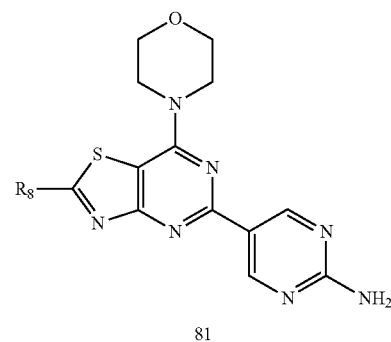

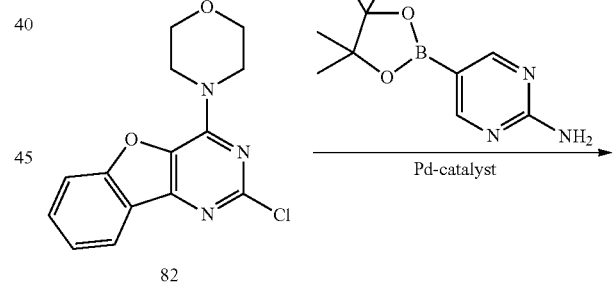

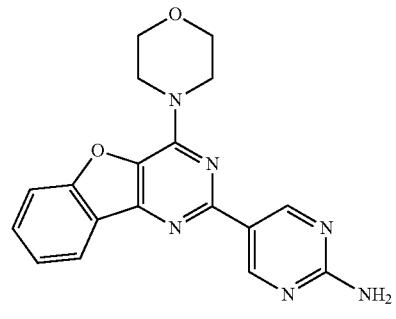

The Suzuki-type coupling reaction is useful to attach a cyclic heteroaryl at the 6-position of the triazine or pyridine ring (see Schemes 7 and 27), 5- or 6-position of the pyrimidine ring (see Schemes 46 and 51). Generally, 4,4'-(6-chloro-1,3,5-triazine-2,4-diyl)dimorpholine (77), 4,4'-(6-chloropyridine-2,4-diyl)dimorpholine (79), 4-(5-chlorothiazolo[4,5-d]pyrimidin-7-yl)morpholine (81) and 2-chloro-4-morpholinobenzofuro[3,2-d]pyrimidine (83) may be combined with boronic acid pinacol ester (4.0 eq.) in 1,2-dimethoxyethane and 2M $Na_2CO_3$ (3:1) for 15 minutes. A catalytic amount, or more, of a palladium reagent, such as dichloro 1,1'-bis(diphenylphosphino)ferrocene palladium (II) (0.025 eq.) was added and the high pressure glass vessel containing the mixture was bubbled with argon gas and sealed. A variety of boronic acids or boronic esters can be used in place of the pinacol boronic ester indicated. Also alternatively, the nitrogen of the pyrimidin-2-amine may be protected, for example with a tetrahydropyranyl group. The reaction mixture was then heated at 90° C. for 15 h or more, cooled down and diluted with ethyl acetate. The organic solution was washed with mixture of water:$Na_2CO_3$:$NH_4OH$ ($NH_4OH$ conc. 32% in water)=5:4:1, $NH_4Cl$ (sat.) and brine, dried over $MgSO_4$, filtered and concentrated. The residue was purified by silica gel flash column chromatography or if necessary by reverse phase HPLC.

General Procedure C Amide Coupling:

7-morpholino-5-(pyrimidin-5-yl)thiazolo[4,5-d]pyrimidine-2-carboxylic acid (84) or pyridinylfuranopyrimidine 86 is treated with 1.5 eq. HATU, 3 eq. of an alkylamine (R—$NH_2$) and 3 eq. of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via silica column chromatography or preparative TLC to yield product 85 or 87.

General Procedure C-1 Amide Coupling:

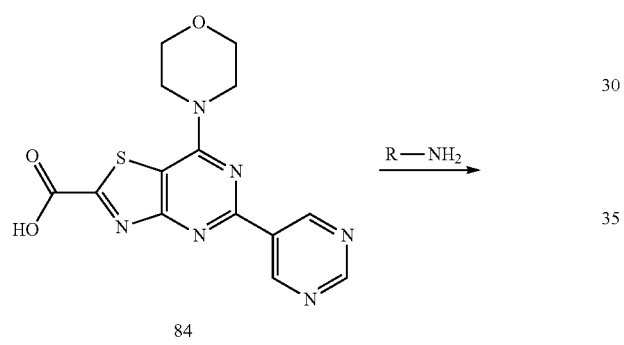

69

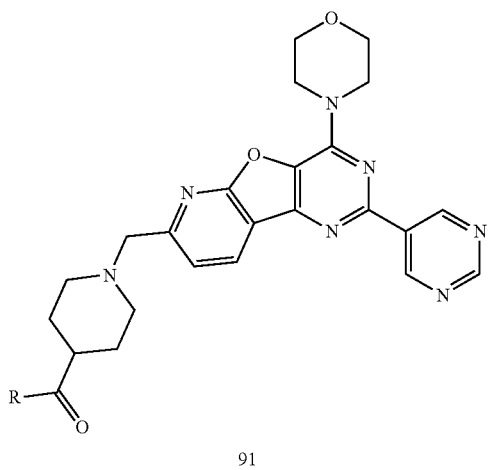

91

4-(2-(piperazin-1-ylmethyl)-5-(pyrimidin-5-yl)thiazolo[4,5-d]pyrimidin-7-yl)morpholine (88) or pyridinylfuropyrimidine 90 is treated with 1.5 eq. HATU, 3 eq. of carboxylic acid (RCO₂H) and 3 eq. of DIPEA in DMF to approximately 0.1 M concentration. The reaction is stirred until complete and extracted in ethyl acetate with saturated bicarbonate solution one time. The organic layer is dried, filtered and concentrated to yield the crude intermediate that was used without further purification or if necessary that was purified by preparative TLC.

General Procedure D Reductive Amination:

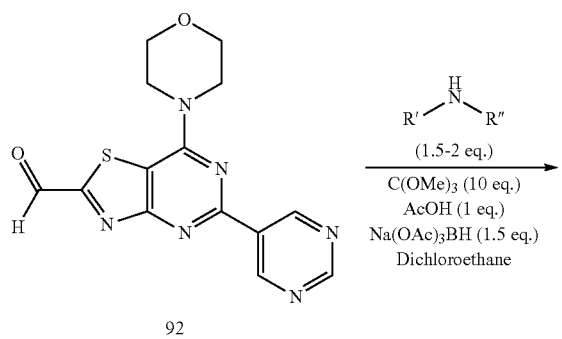

92

93

70

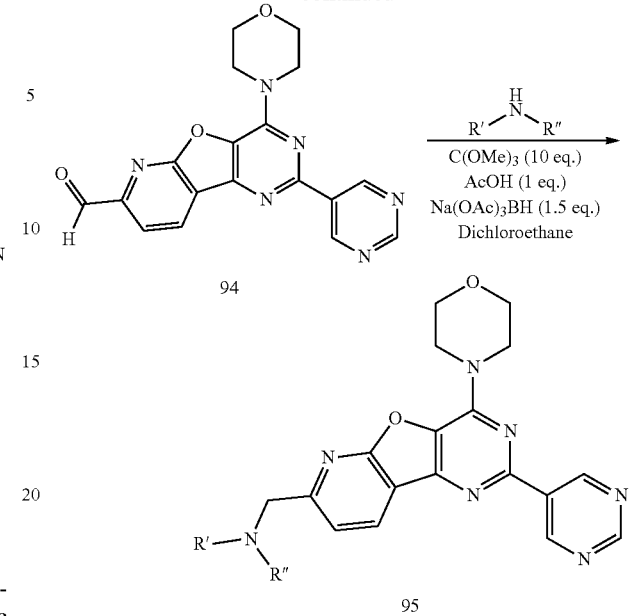

94

95

7-morpholino-5-(pyrimidin-5-yl)thiazolo[4,5-d]pyrimidine-2-carbaldehyde (92) or pyridinylfuropyrimidine 94 was dissolved to a 0.2 M concentration in dichloroethane. To this solution was added 1.5 to 2.0 equivalents of an amine (R'R"NH), 10 equivalents of trimethylorthoformate, and 1 equivalent of acetic acid. The mixture was allowed to stir for 2-6 hours prior to adding 1.5 equivalents of sodium triacetoxyborohydride. Following 12 to 16 hours of stirring the reaction was poured into saturated sodium bicarbonate and extracted several times with ethyl acetate. This intermediate was either purified on silica gel or used crude in the next reaction.

General procedure E Sulfonamide Formation:

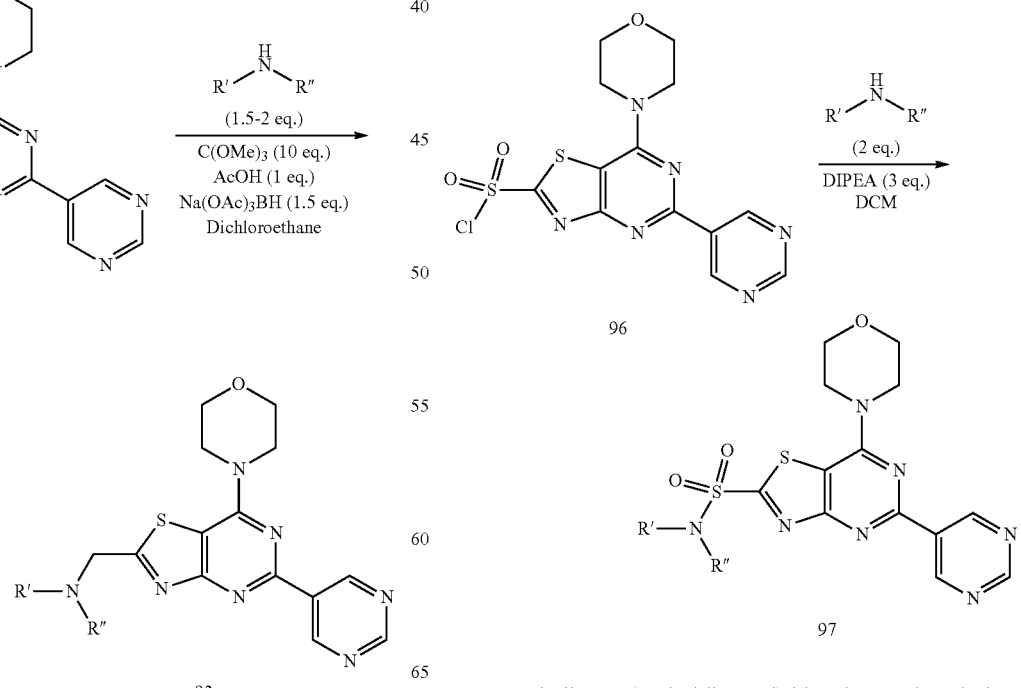

96

97

7-morpholino-5-(pyrimidin-5-yl)thiazolo[4,5-d]pyrimidine-2-sulfonyl chloride (96) was suspended in 1 mL of methylene chloride before addition of 2 eq. of amine (R'R"NH) and 3 eq. of DIPEA. The reactions were monitored by TLC until complete. The crude reaction mixtures were diluted with ethyl acetate, extracted with saturated ammonium chloride and back-extracted once with ethyl acetate. The organic layers were combined and concentrated to dryness. The crude sulfonamide intermediates 97 were used directly in the subsequent Suzuki couplings General Procedure F Aldehyde Synthesis:

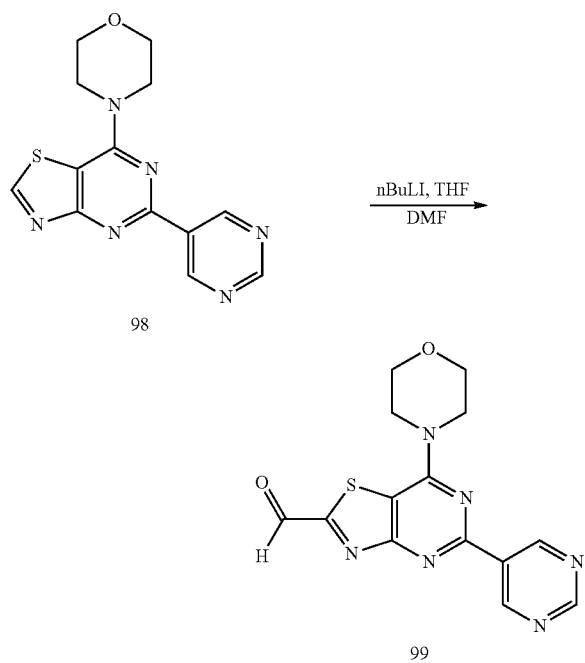

To a suspension of 4-(5-(pyrimidin-5-yl)thiazolo[4,5-d]pyrimidin-7-yl)morpholine (6.85 mmol, 1.0 eq.) in dry THF (40 mL) at −78° C. was added a 2.5 M solution of n-butyllithium (nBuLi) in hexane (1.2 eq.). After stirring for 1 h, dry DMF (1.5 eq.) was added. The reaction mixture was stirred for 1 h at −78° C. and then warmed slowly to room temperature. After a further 2 h at room temperature the reaction mixture was poured onto ice/water yielding a precipitate that was collected by filtration and air-dried to yield the title compound.

Methods of Separation

In the methods of preparing the compounds of this invention, it may be advantageous to separate reaction products from one another and/or from starting materials. The desired products of each step or series of steps are separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Administration of Compounds of the Invention

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of formula Ia-d compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Compounds of the Invention

Compounds of the present invention are useful for treating diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of formula Ia-d, or a stereoisomer, geometric isomer, tautomer, solvate, metabolite, N-oxide derivative or pharmaceutically acceptable salt or prodrug thereof.

Diseases and conditions treatable according to the methods of this invention include, but are not limited to, cancer, stroke, diabetes, hepatomegaly, cardiovascular disease, Alzheimer's disease, cystic fibrosis, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of formula Ia-d and a pharmaceutically acceptable carrier, adjuvant, or vehicle, wherein said compound of formula Ia-d is present in an amount to detectably inhibit PB kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are nontoxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of formula Ia-d having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution, formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of formula Ia-d may be prepared. Suitable examples of sustained-release preparations include semipermeable matrices of solid hydrophobic polymers containing a compound of formula Ia-d, which matrices are in the form of shaped articles, e.g., films, or microcapsules. Examples of sustained-release matrices include polyesters, hydrogels (for example, poly(2-hydroxyethyl-methacrylate), or polyvinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy.

Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of formula Ia-d suitable for oral administration may be prepared as discrete units such as pills, capsules, cachets or tablets each containing a predetermined amount of a compound of formula Ia-d.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use, formulations of compounds of formula Ia-d intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of formula Ia-d compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 niL/hr can occur.

Formulations suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. [00180] formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of the invention may be employed alone or in combination with other therapeutic agents for the treatment of a disease or disorder described herein, such as a hyperproliferative disorder (e.g., cancer). In certain embodiments, a compound of formula Ia-d is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula Ia-d such that they do not adversely affect each other. Such compounds are suitably present in combination in amounts that are effective for the purpose intended. In one embodiment, a composition of this invention comprises a compound of formula Ia-d, or a stereoisomer, geometric isomer, tautomer, solvate, metabolite, a N-oxide derivative or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of formula Ia-d, or a stereoisomer, geometric isomer, tautomer, solvate, metabolite, N-oxide derivative or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of formula Ia-d, or a stereoisomer, geometric isomer, tautomer, solvate, metabolite, N-oxide derivative or pharmaceutically acceptable salt or prodrug thereof, and the use of at least one other cancer treatment method. The amounts of the compound(s) of formula Ia-d and the other pharmaceutically active chemotherapeutic agent(s) and the relative timings of administration will be selected in order to achieve the desired combined therapeutic effect.

Metabolites of Compounds of the Invention

Also falling within the scope of this invention are the in vivo metabolic products of formulas (I) and (Ia) to (Ii) described herein. Such products may result for example from the oxidation, reduction, hydrolysis, amidation, deamidation, esterification, deesterification, enzymatic cleavage, and the like, of the administered compound. Accordingly, the invention includes metabolites of compounds of formulas (I) and (Ia) to (Ii), including compounds produced by a process comprising contacting a compound of this invention with a mammal for a period of time sufficient to yield a metabolic product thereof.

Metabolite products typically are identified by preparing a radiolabeled (e.g., C or H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Prodrugs of the Compounds of the Invention

In addition to compounds of the invention, the invention also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, (1996) 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1\text{-}C_6)$alkanoyloxymethyl, 1-(($Ci\text{-}C_6$)alkanoyloxy)ethyl, 1-methyl-1-(($C_1\text{-}C_6$)alkanoyloxy)ethyl, ($Ci\text{-}C_6$)alkoxycarbonyloxymethyl, N—(C]-C_6)alkoxycarbonylaminomethyl, succinoyl, ($CrC_6$)alkanoyl, α-amino($C_1\text{-}C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1\text{-}C_6)\text{alkyl})_2$ or glycosyl (the radical resulting from the removal of a hydroxyl group of the hemiacetal form of a carbohydrate). [00196] For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Articles of Manufacture

In another embodiment of the invention, an article of manufacture, or "kit", containing materials useful for the treatment of the diseases and disorders described above is provided. In one embodiment, the kit comprises a container comprising a compound of formula Ia-d, or a stereoisomer, geometric isomer, tautomer, solvate, metabolite, N-oxide derivative or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula Ia-d or a formulation thereof which is effective for treating the condition and may have a sterile access port (for example, the container may be an intravenous solution bag or a vial having a stopper pierceable by a hypodermic injection needle). At least one active agent in the composition is a compound of formula Ia-d. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of formula Ia-d can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of formula Ia-d and, if present, the second pharmaceutical formulation. For example, if the kit comprises a first composition comprising a compound of formula Ia-d and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of formula Ia-d, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of formula Ia-d contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of formula Ia-d and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Example of Biological Evaluation

Determination of the potential to target PI3K/PI3K-related kinases (PIKK) of a compound of formula I is possible by a number of direct and indirect detection methods. Certain exemplary compounds described herein were assayed for their phospho PKB blocking activity and their in vitro activity against tumor cells. The range of phospho PKB activities was less than 1 nM (nanomolar) to about 10 μM (micromolar). Other exemplary compounds of the invention had phospho PKB blocking activity $IC_{50}$ values less than 10 nM. Certain compounds of the invention had tumor cell-based activity $IC_{50}$ values less than 100 nM.

The cytotoxic or cytostatic activity of formula I exemplary compounds was measured by: establishing a proliferating mammalian tumor cell lines in a cell culture medium, adding a formula I compound, culturing the cells for a period from about 6 hours to about 3 days; and measuring cell viability. Cell-based assays were used to measure viability, i.e. proliferation ($IC_{50}$), cytotoxicity ($EC_{50}$), and induction of apoptosis (caspase activation).

The in vitro potency of formula I compounds was measured by the in-cell Western assay designed in laboratories at University of Basel. This assay method was conducted in microtiter plate formats, making it amenable to high-throughput screening (HTS). Inhibitors were added to the medium and incubated. Antibodies diluted in PBS/T against pPKB Ser473 (Cell Signalling) and PKB (gift from E. Hirsch) or pS6 Ser 235/236 (Cell Signalling) were incubated overnight and then secondary fluorescently labelled antibodies (LI-COR) were applied and plates were scanned on an Odyssey reader to detect pPKB/PKB ratios.

The following compounds have shown particularly interesting biological activities:

4,4'-(6-(pyridin-3-yl)-1,3,5-triazine-2,4-diyl)dimorpholine,
3-(4,6-dimorpholino-1,3,5-triazin-2-yl)phenol,
5-(4,6-dimorpholino-1,3,5-triazin-2-yl)pyridin-3-ol,
5-(4,6-dimorpholino-1,3,5-triazin-2-yl)pyridin-2-amine,
5-(4,6-dimorpholino-1,3,5-triazin-2-yl)pyrimidin-2-amine,
5-(4,6-dimorpholino-1,3,5-triazin-2-yl)-4-(trifluoromethyl)pyridin-2-amine,
5-(4,6-dimorpholino-1,3,5-triazin-2-yl)-4-(trifluoromethyl)pyrimidin-2-amine,
N-(5-(4,6-dimorpholino-1,3,5-triazin-2-yl)pyridin-2-yl)acetamide,
N-(5-(4,6-dimorpholino-1,3,5-triazin-2-yl)pyrimidin-2-yl)acetamide,
N-(5-(4,6-dimorpholino-1,3,5-triazin-2-yl)-4-(trifluoromethyl)pyrimidin-2-yl)acetamide,
N-(5-(4,6-dimorpholino-1,3,5-triazin-2-yl)-4-(trifluoromethyl)pyridin-2-yl)acetamide,
5-(4,6-dimorpholino-1,3,5-triazin-2-yl)-6-(trifluoromethyl)pyridin-2-amine,
4,4'-(6-(1H-indazol-5-yl)-1,3,5-triazine-2,4-diyl)dimorpholine,
4,4'-(6-(1H-indol-5-yl)-1,3,5-triazine-2,4-diyl)dimorpholine,
4,4'-(6-(1H-benzo[d]imidazol-5-yl)-1,3,5-triazine-2,4-diyl)dimorpholine,
4,4'-(6-(1H-benzo[d]imidazol-4-yl)-1,3,5-triazine-2,4-diyl)dimorpholine,
4,4'-(6-(1H-indol-4-yl)-1,3,5-triazine-2,4-diyl)dimorpholine,
4,4'-(6-(1H-indazol-4-yl)-1,3,5-triazine-2,4-diyl)dimorpholine,
4,4'-(6-(1H-indazol-6-yl)-1,3,5-triazine-2,4-diyl)dimorpholine,
5-(4-morpholino-6-(pyridin-2-ylmethoxy)-1,3,5-triazin-2-yl)pyridin-2-amine,
5-(4-morpholino-6-(pyridin-2-ylmethoxy)-1,3,5-triazin-2-yl)pyrimidin-2-amine,
4-(4-(1H-indol-4-yl)-6-(pyridin-2-ylmethoxy)-1,3,5-triazin-2-yl)morpholine,
4-(4-(1H-indazol-4-yl)-6-(pyridin-2-ylmethoxy)-1,3,5-triazin-2-yl)morpholine,
4-(4-(1H-benzo[d]imidazol-4-yl)-6-(pyridin-2-ylmethoxy)-1,3,5-triazin-2-yl)morpholine,
4-(4-(1H-benzo[d]imidazol-5-yl)-6-(pyridin-2-ylmethoxy)-1,3,5-triazin-2-yl)morpholine,
4-(4-(1H-indazol-5-yl)-6-(pyridin-2-ylmethoxy)-1,3,5-triazin-2-yl)morpholine,
4-(4-(1H-indol-5-yl)-6-(pyridin-2-ylmethoxy)-1,3,5-triazin-2-yl)morpholine,
3-(4-morpholino-6-(pyridin-2-ylmethylamino)-1,3,5-triazin-2-yl)phenol,
4-(6-aminopyridin-3-yl)-6-morpholino-N-(pyridin-2-ylmethyl)-1,3,5-triazin-2-amine,
4-(2-aminopyrimidin-5-yl)-6-morpholino-N-(pyridin-2-ylmethyl)-1,3,5-triazin-2-amine,
4-(1H-indol-5-yl)-6-morpholino-N-(pyridin-2-ylmethyl)-1,3,5-triazin-2-amine,
4-(1H-indazol-5-yl)-6-morpholino-N-(pyridin-2-ylmethyl)-1,3,5-triazin-2-amine,
4-(1H-benzo[d]imidazol-5-yl)-6-morpholino-N-(pyridin-2-ylmethyl)-1,3,5-triazin-2-amine,
4-(1H-benzo[d]imidazol-4-yl)-6-morpholino-N-(pyridin-2-ylmethyl)-1,3,5-triazin-2-amine, 4-(1H-indol-4-yl)-6-morpholino-N-(pyridin-2-ylmethyl)-1,
  3,5-triazin-2-amine,
4-(1H-indazol-4-yl)-6-morpholino-N-(pyridin-2-ylmethyl)-
  1,3,5-triazin-2-amine,
3-(7-morpholinothiazolo[4,5-d]pyrimidin-5-yl)phenol,
3-(7-morpholinooxazolo[4,5-d]pyrimidin-5-yl)phenol,
3-(2-((4-methylpiperazin-1-yl)methyl)-7-morpholinoox-
  azolo[4,5-d]pyrimidin-5-yl)phenol,
3-(2-((4-methylpiperazin-1-yl)methyl)-7-morpholinothia-
  zolo[4,5-d]pyrimidin-5-yl)phenol,
3-(2-((4-(methylsulfonyl)piperazin-1-yl)methyl)-7-mor-
  pholinothiazolo[4,5-d]pyrimidin-5-yl)phenol,
5-(7-morpholinothiazolo[4,5-d]pyrimidin-5-yl)pyrimidin-2-
  amine,
5-(7-morpholinothiazolo[4,5-d]pyrimidin-5-yl)pyridin-2-
  amine,
5-(2(4-methylpiperazin-1-yl)methyl)-7-morpholinothia-
  zolo[4,5-d]pyrimidin-5-yl)pyrimidin-2-amine,
5-(2-((4-methylpiperazin-1-yl)methyl)-7-morpholinoox-
  azolo[4,5-d]pyrimidin-5-yl)pyrimidin-2-amine,
4-(5-(1H-indazol-4-yl)thiazolo[4,5-d]pyrimidin-7-yl)mor-
  pholine,
4-(5-(1H-indazol-4-yl)-2-((4-methylpiperazin-1-yl)methyl)
  thiazolo[4,5-d]pyrimidin-7-yl)morpholine,
4-(5-(1H-indazol-4-yl)-2-((4-(methylsulfonyl)piperazin-1-
  yl)methyl)thiazolo[4,5-d]pyrimidin-7-yl)morpholine,
4-(5-(1H-indol-4-yl)thiazolo[4,5-d]pyrimidin-7-yl)morpho-
  line,
4-(5-(1H-benzo[d]imidazol-4-yl)thiazolo[4,5-d]pyrimidin-
  7-yl)morpholine,
4-(5-(1H-benzo[d]imidazol-5-yl)thiazolo[4,5-d]pyrimidin-
  7-yl)morpholine,
4-(5-(1H-indol-5-yl)thiazolo[4,5-d]pyrimidin-7-yl)morpho-
  line,
4-(5-(1H-indol-5-yl)-2-((4-methylpiperazin-1-yl)methyl)
  thiazolo[4,5-d]pyrimidin-7-yl)morpholine,
4-(5-(1H-indazol-5-yl)thiazolo[4,5-d]pyrimidin-7-yl)mor-
  pholine,
2-(1H-benzo[d]imidazol-5-yl)-4-morpholinobenzofuro[3,2-
  d]pyrimidine,
2-(1H-indol-5-yl)-4-morpholinobenzofuro[3,2-d]pyrimi-
  dine,
2-(1H-indazol-5-yl)-4-morpholinobenzofuro[3,2-d]pyrimi-
  dine,
6-(1H-Indazol-5-yl)-8-morpholin-4-yl-9-oxa-1,5,7-triaza-
  fluorene,
6-(1H-Benzoimidazol-5-yl)-8-morpholin-4-yl-9-oxa-1,5,7-
  triaza-fluorene,
6-(1H-Indol-5-yl)-8-morpholin-4-yl-9-oxa-1,5,7-triaza-
  fluorene,
2-(1H-indol-4-yl)-4-morpholinobenzofuro[3,2-d]pyrimi-
  dine,
2-(1H-indazol-4-yl)-4-morpholinobenzofuro[3,2-d]pyrimi-
  dine,
2-(1H-benzo[d]imidazol-4-yl)-4-morpholinobenzofuro[3,2-
  d]pyrimidine,
6-(1H-Indazol-4-yl)-8-morpholin-4-yl-9-oxa-1,5,7-triaza-
  fluorene,
6-(1H-Indazol-4-yl)-2-(4-methyl-piperazin-1-ylmethyl)-8-
  morpholin-4-yl-9-oxa-1,5,7-triaza-fluorene,
6-(1H-Benzoimidazol-4-yl)-8-morpholin-4-yl-9-oxa-1,5,7-
  triaza-fluorene,
6-(1H-Indol-4-yl)-8-morpholin-4-yl-9-oxa-1,5,7-triaza-
  fluorene,
5-(8-Morpholin-4-yl-9-oxa-1,5,7-triaza-fluoren-6-yl)-pyri-
  midin-2-ylamine,
3-[2-(4-Methyl-piperazin-1-ylmethyl)-8-morpholin-4-yl-9-
  oxa-1,5,7-triaza-fluoren-6-yl]-phenol,
5-(8-Morpholin-4-yl-9-oxa-1,5,7-triaza-fluoren-6-yl)-pyri-
  din-2-ylamine,
5-(4-morpholinobenzofuro[3,2-d]pyrimidin-2-yl)pyridin-2-
  amine,
5-(4-morpholinobenzofuro[3,2-d]pyrimidin-2-yl)pyrimidin-
  2-amine, and
3-(4-morpholinobenzofuro[3,2-d]pyrimidin-2-yl)phenol.

Among the above recited compounds 5-(4,6-dimor-
pholino-1,3,5-triazin-2-yl)-4-(trifluoromethyl)pyridin-
2-amine and 5-(4,6-dimorpholino-1,3,5-triazin-2-yl)-4-
(trifluoromethyl)pyrimidin-2-amine have excellent
biological properties which make them very promising
as therapeutic agents (see Table 6 below).

DETAILED DESCRIPTION OF THE INVENTION

The invention will be now described in a more detailed fashion with regard to specific embodiments and examples of the invention, which have an exemplary but not a limitative character.

Table 1 gives the structures and the corresponding IUPAC names (using ChemDraw Ultra, Version 11.0.1 as well as lower and upper software versions thereof, CambridgeSoft Corp., Cambridge Mass.) of exemplary compounds Nos. 1-259 of formula (Ia), (Ib) or (Id).

TABLE 1

| Cpd No. | Structure | Name |
|---|---|---|
| 1 | 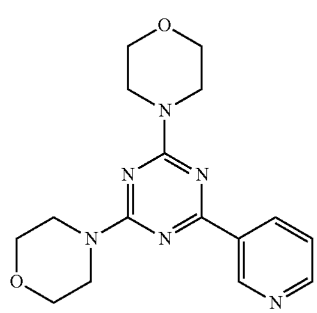 [SMILES: c1cncc(-c2nc(N3CCOCC3)nc(N3CCOCC3)n2)c1] | 4,4'-(6-(pyridin-3-yl)-1,3,5-triazine-2,4-diyl)dimorpholine |

TABLE 1-continued

| Cpd No. | Structure | Name |
|---|---|---|
| 2 | 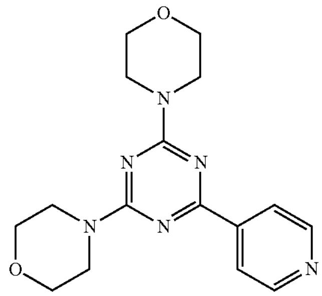 [SMILES: c1cc(-c2nc(N3CCOCC3)nc(N3CCOCC3)n2)ccn1] | 4,4'-(6-(pyridin-4-yl)-1,3,5-triazine-2,4-diyl)dimorpholine |
| 3 | 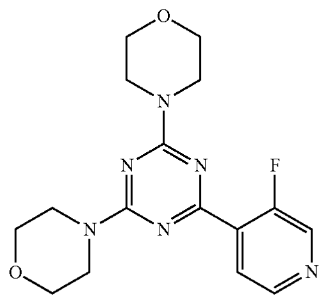 [SMILES: Fc1cnccc1-c1nc(N2CCOCC2)nc(N2CCOCC2)n1] | 4,4'-(6-(3-fluoropyridin-4-yl)-1,3,5-triazine-2,4-diyl)dimorpholine |
| 4 | 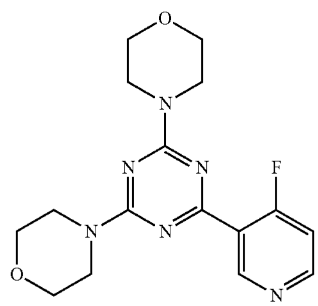 [SMILES: Fc1ccncc1-c1nc(N2CCOCC2)nc(N2CCOCC2)n1] | 4,4'-(6-(4-fluoropyridin-3-yl)-1,3,5-triazine-2,4-diyl)dimorpholine |
| 5 | 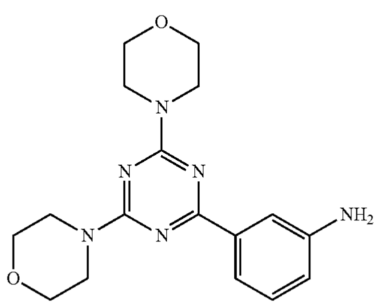 [SMILES: Nc1cccc(-c2nc(N3CCOCC3)nc(N3CCOCC3)n2)c1] | 3-(4,6-dimorpholino-1,3,5-triazin-2-yl)aniline |
| 6 | 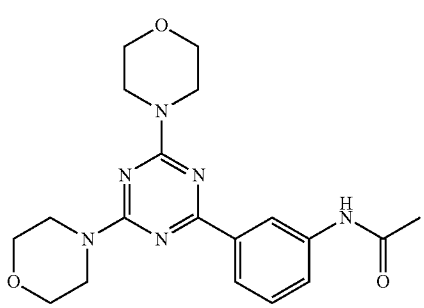 [SMILES: CC(=O)Nc1cccc(-c2nc(N3CCOCC3)nc(N3CCOCC3)n2)c1] | N-(3-(4,6-dimorpholino-1,3,5-triazin-2-yl)phenyl)acetamide |

TABLE 1-continued

| Cpd No. | Structure | Name |
|---|---|---|
| 6.1 | 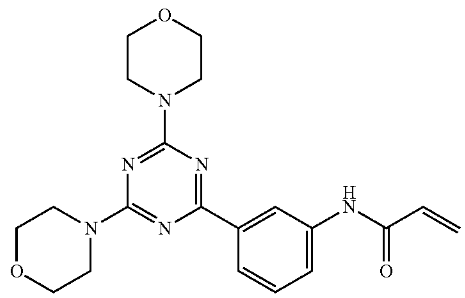 [SMILES: C=CC(=O)Nc1cccc(-c2nc(N3CCOCC3)nc(N3CCOCC3)n2)c1] | N-(3-(4,6-dimorpholino-1,3,5-triazin-2-yl)phenyl)acrylamide |
| 6.2 | 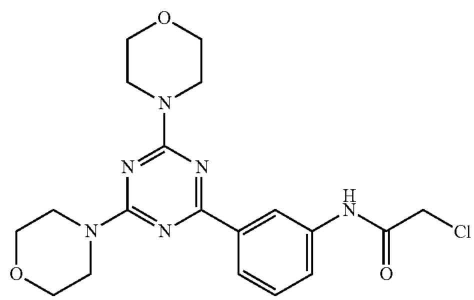 [SMILES: O=C(CCl)Nc1cccc(-c2nc(N3CCOCC3)nc(N3CCOCC3)n2)c1] | 2-chloro-N-(3-(4,6-dimorpholino-1,3,5-triazin-2-yl)phenyl)acetamide |
| 6.3 | 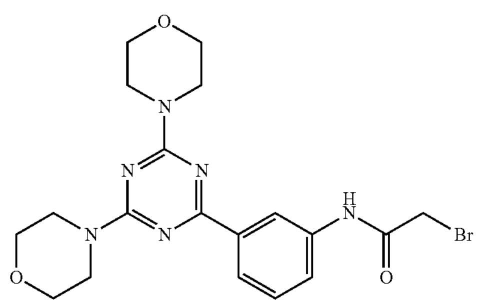 [SMILES: O=C(CBr)Nc1cccc(-c2nc(N3CCOCC3)nc(N3CCOCC3)n2)c1] | 2-bromo-N-(3-(4,6-dimorpholino-1,3,5-triazin-2-yl)phenyl)acetamide |
| 6.4 | 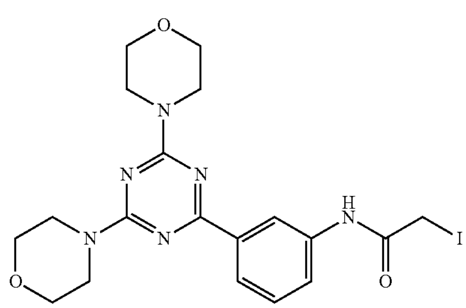 [SMILES: O=C(CI)Nc1cccc(-c2nc(N3CCOCC3)nc(N3CCOCC3)n2)c1] | N-(3-(4,6-dimorpholino-1,3,5-triazin-2-yl)phenyl)-2-iodoacetamide |
| 6.5 | 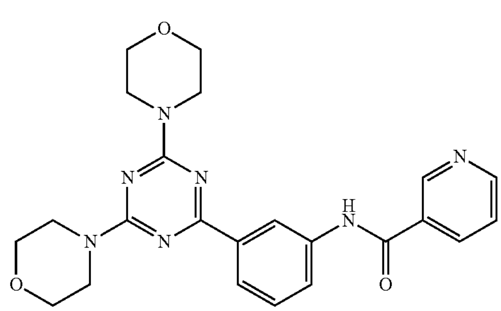 [SMILES: O=C(Nc1cccc(-c2nc(N3CCOCC3)nc(N3CCOCC3)n2)c1)c1cccnc1] | N-(3-(4,6-dimorpholino-1,3,5-triazin-2-yl)phenyl)nicotinamide |

TABLE 1-continued
| Cpd No. | Structure | Name |
|---|---|---|
| 6.6 | 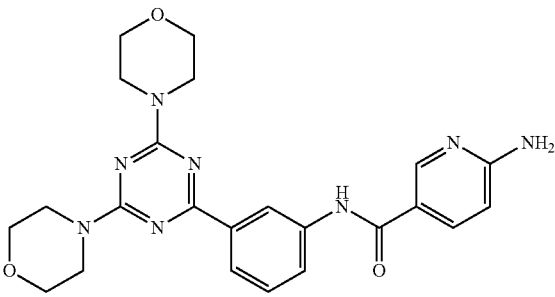 [SMILES: Nc1ccc(C(=O)Nc2cccc(-c3nc(N4CCOCC4)nc(N4CCOCC4)n3)c2)cn1] | 6-amino-N-(3-(4,6-dimorpholino-1,3,5-triazin-2-yl)phenyl)nicotinamide |
| 6.7 | 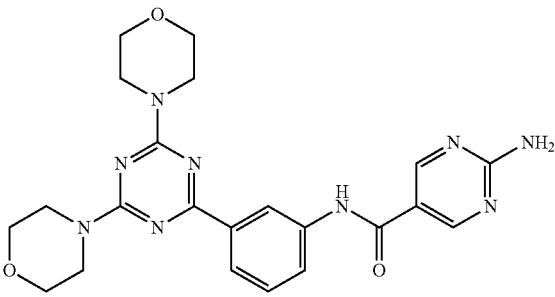 [SMILES: Nc1ncc(C(=O)Nc2cccc(-c3nc(N4CCOCC4)nc(N4CCOCC4)n3)c2)cn1] | 2-amino-N-(3-(4,6-dimorpholino-1,3,5-triazin-2-yl)phenyl)pyrimidine-5-carboxamide |
| 7 | 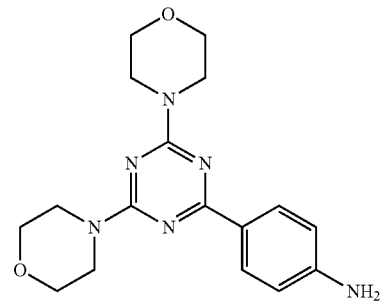 [SMILES: Nc1ccc(-c2nc(N3CCOCC3)nc(N3CCOCC3)n2)cc1] | 4-(4,6-dimorpholino-1,3,5-triazin-2-yl)aniline |
| 8 | 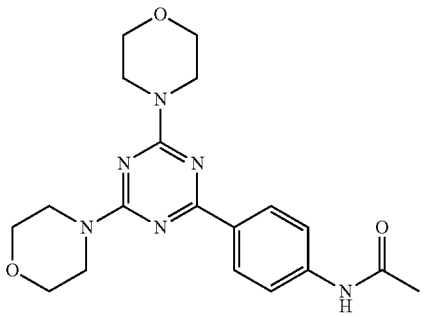 [SMILES: CC(=O)Nc1ccc(-c2nc(N3CCOCC3)nc(N3CCOCC3)n2)cc1] | N-(4-(4,6-dimorpholino-1,3,5-triazin-2-yl)phenyl)acetamide |
| 8.1 | 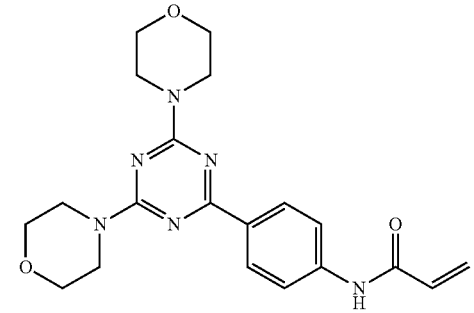 [SMILES: C=CC(=O)Nc1ccc(-c2nc(N3CCOCC3)nc(N3CCOCC3)n2)cc1] | N-(4-(4,6-dimorpholino-1,3,5-triazin-2-yl)phenyl)acrylamide |

TABLE 1-continued

| Cpd No. | Structure | Name |
|---|---|---|
| 8.2 | 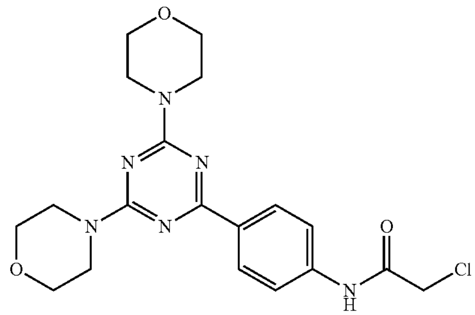 [SMILES: O=C(CCl)Nc1ccc(-c2nc(N3CCOCC3)nc(N3CCOCC3)n2)cc1] | 2-chloro-N-(4-(4,6-dimorpholino-1,3,5-triazin-2-yl)phenyl)acetamide |
| 8.3 | 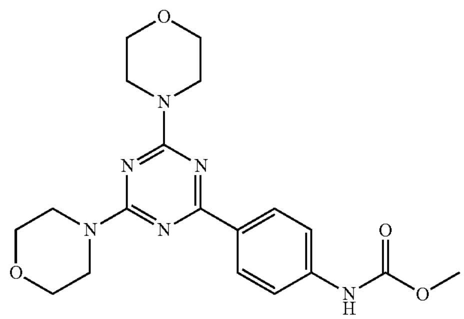 [SMILES: COC(=O)Nc1ccc(-c2nc(N3CCOCC3)nc(N3CCOCC3)n2)cc1] | N-(4-(4,6-dimorpholino-1,3,5-triazin-2-yl)phenyl)acrylamide |
| 8.4 | 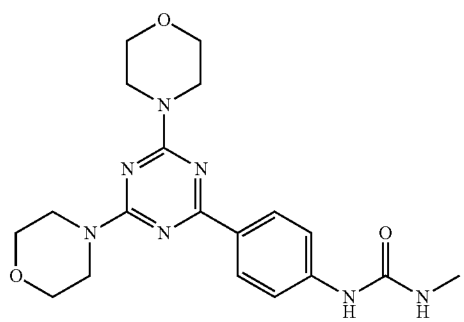 [SMILES: CNC(=O)Nc1ccc(-c2nc(N3CCOCC3)nc(N3CCOCC3)n2)cc1] | 1-(4-(4,6-dimorpholino-1,3,5-triazin-2-yl)phenyl)-3-methylurea |
| 9 | 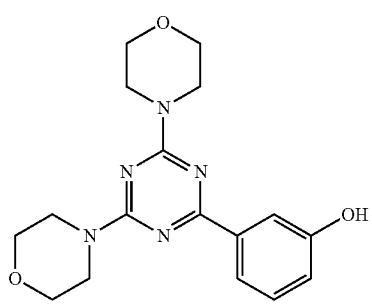 [SMILES: Oc1cccc(-c2nc(N3CCOCC3)nc(N3CCOCC3)n2)c1] | 3-(4,6-dimorpholino-1,3,5-triazin-2-yl)phenol |
| 9.1 | 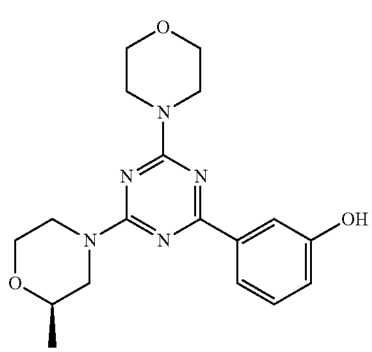 [SMILES: C[C@@H]1CN(c2nc(-c3cccc(O)c3)nc(N3CCOCC3)n2)CCO1] | (R)-3-(4-(2-methylmorpholino)-6-morpholino-1,3,5-triazin-2-yl)phenol |

TABLE 1-continued

| Cpd No. | Structure | Name |
|---|---|---|
| 9.2 | 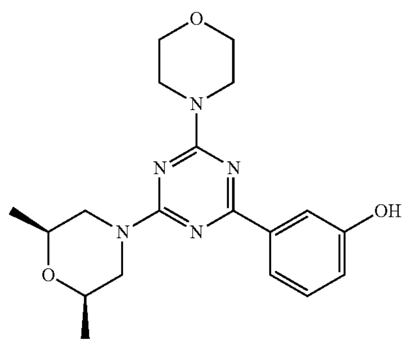 [SMILES: C[C@@H]1CN(c2nc(-c3cccc(O)c3)nc(N3CCOCC3)n2)C[C@H](C)O1] | 3-(4-((2R,6S)-2,6-dimethylmorpholino)-6-morpholino-1,3,5-triazin-2-yl)phenol |
| 9.3 | 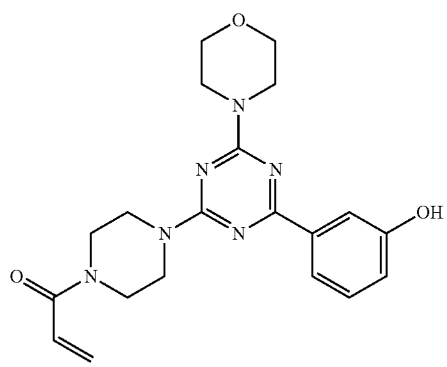 [SMILES: C=CC(=O)N1CCN(c2nc(-c3cccc(O)c3)nc(N3CCOCC3)n2)CC1] | 1-(4-(4-(3-hydroxyphenyl)-6-morpholino-1,3,5-triazin-2-yl)piperazin-1-yl)prop-2-en-1-one |
| 9.4 | 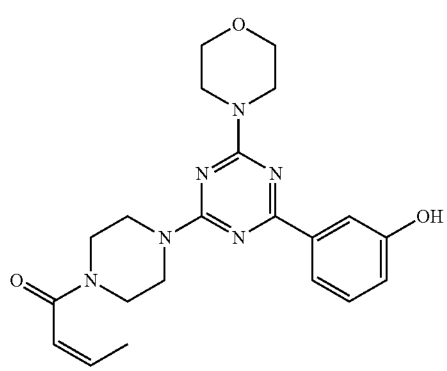 [SMILES: C/C=C\C(=O)N1CCN(c2nc(-c3cccc(O)c3)nc(N3CCOCC3)n2)CC1] | (Z)-1-(4-(4-(3-hydroxyphenyl)-6-morpholino-1,3,5-triazin-2-yl)piperazin-1-yl)but-2-en-1-one |
| 9.5 | 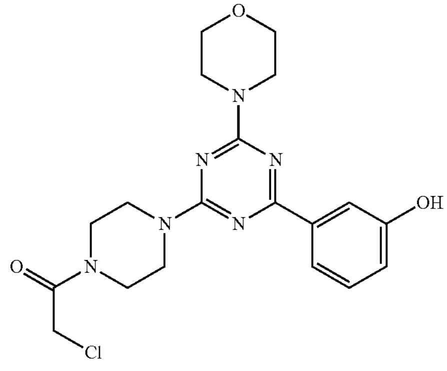 [SMILES: O=C(CCl)N1CCN(c2nc(-c3cccc(O)c3)nc(N3CCOCC3)n2)CC1] | 2-2-chloro-1-(4-(4-(3-hydroxyphenyl)-6-morpholino-1,3,5-triazin-2-yl)piperazin-1-yl)ethanone |

TABLE 1-continued

| Cpd No. | Structure | Name |
|---|---|---|
| 10 | 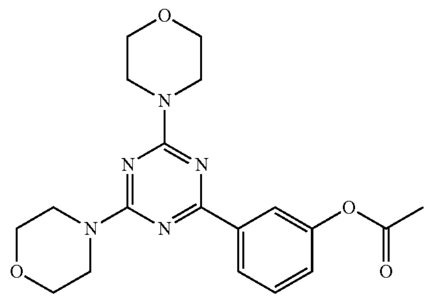 [SMILES: CC(=O)Oc1cccc(-c2nc(N3CCOCC3)nc(N3CCOCC3)n2)c1] | 3-(4,6-dimorpholino-1,3,5-triazin-2-yl)phenyl acetate |
| 11 | 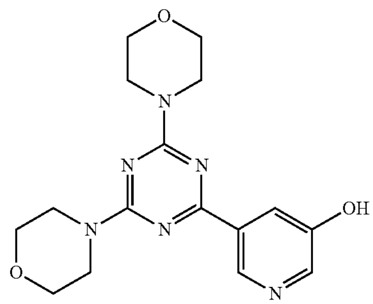 [SMILES: Oc1cncc(-c2nc(N3CCOCC3)nc(N3CCOCC3)n2)c1] | 5-(4,6-dimorpholino-1,3,5-triazin-2-yl)pyridin-3-ol |
| 12 | 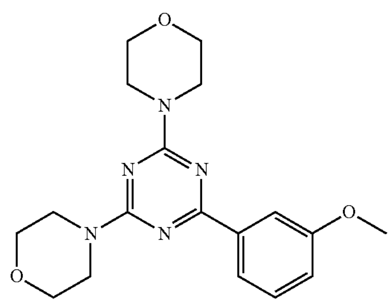 [SMILES: COc1cccc(-c2nc(N3CCOCC3)nc(N3CCOCC3)n2)c1] | 4,4'-(6-(3-methoxyphenyl)-1,3,5-triazine-2,4-diyl)dimorpholine |
| 13 | 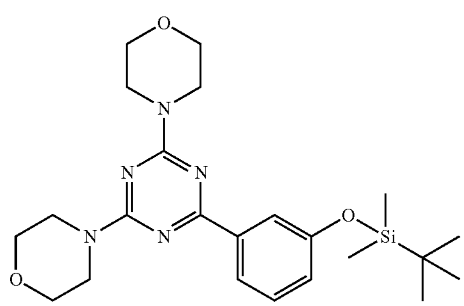 [SMILES: CC(C)(C)[Si](C)(C)Oc1cccc(-c2nc(N3CCOCC3)nc(N3CCOCC3)n2)c1] | 4,4'-(6-(3-(tert-butyldimethylsilyloxy)phenyl)-1,3,5-triazine-2,4-diyl)dimorpholine |
| 14 | 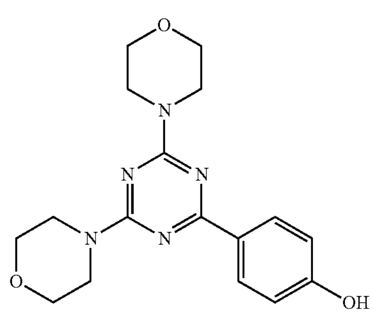 [SMILES: Oc1ccc(-c2nc(N3CCOCC3)nc(N3CCOCC3)n2)cc1] | 4-(4,6-dimorpholino-1,3,5-triazin-2-yl)phenol |

TABLE 1-continued

| Cpd No. | Structure | Name |
|---|---|---|
| 15 | 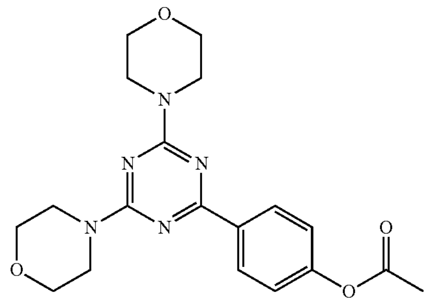 [SMILES: CC(=O)Oc1ccc(-c2nc(N3CCOCC3)nc(N3CCOCC3)n2)cc1] | 4-(4,6-dimorpholino-1,3,5-triazin-2-yl)phenyl acetate |
| 16 | 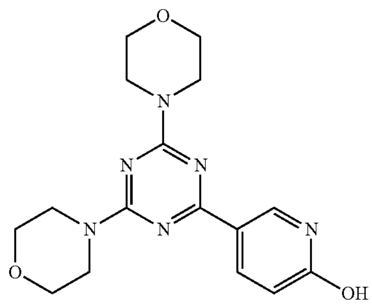 [SMILES: Oc1ccc(-c2nc(N3CCOCC3)nc(N3CCOCC3)n2)cn1] | 5-(4,6-dimorpholino-1,3,5-triazin-2-yl)pyridin-2-ol |
| 17 | 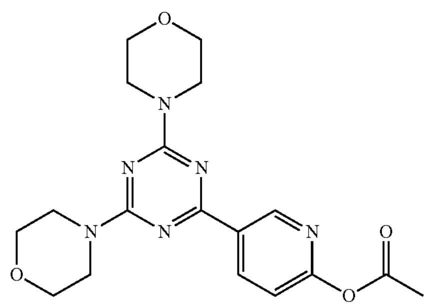 [SMILES: CC(=O)Oc1ccc(-c2nc(N3CCOCC3)nc(N3CCOCC3)n2)cn1] | 5-(4,6-dimorpholino-1,3,5-triazin-2-yl)pyridin-2-yl acetate |
| 18 | 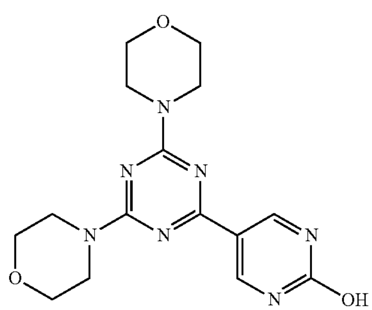 [SMILES: Oc1ncc(-c2nc(N3CCOCC3)nc(N3CCOCC3)n2)cn1] | 5-(4,6-dimorpholino-1,3,5-triazin-2-yl)pyrimidin-2-ol |
| 19 | 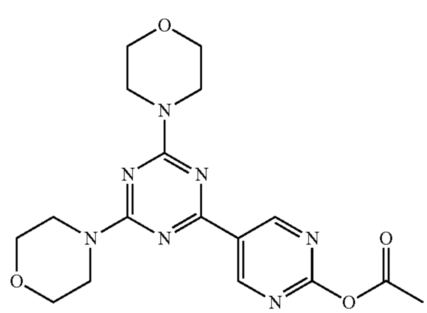 [SMILES: CC(=O)Oc1ncc(-c2nc(N3CCOCC3)nc(N3CCOCC3)n2)cn1] | 5-(4,6-dimorpholino-1,3,5-triazin-2-yl)pyrimidin-2-yl acetate |

TABLE 1-continued

| Cpd No. | Structure | Name |
|---|---|---|
| 20 | 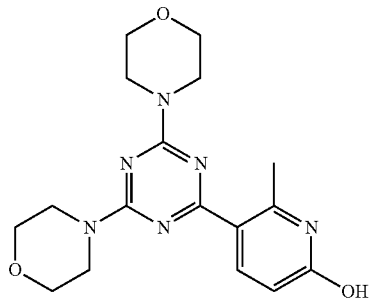 [SMILES: Cc1nc(O)ccc1-c1nc(N2CCOCC2)nc(N2CCOCC2)n1] | 5-(4,6-dimorpholino-1,3,5-triazin-2-yl)-6-methylpyridin-2-ol |
| 21 | 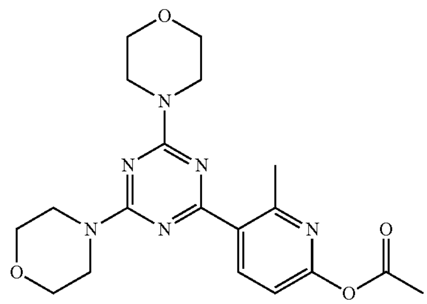 [SMILES: CC(=O)Oc1ccc(-c2nc(N3CCOCC3)nc(N3CCOCC3)n2)c(C)n1] | 5-(4,6-dimorpholino-1,3,5-triazin-2-yl)-6-methylpyridin-2-yl acetate |
| 22 | 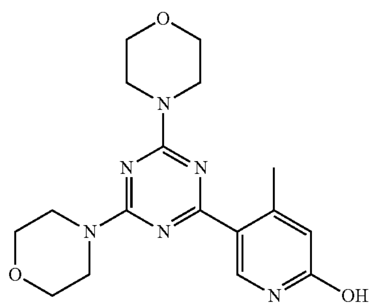 [SMILES: Cc1cc(O)ncc1-c1nc(N2CCOCC2)nc(N2CCOCC2)n1] | 5-(4,6-dimorpholino-1,3,5-triazin-2-yl)-4-methylpyridin-2-ol |
| 23 | 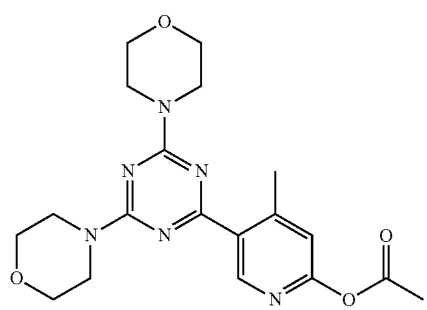 [SMILES: CC(=O)Oc1cc(C)c(-c2nc(N3CCOCC3)nc(N3CCOCC3)n2)cn1] | 5-(4,6-dimorpholino-1,3,5-triazin-2-yl)-4-methylpyridin-2-yl acetate |
| 24 | 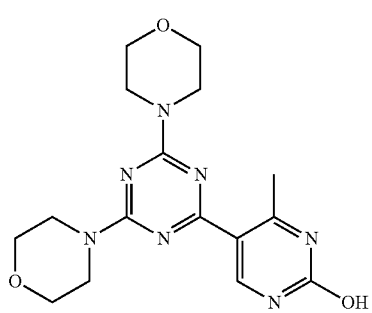 [SMILES: Cc1nc(O)ncc1-c1nc(N2CCOCC2)nc(N2CCOCC2)n1] | 5-(4,6-dimorpholino-1,3,5-triazin-2-yl)-4-methylpyrimidin-2-ol |

TABLE 1-continued

| Cpd No. | Structure | Name |
|---|---|---|
| 25 | 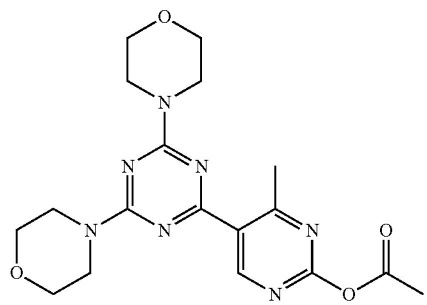 [SMILES: CC(=O)Oc1ncc(-c2nc(N3CCOCC3)nc(N3CCOCC3)n2)c(C)n1] | 5-(4,6-dimorpholino-1,3,5-triazin-2-yl)-4-methylpyrimidin-2-yl acetate |
| 26 | 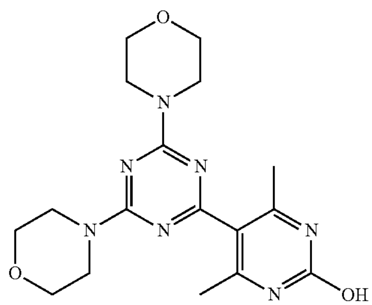 [SMILES: Cc1nc(O)nc(C)c1-c1nc(N2CCOCC2)nc(N2CCOCC2)n1] | 5-(4,6-dimorpholino-1,3,5-triazin-2-yl)-4,6-dimethylpyrimidin-2-ol |
| 27 | 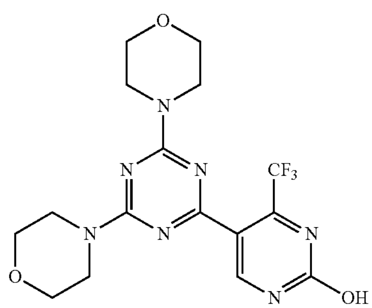 [SMILES: Oc1ncc(-c2nc(N3CCOCC3)nc(N3CCOCC3)n2)c(C(F)(F)F)n1] | 5-(4,6-dimorpholino-1,3,5-triazin-2-yl)-4-(trifluoromethyl)pyrimidin-2-ol |
| 28 | 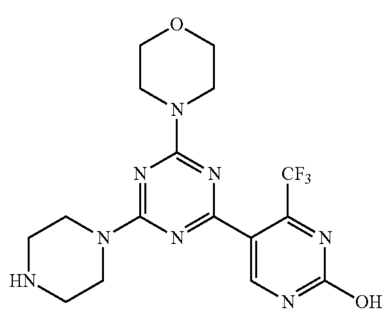 [SMILES: Oc1ncc(-c2nc(N3CCNCC3)nc(N3CCOCC3)n2)c(C(F)(F)F)n1] | 5-(4-morpholino-6-(piperazin-1-yl)-1,3,5-triazin-2-yl)-4-trifluoromethyl)pyrimidin-2-ol |
| 29 | 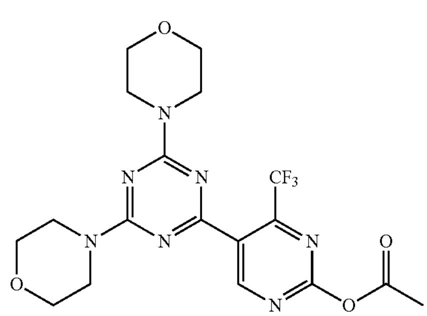 [SMILES: CC(=O)Oc1ncc(-c2nc(N3CCOCC3)nc(N3CCOCC3)n2)c(C(F)(F)F)n1] | 5-(4,6-dimorpholino-1,3,5-triazin-2-yl)-4-(trifluoromethyl)pyrimidin-2-yl acetate |

TABLE 1-continued

| Cpd No. | Structure | Name |
|---|---|---|
| 30 | 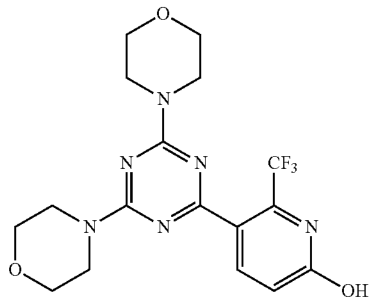 [SMILES: Oc1ccc(-c2nc(N3CCOCC3)nc(N3CCOCC3)n2)c(C(F)(F)F)n1] | 5-(4,6-dimorpholino-1,3,5-triazin-2-yl)-6-(trifluoromethyl)pyridin-2-ol |
| 31 | 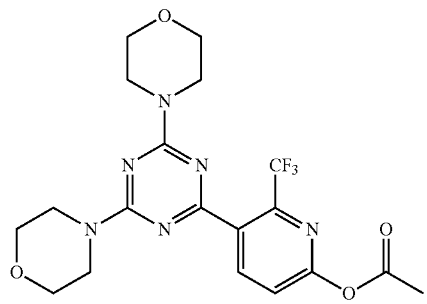 [SMILES: CC(=O)Oc1ccc(-c2nc(N3CCOCC3)nc(N3CCOCC3)n2)c(C(F)(F)F)n1] | 5-(4,6-dimorpholino-1,3,5-triazin-2-yl)-6-(trifluoromethyl)pyridin-2-yl acetate |
| 32 | 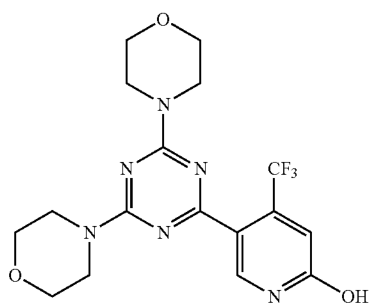 [SMILES: Oc1cc(C(F)(F)F)c(-c2nc(N3CCOCC3)nc(N3CCOCC3)n2)cn1] | 5-(4,6-dimorpholino-1,3,5-triazin-2-yl)-4-(trifluoromethyl)pyridin-2-ol |
| 33 | 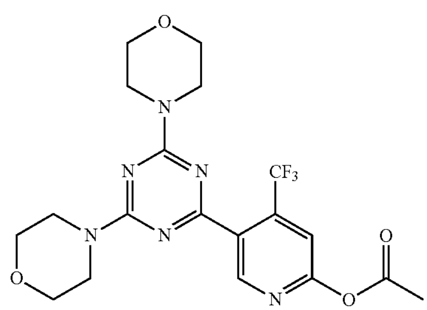 [SMILES: CC(=O)Oc1cc(C(F)(F)F)c(-c2nc(N3CCOCC3)nc(N3CCOCC3)n2)cn1] | 5-(4,6-dimorpholino-1,3,5-triazin-2-yl)-4-(trifluoromethyl)pyridin-2-yl acetate |
| 34 | 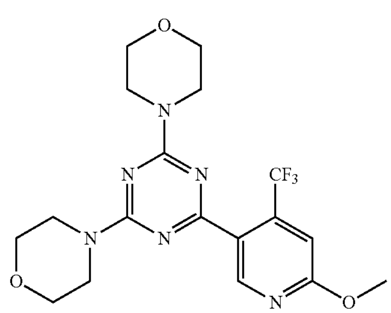 [SMILES: COc1cc(C(F)(F)F)c(-c2nc(N3CCOCC3)nc(N3CCOCC3)n2)cn1] | 4,4'-(6-(6-methoxy-4-(trifluoromethyl)pyridin-3-yl)-1,3,5-triazine-2,4-diyl)dimorpholine |

TABLE 1-continued

| Cpd No. | Structure | Name |
|---|---|---|
| 35 | 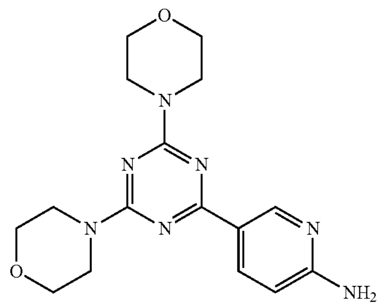 [SMILES: Nc1ccc(-c2nc(N3CCOCC3)nc(N3CCOCC3)n2)cn1] | 5-(4,6-dimorpholino-1,3,5-triazin-2-yl)pyridin-2-amine |
| 36 | 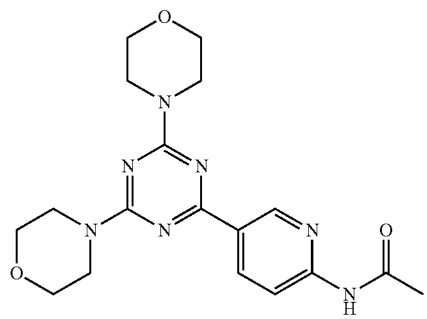 [SMILES: CC(=O)Nc1ccc(-c2nc(N3CCOCC3)nc(N3CCOCC3)n2)cn1] | N-(5-(4,6-dimorpholino-1,3,5-triazin-2-yl)pyridin-2-yl)acetamide |
| 37 | 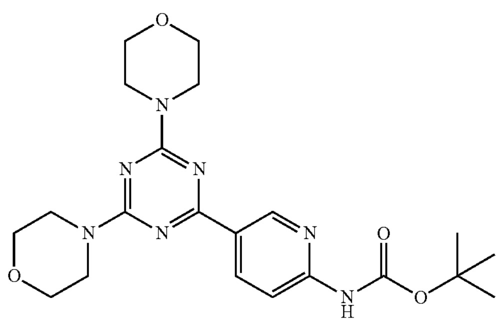 [SMILES: CC(C)(C)OC(=O)Nc1ccc(-c2nc(N3CCOCC3)nc(N3CCOCC3)n2)cn1] | tert-butyl 5-(4,6-dimorpholino-1,3,5-triazin-2-yl)pyridin-2-ylcarbamate |
| 38 | 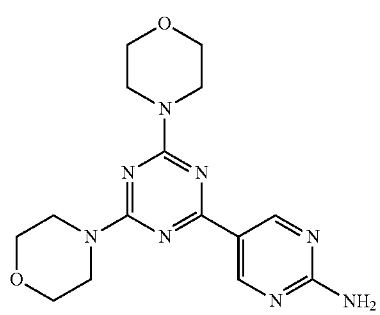 [SMILES: Nc1ncc(-c2nc(N3CCOCC3)nc(N3CCOCC3)n2)cn1] | 5-(4,6-dimorpholino-1,3,5-triazin-2-yl)pyrimidin-2-amine |
| 38.1 | 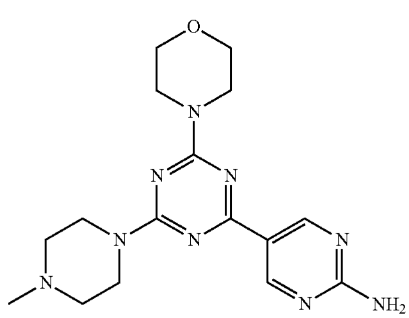 [SMILES: CN1CCN(c2nc(-c3cnc(N)nc3)nc(N3CCOCC3)n2)CC1] | 5-(4-(4-methylpiperazin-1-yl)-6-morpholino-1,3,5-triazin-2-yl)pyrimidin-2-amine |

TABLE 1-continued

| Cpd No. | Structure | Name |
|---|---|---|
| 38.2 | 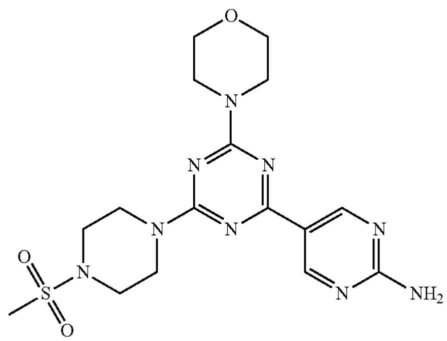 [SMILES: CS(=O)(=O)N1CCN(c2nc(-c3cnc(N)nc3)nc(N3CCOCC3)n2)CC1] | 5-(4-(4-(methylsulfonyl)piperazin-1-yl)-6-morpholino-1,3,5-triazin-2-yl)pyrimidin-2-amine |
| 38.3 | 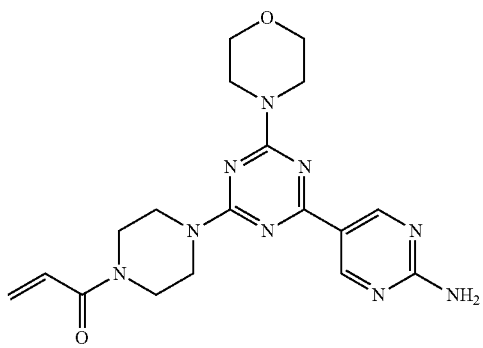 [SMILES: C=CC(=O)N1CCN(c2nc(-c3cnc(N)nc3)nc(N3CCOCC3)n2)CC1] | 1-(4-(4-(2-aminopyrimidin-5-yl)-6-morpholino-1,3,5-triazin-2-yl)piperazin-1-yl)prop-2-en-1-one |
| 38.4 | 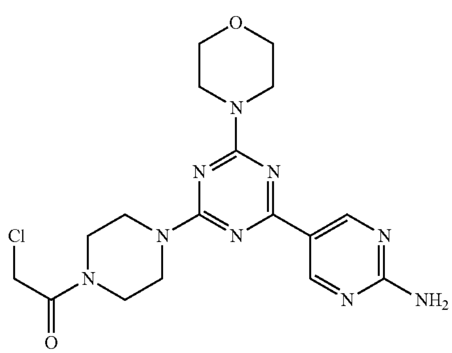 [SMILES: Nc1ncc(-c2nc(N3CCOCC3)nc(N3CCN(C(=O)CCl)CC3)n2)cn1] | 1-(4-(4-(2-aminopyrimidin-5-yl)-6-morpholino-1,3,5-triazin-2-yl)piperazin-1-yl)-2-chloroethanone |
| 38.5 | 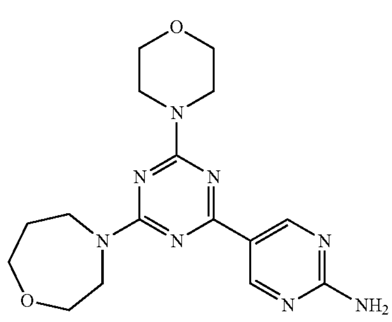 [SMILES: Nc1ncc(-c2nc(N3CCCOCC3)nc(N3CCOCC3)n2)cn1] | 5-(4-morpholino-6-(1,4-oxazepan-4-yl)-1,3,5-triazin-2-yl)pyrimidin-2-amine |

TABLE 1-continued

| Cpd No. | Structure | Name |
|---|---|---|
| 39 | 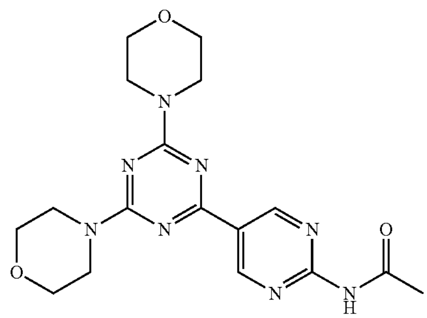 [SMILES: CC(=O)Nc1ncc(-c2nc(N3CCOCC3)nc(N3CCOCC3)n2)cn1] | N-(5-(4,6-dimorpholino-1,3,5-triazin-2-yl)pyrimidin-2-yl)acetamide |
| 40 | 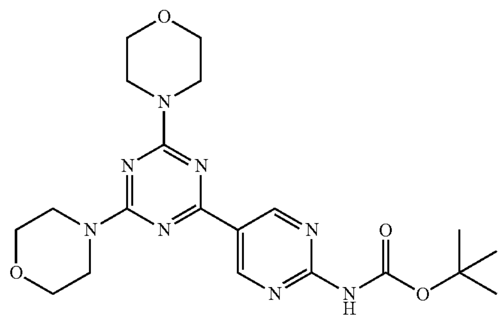 [SMILES: CC(C)(C)OC(=O)Nc1ncc(-c2nc(N3CCOCC3)nc(N3CCOCC3)n2)cn1] | tert-butyl 5-(4,6-dimorpholino-1,3,5-triazin-2-yl)pyrimidin-2-ylcarbamate |
| 41 | 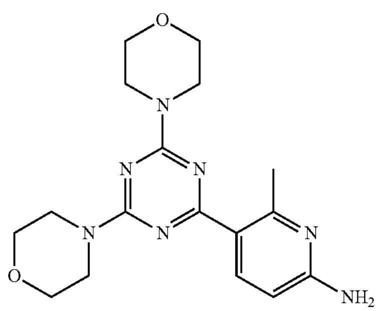 [SMILES: Cc1nc(N)ccc1-c1nc(N2CCOCC2)nc(N2CCOCC2)n1] | 5-(4,6-dimorpholino-1,3,5-triazin-2-yl)-6-methylpyridin-2-amine |
| 42 | 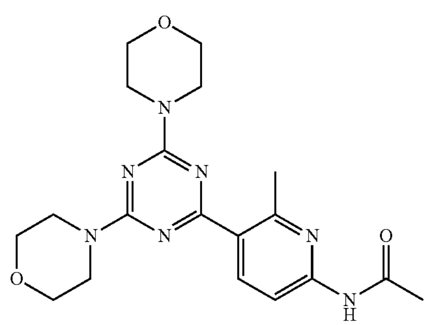 [SMILES: CC(=O)Nc1ccc(-c2nc(N3CCOCC3)nc(N3CCOCC3)n2)c(C)n1] | N-(5-(4,6-dimorpholino-1,3,5-triazin-2-yl)-6-methylpyridin-2-yl)acetamide |
| 43 | 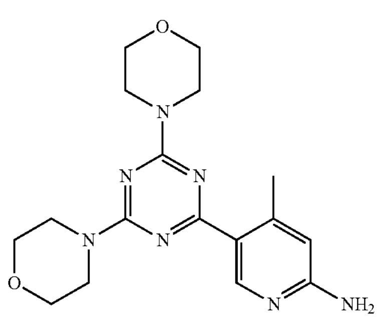 [SMILES: Cc1cc(N)ncc1-c1nc(N2CCOCC2)nc(N2CCOCC2)n1] | 5-(4,6-dimorpholino-1,3,5-triazin-2-yl)-4-methylpyridin-2-amine |

TABLE 1-continued

| Cpd No. | Structure | Name |
|---|---|---|
| 43.1 | 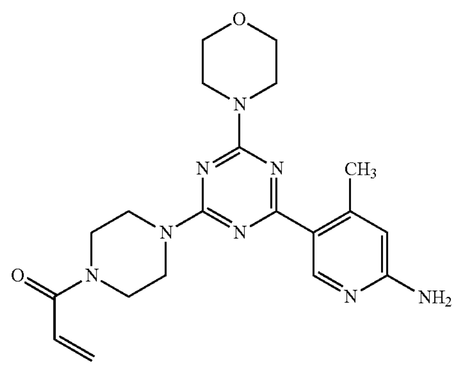 [SMILES: C=CC(=O)N1CCN(c2nc(-c3cnc(N)cc3C)nc(N3CCOCC3)n2)CC1] | 1-(4-(4-(6-amino-4-methylpyridin-3-yl)-6-morpholino-1,3,5-triazin-2-yl)piperazin-1-yl)prop-2-en-1-one |
| 43.2 | 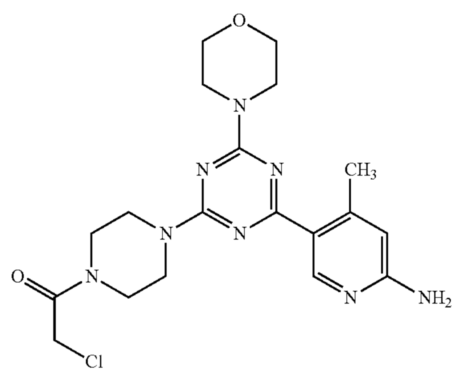 [SMILES: Cc1cc(N)ncc1-c1nc(N2CCOCC2)nc(N2CCN(C(=O)CCl)CC2)n1] | 1-(4-(4-(6-amino-4-methylpyridin-3-yl)-6-morpholino-1,3,5-triazin-2-yl)piperazin-1-yl)-2-chloroethanone |
| 43.3 | 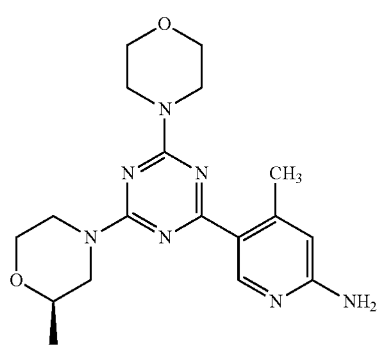 [SMILES: Cc1cc(N)ncc1-c1nc(N2CCOCC2)nc(N2CCO[C@H](C)C2)n1] | (R)-4-methyl-5-(4-(2-methylmorpholino)-6-morpholino-1,3,5-triazin-2-yl)pyridin-2-amine |
| 43.4 | 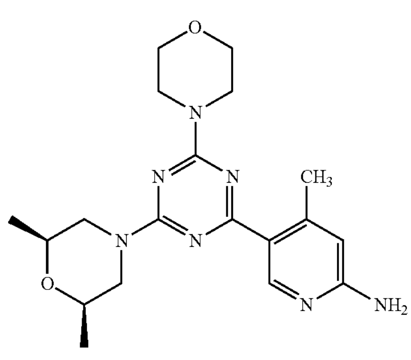 [SMILES: Cc1cc(N)ncc1-c1nc(N2CCOCC2)nc(N2C[C@@H](C)O[C@@H](C)C2)n1] | 5-(4-((2R,6S)-2,6-dimethylmorpholino)-6-morpholino-1,3,5-triazin-2-yl)-4-methylpyridin-2-amine |

TABLE 1-continued

| Cpd No. | Structure | Name |
|---|---|---|
| 43.5 | 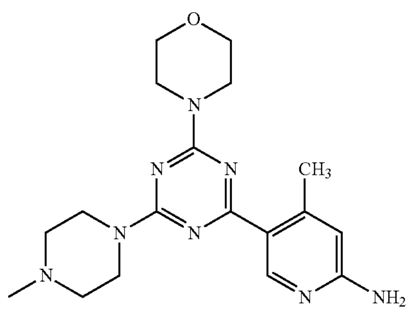 [SMILES: Cc1cc(N)ncc1-c1nc(N2CCOCC2)nc(N2CCN(C)CC2)n1] | 4-methyl-5-(4-(4-methylpiperazin-1-yl)-6-morpholino-1,3,5-triazin-2-yl)pyridin-2-amine |
| 43.6 | 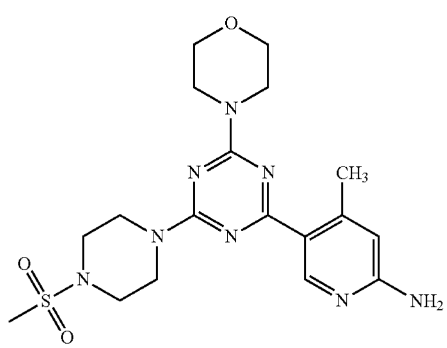 [SMILES: Cc1cc(N)ncc1-c1nc(N2CCOCC2)nc(N2CCN(S(C)(=O)=O)CC2)n1] | 4-methyl-5-(4-(4-(methylsulfonyl)piperazin-1-yl)-6-morpholino-1,3,5-triazin-2-yl)pyridin-2-amine |
| 44 | 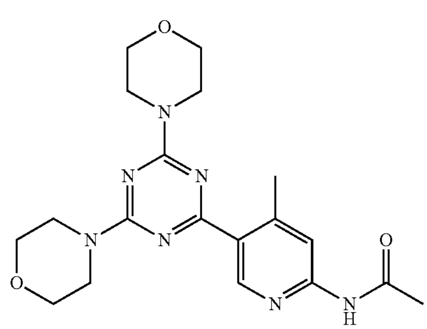 [SMILES: CC(=O)Nc1cc(C)c(-c2nc(N3CCOCC3)nc(N3CCOCC3)n2)cn1] | N-(5-(4,6-dimorpholino-1,3,5-triazin-2-yl)-4-methylpyridin-2-yl)acetamide |
| 45 | 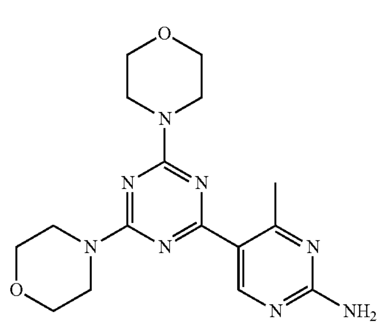 [SMILES: Cc1nc(N)ncc1-c1nc(N2CCOCC2)nc(N2CCOCC2)n1] | 5-(4,6-dimorpholino-1,3,5-triazin-2-yl)-4-methylpyrimidin-2-amine |

TABLE 1-continued

| Cpd No. | Structure | Name |
|---|---|---|
| 45.1 | 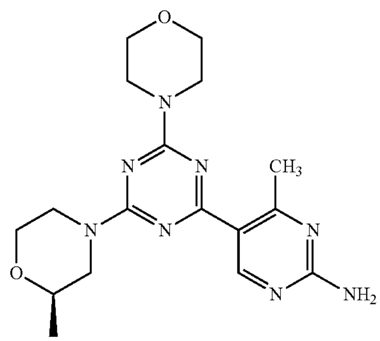 [SMILES: Cc1nc(N)ncc1-c1nc(N2CCOCC2)nc(N2CCO[C@H](C)C2)n1] | (R)-4-methyl-5-(4-(2-methylmorpholino)-6-morpholino-1,3,5-triazin-2-yl)pyrimidin-2-amine |
| 45.2 | 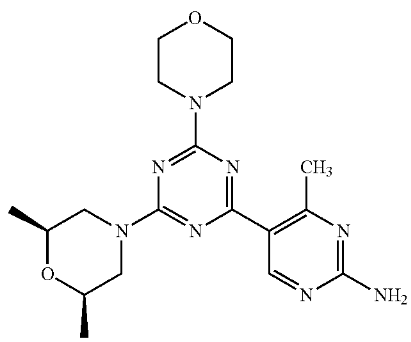 [SMILES: Cc1nc(N)ncc1-c1nc(N2CCOCC2)nc(N2C[C@@H](C)O[C@@H](C)C2)n1] | 5-(4-((2R,6S)-2,6-dimethylmorpholino)-6-morpholino-1,3,5-triazin-2-yl)-4-methylpyrimidin-2-amine |
| 45.3 | 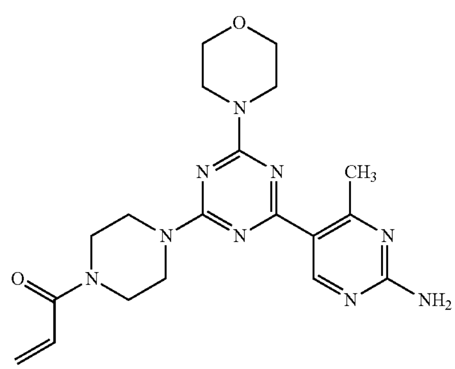 [SMILES: C=CC(=O)N1CCN(c2nc(-c3cnc(N)nc3C)nc(N3CCOCC3)n2)CC1] | 1-(4-(4-(2-amino-4-methylpyrimidin-5-yl)-6-morpholino-1,3,5-triazin-2-yl)piperazin-1-yl)prop-2-en-1-one |
| 45.4 | 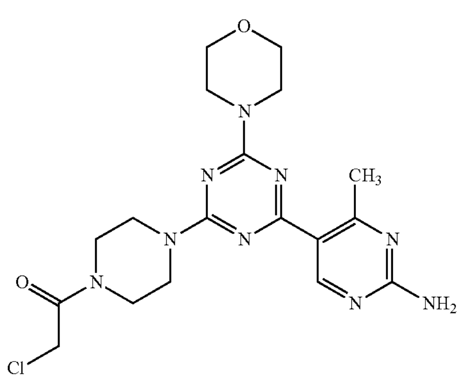 [SMILES: Cc1nc(N)ncc1-c1nc(N2CCOCC2)nc(N2CCN(C(=O)CCl)CC2)n1] | 1-(4-(4-(2-amino-4-methylpyrimidin-5-yl)-6-morpholino-1,3,5-triazin-2-yl)piperazin-1-yl)-2-chloroethanone |

TABLE 1-continued

| Cpd No. | Structure | Name |
|---|---|---|
| 45.5 | 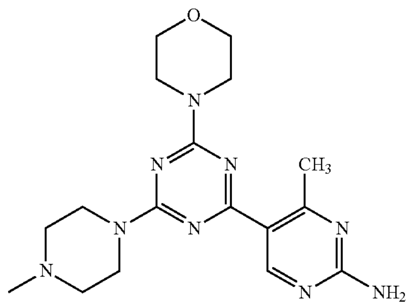 | 4-methyl-5-(4-(4-methylpiperazin-1-yl)-6-morpholino-1,3,5-triazin-2-yl)pyrimidin-2-amine |
| 45.6 | 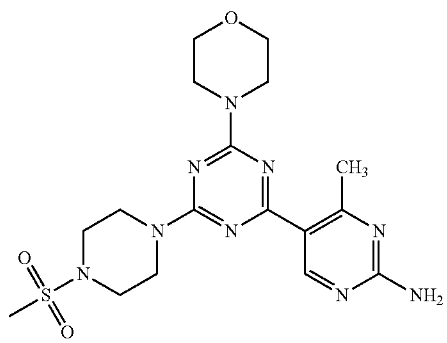 [SMILES: Cc1nc(N)ncc1-c1nc(N2CCOCC2)nc(N2CCN(S(C)(=O)=O)CC2)n1] | 4-methyl-5-(4-(4-(methylsulfonyl)piperazin-1-yl)-6-morpholino-1,3,5-triazin-2-yl)pyrimidin-2-amine |
| 45.7 | 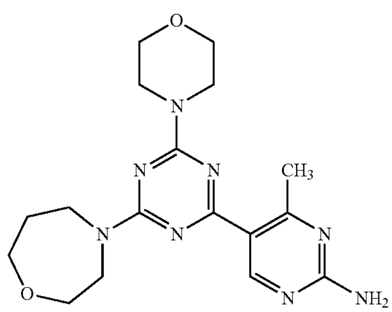 [SMILES: Cc1nc(N)ncc1-c1nc(N2CCCOCC2)nc(N2CCOCC2)n1] | 4-methyl-5-(4-morpholino-6-(1,4-oxazepan-4-yl)-1,3,5-triazin-2-yl)pyrimidin-2-amine |
| 45.8 | 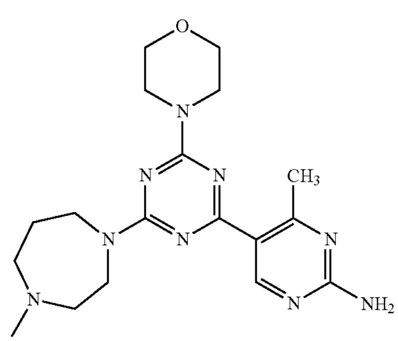 [SMILES: Cc1nc(N)ncc1-c1nc(N2CCOCC2)nc(N2CCCN(C)CC2)n1] | 4-methyl-5-(4-(4-methyl-1,4-diazepan-1-yl)-6-morpholino-1,3,5-triazin-2-yl)pyrimidin-2-amine |

TABLE 1-continued

| Cpd No. | Structure | Name |
|---|---|---|
| 46 | 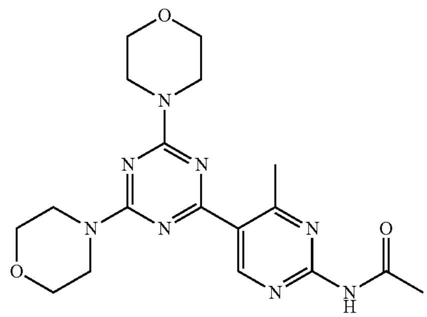 [SMILES: CC(=O)Nc1ncc(-c2nc(N3CCOCC3)nc(N3CCOCC3)n2)c(C)n1] | N-(5-(4,6-dimorpholino-1,3,5-triazin-2-yl)-4-methylpyrimidin-2-yl)acetamide |
| 47 | 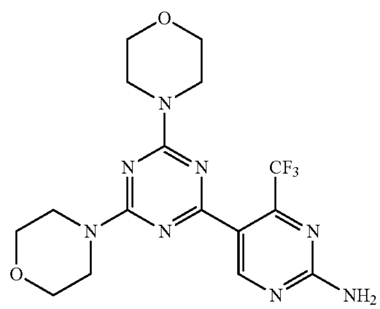 | 5-(4,6-dimorpholino-1,3,5-triazin-2-yl)-4-(trifluoromethyl)pyrimidin-2-amine |
| 47a | 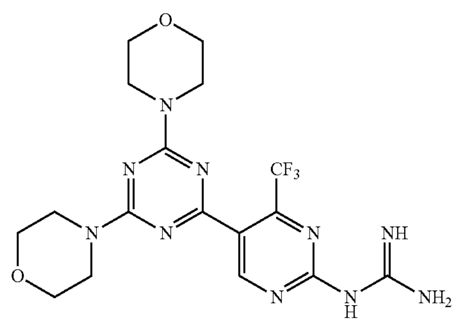 [SMILES: N=C(N)Nc1ncc(-c2nc(N3CCOCC3)nc(N3CCOCC3)n2)c(C(F)(F)F)n1] | 1-(5-(4,6-dimorpholino-1,3,5-triazin-2-yl)-4-(trifluoromethyl)pyrimidin-2-yl)guanidine |
| 48 | 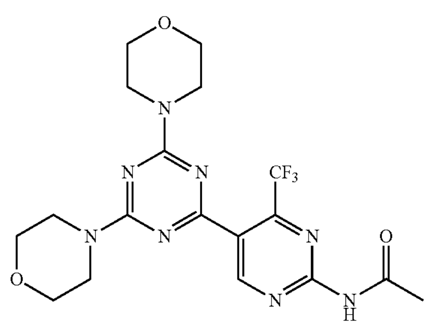 [SMILES: CC(=O)Nc1ncc(-c2nc(N3CCOCC3)nc(N3CCOCC3)n2)c(C(F)(F)F)n1] | N-(5-(4,6-dimorpholino-1,3,5-triazin-2-yl)-4-(trifluoromethyl)pyrimidin-2-yl)acetamide |
| 49 | 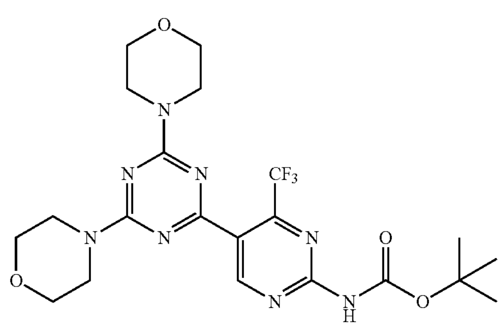 [SMILES: CC(C)(C)OC(=O)Nc1ncc(-c2nc(N3CCOCC3)nc(N3CCOCC3)n2)c(C(F)(F)F)n1] | tert-butyl 5-(4,6-dimorpholino-1,3,5-triazin-2-yl)-4-(trifluoromethyl)pyrimidin-2-ylcarbamate |

TABLE 1-continued

| Cpd No. | Structure | Name |
| --- | --- | --- |
| 50 | 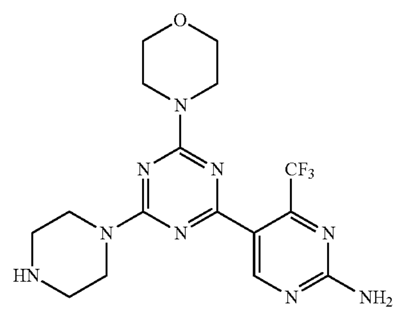 | 5-(4-morpholino-6-(piperazin-1-yl)-1,3,5-triazin-2-yl)-4-(trifluoromethyl)pyrimidin-2-amine |
| 51 | 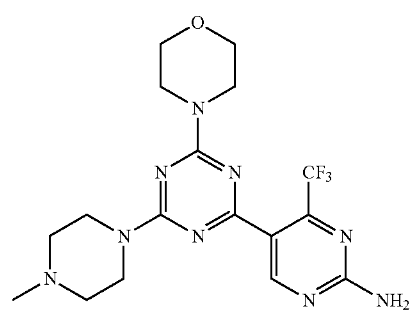 [SMILES: CN1CCN(c2nc(-c3cnc(N)nc3C(F)(F)F)nc(N3CCOCC3)n2)CC1] | 5-(4-(4-methylpiperazin-1-yl)-6-morpholino-1,3,5-triazin-2-yl)-4-(trifluoromethyl)pyrimidin-2-amine |
| 51.1 | 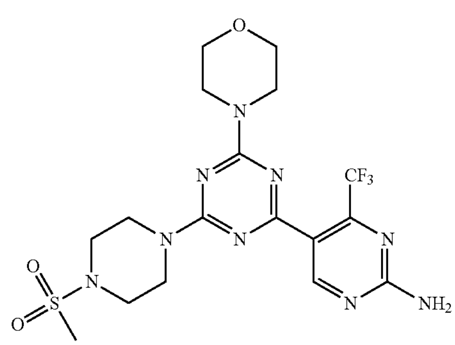 [SMILES: CS(=O)(=O)N1CCN(c2nc(-c3cnc(N)nc3C(F)(F)F)nc(N3CCOCC3)n2)CC1] | 5-(4-(4-(methylsulfonyl)piperazin-1-yl)-6-morpholino-1,3,5-triazin-2-yl)-4-(trifluoromethyl)pyrimidin-2-amine |
| 52 | 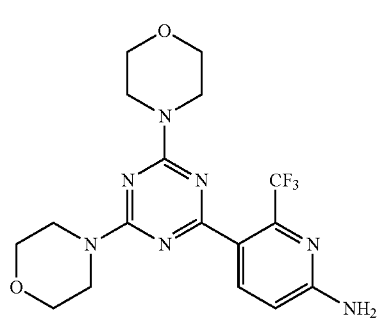 [SMILES: Nc1ccc(-c2nc(N3CCOCC3)nc(N3CCOCC3)n2)c(C(F)(F)F)n1] | 5-(4,6-dimorpholino-1,3,5-triazin-2-yl)-6-(trifluoromethyl)pyridin-2-amine |

TABLE 1-continued

| Cpd No. | Structure | Name |
|---|---|---|
| 53 | 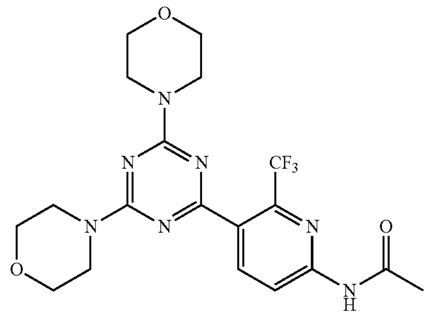 [SMILES: CC(=O)Nc1ccc(-c2nc(N3CCOCC3)nc(N3CCOCC3)n2)c(C(F)(F)F)n1] | N-(5-(4,6-dimorpholino-1,3,5-triazin-2-yl)-6-(trifluoromethyl)pyridin-2-yl)acetamide |
| 54 | 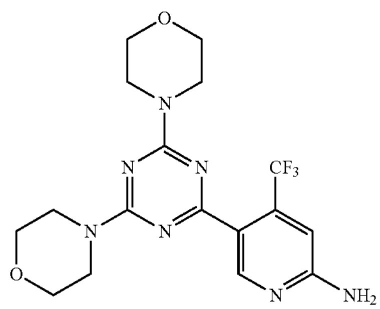 [SMILES: Nc1cc(C(F)(F)F)c(-c2nc(N3CCOCC3)nc(N3CCOCC3)n2)cn1] | 5-(4,6-dimorpholino-1,3,5-triazin-2-yl)-4-(trifluoromethyl)pyridin-2-amine |
| 54a | 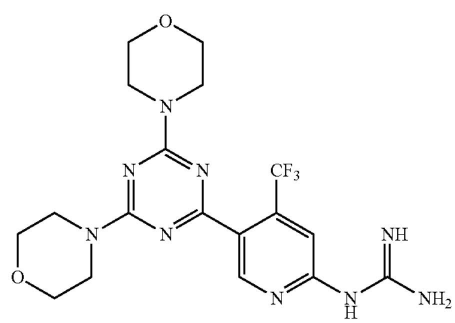 [SMILES: N=C(N)Nc1cc(C(F)(F)F)c(-c2nc(N3CCOCC3)nc(N3CCOCC3)n2)cn1] | 1-(5-(4,6-dimorpholino-1,3,5-triazin-2-yl)-4-(trifluoromethyl)pyridin-2-yl)guanidine |
| 55 | 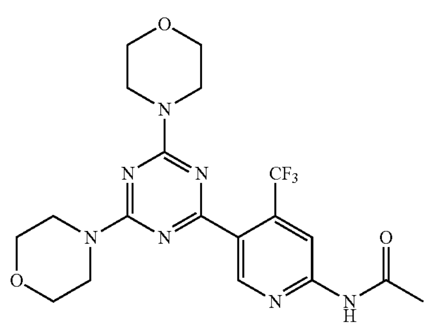 [SMILES: CC(=O)Nc1cc(C(F)(F)F)c(-c2nc(N3CCOCC3)nc(N3CCOCC3)n2)cn1] | N-(5-(4,6-dimorpholino-1,3,5-triazin-2-yl)-6-(trifluoromethyl)pyridin-2-yl)acetamide |
| 56 | 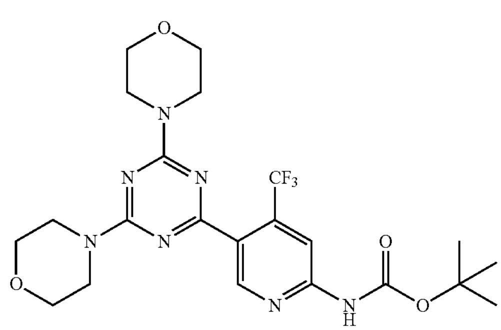 [SMILES: CC(C)(C)OC(=O)Nc1cc(C(F)(F)F)c(-c2nc(N3CCOCC3)nc(N3CCOCC3)n2)cn1] | tert-butyl 5-(4,6-dimorpholino-1,3,5-triazin-2-yl)-4-(trifluoromethyl)pyridin-2-ylcarbamate |

TABLE 1-continued

| Cpd No. | Structure | Name |
|---|---|---|
| 57 | 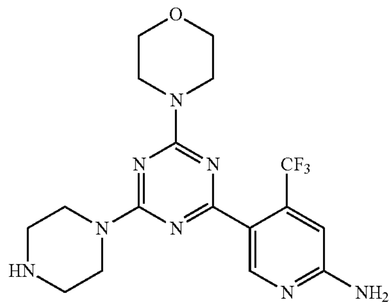 [SMILES: Nc1cc(C(F)(F)F)c(-c2nc(N3CCNCC3)nc(N3CCOCC3)n2)cn1] | 5-(4-morpholino-6-(piperazin-1-yl)-1,3,5-triazin-2-yl)-4-(trifluoromethyl)pyridin-2-amine |
| 58 | 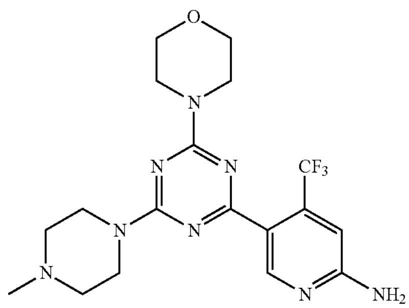 [SMILES: CN1CCN(c2nc(-c3cnc(N)cc3C(F)(F)F)nc(N3CCOCC3)n2)CC1] | 5-(4-(4-methylpiperazin-1-yl)-6-morpholino-1,3,5-triazin-2-yl)-4-(trifluoromethyl)pyridin-2-amine |
| 58.1 | 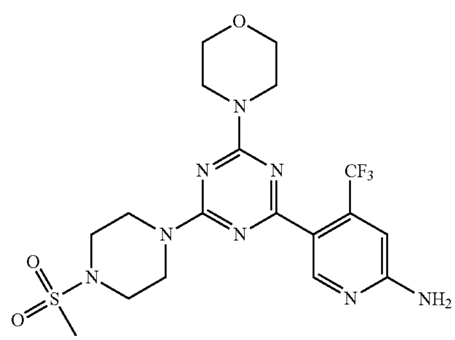 [SMILES: CS(=O)(=O)N1CCN(c2nc(-c3cnc(N)cc3C(F)(F)F)nc(N3CCOCC3)n2)CC1] | 5-(4-(4-(methylsulfonyl)piperazin-1-yl)-6-morpholino-1,3,5-triazin-2-yl)-4-(trifluoromethyl)pyridin-2-amine |
| 59 | 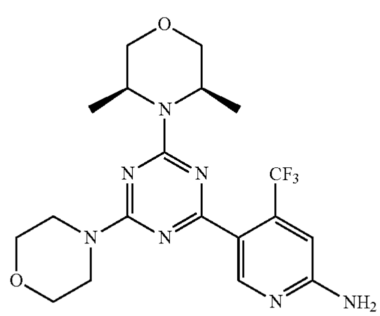 [SMILES: C[C@@H]1COC[C@H](C)N1c1nc(-c2cnc(N)cc2C(F)(F)F)nc(N2CCOCC2)n1] | 5-(4-((3R,5S)-3,5-dimethylmorpholino)-6-morpholino-1,3,5-triazin-2-yl)-4-(trifluoromethyl)pyridin-2-amine |
| 60 | 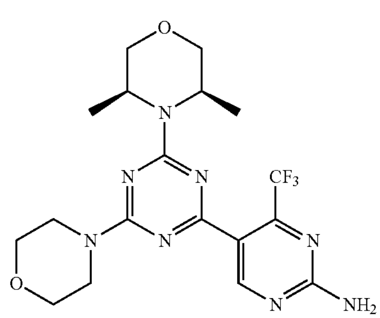 [SMILES: C[C@@H]1COC[C@H](C)N1c1nc(-c2cnc(N)nc2C(F)(F)F)nc(N2CCOCC2)n1] | 5-(4-((3R,5S)-3,5-dimethylmorpholino)-6-morpholino-1,3,5-triazin-2-yl)-4-(trifluoromethyl)pyrimidin-2-amine |

TABLE 1-continued

| Cpd No. | Structure | Name |
|---|---|---|
| 61 | 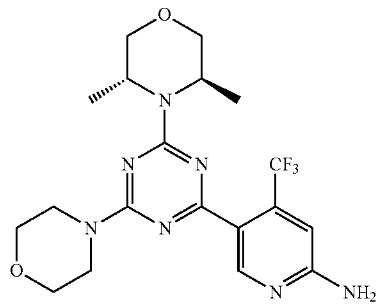 [SMILES: C[C@@H]1COC[C@@H](C)N1c1nc(-c2cnc(N)cc2C(F)(F)F)nc(N2CCOCC2)n1] | 5-(4-((3R,5R)-3,5-dimethylmorpholino)-6-morpholino-1,3,5-triazin-2-yl)-4-(trifluoromethyl)pyridin-2-amine |
| 62 | 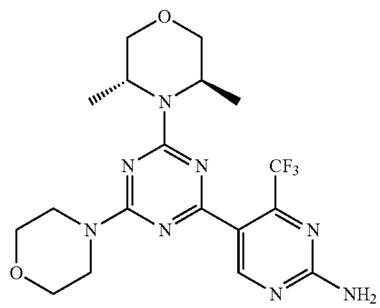 [SMILES: C[C@@H]1COC[C@@H](C)N1c1nc(-c2cnc(N)nc2C(F)(F)F)nc(N2CCOCC2)n1] | 5-(4-((3R,5R)-3,5-dimethylmorpholino)-6-morpholino-1,3,5-triazin-2-yl)-4-(trifluoromethyl)pyrimidin-2-amine |
| 63 | 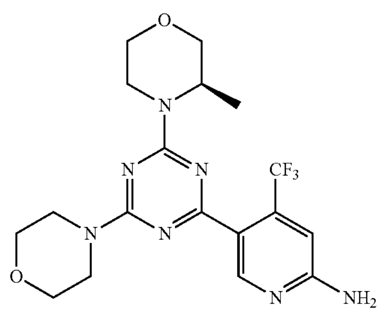 [SMILES: C[C@@H]1COCCN1c1nc(-c2cnc(N)cc2C(F)(F)F)nc(N2CCOCC2)n1] | (R)-5-(4-(3-methylmorpholino)-6-morpholino-1,3,5-triazin-2-yl)-4-(trifluoromethyl)pyridin-2-amine |
| 64 | 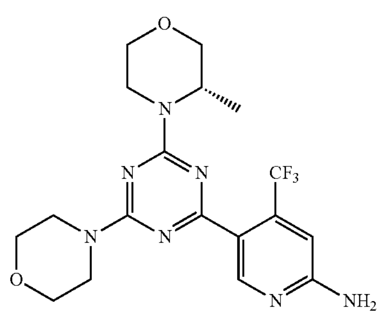 [SMILES: C[C@H]1COCCN1c1nc(-c2cnc(N)cc2C(F)(F)F)nc(N2CCOCC2)n1] | (S)-5-(4-(3-methylmorpholino)-6-morpholino-1,3,5-triazin-2-yl)-4-(trifluoromethyl)pyridin-2-amine |
| 65 | 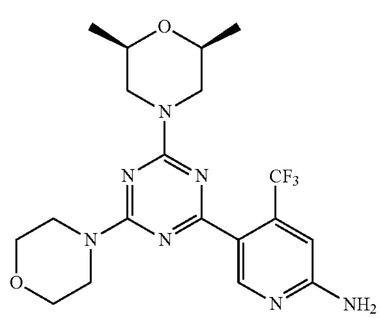 [SMILES: C[C@@H]1CN(c2nc(-c3cnc(N)cc3C(F)(F)F)nc(N3CCOCC3)n2)C[C@H](C)O1] | 5-(4-((2S,6R)-2,6-dimethylmorpholino)-6-morpholino-1,3,5-triazin-2-yl)-4-(trifluoromethyl)pyridin-2-amine |

TABLE 1-continued

| Cpd No. | Structure | Name |
|---|---|---|
| 66 | 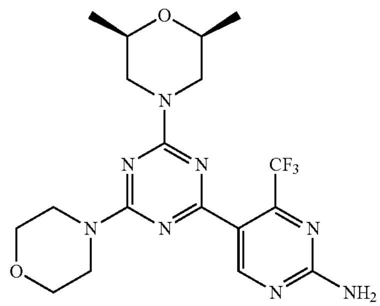 [SMILES: C[C@@H]1CN(c2nc(-c3cnc(N)nc3C(F)(F)F)nc(N3CCOCC3)n2)C[C@H](C)O1] | 5-(4-((2S,6R)-2,6-dimethylmorpholino)-6-morpholino-1,3,5-triazin-2-yl)-4-(trifluoromethyl)pyrimidin-2-amine |
| 67 | 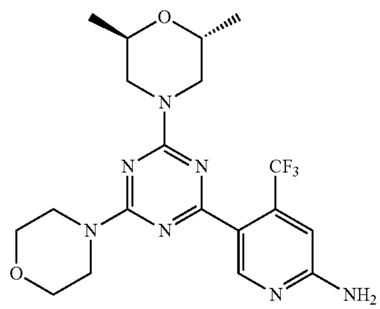 [SMILES: C[C@@H]1CN(c2nc(-c3cnc(N)cc3C(F)(F)F)nc(N3CCOCC3)n2)C[C@@H](C)O1] | 5-(4-((2R,6R)-2,6-dimethylmorpholino)-6-morpholino-1,3,5-triazin-2-yl)-4-(trifluoromethyl)pyridin-2-amine |
| 68 | 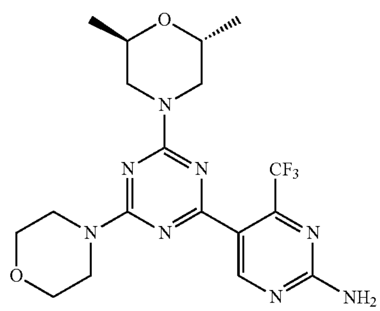 [SMILES: C[C@@H]1CN(c2nc(-c3cnc(N)nc3C(F)(F)F)nc(N3CCOCC3)n2)C[C@@H](C)O1] | 5-(4-((2R,6R)-2,6-dimethylmorpholino)-6-morpholino-1,3,5-triazin-2-yl)-4-(trifluoromethyl)pyrimidin-2-amine |
| 69 | 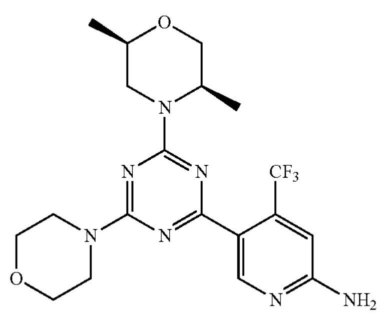 [SMILES: C[C@@H]1CN(c2nc(-c3cnc(N)cc3C(F)(F)F)nc(N3CCOCC3)n2)[C@H](C)CO1] | 5-(4-((2R,5R)-2,5-dimethylmorpholino)-6-morpholino-1,3,5-triazin-2-yl)-4-(trifluoromethyl)pyridin-2-amine |
| 70 | 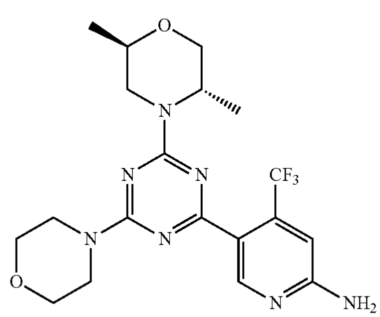 [SMILES: C[C@@H]1CN(c2nc(-c3cnc(N)cc3C(F)(F)F)nc(N3CCOCC3)n2)[C@@H](C)CO1] | 5-(4-((2R,5S)-2,5-dimethylmorpholino)-6-morpholino-1,3,5-triazin-2-yl)-4-(trifluoromethyl)pyridin-2-amine |

TABLE 1-continued

| Cpd No. | Structure | Name |
|---|---|---|
| 71 | 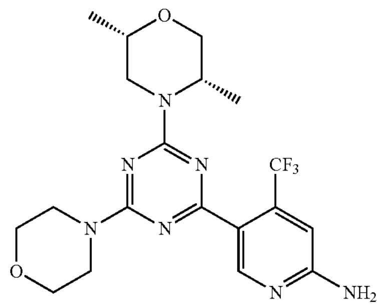 [SMILES: C[C@H]1CN(c2nc(-c3cnc(N)cc3C(F)(F)F)nc(N3CCOCC3)n2)[C@@H](C)CO1] | 5-(4-((2S,5S)-2,5-dimethylmorpholino)-6-morpholino-1,3,5-triazin-2-yl)-4-(trifluoromethyl)pyridin-2-amine |
| 72 | 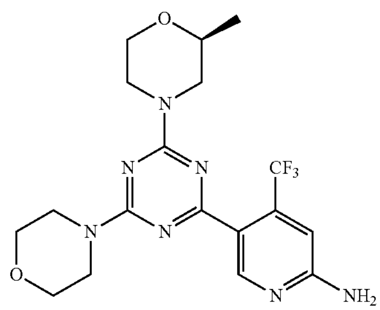 [SMILES: C[C@H]1CN(c2nc(-c3cnc(N)cc3C(F)(F)F)nc(N3CCOCC3)n2)CCO1] | (S)-5-(4-(2-methylmorpholino)-6-morpholino-1,3,5-triazin-2-yl)-4-(trifluoromethyl)pyridin-2-amine |
| 73 | 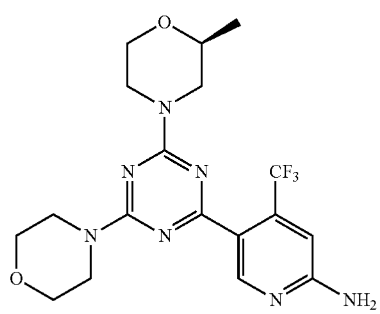 [SMILES: C[C@H]1CN(c2nc(-c3cnc(N)cc3C(F)(F)F)nc(N3CCOCC3)n2)CCO1] | (S)-5-(4-(2-methylmorpholino)-6-morpholino-1,3,5-triazin-2-yl)-4-(trifluoromethyl)pyridin-2-amine |
| 74 | 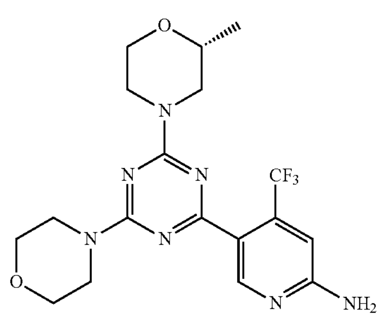 [SMILES: C[C@@H]1CN(c2nc(-c3cnc(N)cc3C(F)(F)F)nc(N3CCOCC3)n2)CCO1] | (R)-5-(4-(2-methylmorpholino)-6-morpholino-1,3,5-triazin-2-yl)-4-(trifluoromethyl)pyridin-2-amine |
| 75 | 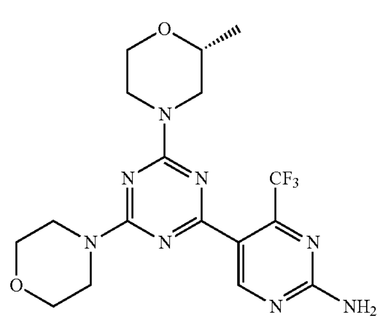 [SMILES: C[C@@H]1CN(c2nc(-c3cnc(N)nc3C(F)(F)F)nc(N3CCOCC3)n2)CCO1] | (R)-5-(4-(2-methylmorpholino)-6-morpholino-1,3,5-triazin-2-yl)-4-(trifluoromethyl)pyrimidin-2-amine |

TABLE 1-continued

| Cpd No. | Structure | Name |
|---|---|---|
| 76 | 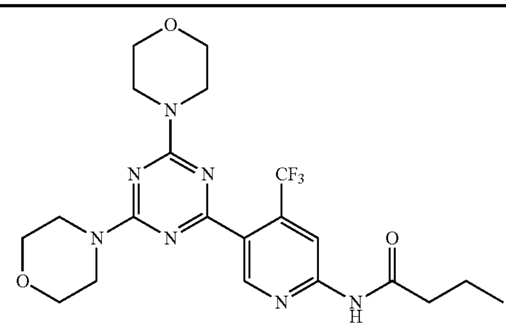 | N-(5-(4,6-dimorpholino-1,3,5-triazin-2-yl)-4-(trifluoromethyl)pyridin-2-yl)butyramide |
| 77 | 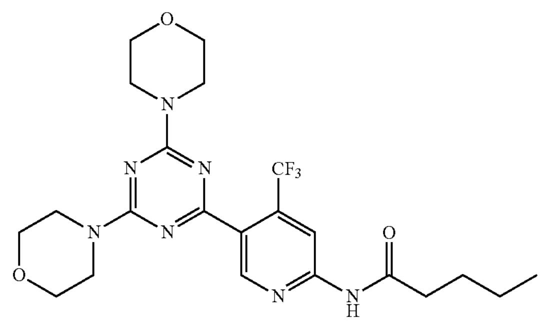 [SMILES: CCCCC(=O)Nc1cc(C(F)(F)F)c(-c2nc(N3CCOCC3)nc(N3CCOCC3)n2)cn1] | N-(5-(4,6-dimorpholino-1,3,5-triazin-2-yl)-4-(trifluoromethyl)pyridin-2-yl)pentanamide |
| 78 | 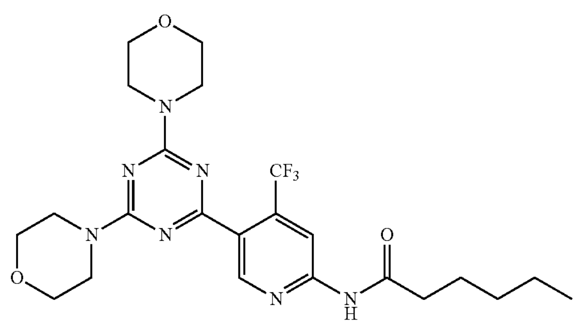 [SMILES: CCCCCC(=O)Nc1cc(C(F)(F)F)c(-c2nc(N3CCOCC3)nc(N3CCOCC3)n2)cn1] | N-(5-(4,6-dimorpholino-1,3,5-triazin-2-yl)-4-(trifluoromethyl)pyridin-2-yl)hexanamide |
| 79 | 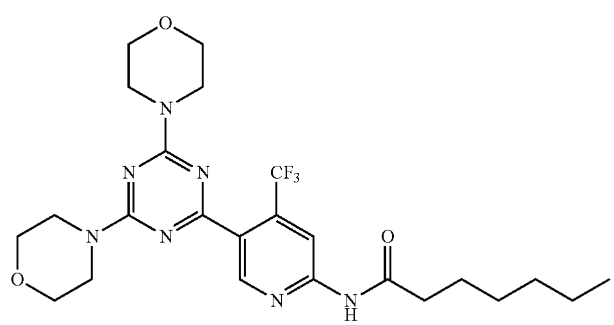 [SMILES: CCCCCCC(=O)Nc1cc(C(F)(F)F)c(-c2nc(N3CCOCC3)nc(N3CCOCC3)n2)cn1] | N-(5-(4,6-dimorpholino-1,3,5-triazin-2-yl)-4-(trifluoromethyl)pyridin-2-yl)heptanamide |
| 80 | 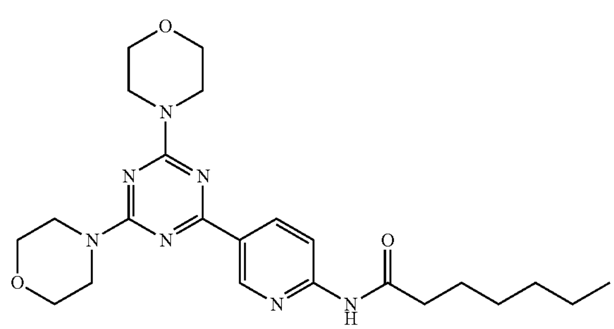 [SMILES: CCCCCCC(=O)Nc1ccc(-c2nc(N3CCOCC3)nc(N3CCOCC3)n2)cn1] | N-(5-(4,6-dimorpholino-1,3,5-triazin-2-yl)pyridin-2-yl)heptanamide |

TABLE 1-continued

| Cpd No. | Structure | Name |
|---|---|---|
| 81 | 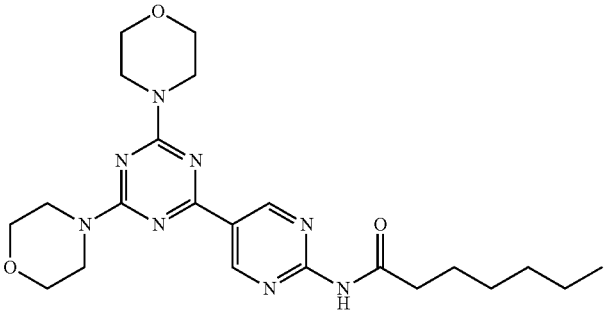 [SMILES: CCCCCCC(=O)Nc1ncc(-c2nc(N3CCOCC3)nc(N3CCOCC3)n2)cn1] | N-(5-(4,6-dimorpholino-1,3,5-triazin-2-yl)pyrimidin-2-yl)heptanamide |
| 82 | 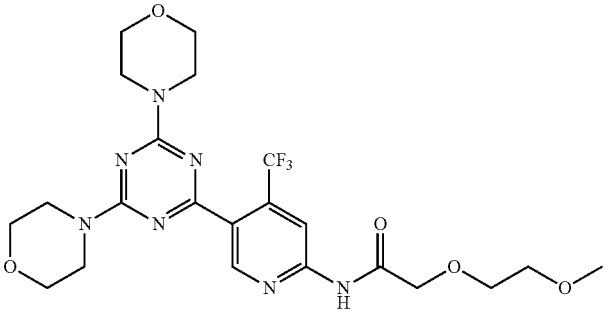 [SMILES: COCCOCC(=O)Nc1cc(C(F)(F)F)c(-c2nc(N3CCOCC3)nc(N3CCOCC3)n2)cn1] | N-(5-(4,6-dimorpholino-1,3,5-triazin-2-yl)-4-(trifluoromethyl)pyridin-2-yl)-2-(2-methoxyethoxy)acetamide |
| 83 | 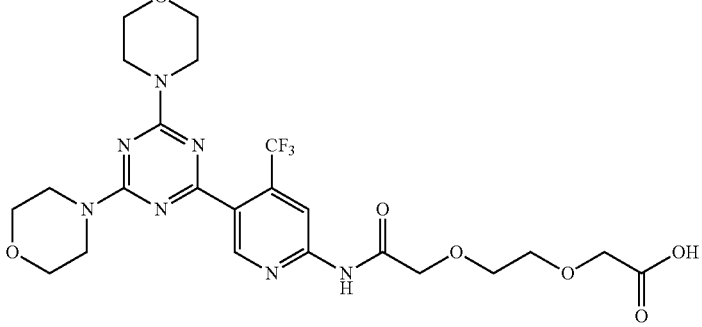 | 2-(2-(2-(5-(4,6-dimorpholino-1,3,5-triazin-2-yl)-4-(trifluoromethyl)pyridin-2-ylamino)-2-oxoethoxy)ethoxy)acetic acid |
| 84 | 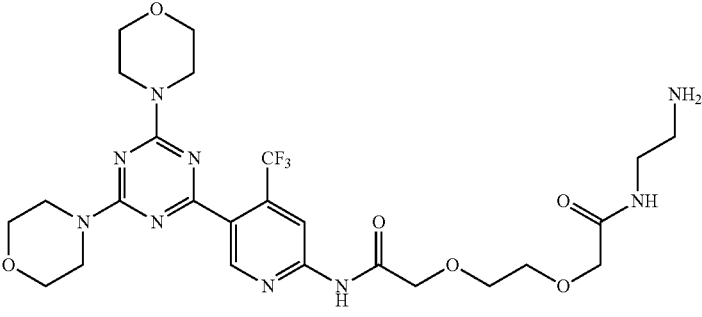 [SMILES: NCCNC(=O)COCCOCC(=O)Nc1cc(C(F)(F)F)c(-c2nc(N3CCOCC3)nc(N3CCOCC3)n2)cn1] | N-(2-aminoethyl)-2-(2-(2-(5-(4,6-dimorpholino-1,3,5-triazin-2-yl)-4-(trifluoromethyl)pyridin-2-ylamino)-2-oxoethoxy)ethoxy)acetamide |

TABLE 1-continued
| Cpd No. | Structure | Name |
|---|---|---|
| 85 | 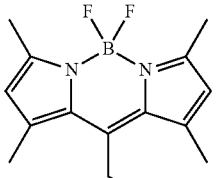 | Bodipy = Tag molecule |
| 86 | 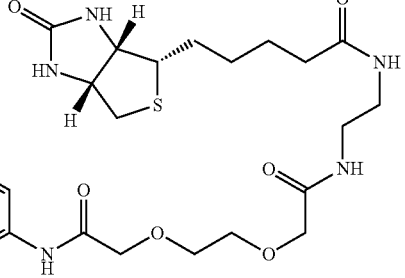 | N-(2-(2-(2-(2-(5-(4,6-dimorpholino-1,3,5-triazin-2-yl)-4-(trifluoromethyl)pyridin-2-ylamino)-2-oxoethoxy)ethoxy)acetamido)ethyl)-5-((3aS,4S,6aR)-2-oxohexahydro-1H-thieno[3,4-d]imidazol-4-yl)pentanamide<br>Biotin = Tag molecule |
| 87 | 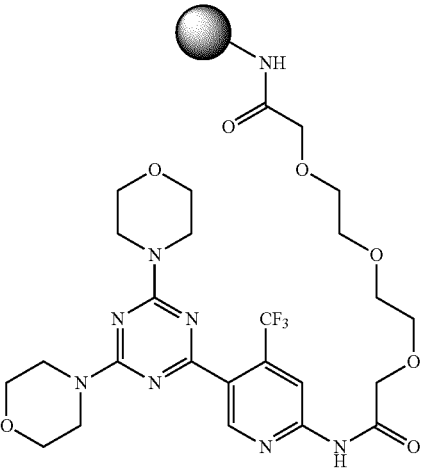 [SMILES: CNC(=O)COCCOCCOCC(=O)Nc1cc(C(F)(F)F)c(-c2nc(N3CCOCC3)nc(N3CCOCC3)n2)cn1] | |
| 88 | 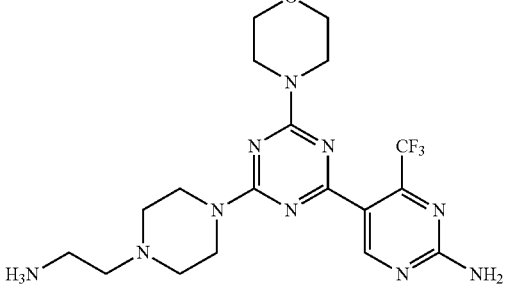 | 5-(4-(4-(2-aminoethyl)piperazin-1-yl)-6-morpholino-1,3,5-triazin-2-yl)-4-(trifluoromethyl)pyrimidin-2-amine |

| Cpd No. | Structure | Name |
|---|---|---|
| 89 | 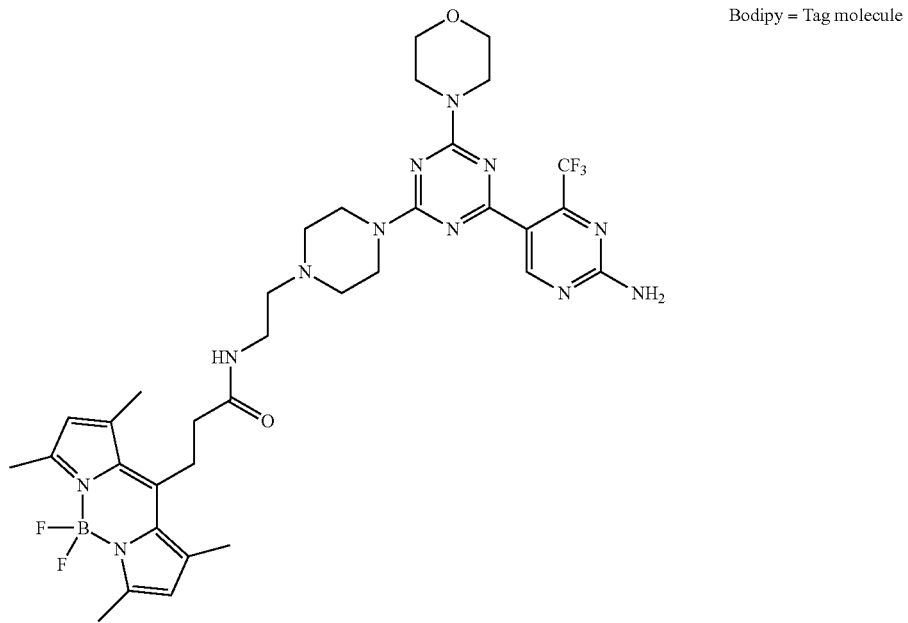 | Bodipy = Tag molecule |
| 90 | 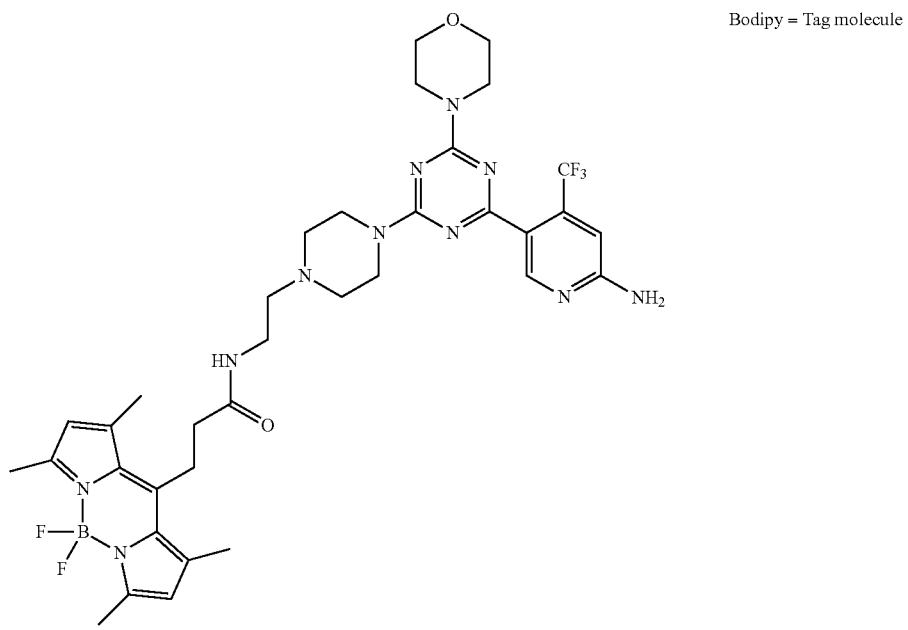 | Bodipy = Tag molecule |

TABLE 1-continued

| Cpd No. | Structure | Name |
|---|---|---|
| 91 | 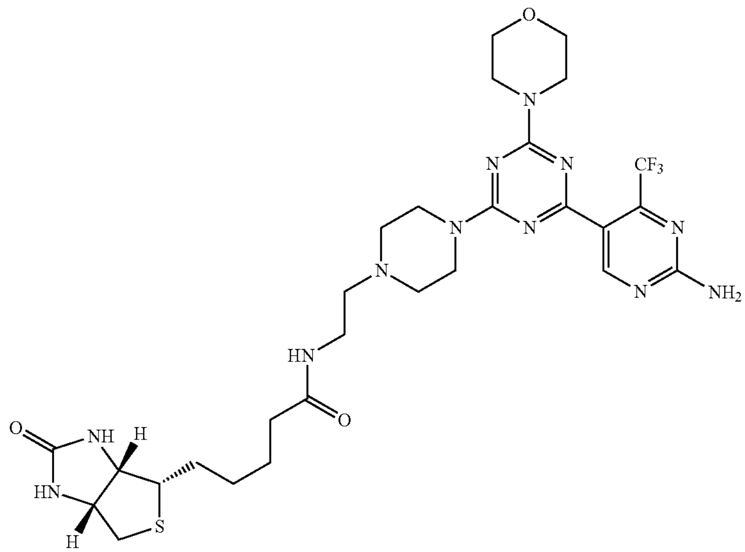 [SMILES: Nc1ncc(-c2nc(N3CCOCC3)nc(N3CCN(CCNC(=O)CCCC[C@@H]4SC[C@@H]5NC(=O)N[C@@H]54)CC3)n2)c(C(F)(F)F)n1] | N-(2-(4-(4-(2-amino-4-(trifluoromethyl)pyrimidin-5-yl)-6-morpholino-1,3,5-triazin-2-yl)piperazin-1-yl)ethyl)-5-((3aS,4S,6aR)-2-oxohexahydro-1H-thieno[3,4-d]imidazol-4-yl)pentanamide<br>Biotin = Tag molecule |
| 92 | 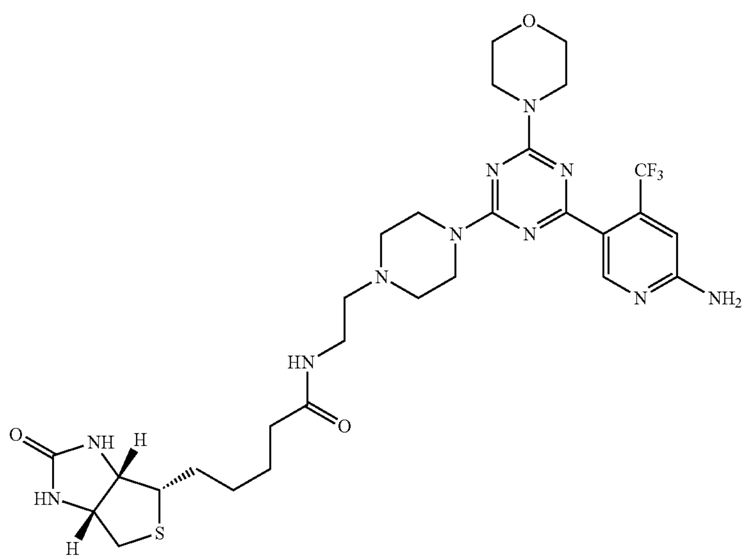 [SMILES: Nc1cc(C(F)(F)F)c(-c2nc(N3CCOCC3)nc(N3CCN(CCNC(=O)CCCC[C@@H]4SC[C@@H]5NC(=O)N[C@@H]54)CC3)n2)cn1] | N-(2-(4-(4-(6-amino-4-(trifluoromethyl)pyridin-3-yl)-6-morpholino-1,3,5-triazin-2-yl)piperazin-1-yl)ethyl)-5-((3aS,4S,6aR)-2-oxohexahydro-1H-thieno[3,4-d]imidazol-4-yl)pentanamide<br>Biotin = Tag molecule |
| 93 | 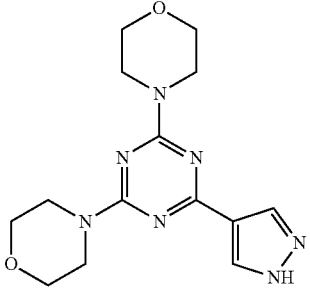 [SMILES: c1n[nH]cc1-c1nc(N2CCOCC2)nc(N2CCOCC2)n1] | 4,4'-(6-(1H-pyrazol-4-yl)-1,3,5-triazine-2,4-diyl)dimorpholine |

TABLE 1-continued

| Cpd No. | Structure | Name |
|---|---|---|
| 94 | 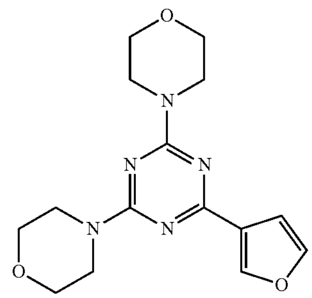 [SMILES: c1cc(-c2nc(N3CCOCC3)nc(N3CCOCC3)n2)co1] | 4,4'-(6-(furan-3-yl)-1,3,5-triazine-2,4-diyl)dimorpholine |
| 95 | 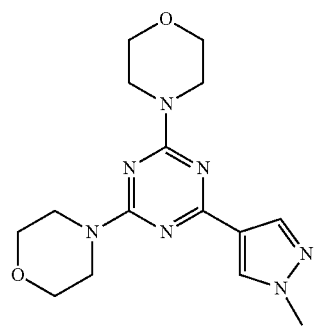 [SMILES: Cn1cc(-c2nc(N3CCOCC3)nc(N3CCOCC3)n2)cn1] | 4,4'-(6-(1-methyl-1H-pyrazol-4-yl)-1,3,5-triazine-2,4-diyl)dimorpholine |
| 96 | 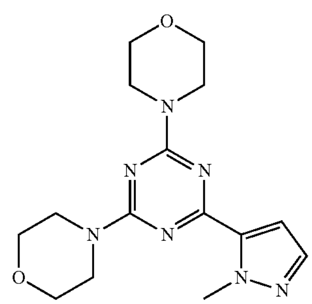 [SMILES: Cn1nccc1-c1nc(N2CCOCC2)nc(N2CCOCC2)n1] | 4,4'-(6-(1-methyl-1H-pyrazol-5-yl)-1,3,5-triazine-2,4-diyl)dimorpholine |
| 97 | 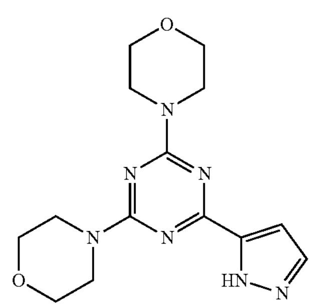 [SMILES: c1cc(-c2nc(N3CCOCC3)nc(N3CCOCC3)n2)[nH]n1] | 4,4'-(6-(1H-pyrazol-5-yl)-1,3,5-triazine-2,4-diyl)dimorpholine |
| 98 | 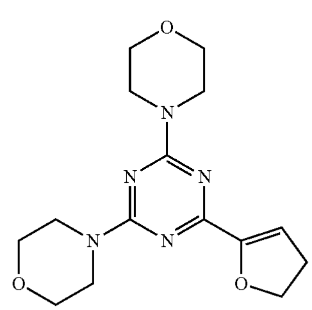 [SMILES: C1=C(c2nc(N3CCOCC3)nc(N3CCOCC3)n2)OCC1] | 4,4'-(6-(4,5-dihydrofuran-2-yl)-1,3,5-triazine-2,4-diyl)dimorpholine |

TABLE 1-continued

| Cpd No. | Structure | Name |
|---|---|---|
| 99 | 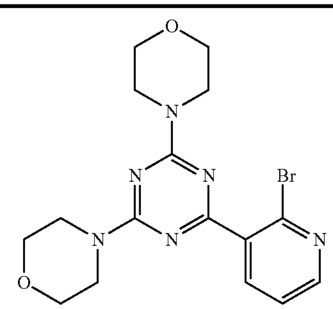 | 4,4'-(6-(2-bromopyridin-3-yl)-1,3,5-triazine-2,4-diyl)dimorpholine |
| 100 | 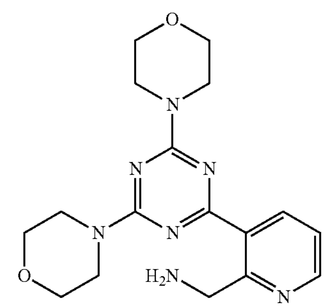 [SMILES: NCc1ncccc1-c1nc(N2CCOCC2)nc(N2CCOCC2)n1] | (3-(4,6-dimorpholino-1,3,5-triazin-2-yl)pyridin-2-yl)methanamine |
| 101 | 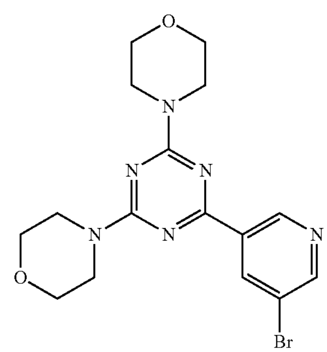 [SMILES: Brc1cncc(-c2nc(N3CCOCC3)nc(N3CCOCC3)n2)c1] | 4,4'-(6-(5-bromopyridin-3-yl)-1,3,5-triazine-2,4-diyl)dimorpholine |
| 102 | 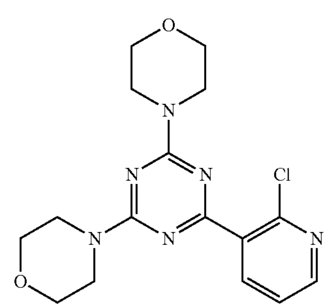 [SMILES: Clc1ncccc1-c1nc(N2CCOCC2)nc(N2CCOCC2)n1] | 4,4'-(6-(2-chloropyridin-3-yl)-1,3,5-triazine-2,4-diyl)dimorpholine |
| 103 | 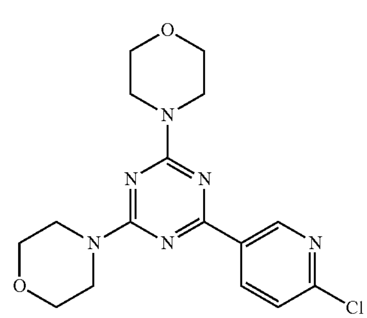 [SMILES: Clc1ccc(-c2nc(N3CCOCC3)nc(N3CCOCC3)n2)cn1] | 4,4'-(6-(6-chloropyridin-3-yl)-1,3,5-triazine-2,4-diyl)dimorpholine |

TABLE 1-continued

| Cpd No. | Structure | Name |
|---|---|---|
| 104 | 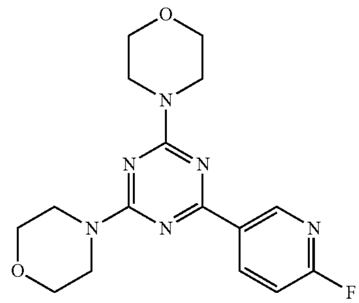 [SMILES: Fc1ccc(-c2nc(N3CCOCC3)nc(N3CCOCC3)n2)cn1] | 4,4'-(6-(6-fluoropyridin-3-yl)-1,3,5-triazine-2,4-diyl)dimorpholine |
| 105 | 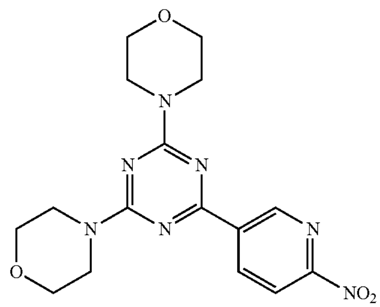 [SMILES: O=[N+]([O-])c1ccc(-c2nc(N3CCOCC3)nc(N3CCOCC3)n2)cn1] | 4,4'-(6-(6-nitropyridin-3-yl)-1,3,5-triazine-2,4-diyl)dimorpholine |
| 106 | 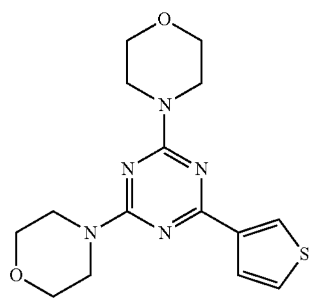 [SMILES: c1cc(-c2nc(N3CCOCC3)nc(N3CCOCC3)n2)cs1] | 4,4'-(6-(thiophen-3-yl)-1,3,5-triazine-2,4-diyl)dimorpholine |
| 107 | 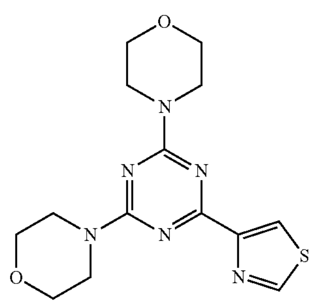 [SMILES: c1nc(-c2nc(N3CCOCC3)nc(N3CCOCC3)n2)cs1] | 4,4'-(6-(thiazol-4-yl)-1,3,5-triazine-2,4-diyl)dimorpholine |
| 108 | 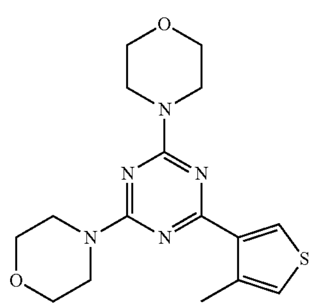 [SMILES: Cc1cscc1-c1nc(N2CCOCC2)nc(N2CCOCC2)n1] | 4,4'-(6-(4-methylthiophen-3-yl)-1,3,5-triazine-2,4-diyl)dimorpholine |

TABLE 1-continued

| Cpd No. | Structure | Name |
|---|---|---|
| 109 | 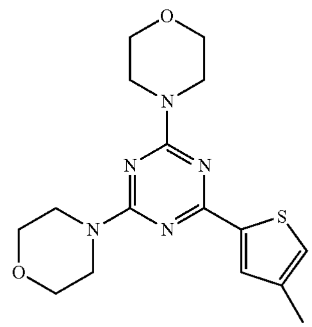 [SMILES: Cc1csc(-c2nc(N3CCOCC3)nc(N3CCOCC3)n2)c1] | 4,4'-(6-(4-methylthiophen-2-yl)-1,3,5-triazine-2,4-diyl)dimorpholine |
| 110 | 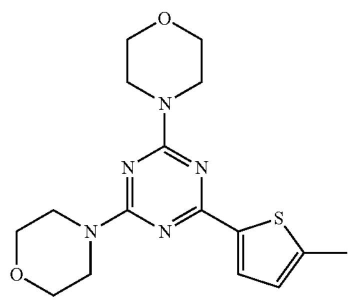 [SMILES: Cc1ccc(-c2nc(N3CCOCC3)nc(N3CCOCC3)n2)s1] | 4,4'-(6-(5-methylthiophen-2-yl)-1,3,5-triazine-2,4-diyl)dimorpholine |
| 111 | 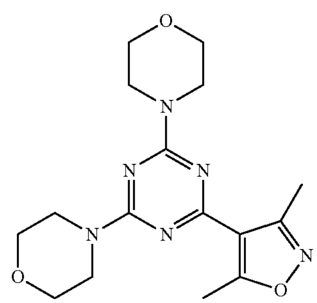 [SMILES: Cc1noc(C)c1-c1nc(N2CCOCC2)nc(N2CCOCC2)n1] | 4,4'-(6-(3,5-dimethylisoxazol-4-yl)-1,3,5-triazine-2,4-diyl)dimorpholine |
| 112 | 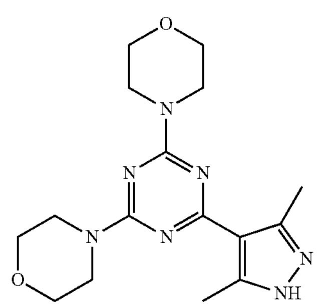 [SMILES: Cc1n[nH]c(C)c1-c1nc(N2CCOCC2)nc(N2CCOCC2)n1] | 4,4'-(6-(3,5-dimethyl-1H-pyrazol-4-yl)-1,3,5-triazine-2,4-diyl)dimorpholine |
| 113 | 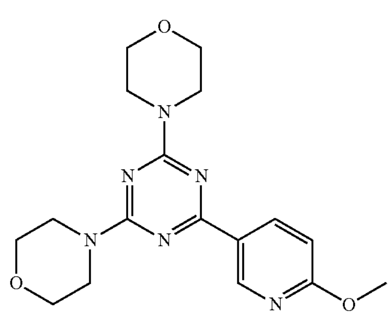 [SMILES: COc1ccc(-c2nc(N3CCOCC3)nc(N3CCOCC3)n2)cn1] | 4,4'-(6-(6-methoxypyridin-3-yl)-1,3,5-triazine-2,4-diyl)dimorpholine |

TABLE 1-continued

| Cpd No. | Structure | Name |
|---|---|---|
| 114 | 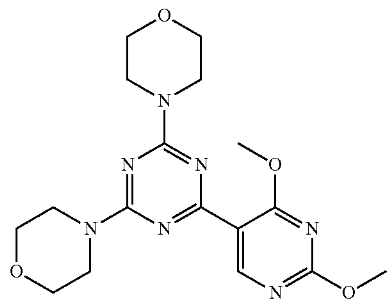 [SMILES: COc1ncc(-c2nc(N3CCOCC3)nc(N3CCOCC3)n2)c(OC)n1] | 4,4'-(6-(2,4-dimethoxypyrimidin-5-yl)-1,3,5-triazine-2,4-diyl)dimorpholine |
| 115 | 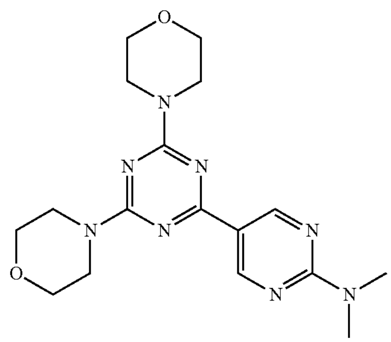 [SMILES: CN(C)c1ncc(-c2nc(N3CCOCC3)nc(N3CCOCC3)n2)cn1] | 5-(4,6-dimorpholino-1,3,5-triazin-2-yl)-N,N-dimethylpyrimidin-2-amine |
| 116 | 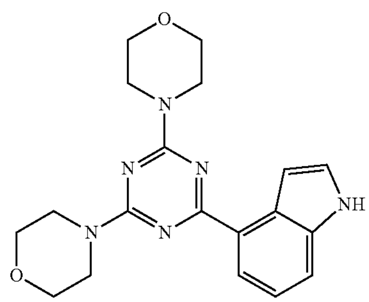 [SMILES: c1cc(-c2nc(N3CCOCC3)nc(N3CCOCC3)n2)c2cc[nH]c2c1] | 4,4'-(6-(1H-indol-4-yl)-1,3,5-triazine-2,4-diyl)dimorpholine |
| 117 | 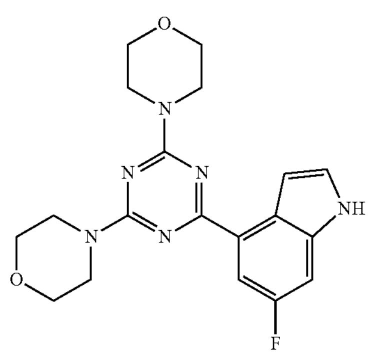 [SMILES: Fc1cc(-c2nc(N3CCOCC3)nc(N3CCOCC3)n2)c2cc[nH]c2c1] | 4,4'-(6-(6-fluoro-1H-indol-4-yl)-1,3,5-triazine-2,4-diyl)dimorpholine |
| 118 | 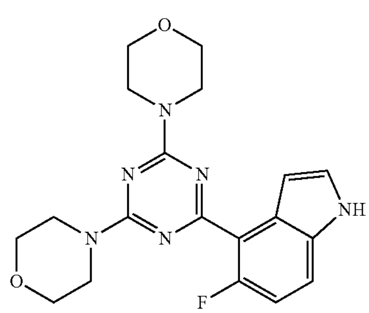 [SMILES: Fc1ccc2[nH]ccc2c1-c1nc(N2CCOCC2)nc(N2CCOCC2)n1] | 4,4'-(6-(5-fluoro-1H-indol-4-yl)-1,3,5-triazine-2,4-diyl)dimorpholine |

TABLE 1-continued

| Cpd No. | Structure | Name |
|---|---|---|
| 119 | 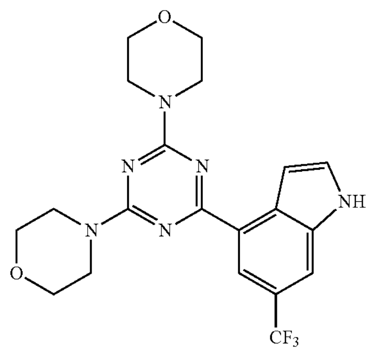 [SMILES: FC(F)(F)c1cc(-c2nc(N3CCOCC3)nc(N3CCOCC3)n2)c2cc[nH]c2c1] | 4,4'-(6-(6-(trifluoromethyl)-1H-indol-4-yl)-1,3,5-triazine-2,4-diyl)dimorpholine |
| 120 | 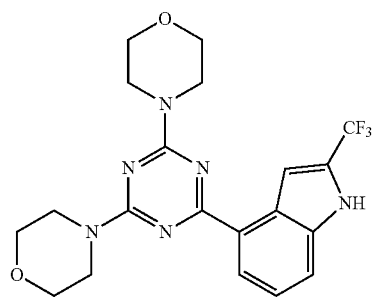 [SMILES: FC(F)(F)c1cc2c(-c3nc(N4CCOCC4)nc(N4CCOCC4)n3)cccc2[nH]1] | 4,4'-(6-(2-(trifluoromethyl)-1H-indol-4-yl)-1,3,5-triazine-2,4-diyl)dimorpholine |
| 121 | 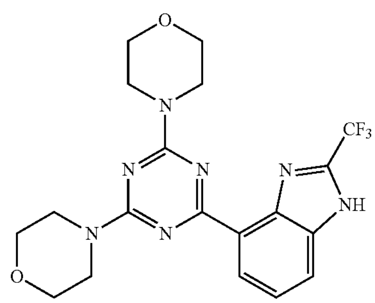 [SMILES: FC(F)(F)c1nc2c(-c3nc(N4CCOCC4)nc(N4CCOCC4)n3)cccc2[nH]1] | 4,4'-(6-(2-(trifluoromethyl)-1H-benzo[d]imidazol-4-yl)-1,3,5-triazine-2,4-diyl)dimorpholine |
| 122 | 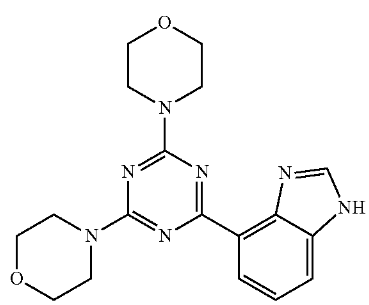 [SMILES: c1cc(-c2nc(N3CCOCC3)nc(N3CCOCC3)n2)c2nc[nH]c2c1] | 4,4'-(6-(1H-benzo[d]imidazol-4-yl)-1,3,5-triazine-2,4-diyl)dimorpholine |
| 123 | 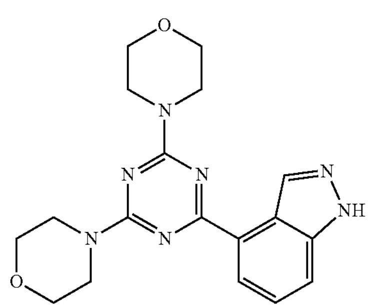 [SMILES: c1cc(-c2nc(N3CCOCC3)nc(N3CCOCC3)n2)c2cn[nH]c2c1] | 4,4'-(6-(1H-indazol-4-yl)-1,3,5-triazine-2,4-diyl)dimorpholine |

TABLE 1-continued

| Cpd No. | Structure | Name |
|---|---|---|
| 124 | 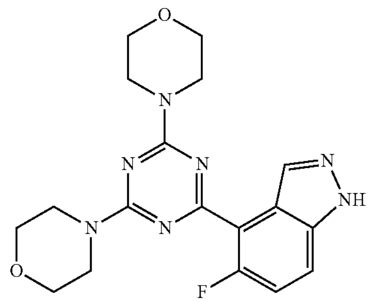 [SMILES: Fc1ccc2[nH]ncc2c1-c1nc(N2CCOCC2)nc(N2CCOCC2)n1] | 4,4'-(6-(5-fluoro-1H-indazol-4-yl)-1,3,5-triazine-2,4-diyl)dimorpholine |
| 125 | 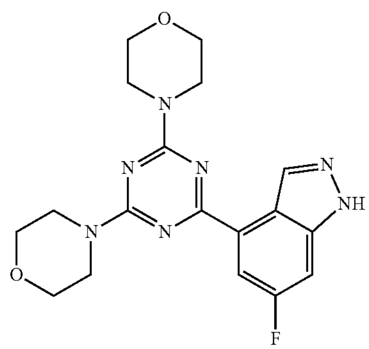 [SMILES: Fc1cc(-c2nc(N3CCOCC3)nc(N3CCOCC3)n2)c2cn[nH]c2c1] | 4,4'-(6-(6-fluoro-1H-indazol-4-yl)-1,3,5-triazine-2,4-diyl)dimorpholine |
| 126 | 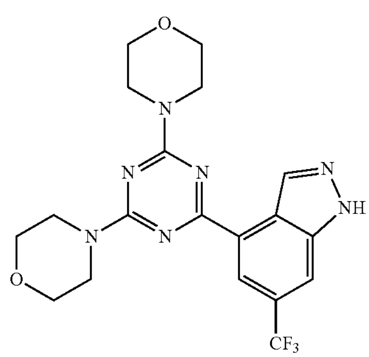 [SMILES: FC(F)(F)c1cc(-c2nc(N3CCOCC3)nc(N3CCOCC3)n2)c2cn[nH]c2c1] | 4,4'-(6-(6-(trifluoromethyl)-1H-indazol-4-yl)-1,3,5-triazine-2,4-diyl)dimorpholine |
| 127 | 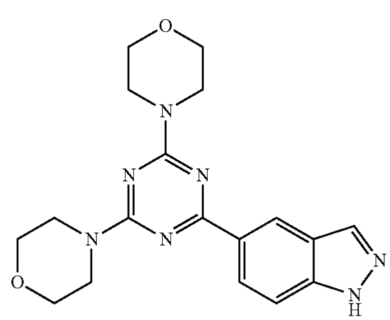 [SMILES: c1cc2[nH]ncc2cc1-c1nc(N2CCOCC2)nc(N2CCOCC2)n1] | 4,4'-(6-(1H-indazol-5-yl)-1,3,5-triazine-2,4-diyl)dimorpholine |

TABLE 1-continued

| Cpd No. | Structure | Name |
|---|---|---|
| 128 | 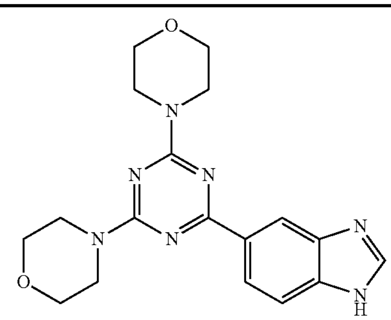 | 4,4'-(6-(1H-benzo[d]imidazol-5-yl)-1,3,5-triazine-2,4-diyl)dimorpholine |
| 129 | 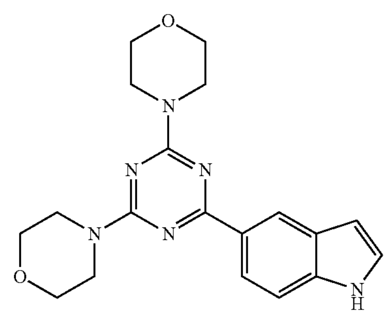 [SMILES: c1cc2cc(-c3nc(N4CCOCC4)nc(N4CCOCC4)n3)ccc2[nH]1] | 4,4'-(6-(1H-indol-5-yl)-1,3,5-triazine-2,4-diyl)dimorpholine |
| 130 | 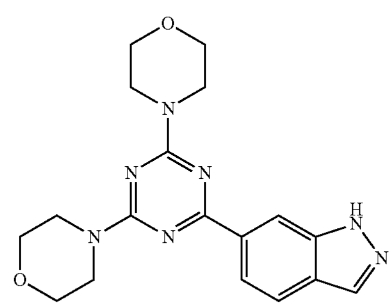 [SMILES: c1cc2cn[nH]c2cc1-c1nc(N2CCOCC2)nc(N2CCOCC2)n1] | 4,4'-(6-(1H-indol-6-yl)-1,3,5-triazine-2,4-diyl)dimorpholine |
| 131 | 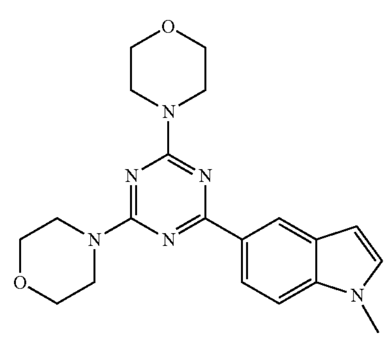 [SMILES: Cn1ccc2cc(-c3nc(N4CCOCC4)nc(N4CCOCC4)n3)ccc21] | 4,4'-(6-(1-methyl-1H-indol-5-yl)-1,3,5-triazine-2,4-diyl)dimorpholine |
| 132 | 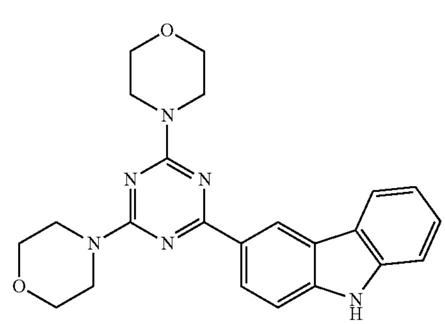 [SMILES: c1ccc2c(c1)[nH]c1ccc(-c3nc(N4CCOCC4)nc(N4CCOCC4)n3)cc12] | 4,4'-(6-(9H-carbazol-3-yl)-1,3,5-triazine-2,4-diyl)dimorpholine |

TABLE 1-continued
| Cpd No. | Structure | Name |
|---|---|---|
| 133 | 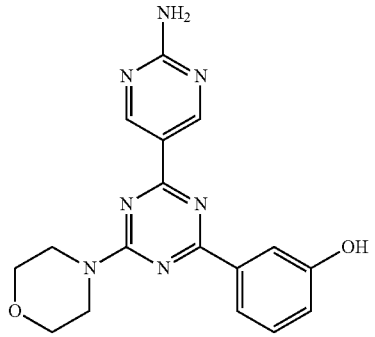 [SMILES: Nc1ncc(-c2nc(-c3cccc(O)c3)nc(N3CCOCC3)n2)cn1] | 3-(4-(2-aminopyrimidin-5-yl)-6-morpholino-1,3,5-triazin-2-yl)phenol |
| 134 | 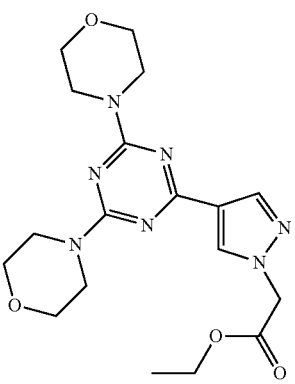 [SMILES: CCOC(=O)Cn1cc(-c2nc(N3CCOCC3)nc(N3CCOCC3)n2)cn1] | ethy 2-(4-(4,6-dimorpholino-1,3,5-triazin-2-yl)-1H-pyrazol-1-yl)acetate |
| 135 | 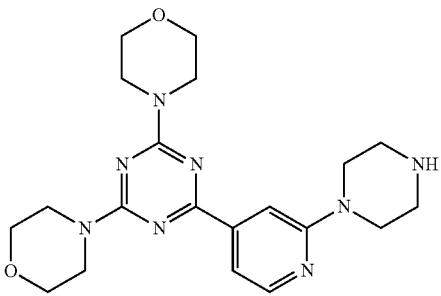 [SMILES: c1cc(-c2nc(N3CCOCC3)nc(N3CCOCC3)n2)cc(N2CCNCC2)n1] | 4,4'-(6-(2-(piperazin-1-yl)pyridin-4-yl)-1,3,5-triazine-2,4-diyl)dimorpholine |
| 136 | 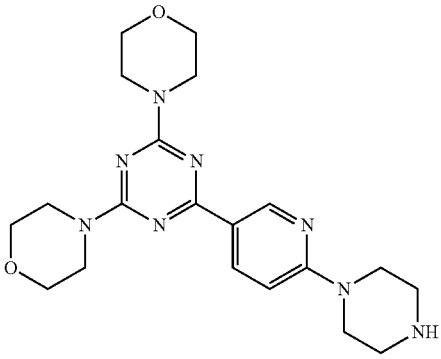 [SMILES: c1cc(N2CCNCC2)ncc1-c1nc(N2CCOCC2)nc(N2CCOCC2)n1] | 4,4'-(6-(6-(piperazin-1-yl)pyridin-3-yl)-1,3,5-triazine-2,4-diyl)dimorpholine |

TABLE 1-continued

| Cpd No. | Structure | Name |
|---|---|---|
| 137 | 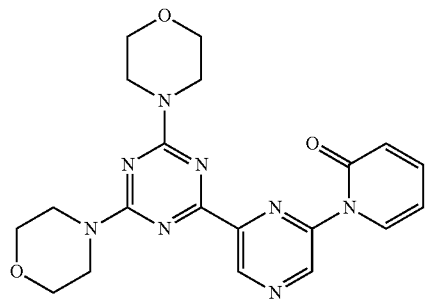 [SMILES: O=c1ccccn1-c1cncc(-c2nc(N3CCOCC3)nc(N3CCOCC3)n2)n1] | 1-(6-(4,6-dimorpholino-1,3,5-triazin-2-yl)pyrazin-2-yl)pyridin-2(1H)-one |
| 138 | 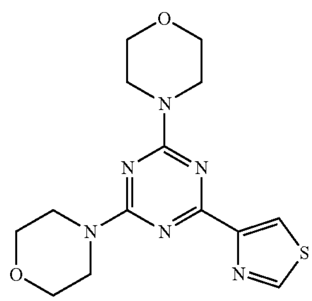 [SMILES: c1nc(-c2nc(N3CCOCC3)nc(N3CCOCC3)n2)cs1] | 4,4'-(6-(thiazol-4-yl)-1,3,5-triazine-2,4-diyl)dimorpholine |
| 139 | 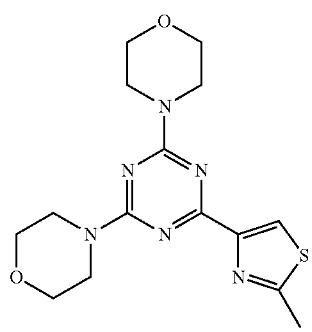 [SMILES: Cc1nc(-c2nc(N3CCOCC3)nc(N3CCOCC3)n2)cs1] | 4,4'-(6-(2-methylthiazol-4-yl)-1,3,5-triazine-2,4-diyl)dimorpholine |
| 140 | 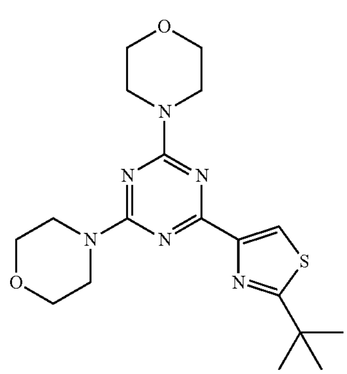 [SMILES: CC(C)(C)c1nc(-c2nc(N3CCOCC3)nc(N3CCOCC3)n2)cs1] | 4,4'-(6-(2-tert-butylthiazol-4-yl)-1,3,5-triazine-2,4-diyl)dimorpholine |

TABLE 1-continued

| Cpd No. | Structure | Name |
|---|---|---|
| 141 | 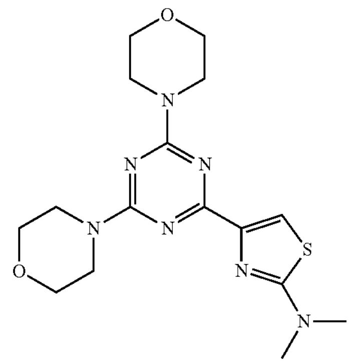 [SMILES: CN(C)c1nc(-c2nc(N3CCOCC3)nc(N3CCOCC3)n2)cs1] | 4-(4,6-dimorpholino-1,3,5-triazin-2-yl)-N,N-dimethylthiazol-2-amine |
| 142 | 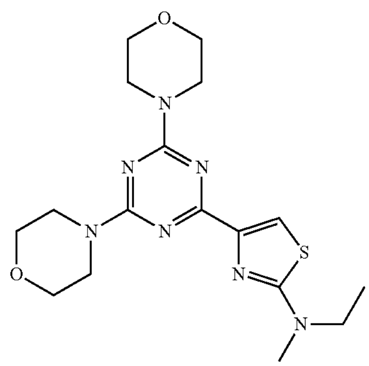 [SMILES: CCN(C)c1nc(-c2nc(N3CCOCC3)nc(N3CCOCC3)n2)cs1] | 4-(4,6-dimorpholino-1,3,5-triazin-2-yl)-N-ethyl-N-methylthiazol-2-amine |
| 143 | 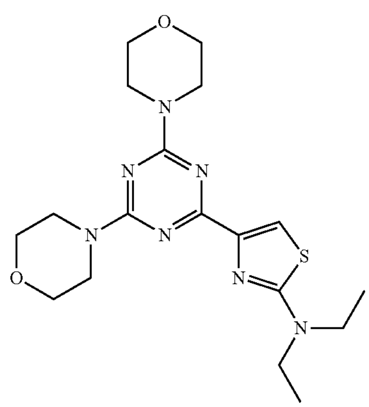 [SMILES: CCN(CC)c1nc(-c2nc(N3CCOCC3)nc(N3CCOCC3)n2)cs1] | 4-(4,6-dimorpholino-1,3,5-triazin-2-yl)-N,N-diethylthiazol-2-amine |
| 144 | 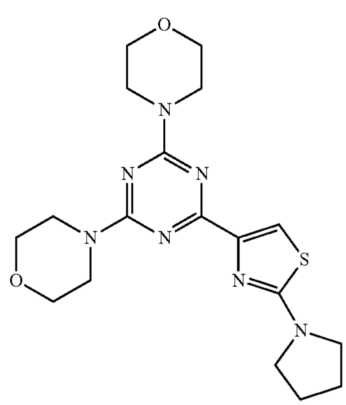 [SMILES: c1sc(N2CCCC2)nc1-c1nc(N2CCOCC2)nc(N2CCOCC2)n1] | 4,4'-(6-(2-(pyrrolidin-1-yl)thiazol-4-yl)-1,3,5-triazine-2,4-diyl)dimorpholine |

TABLE 1-continued

| Cpd No. | Structure | Name |
|---|---|---|
| 145 | 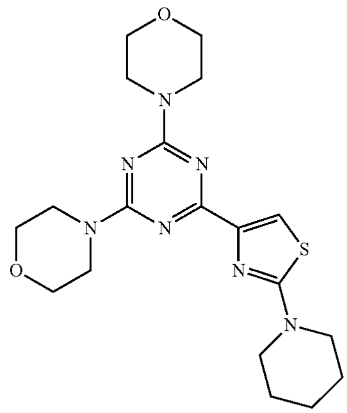 [SMILES: c1sc(N2CCCCC2)nc1-c1nc(N2CCOCC2)nc(N2CCOCC2)n1] | 4,4'-(6-(2-(piperidin-1-yl)thiazol-4-yl)-1,3,5-triazine-2,4-diyl)dimorpholine |
| 146 | 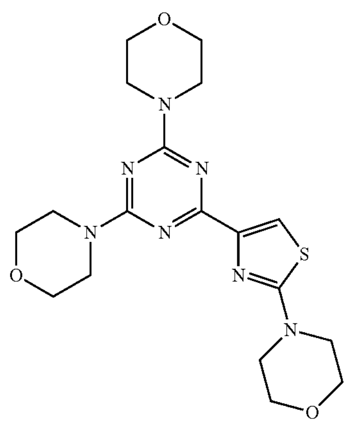 [SMILES: c1sc(N2CCOCC2)nc1-c1nc(N2CCOCC2)nc(N2CCOCC2)n1] | 4,4'-(6-(2-morpholinothiazol-4-yl)-1,3,5-triazine-2,4-diyl)dimorpholine |
| 147 | 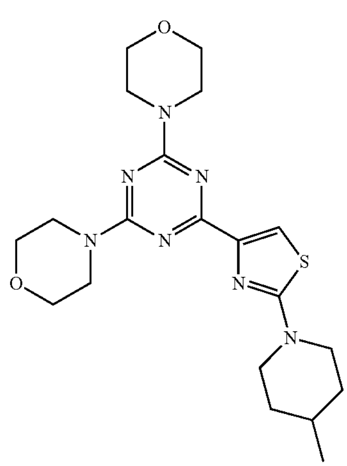 [SMILES: CC1CCN(c2nc(-c3nc(N4CCOCC4)nc(N4CCOCC4)n3)cs2)CC1] | 4,4'-(6-(2-(4-methylpiperidin-1-yl)thiazol-4-yl)-1,3,5-triazine-2,4-diyl)dimorpholine |

TABLE 1-continued

| Cpd No. | Structure | Name |
|---|---|---|
| 148 | 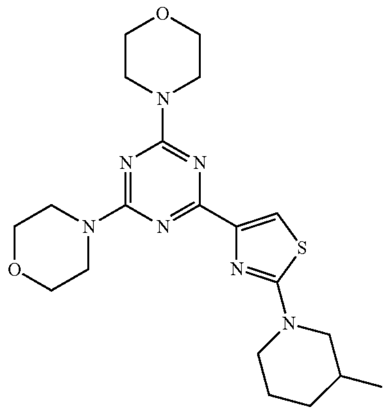 [SMILES: CC1CCCN(c2nc(-c3nc(N4CCOCC4)nc(N4CCOCC4)n3)cs2)C1] | 4,4'-(6-(2-(3-methylpiperidin-1-yl)thiazol-4-yl)-1,3,5-triazine-2,4-diyl)dimorpholine |
| 149 | 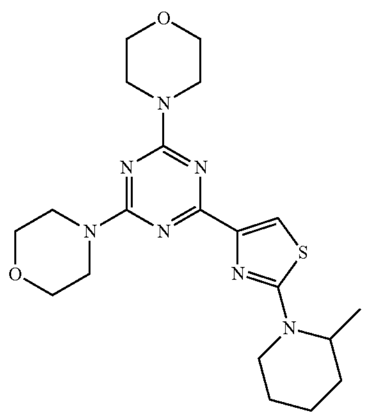 [SMILES: CC1CCCCN1c1nc(-c2nc(N3CCOCC3)nc(N3CCOCC3)n2)cs1] | 4,4'-(6-(2-(2-methylpiperidin-1-yl)thiazol-4-yl)-1,3,5-triazine-2,4-diyl)dimorpholine |
| 150 | 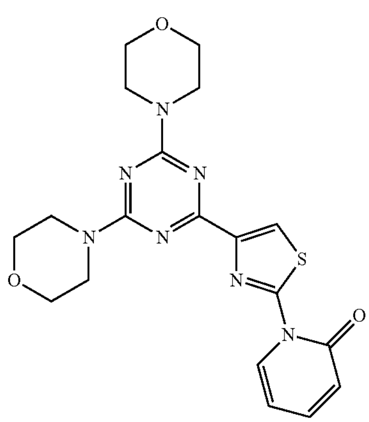 [SMILES: O=c1ccccn1-c1nc(-c2nc(N3CCOCC3)nc(N3CCOCC3)n2)cs1] | 1-(4-(4,6-dimorpholino-1,3,5-triazin-2-yl)thiazol-2-yl)pyridin-2(1H)-one |

TABLE 1-continued

| Cpd No. | Structure | Name |
| --- | --- | --- |
| 151 | 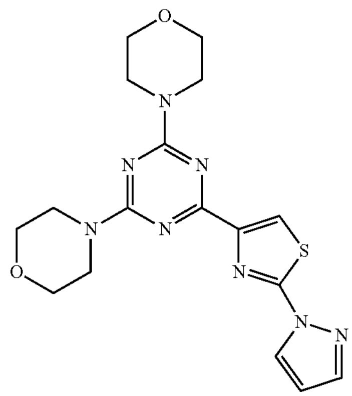 [SMILES: c1cnn(-c2nc(-c3nc(N4CCOCC4)nc(N4CCOCC4)n3)cs2)c1] | 4,4'-(6-(2-(1H-pyrazol-1-yl)thiazol-4-yl)-1,3,5-triazine-2,4-diyl)dimorpholine |
| 152 | 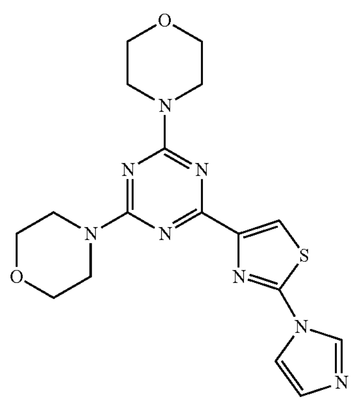 [SMILES: c1cn(-c2nc(-c3nc(N4CCOCC4)nc(N4CCOCC4)n3)cs2)cn1] | 4,4'-(6-(2-(1H-imidazol-1-yl)thiazol-4-yl)-1,3,5-triazine-2,4-diyl)dimorpholine |
| 153 | 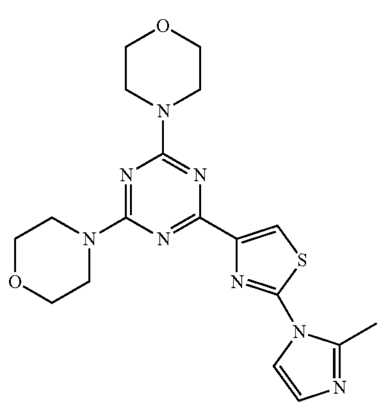 [SMILES: Cc1nccn1-c1nc(-c2nc(N3CCOCC3)nc(N3CCOCC3)n2)cs1] | 4,4'-(6-(2-(2-methyl-1H-imidazol-1-yl)thiazol-4-yl)-1,3,5-triazine-2,4-diyl)dimorpholine |

TABLE 1-continued

| Cpd No. | Structure | Name |
|---|---|---|
| 154 | 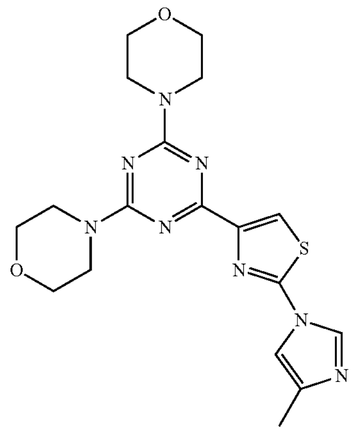 [SMILES: Cc1cn(-c2nc(-c3nc(N4CCOCC4)nc(N4CCOCC4)n3)cs2)cn1] | 4,4'-(6-(2-(4-methyl-1H-imidazol-1-yl)thiazol-4-yl)-1,3,5-triazine-2,4-diyl)dimorpholine |
| 155 | 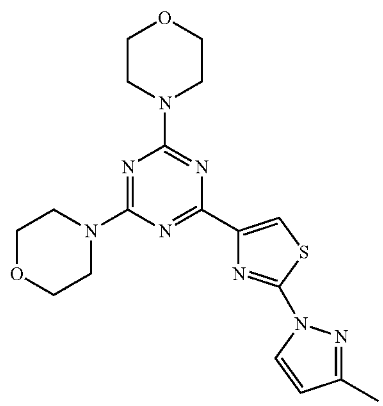 [SMILES: Cc1ccn(-c2nc(-c3nc(N4CCOCC4)nc(N4CCOCC4)n3)cs2)n1] | 4,4'-(6-(2-(3-methyl-1H-pyrazol-1-yl)thiazol-4-yl)-1,3,5-triazine-2,4-diyl)dimorpholine |
| 156 | 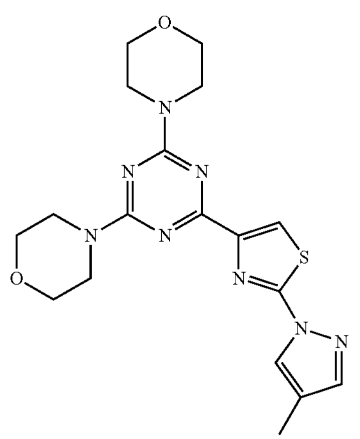 [SMILES: Cc1cnn(-c2nc(-c3nc(N4CCOCC4)nc(N4CCOCC4)n3)cs2)c1] | 4,4'-(6-(2-(4-methyl-1H-pyrazol-1-yl)thiazol-4-yl)-1,3,5-triazine-2,4-diyl)dimorpholine |

TABLE 1-continued
| Cpd No. | Structure | Name |
|---|---|---|
| 157 | 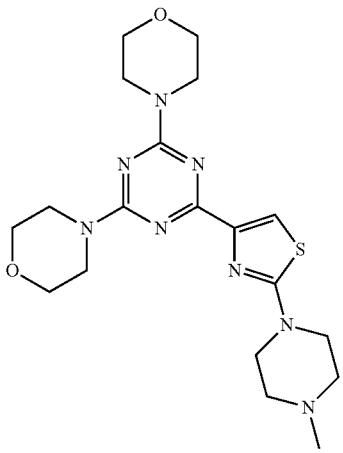 [SMILES: CN1CCN(c2nc(-c3nc(N4CCOCC4)nc(N4CCOCC4)n3)cs2)CC1] | 4,4'-(6-(2-(4-methylpiperazin-1-yl)thiazol-4-yl)-1,3,5-triazine-2,4-diyl)dimorpholine |
| 157.1 | 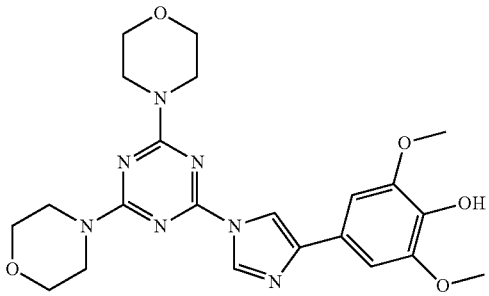 [SMILES: COc1cc(-c2cn(-c3nc(N4CCOCC4)nc(N4CCOCC4)n3)cn2)cc(OC)c1O] | 4-(1-(4,6-dimorpholino-1,3,5-triazin-2-yl)-1H-imidazol-4-yl)-2,6-dimethoxyphenol |
| 157.2 | 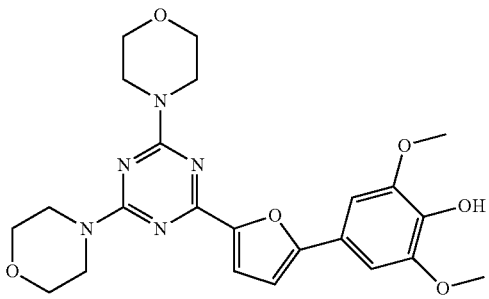 [SMILES: COc1cc(-c2ccc(-c3nc(N4CCOCC4)nc(N4CCOCC4)n3)o2)cc(OC)c1O] | 4-(5-(4,6-dimorpholino-1,3,5-triazin-2-yl)furan-2-yl)-2,6-dimethoxyphenol |
| 157.3 | 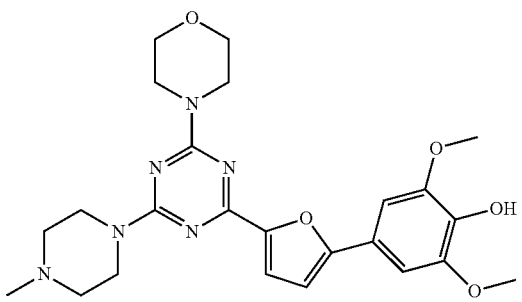 | 2,6-dimethoxy-4-(5-(4-(4-methylpiperazin-1-yl)-6-morpholino-1,3,5-triazin-2-yl)furan-2-yl)phenol |

TABLE 1-continued

| Cpd No. | Structure | Name |
| --- | --- | --- |
| 157.4 | 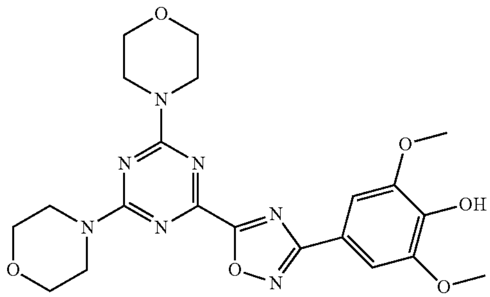 [SMILES: COc1cc(-c2noc(-c3nc(N4CCOCC4)nc(N4CCOCC4)n3)n2)cc(OC)c1O] | 4-(5-(4,6-dimorpholino-1,3,5-triazin-2-yl)-1,2,4-oxadiazol-3-yl)-2,6-dimethoxyphenol |
| 157.5 | 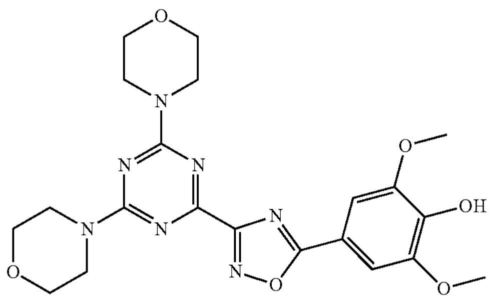 [SMILES: COc1cc(-c2nc(-c3nc(N4CCOCC4)nc(N4CCOCC4)n3)no2)cc(OC)c1O] | 4-(3-(4,6-dimorpholino-1,3,5-triazin-2-yl)-1,2,4-oxadiazol-5-yl)-2,6-dimethoxyphenol |
| 157.6 | 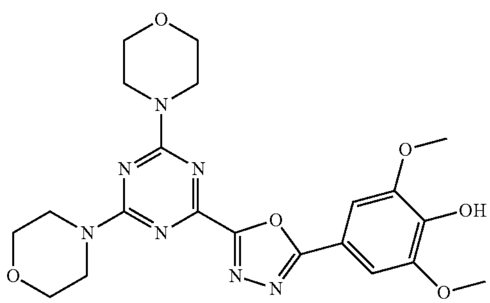 [SMILES: COc1cc(-c2nnc(-c3nc(N4CCOCC4)nc(N4CCOCC4)n3)o2)cc(OC)c1O] | 4-(5-(4,6-dimorpholino-1,3,5-triazin-2-yl)-1,3,4-oxadiazol-2-yl)-2,6-dimethoxyphenol |
| 157.7 | 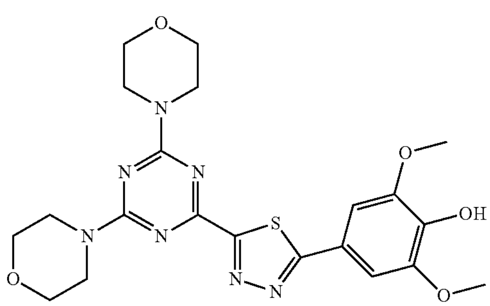 | 4-(5-(4,6-dimorpholino-1,3,5-triazin-2-yl)-1,3,4-thiadiazol-2-yl)-2,6-dimethoxyphenol |
| 158 | 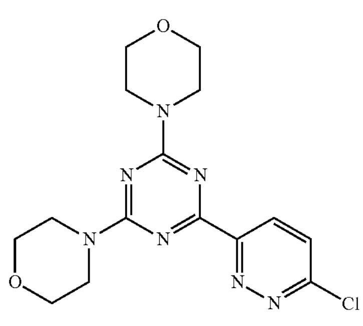 [SMILES: Clc1ccc(-c2nc(N3CCOCC3)nc(N3CCOCC3)n2)nn1] | 4,4'-(6-(6-chloropyridazin-3-yl)-1,3,5-triazine-2,4-diyl)dimorpholine |

TABLE 1-continued

| Cpd No. | Structure | Name |
|---|---|---|
| 159 | 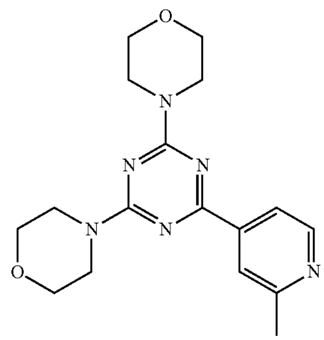 [SMILES: Cc1cc(-c2nc(N3CCOCC3)nc(N3CCOCC3)n2)ccn1] | 4,4'-(6-(2-methylpyridin-4-yl)-1,3,5-triazine-2,4-diyl)dimorpholine |
| 160 | 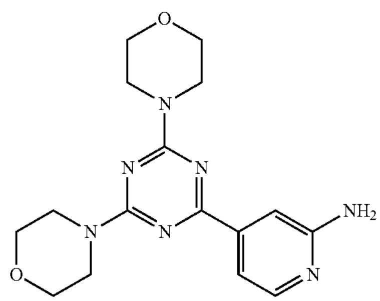 [SMILES: Nc1cc(-c2nc(N3CCOCC3)nc(N3CCOCC3)n2)ccn1] | 4-(4,6-dimorpholino-1,3,5-triazin-2-yl)pyridin-2-amine |
| 161 | 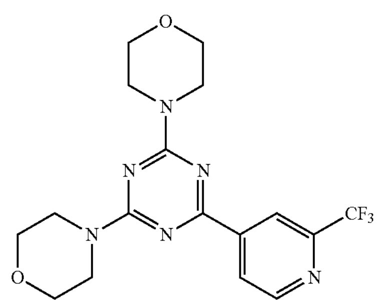 [SMILES: FC(F)(F)c1cc(-c2nc(N3CCOCC3)nc(N3CCOCC3)n2)ccn1] | 4,4'-(6-(2-(trifluoromethyl)pyridin-4-yl)-1,3,5-triazine-2,4-diyl)dimorpholine |
| 162 | 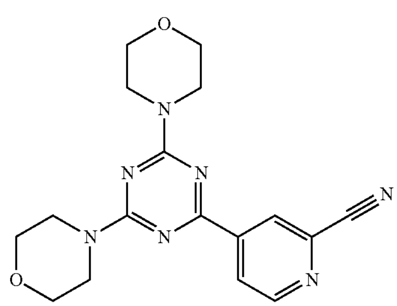 [SMILES: N#Cc1cc(-c2nc(N3CCOCC3)nc(N3CCOCC3)n2)ccn1] | 4-(4,6-dimorpholino-1,3,5-triazin-2-yl)picolinonitrile |
| 163 | 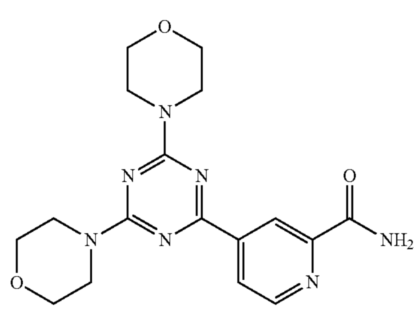 [SMILES: NC(=O)c1cc(-c2nc(N3CCOCC3)nc(N3CCOCC3)n2)ccn1] | 4-(4,6-dimorpholino-1,3,5-triazin-2-yl)picolinamide |

TABLE 1-continued

| Cpd No. | Structure | Name |
|---|---|---|
| 164 | 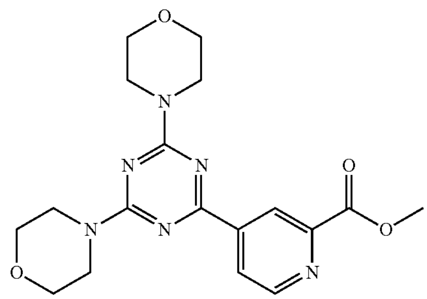 [SMILES: COC(=O)c1cc(-c2nc(N3CCOCC3)nc(N3CCOCC3)n2)ccn1] | methyl 4-(4,6-dimorpholino-1,3,5-triazin-2-yl)picolinate |
| 165 | 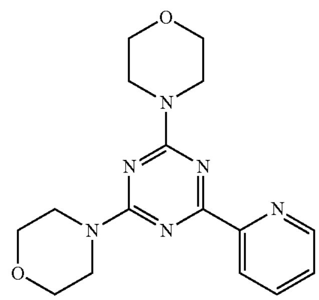 [SMILES: c1ccc(-c2nc(N3CCOCC3)nc(N3CCOCC3)n2)nc1] | 4,4'-(6-(pyridin-2-yl)-1,3,5-triazine-2,4-diyl)dimorpholine |
| 166 | 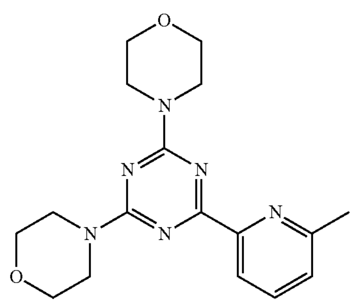 [SMILES: Cc1cccc(-c2nc(N3CCOCC3)nc(N3CCOCC3)n2)n1] | 4,4'-(6-(6-methylpyridin-2-yl)-1,3,5-triazine-2,4-diyl)dimorpholine |
| 167 | 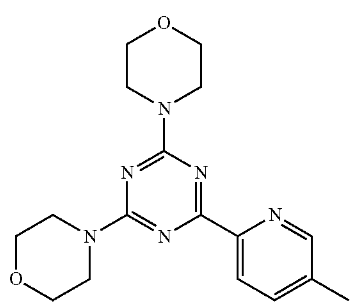 [SMILES: Cc1ccc(-c2nc(N3CCOCC3)nc(N3CCOCC3)n2)nc1] | 4,4'-(6-(5-methylpyridin-2-yl)-1,3,5-triazine-2,4-diyl)dimorpholine |
| 168 | 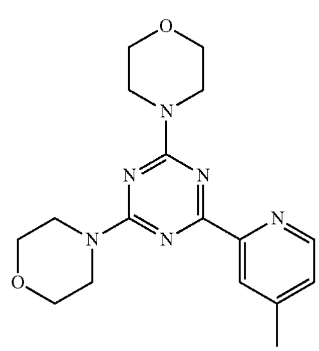 [SMILES: Cc1ccnc(-c2nc(N3CCOCC3)nc(N3CCOCC3)n2)c1] | 4,4'-(6-(4-methylpyridin-2-yl)-1,3,5-triazine-2,4-diyl)dimorpholine |

TABLE 1-continued

| Cpd No. | Structure | Name |
|---|---|---|
| 169 | 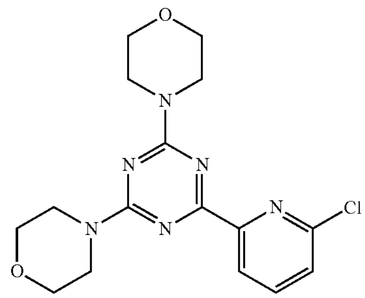 [SMILES: Clc1cccc(-c2nc(N3CCOCC3)nc(N3CCOCC3)n2)n1] | 4,4'-(6-(6-chloropyridin-2-yl)-1,3,5-triazine-2,4-diyl)dimorpholine |
| 170 | 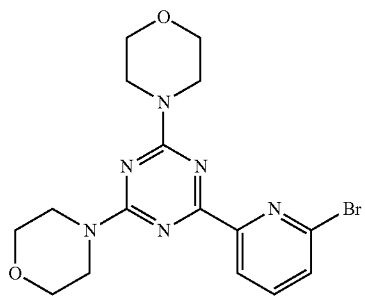 [SMILES: Brc1cccc(-c2nc(N3CCOCC3)nc(N3CCOCC3)n2)n1] | 4,4'-(6-(6-bromopyridin-2-yl)-1,3,5-triazine-2,4-diyl)dimorpholine |
| 171 | 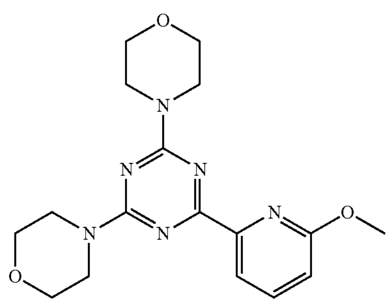 [SMILES: COc1cccc(-c2nc(N3CCOCC3)nc(N3CCOCC3)n2)n1] | 4,4'-(6-(6-methoxypyridin-2-yl)-1,3,5-triazine-2,4-diyl)dimorpholine |
| 172 | 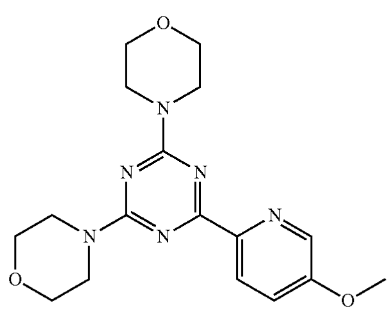 [SMILES: COc1ccc(-c2nc(N3CCOCC3)nc(N3CCOCC3)n2)nc1] | 4,4'-(6-(5-methoxypyridin-2-yl)-1,3,5-triazine-2,4-diyl)dimorpholine |
| 173 | 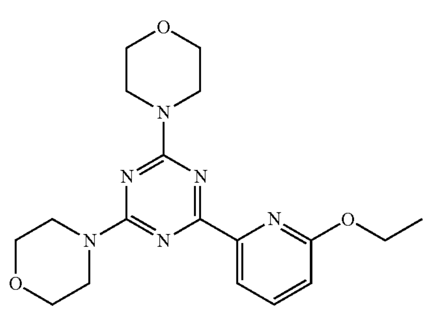 [SMILES: CCOc1cccc(-c2nc(N3CCOCC3)nc(N3CCOCC3)n2)n1] | 4,4'-(6-(6-ethoxypyridin-2-yl)-1,3,5-triazine-2,4-diyl)dimorpholine |

TABLE 1-continued

| Cpd No. | Structure | Name |
|---|---|---|
| 174 | 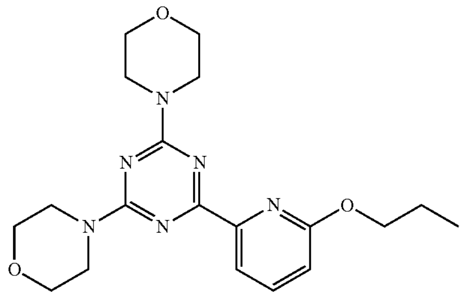 [SMILES: CCCOc1cccc(-c2nc(N3CCOCC3)nc(N3CCOCC3)n2)n1] | 4,4'-(6-(6-propoxypyridin-2-yl)-1,3,5-triazine-2,4-diyl)dimorpholine |
| 175 | 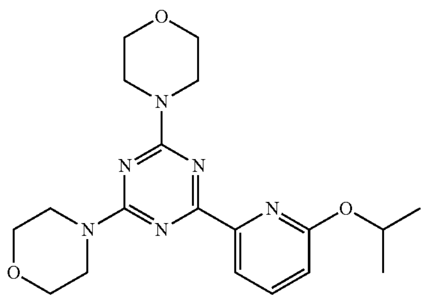 [SMILES: CC(C)Oc1cccc(-c2nc(N3CCOCC3)nc(N3CCOCC3)n2)n1] | 4,4'-(6-(6-isopropoxypyridin-2-yl)-1,3,5-triazine-2,4-diyl)dimorpholine |
| 176 | 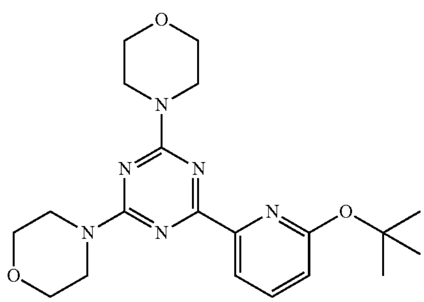 [SMILES: CC(C)(C)Oc1cccc(-c2nc(N3CCOCC3)nc(N3CCOCC3)n2)n1] | 4,4'-(6-(6-tert-butoxypyridin-2-yl)-1,3,5-triazine-2,4-diyl)dimorpholine |
| 177 | 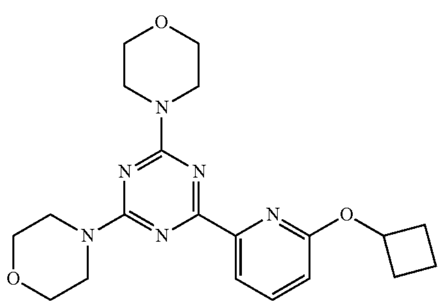 [SMILES: c1cc(OC2CCC2)nc(-c2nc(N3CCOCC3)nc(N3CCOCC3)n2)c1] | 4,4'-(6-(6-cyclobutoxypyridin-2-yl)-1,3,5-triazine-2,4-diyl)dimorpholine |
| 178 | 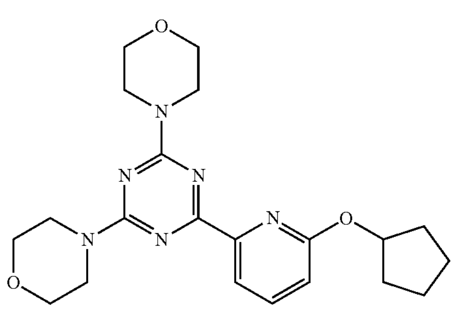 [SMILES: c1cc(OC2CCCC2)nc(-c2nc(N3CCOCC3)nc(N3CCOCC3)n2)c1] | 4,4'-(6-(6-cyclopentyloxy)pyridin-2-yl)-1,3,5-triazine-2,4-diyl)dimorpholine |

TABLE 1-continued

| Cpd No. | Structure | Name |
|---|---|---|
| 179 | 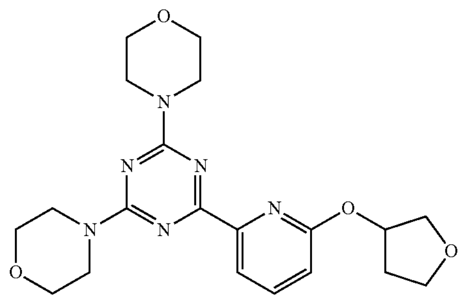 [SMILES: c1cc(OC2CCOC2)nc(-c2nc(N3CCOCC3)nc(N3CCOCC3)n2)c1] | 4,4'-(6-(6-(tetrahydrofuran-3-yloxy)pyridin-2-yl)-1,3,5-triazine-2,4-diyl)dimorpholine |
| 180 | 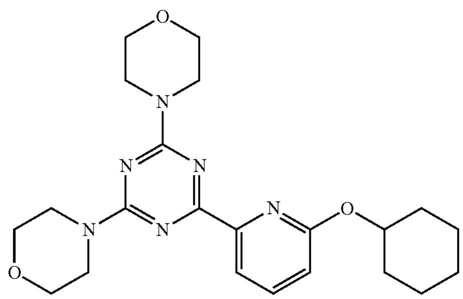 [SMILES: c1cc(OC2CCCCC2)nc(-c2nc(N3CCOCC3)nc(N3CCOCC3)n2)c1] | 4,4'-(6-(6-cyclohexyloxy)pyridin-2-yl)-1,3,5-triazine-2,4-diyl)dimorpholine |
| 181 | 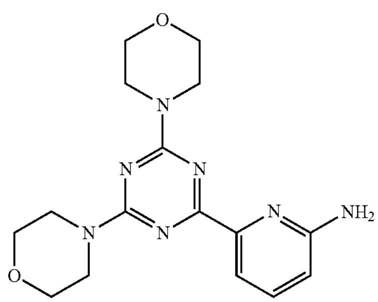 [SMILES: Nc1cccc(-c2nc(N3CCOCC3)nc(N3CCOCC3)n2)n1] | 6-(4,6-dimorpholino-1,3,5-triazin-2-yl)pyridin-2-amine |
| 182 | 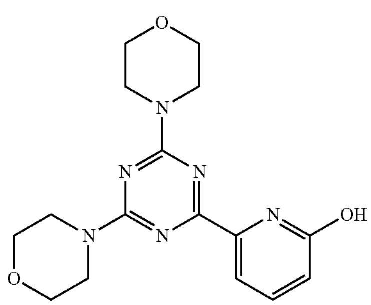 [SMILES: Oc1cccc(-c2nc(N3CCOCC3)nc(N3CCOCC3)n2)n1] | 6-(4,6-dimorpholino-1,3,5-triazin-2-yl)pyridin-2-ol |
| 183 | 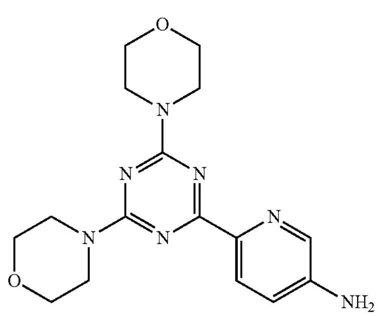 [SMILES: Nc1ccc(-c2nc(N3CCOCC3)nc(N3CCOCC3)n2)nc1] | 6-(4,6-dimorpholino-1,3,5-triazin-2-yl)pyridin-3-amine |

TABLE 1-continued

| Cpd No. | Structure | Name |
|---|---|---|
| 184 | | N-(6-(4,6-dimorpholino-1,3,5-triazin-2-yl)pyridin-3-yl)acetamide |
| 184 | | tert-butyl 6-(4,6-dimorpholino-1,3,5-triazin-2-yl)pyridin-3-ylcarbamate |
| 185 | 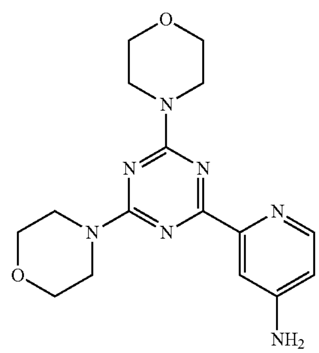 [SMILES: Nc1ccnc(-c2nc(N3CCOCC3)nc(N3CCOCC3)n2)c1] | 2-(4,6-dimorpholino-1,3,5-triazin-2-yl)pyridin-4-amine |
| 186 | 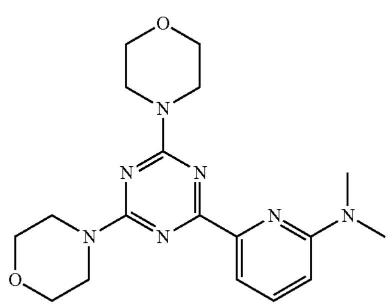 [SMILES: CN(C)c1cccc(-c2nc(N3CCOCC3)nc(N3CCOCC3)n2)n1] | 6-(4,6-dimorpholino-1,3,5-triazin-2-yl)-N,N-dimethylpyridin-2-amine |
| 187 | 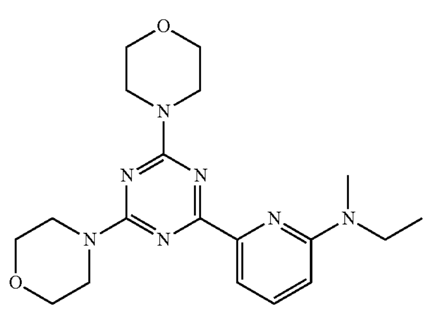 [SMILES: CCN(C)c1cccc(-c2nc(N3CCOCC3)nc(N3CCOCC3)n2)n1] | 6-(4,6-dimorpholino-1,3,5-triazin-2-yl)-N-ethyl-N-methylpyridin-2-amine |

TABLE 1-continued

| Cpd No. | Structure | Name |
|---|---|---|
| 188 | 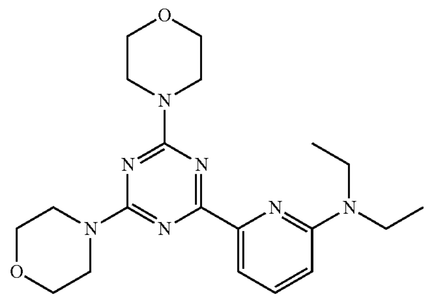 [SMILES: CCN(CC)c1cccc(-c2nc(N3CCOCC3)nc(N3CCOCC3)n2)n1] | 6-(4,6-dimorpholino-1,3,5-triazin-2-yl)-N,N-diethylpyridin-2-amine |
| 189 | 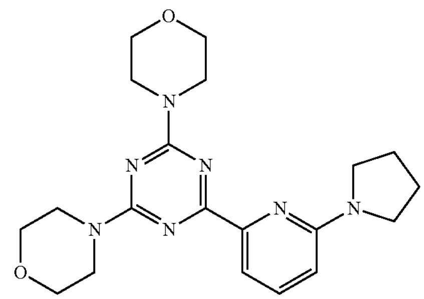 [SMILES: c1cc(-c2nc(N3CCOCC3)nc(N3CCOCC3)n2)nc(N2CCCC2)c1] | 4,4'-(6-(6-(pyrrolidin-1-yl)pyridin-2-yl)-1,3,5-triazine-2,4-diyl)dimorpholine |
| 190 | 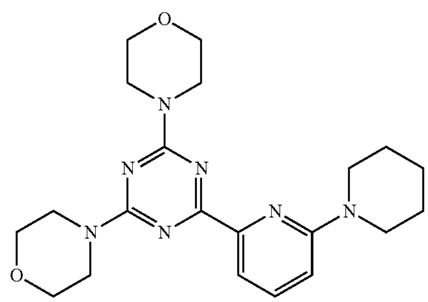 [SMILES: c1cc(-c2nc(N3CCOCC3)nc(N3CCOCC3)n2)nc(N2CCCCC2)c1] | 4,4'-(6-(6-(piperidin-1-yl)pyridin-2-yl)-1,3,5-triazine-2,4-diyl)dimorpholine |
| 191 | 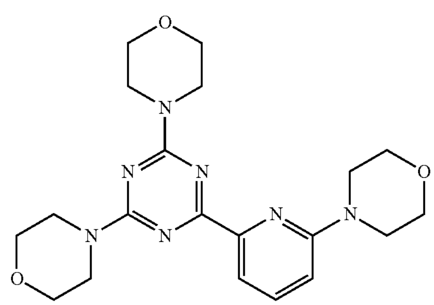 [SMILES: c1cc(-c2nc(N3CCOCC3)nc(N3CCOCC3)n2)nc(N2CCOCC2)c1] | 4,4'-(6-(6-morpholinopyridin-2-yl)-1,3,5-triazine-2,4-diyl)dimorpholine |
| 192 | 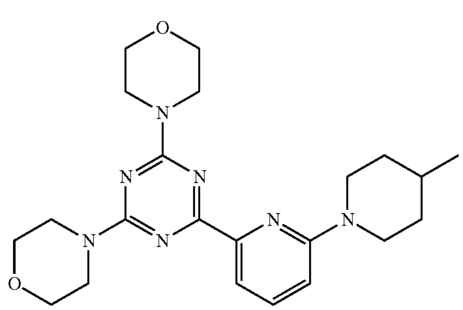 [SMILES: CC1CCN(c2cccc(-c3nc(N4CCOCC4)nc(N4CCOCC4)n3)n2)CC1] | 4,4'-(6-(6-(4-methylpiperidin-1-yl)pyridin-2-yl)-1,3,5-triazine-2,4-diyl)dimorpholine |

TABLE 1-continued

| Cpd No. | Structure | Name |
| --- | --- | --- |
| 193 | 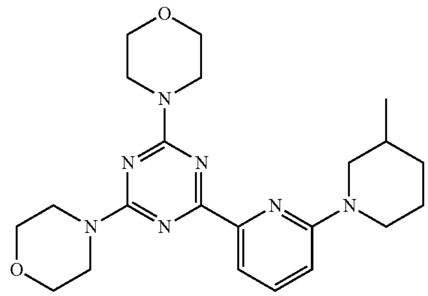 [SMILES: CC1CCCN(c2cccc(-c3nc(N4CCOCC4)nc(N4CCOCC4)n3)n2)C1] | 4,4'-(6-(6-(3-methylpiperidin-1-yl)pyridin-2-yl)-1,3,5-triazine-2,4-diyl)dimorpholine |
| 194 | 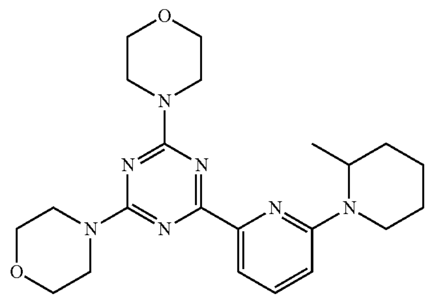 [SMILES: CC1CCCCN1c1cccc(-c2nc(N3CCOCC3)nc(N3CCOCC3)n2)n1] | 4,4'-(6-(6-(2-methylpiperidin-1-yl)pyridin-2-yl)-1,3,5-triazine-2,4-diyl)dimorpholine |
| 195 | 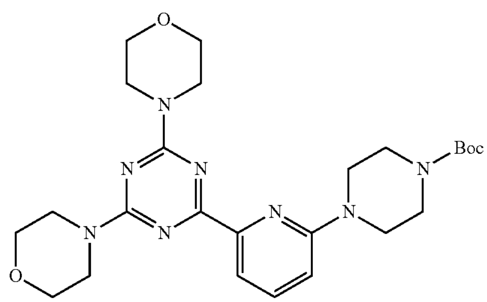 [SMILES: CC(C)(C)OC(=O)N1CCN(c2cccc(-c3nc(N4CCOCC4)nc(N4CCOCC4)n3)n2)CC1] | tert-butyl 4-(6-(4,6-dimorpholino-1,3,5-triazin-2-yl)pyridin-2-yl)piperazine-1-carboxylate |
| 196 | 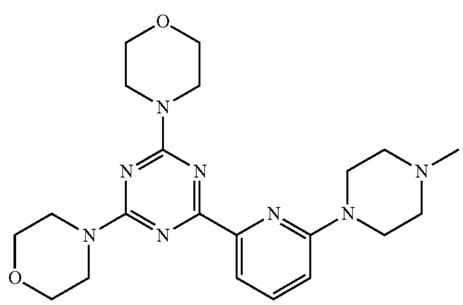 [SMILES: CN1CCN(c2cccc(-c3nc(N4CCOCC4)nc(N4CCOCC4)n3)n2)CC1] | 4,4'-(6-(6-(4-methylpiperazin-1-yl)pyridin-2-yl)-1,3,5-triazine-2,4-diyl)dimorpholine |
| 197 | 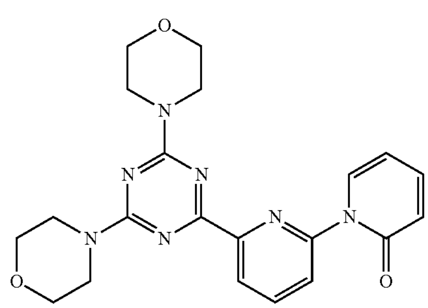 [SMILES: O=c1ccccn1-c1cccc(-c2nc(N3CCOCC3)nc(N3CCOCC3)n2)n1] | 1-(6-(4,6-dimorpholino-1,3,5-triazin-2-yl)pyridin-2-yl)pyridin-2(1H)-one |

TABLE 1-continued

| Cpd No. | Structure | Name |
|---|---|---|
| 198 | 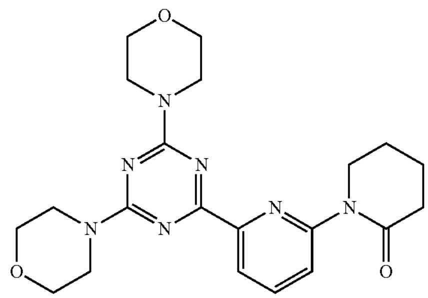 [SMILES: O=C1CCCCN1c1cccc(-c2nc(N3CCOCC3)nc(N3CCOCC3)n2)n1] | 1-(6-(4,6-dimorpholino-1,3,5-triazin-2-yl)pyridin-2-yl)piperidin-2-one |
| 199 | 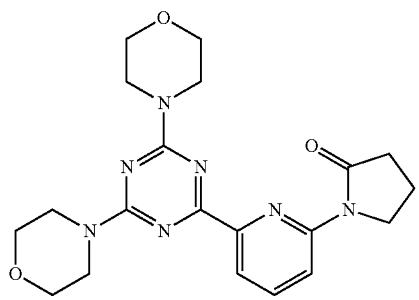 [SMILES: O=C1CCCN1c1cccc(-c2nc(N3CCOCC3)nc(N3CCOCC3)n2)n1] | 1-(6-(4,6-dimorpholino-1,3,5-triazin-2-yl)pyridin-2-yl)pyrrolidin-2-one |
| 200 | 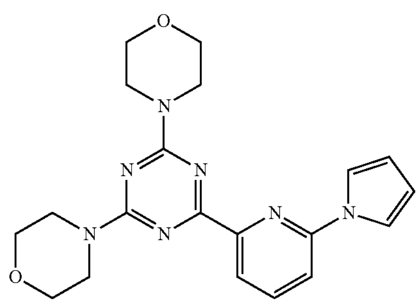 [SMILES: c1cc(-c2nc(N3CCOCC3)nc(N3CCOCC3)n2)nc(-n2cccc2)c1] | 4,4'-(6-(6-(1H-pyrrol-1-yl)pyridin-2-yl)-1,3,5-triazine-2,4-diyl)dimorpholine |
| 201 | 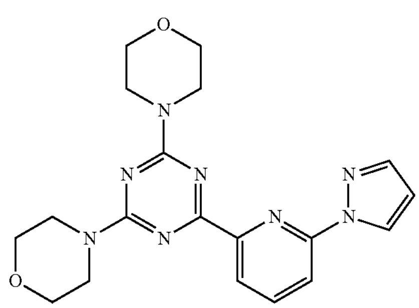 [SMILES: c1cc(-c2nc(N3CCOCC3)nc(N3CCOCC3)n2)nc(-n2cccn2)c1] | 4,4'-(6-(6-(1H-pyrazol-1-yl)pyridin-2-yl)-1,3,5-triazine-2,4-diyl)dimorpholine |
| 202 | 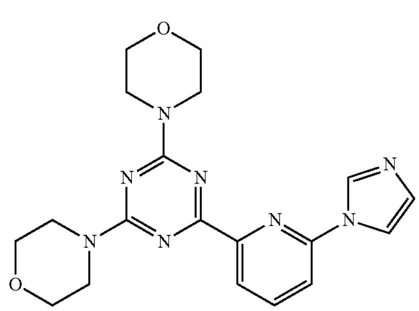 [SMILES: c1cc(-c2nc(N3CCOCC3)nc(N3CCOCC3)n2)nc(-n2ccnc2)c1] | 4,4'-(6-(6-(1H-imidazol-1-yl)pyridin-2-yl)-1,3,5-triazine-2,4-diyl)dimorpholine |

TABLE 1-continued

| Cpd No. | Structure | Name |
|---|---|---|
| 203 | 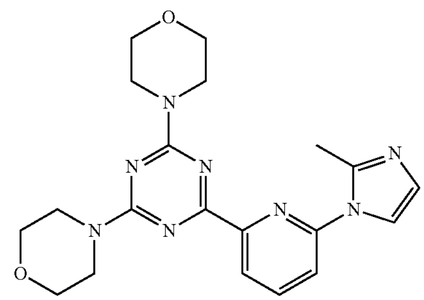 [SMILES: Cc1nccn1-c1cccc(-c2nc(N3CCOCC3)nc(N3CCOCC3)n2)n1] | 4,4'-(6-(6-(2-methyl-1H-imidazol-1-yl)pyridin-2-yl)-1,3,5-triazine-2,4-diyl)dimorpholine |
| 204 | 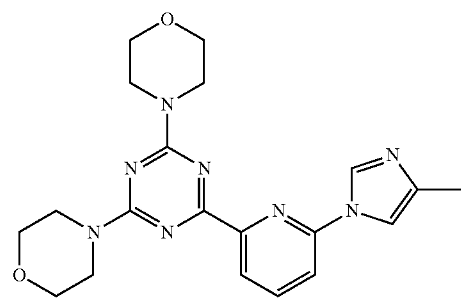 [SMILES: Cc1cn(-c2cccc(-c3nc(N4CCOCC4)nc(N4CCOCC4)n3)n2)cn1] | 4,4'-(6-(6-(4-methyl-1H-imidazol-1-yl)pyridin-2-yl)-1,3,5-triazine-2,4-diyl)dimorpholine |
| 205 | 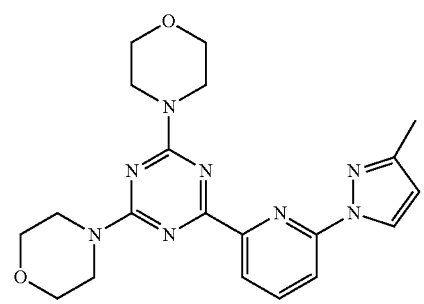 [SMILES: Cc1ccn(-c2cccc(-c3nc(N4CCOCC4)nc(N4CCOCC4)n3)n2)n1] | 4,4'-(6-(6-(3-methyl-1H-pyrazol-1-yl)pyridin-2-yl)-1,3,5-triazine-2,4-diyl)dimorpholine |
| 206 | 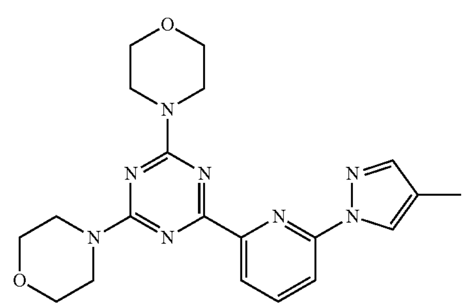 [SMILES: Cc1cnn(-c2cccc(-c3nc(N4CCOCC4)nc(N4CCOCC4)n3)n2)c1] | 4,4'-(6-(6-(4-methyl-1H-pyrazol-1-yl)pyridin-2-yl)-1,3,5-triazine-2,4-diyl)dimorpholine |
| 207 | 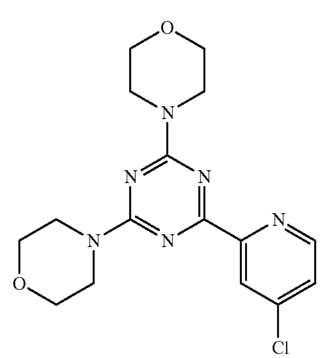 [SMILES: Clc1ccnc(-c2nc(N3CCOCC3)nc(N3CCOCC3)n2)c1] | 4,4'-(6-(4-chloropyridin-2-yl)-1,3,5-triazine-2,4-diyl)dimorpholine |

TABLE 1-continued

| Cpd No. | Structure | Name |
|---|---|---|
| 208 | 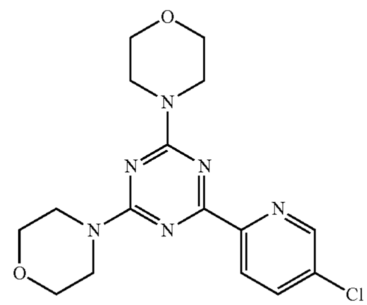 [SMILES: Clc1ccc(-c2nc(N3CCOCC3)nc(N3CCOCC3)n2)nc1] | 4,4'-(6-(5-chloropyridin-2-yl)-1,3,5-triazine-2,4-diyl)dimorpholine |
| 209 | 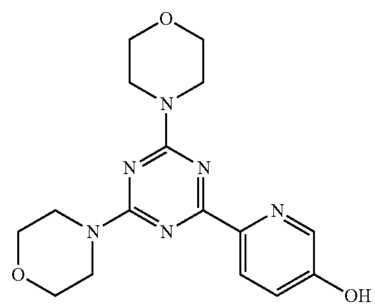 [SMILES: Oc1ccc(-c2nc(N3CCOCC3)nc(N3CCOCC3)n2)nc1] | 6-(4,6-dimorpholino-1,3,5-triazin-2-yl)pyridin-3-ol |
| 210 | 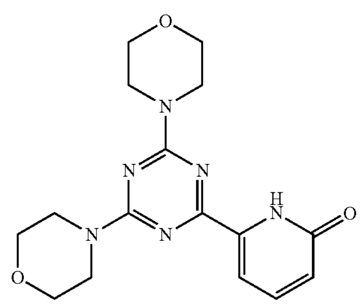 [SMILES: O=c1cccc(-c2nc(N3CCOCC3)nc(N3CCOCC3)n2)[nH]1] | 6-(4,6-dimorpholino-1,3,5-triazin-2-yl)pyridin-2(1H)-one |
| 211 | 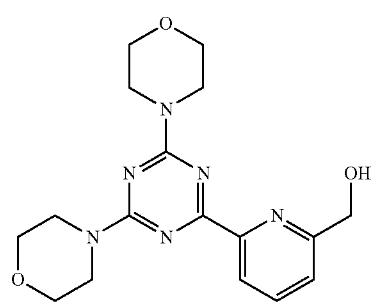 [SMILES: OCc1cccc(-c2nc(N3CCOCC3)nc(N3CCOCC3)n2)n1] | (6-(4,6-dimorpholino-1,3,5-triazin-2-yl)pyridin-2-yl)methanol |
| 212 | 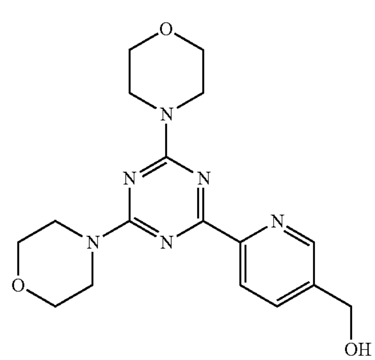 [SMILES: OCc1ccc(-c2nc(N3CCOCC3)nc(N3CCOCC3)n2)nc1] | (6-(4,6-dimorpholino-1,3,5-triazin-2-yl)pyridin-3-yl)methanol |

TABLE 1-continued

| Cpd No. | Structure | Name |
|---|---|---|
| 213 | 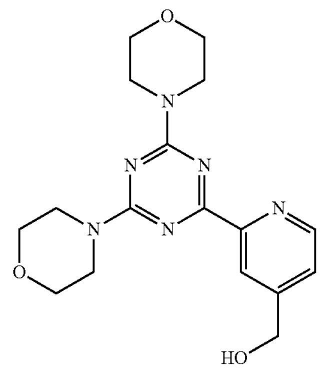 [SMILES: OCc1ccnc(-c2nc(N3CCOCC3)nc(N3CCOCC3)n2)c1] | (2-(4,6-dimorpholino-1,3,5-triazin-2-yl)pyridin-4-yl)methanol |
| 214 | 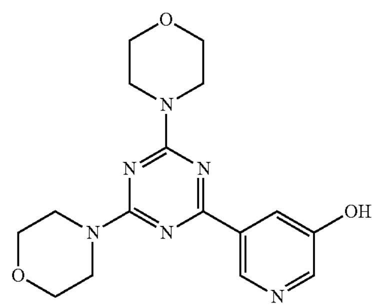 [SMILES: Oc1cncc(-c2nc(N3CCOCC3)nc(N3CCOCC3)n2)c1] | 5-(4,6-dimorpholino-1,3,5-triazin-2-yl)pyridin-3-ol |
| 215 | 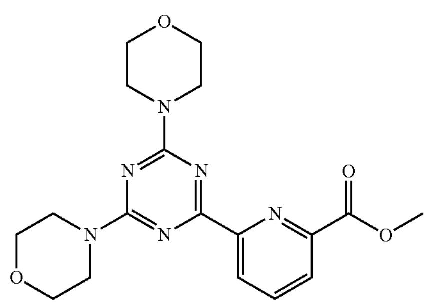 [SMILES: COC(=O)c1cccc(-c2nc(N3CCOCC3)nc(N3CCOCC3)n2)n1] | methyl 6-(4,6-dimorpholino-1,3,5-triazin-2-yl)picolinate |
| 216 | 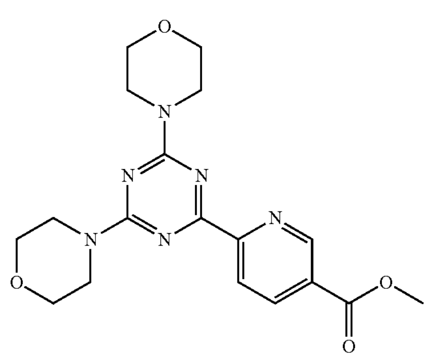 [SMILES: COC(=O)c1ccc(-c2nc(N3CCOCC3)nc(N3CCOCC3)n2)nc1] | methyl 6-(4,6-dimorpholino-1,3,5-triazin-2-yl)nicotinate |

TABLE 1-continued

| Cpd No. | Structure | Name |
|---|---|---|
| 217 | 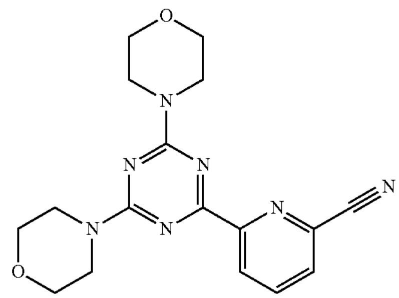 [SMILES: N#Cc1cccc(-c2nc(N3CCOCC3)nc(N3CCOCC3)n2)n1] | 6-(4,6-dimorpholino-1,3,5-triazin-2-yl)picolinonitrile |
| 218 | 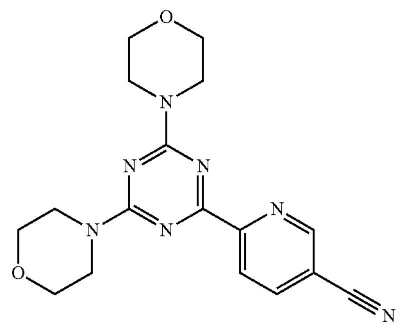 [SMILES: N#Cc1ccc(-c2nc(N3CCOCC3)nc(N3CCOCC3)n2)nc1] | 6-(4,6-dimorpholino-1,3,5-triazin-2-yl)nicotinonitrile |
| 219 | 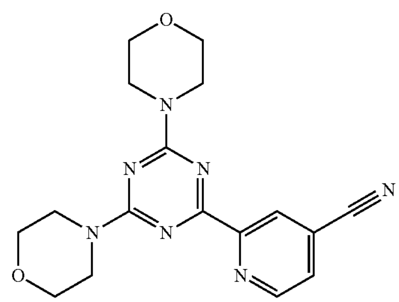 [SMILES: N#Cc1ccnc(-c2nc(N3CCOCC3)nc(N3CCOCC3)n2)c1] | 6-(4,6-dimorpholino-1,3,5-triazin-2-yl)isoniconitrile |
| 220 | 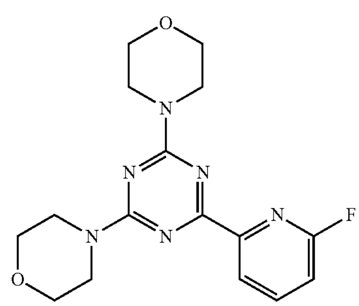 [SMILES: Fc1cccc(-c2nc(N3CCOCC3)nc(N3CCOCC3)n2)n1] | 4,4'-(6-(6-fluoropyridin-2-yl)-1,3,5-triazine-2,4-diyl)dimorpholine |
| 221 | 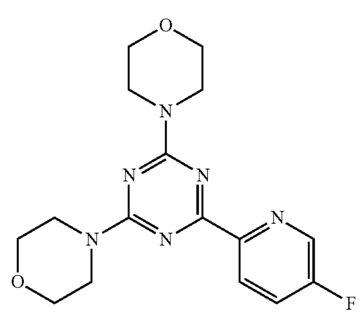 [SMILES: Fc1ccc(-c2nc(N3CCOCC3)nc(N3CCOCC3)n2)nc1] | 4,4'-(6-(5-fluoropyridin-2-yl)-1,3,5-triazine-2,4-diyl)dimorpholine |

TABLE 1-continued

| Cpd No. | Structure | Name |
|---|---|---|
| 222 | 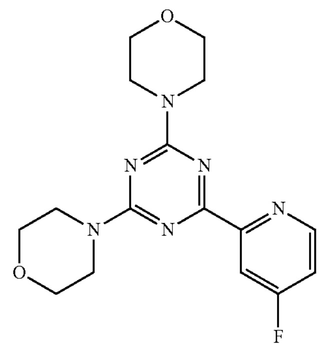 [SMILES: Fc1ccnc(-c2nc(N3CCOCC3)nc(N3CCOCC3)n2)c1] | 4,4'-(6-(4-fluoropyridin-2-yl)-1,3,5-triazine-2,4-diyl)dimorpholine |
| 223 | 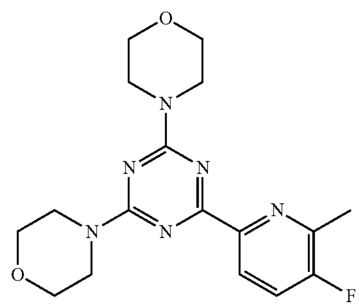 [SMILES: Cc1nc(-c2nc(N3CCOCC3)nc(N3CCOCC3)n2)ccc1F] | 4,4'-(6-(5-fluoro-6-methylpyridin-2-yl)-1,3,5-triazine-2,4-diyl)dimorpholine |
| 224 | 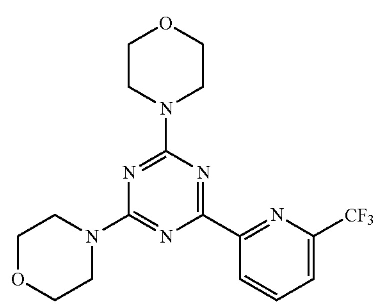 [SMILES: FC(F)(F)c1cccc(-c2nc(N3CCOCC3)nc(N3CCOCC3)n2)n1] | 4,4'-(6-(6-(trifluoromethyl)pyridin-2-yl)-1,3,5-triazine-2,4-diyl)dimorpholine |
| 225 | 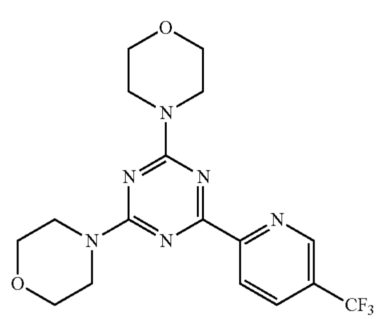 [SMILES: FC(F)(F)c1ccc(-c2nc(N3CCOCC3)nc(N3CCOCC3)n2)nc1] | 4,4'-(6-(5-(trifluoromethyl)pyridin-2-yl)-1,3,5-triazine-2,4-diyl)dimorpholine |

TABLE 1-continued

| Cpd No. | Structure | Name |
|---|---|---|
| 226 | 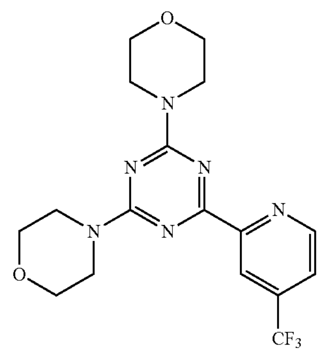 [SMILES: FC(F)(F)c1ccnc(-c2nc(N3CCOCC3)nc(N3CCOCC3)n2)c1] | 4,4'-(6-(4-(trifluoromethyl)pyridin-2-yl)-1,3,5-triazine-2,4-diyl)dimorpholine |
| 227 | 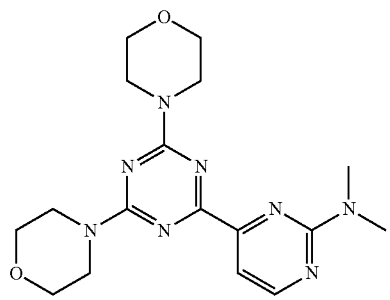 [SMILES: CN(C)c1nccc(-c2nc(N3CCOCC3)nc(N3CCOCC3)n2)n1] | 4-(4,6-dimorpholino-1,3,5-triazin-2-yl)-N,N-dimethylpyrimidin-2-amine |
| 228 | 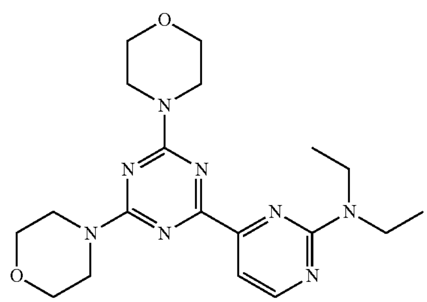 [SMILES: CCN(CC)c1nccc(-c2nc(N3CCOCC3)nc(N3CCOCC3)n2)n1] | 4-(4,6-dimorpholino-1,3,5-triazin-2-yl)-N,N-diethylpyrimidin-2-amine |
| 229 | 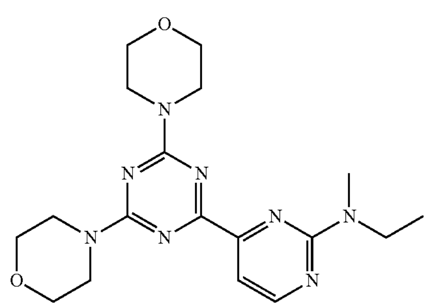 [SMILES: CCN(C)c1nccc(-c2nc(N3CCOCC3)nc(N3CCOCC3)n2)n1] | 4-(4,6-dimorpholino-1,3,5-triazin-2-yl)-N-ethyl-N-methylpyrimidin-2-amine |
| 230 | 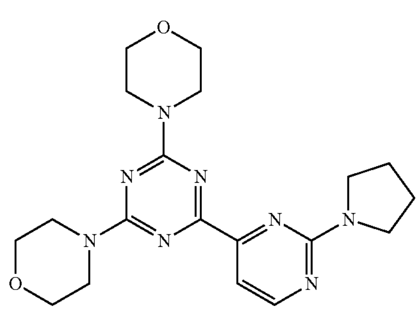 [SMILES: c1cc(-c2nc(N3CCOCC3)nc(N3CCOCC3)n2)nc(N2CCCC2)n1] | 4,4'-(6-(2-(pyrrolidin-1-yl)pyrimidin-4-yl)-1,3,5-triazine-2,4-diyl)dimorpholine |

TABLE 1-continued

| Cpd No. | Structure | Name |
|---|---|---|
| 231 | 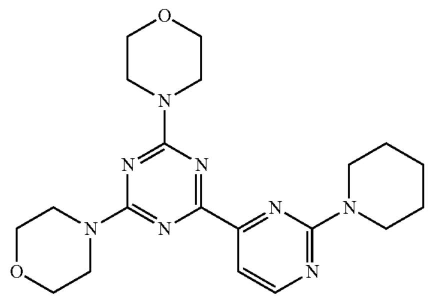 [SMILES: c1cc(-c2nc(N3CCOCC3)nc(N3CCOCC3)n2)nc(N2CCCCC2)n1] | 4,4'-(6-(2-(piperidin-1-yl)pyrimidin-4-yl)-1,3,5-triazine-2,4-diyl)dimorpholine |
| 232 | 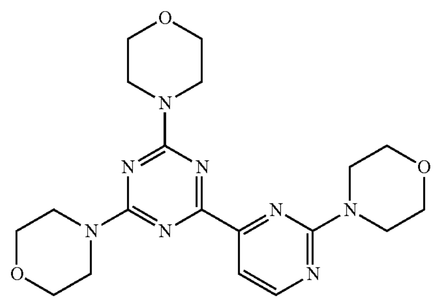 [SMILES: c1cc(-c2nc(N3CCOCC3)nc(N3CCOCC3)n2)nc(N2CCOCC2)n1] | 4,4'-(6-(2-morpholinopyrimidin-4-yl)-1,3,5-triazine-2,4-diyl)dimorpholine |
| 233 | 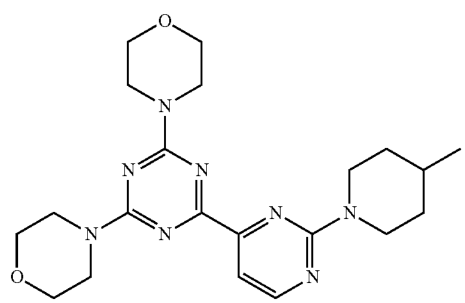 [SMILES: CC1CCN(c2nccc(-c3nc(N4CCOCC4)nc(N4CCOCC4)n3)n2)CC1] | 4,4'-(6-(2-(4-methylpiperidin-1-yl)pyrimidin-4-yl)-1,3,5-triazine-2,4-diyl)dimorpholine |
| 234 | 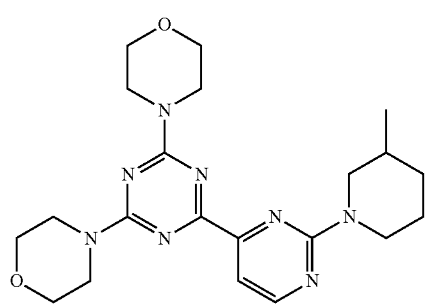 [SMILES: CC1CCCN(c2nccc(-c3nc(N4CCOCC4)nc(N4CCOCC4)n3)n2)C1] | 4,4'-(6-(2-(3-methylpiperidin-1-yl)pyrimidin-4-yl)-1,3,5-triazine-2,4-diyl)dimorpholine |
| 235 | 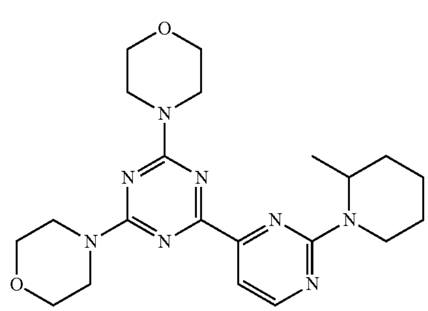 [SMILES: CC1CCCCN1c1nccc(-c2nc(N3CCOCC3)nc(N3CCOCC3)n2)n1] | 4,4'-(6-(2-(2-methylpiperidin-1-yl)pyrimidin-4-yl)-1,3,5-triazine-2,4-diyl)dimorpholine |

TABLE 1-continued

| Cpd No. | Structure | Name |
|---|---|---|
| 236 | 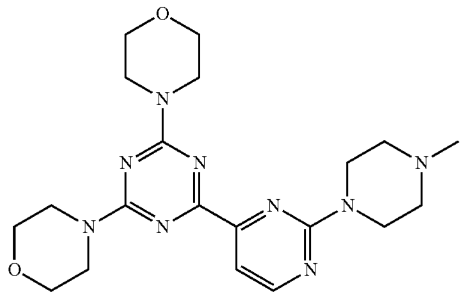 [SMILES: CN1CCN(c2nccc(-c3nc(N4CCOCC4)nc(N4CCOCC4)n3)n2)CC1] | 4,4'-(6-(2-(4-methylpiperazin-1-yl)pyrimidin-4-yl)-1,3,5-triazine-2,4-diyl)dimorpholine |
| 237 | 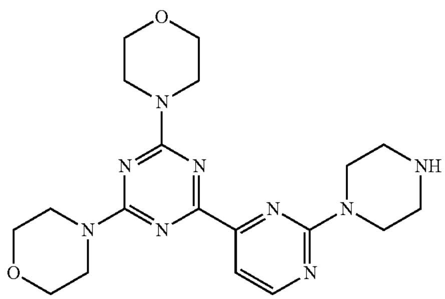 [SMILES: c1cc(-c2nc(N3CCOCC3)nc(N3CCOCC3)n2)nc(N2CCNCC2)n1] | 4,4'-(6-(2-(piperazin-1-yl)pyrimidin-4-yl)-1,3,5-triazine-2,4-diyl)dimorpholine |
| 238 | 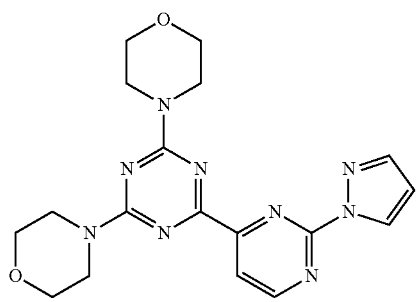 [SMILES: c1cnn(-c2nccc(-c3nc(N4CCOCC4)nc(N4CCOCC4)n3)n2)c1] | 4,4'-(6-(2-(1H-pyrazol-1-yl)pyrimidin-4-yl)-1,3,5-triazine-2,4-diyl)dimorpholine |
| 239 | 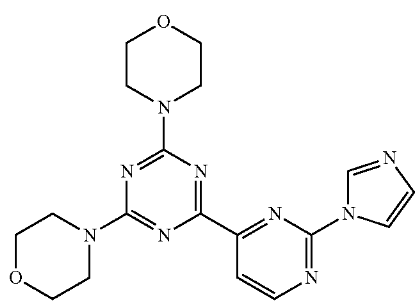 [SMILES: c1cn(-c2nccc(-c3nc(N4CCOCC4)nc(N4CCOCC4)n3)n2)cn1] | 4,4'-(6-(2-(1H-imidazol-1-yl)pyrimidin-4-yl)-1,3,5-triazine-2,4-diyl)dimorpholine |
| 240 | 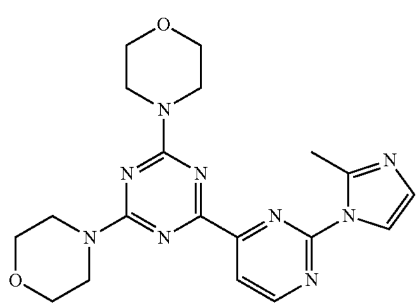 [SMILES: Cc1nccn1-c1nccc(-c2nc(N3CCOCC3)nc(N3CCOCC3)n2)n1] | 4,4'-(6-(2-(2-methyl-1H-imidazol-1-yl)pyrimidin-4-yl)-1,3,5-triazine-2,4-diyl)dimorpholine |

TABLE 1-continued

| Cpd No. | Structure | Name |
|---|---|---|
| 241 | 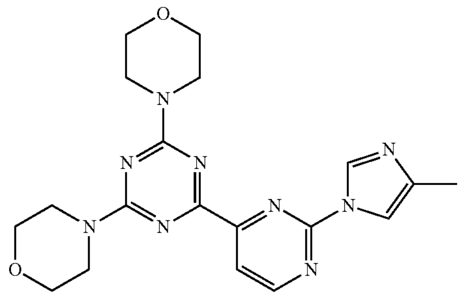 [SMILES: Cc1cn(-c2nccc(-c3nc(N4CCOCC4)nc(N4CCOCC4)n3)n2)cn1] | 4,4'-(6-(2-(4-methyl-1H-imidazol-1-yl)pyrimidin-4-yl)-1,3,5-triazine-2,4-diyl)dimorpholine |
| 242 | 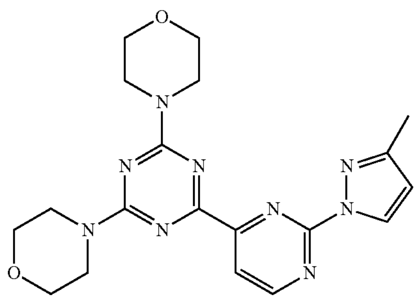 [SMILES: Cc1ccn(-c2nccc(-c3nc(N4CCOCC4)nc(N4CCOCC4)n3)n2)n1] | 4,4'-(6-(2-(3-methyl-1H-pyrazol-1-yl)pyrimidin-4-yl)-1,3,5-triazine-2,4-diyl)dimorpholine |
| 243 | 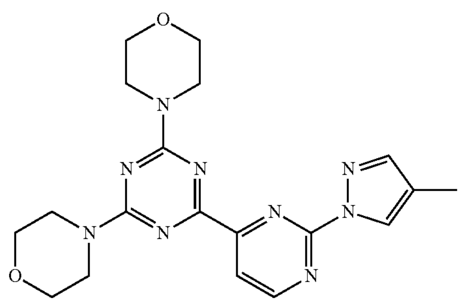 [SMILES: Cc1cnn(-c2nccc(-c3nc(N4CCOCC4)nc(N4CCOCC4)n3)n2)c1] | 4,4'-(6-(2-(4-methyl-1H-pyrazol-1-yl)pyrimidin-4-yl)-1,3,5-triazine-2,4-diyl)dimorpholine |
| 244 | 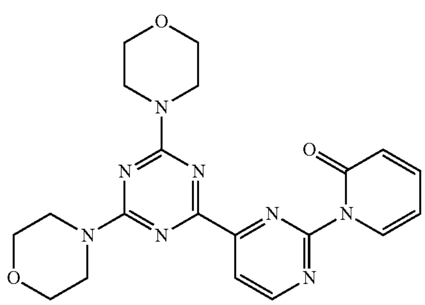 [SMILES: O=c1ccccn1-c1nccc(-c2nc(N3CCOCC3)nc(N3CCOCC3)n2)n1] | 1-(4-(4,6-dimorpholino-1,3,5-triazin-2-yl)pyrimidin-2-yl)pyridin-2(1H)-one |
| 245 | 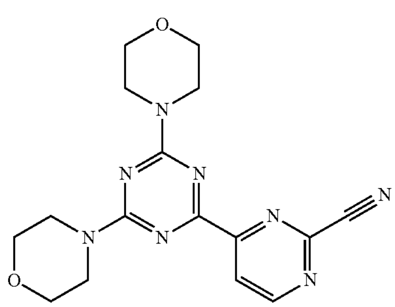 [SMILES: N#Cc1nccc(-c2nc(N3CCOCC3)nc(N3CCOCC3)n2)n1] | 4-(4,6-dimorpholino-1,3,5-triazin-2-yl)pyrimidine-2-carbonitrile |

TABLE 1-continued

| Cpd No. | Structure | Name |
|---|---|---|
| 246 | 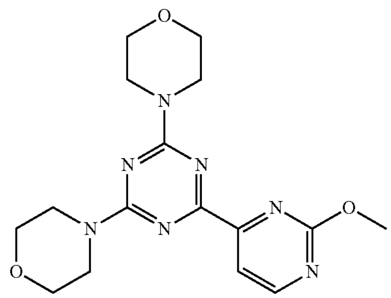 [SMILES: COc1nccc(-c2nc(N3CCOCC3)nc(N3CCOCC3)n2)n1] | 4,4'-(6-(2-methoxypyrimidin-4-yl)-1,3,5-triazine-2,4-diyl)dimorpholine |
| 247 | 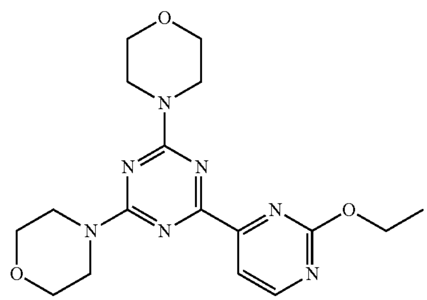 [SMILES: CCOc1nccc(-c2nc(N3CCOCC3)nc(N3CCOCC3)n2)n1] | 4,4'-(6-(2-ethoxypyrimidin-4-yl)-1,3,5-triazine-2,4-diyl)dimorpholine |
| 248 | 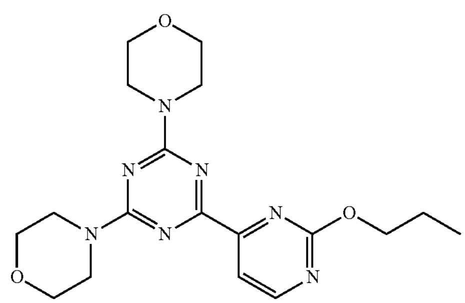 [SMILES: CCCOc1nccc(-c2nc(N3CCOCC3)nc(N3CCOCC3)n2)n1] | 4,4'-(6-(2-propoxypyrimidin-4-yl)-1,3,5-triazine-2,4-diyl)dimorpholine |
| 249 | 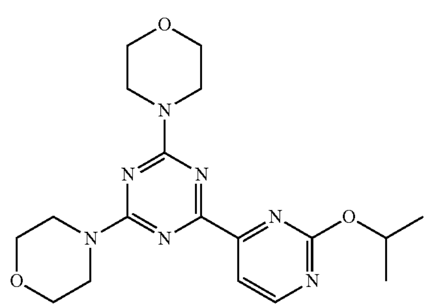 [SMILES: CC(C)Oc1nccc(-c2nc(N3CCOCC3)nc(N3CCOCC3)n2)n1] | 4,4'-(6-(2-isopropoxypyrimidin-4-yl)-1,3,5-triazine-2,4-diyl)dimorpholine |
| 250 | 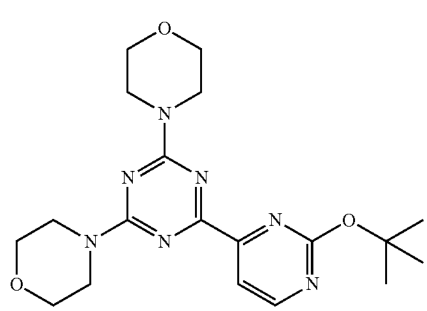 [SMILES: CC(C)(C)Oc1nccc(-c2nc(N3CCOCC3)nc(N3CCOCC3)n2)n1] | 4,4'-(6-(2-tert-butoxypyrimidin-4-yl)-1,3,5-triazine-2,4-diyl)dimorpholine |

TABLE 1-continued

| Cpd No. | Structure | Name |
|---|---|---|
| 251 | 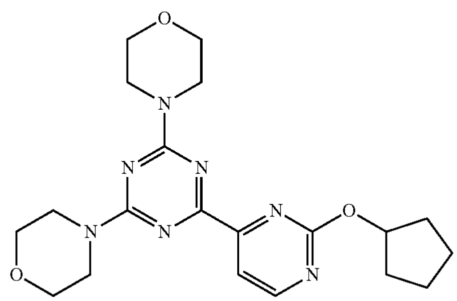 [SMILES: c1cc(-c2nc(N3CCOCC3)nc(N3CCOCC3)n2)nc(OC2CCCC2)n1] | 4,4'-(6-(2-(cyclopentyloxy)pyrimidin-4-yl)-1,3,5-triazine-2,4-diyl)dimorpholine |
| 252 | 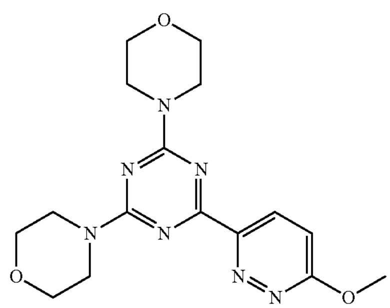 [SMILES: COc1ccc(-c2nc(N3CCOCC3)nc(N3CCOCC3)n2)nn1] | 4,4'-(6-(6-methoxypyridazin-3-yl)-1,3,5-triazine-2,4-diyl)dimorpholine |
| 253 | 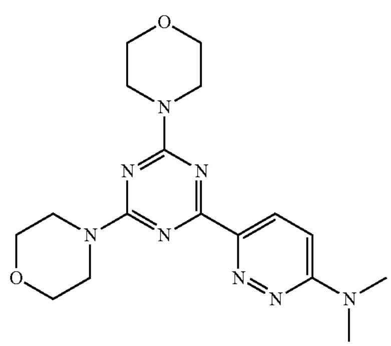 [SMILES: CN(C)c1ccc(-c2nc(N3CCOCC3)nc(N3CCOCC3)n2)nn1] | 6-(4,6-dimorpholino-1,3,5-triazin-2-yl)-N,N-dimethylpyridazin-3-amine |
| 254 | 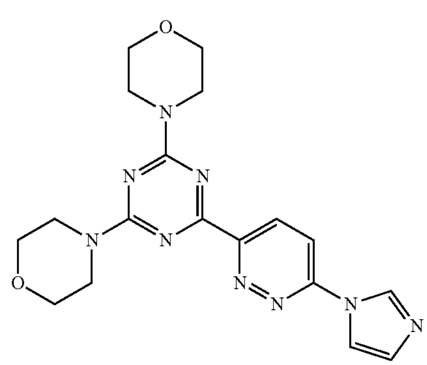 [SMILES: c1cn(-c2ccc(-c3nc(N4CCOCC4)nc(N4CCOCC4)n3)nn2)cn1] | 4,4'-(6-(6-(1H-imidazol-1-yl)pyridazin-3-yl)-1,3,5-triazine-2,4-diyl)dimorpholine |

TABLE 1-continued

| Cpd No. | Structure | Name |
|---|---|---|
| 255 | 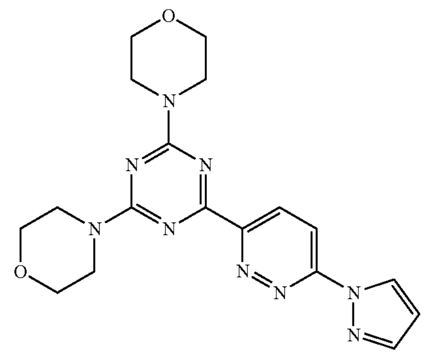 [SMILES: c1cnn(-c2ccc(-c3nc(N4CCOCC4)nc(N4CCOCC4)n3)nn2)c1] | 4,4'-(6-(6-(1H-pyrazol-1-yl)pyridazin-3-yl)-1,3,5-triazine-2,4-diyl)dimorpholine |
| 256 | 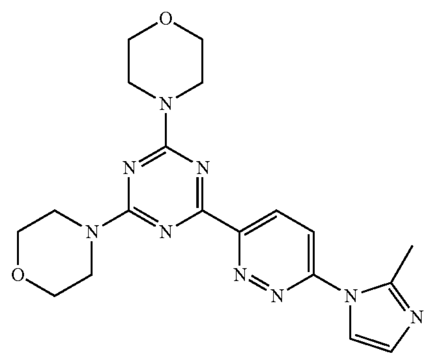 [SMILES: Cc1nccn1-c1ccc(-c2nc(N3CCOCC3)nc(N3CCOCC3)n2)nn1] | 4,4'-(6-(6-(2-methyl-1H-imidazol-1-yl)pyridazin-3-yl)-1,3,5-triazine-2,4-diyl)dimorpholine |
| 257 | 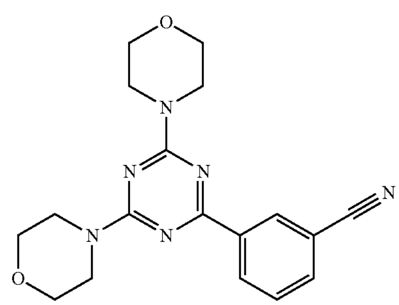 | 3-(4,6-dimorpholino-1,3,5-triazin-2-yl)benzonitrile |
| 258 | 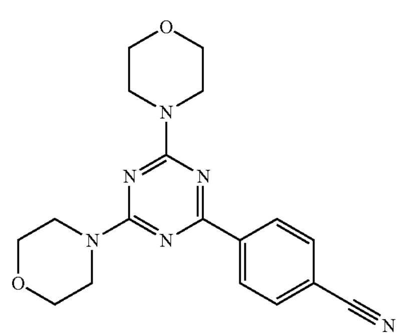 [SMILES: N#Cc1ccc(-c2nc(N3CCOCC3)nc(N3CCOCC3)n2)cc1] | 4-(4,6-dimorpholino-1,3,5-triazin-2-yl)benzonitrile |

TABLE 1-continued

| Cpd No. | Structure | Name |
|---|---|---|
| 259 | 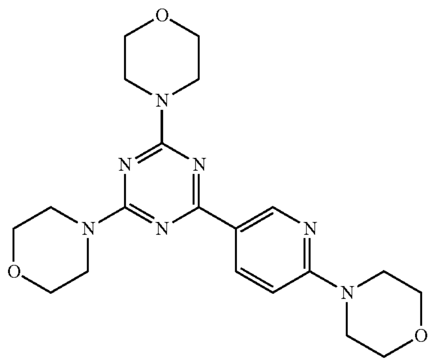 [SMILES: c1cc(N2CCOCC2)ncc1-c1nc(N2CCOCC2)nc(N2CCOCC2)n1] | 4,4'-(6-(6-morpholinopyridin-3-yl)-1,3,5-triazine-2,4-diyl)dimorpholine |

 = solid phase polymers

Table 2 gives the structures and the corresponding IUPAC names (using ChemDraw Ultra, Version 11.0.1 as well as lower and upper software versions thereof, CambridgeSoft Corp., Cambridge Mass.) of exemplary compounds Nos. 260-385 of formula (Ic).

TABLE 2

| Cpd. No. | Structure | Name |
|---|---|---|
| 260 | 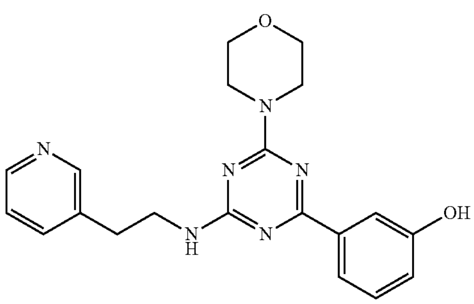 [SMILES: Oc1cccc(-c2nc(NCCc3cccnc3)nc(N3CCOCC3)n2)c1] | 3-(4-morpholino-6-(2-(pyridin-3-yl)ethylamino)-1,3,5-triazin-2-yl)phenol |
| 261 | 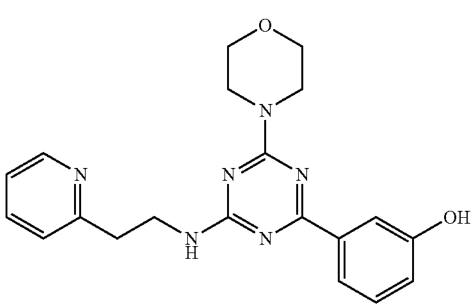 [SMILES: Oc1cccc(-c2nc(NCCc3ccccn3)nc(N3CCOCC3)n2)c1] | 3-(4-morpholino-6-(2-(pyridin-2-yl)ethylamino)-1,3,5-triazin-2-yl)phenol |

TABLE 2-continued

| Cpd. No. | Structure | Name |
|---|---|---|
| 262 | 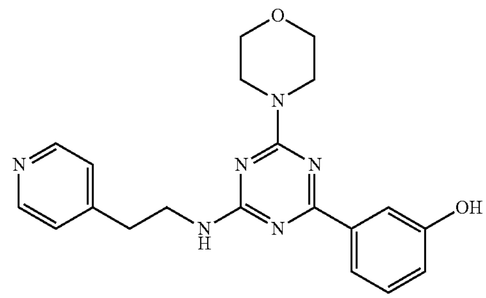 [SMILES: Oc1cccc(-c2nc(NCCc3ccncc3)nc(N3CCOCC3)n2)c1] | 3-(4-morpholino-6-(2-(pyridin-4-yl)ethylamino)-1,3,5-triazin-2-yl)phenol |
| 263 | 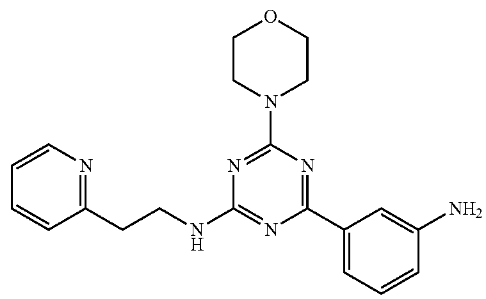 [SMILES: Nc1cccc(-c2nc(NCCc3ccccn3)nc(N3CCOCC3)n2)c1] | 4-(3-aminophenyl)-6-morpholino-N-(2-(pyridin-2-yl)ethyl)-1,3,5-triazin-2-amine |
| 264 | 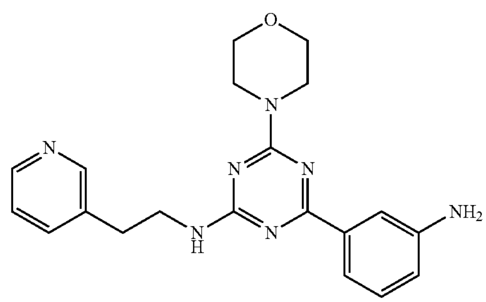 [SMILES: Nc1cccc(-c2nc(NCCc3cccnc3)nc(N3CCOCC3)n2)c1] | 4-(3-aminophenyl)-6-morpholino-N-(2-(pyridin-3-yl)ethyl)-1,3,5-triazin-2-amine |
| 265 | 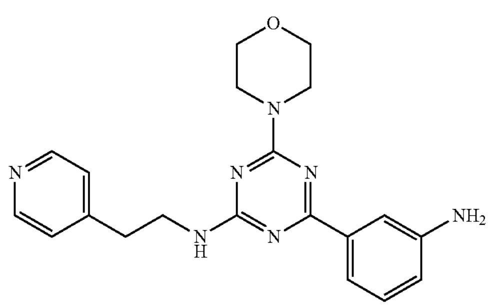 [SMILES: Nc1cccc(-c2nc(NCCc3ccncc3)nc(N3CCOCC3)n2)c1] | 4-(3-aminophenyl)-6-morpholino-N-(2-(pyridin-4-yl)ethyl)-1,3,5-triazin-2-amine |
| 266 | 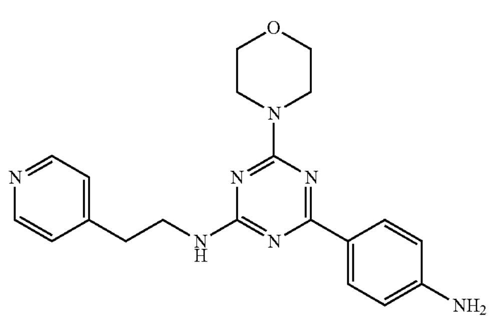 [SMILES: Nc1ccc(-c2nc(NCCc3ccncc3)nc(N3CCOCC3)n2)cc1] | 4-(4-aminophenyl)-6-morpholino-N-(2-(pyridin-4-yl)ethyl)-1,3,5-triazin-2-amine |

TABLE 2-continued

| Cpd. No. | Structure | Name |
|---|---|---|
| 267 | 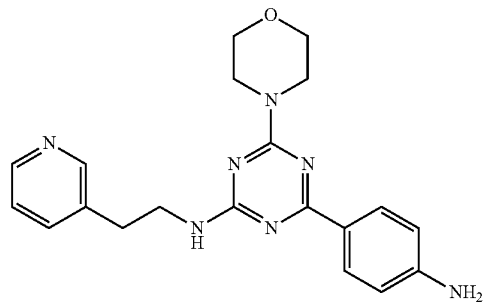 [SMILES: Nc1ccc(-c2nc(NCCc3cccnc3)nc(N3CCOCC3)n2)cc1] | 4-(4-aminophenyl)-6-morpholino-N-(2-(pyridin-3-yl)ethyl)-1,3,5-triazin-2-amine |
| 268 | 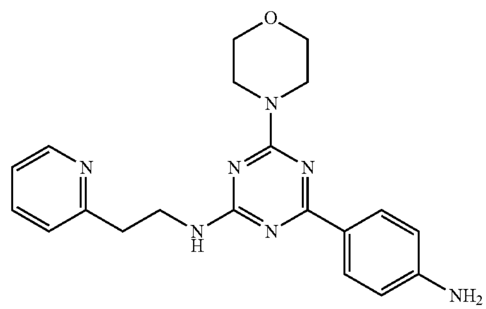 [SMILES: Nc1ccc(-c2nc(NCCc3ccccn3)nc(N3CCOCC3)n2)cc1] | 4-(4-aminophenyl)-6-morpholino-N-(2-(pyridin-2-yl)ethyl)-1,3,5-triazin-2-amine |
| 269 | 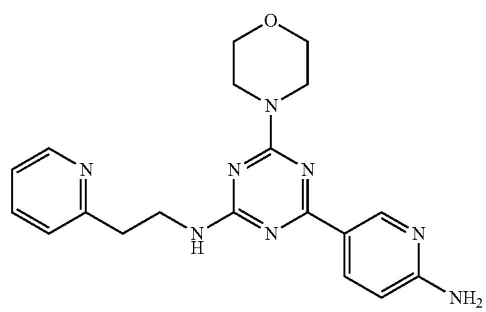 [SMILES: Nc1ccc(-c2nc(NCCc3ccccn3)nc(N3CCOCC3)n2)cn1] | 4-(6-aminopyridin-3-yl)-6-morpholino-N-(2-(pyridin-2-yl)ethyl)-1,3,5-triazin-2-amine |
| 270 | 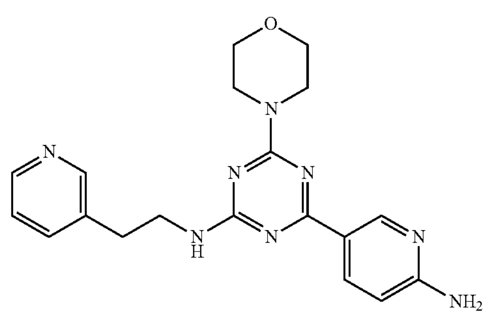 [SMILES: Nc1ccc(-c2nc(NCCc3cccnc3)nc(N3CCOCC3)n2)cn1] | 4-(6-aminopyridin-3-yl)-6-morpholino-N-(2-(pyridin-3-yl)ethyl)-1,3,5-triazin-2-amine |
| 271 | 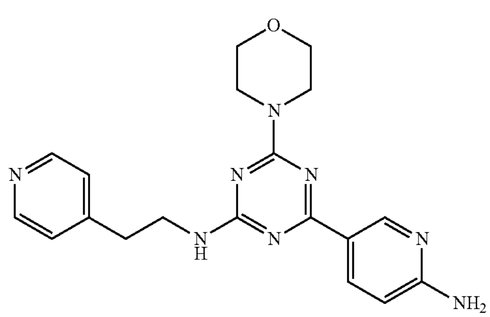 | 4-(6-aminopyridin-3-yl)-6-morpholino-N-(2-(pyridin-4-yl)ethyl)-1,3,5-triazin-2-amine |

TABLE 2-continued

| Cpd. No. | Structure | Name |
|---|---|---|
| 272 | 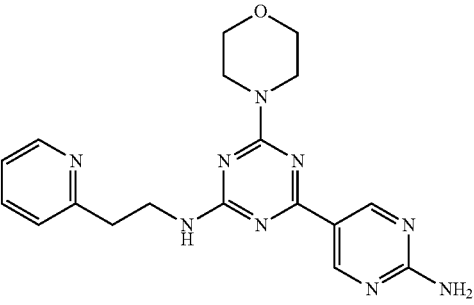 | 4-(2-aminopyrimidin-5-yl)-6-morpholino-N-(2-(pyridin-2-yl)ethyl)-1,3,5-triazin-2-amine |
| 273 | 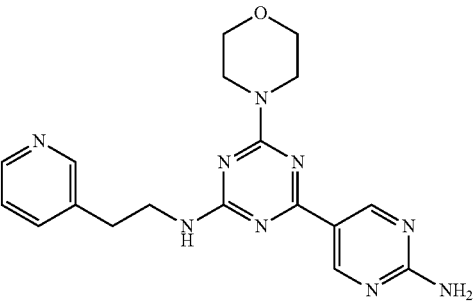 | 4-(2-aminopyrimidin-5-yl)-6-morpholino-N-(2-(pyridin-3-yl)ethyl)-1,3,5-triazin-2-amine |
| 274 | 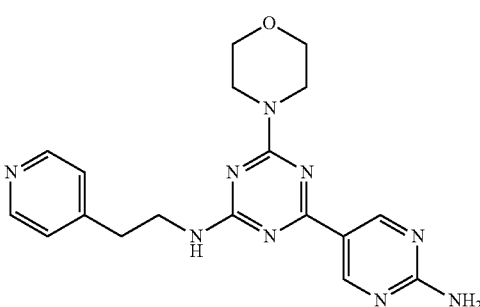 | 4-(2-aminopyrimidin-5-yl)-6-morpholino-N-(2-(pyridin-4-yl)ethyl)-1,3,5-triazin-2-amine |
| 275 | 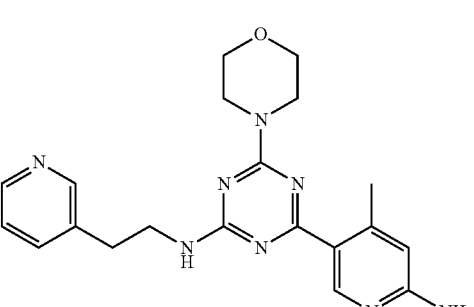 | 4-(6-amino-4-methylpyridin-3-yl)-6-morpholino-N-(2-(pyridin-3-yl)ethyl)-1,3,5-triazin-2-amine |
| 276 | 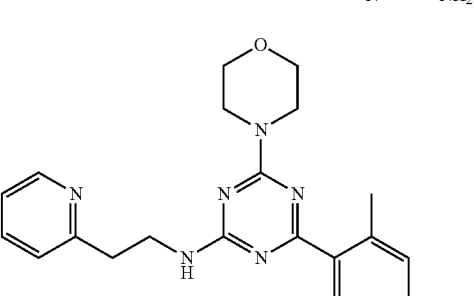 | 4-(6-amino-4-methylpyridin-3-yl)-6-morpholino-N-(2-(pyridin-2-yl)ethyl)-1,3,5-triazin-2-amine |

TABLE 2-continued

| Cpd. No. | Structure | Name |
|---|---|---|
| 277 | 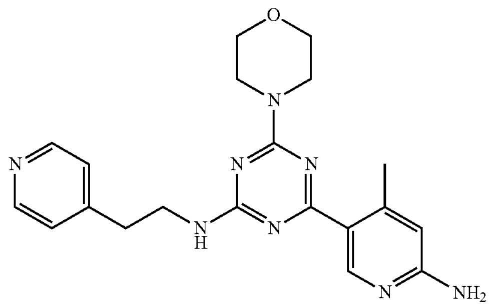 | 4-(6-amino-4-methylpyridin-3-yl)-6-morpholino-N-(2-(pyridin-4-yl)ethyl)-1,3,5-triazin-2-amine |
| 278 | 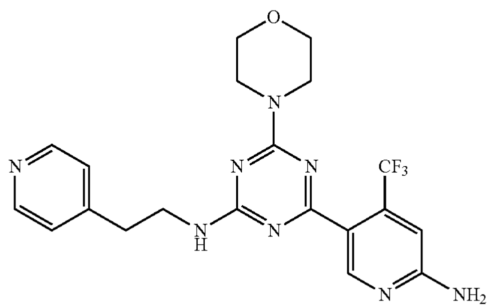 | 4-(6-amino-4-(trifluoromethyl)pyridin-3-yl)-6-morpholino-N-(2-(pyridin-4-yl)ethyl)-1,3,5-triazin-2-amine |
| 279 | 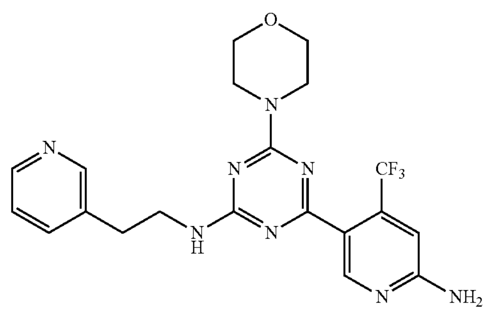 [SMILES: Nc1cc(C(F)(F)F)c(-c2nc(NCCc3cccnc3)nc(N3CCOCC3)n2)cn1] | 4-(6-amino-4-(trifluoromethyl)pyridin-3-yl)-6-morpholino-N-(2-(pyridin-3-yl)ethyl)-1,3,5-triazin-2-amine |
| 280 | 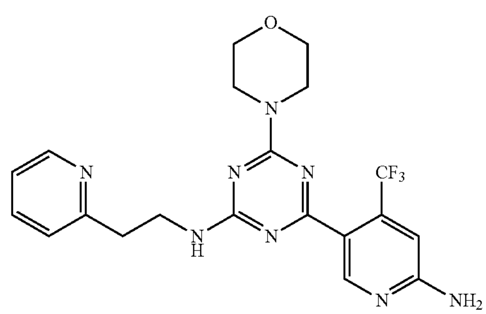 [SMILES: Nc1cc(C(F)(F)F)c(-c2nc(NCCc3ccccn3)nc(N3CCOCC3)n2)cn1] | 4-(6-amino-4-(trifluoromethyl)pyridin-3-yl)-6-morpholino-N-(2-(pyridin-2-yl)ethyl)-1,3,5-triazin-2-amine |
| 281 | 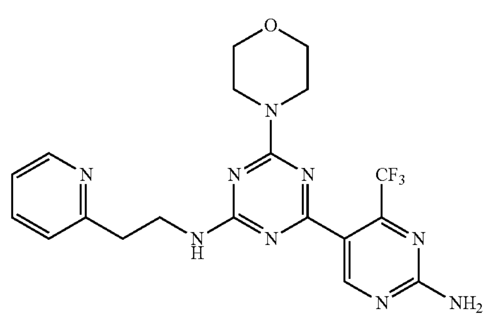 [SMILES: Nc1ncc(-c2nc(NCCc3ccccn3)nc(N3CCOCC3)n2)c(C(F)(F)F)n1] | 4-(2-amino-4-(trifluoromethyl)pyrimidin-5-yl)-6-morpholino-N-(2-(pyridin-2-yl)ethyl)-1,3,5-triazin-2-amine |

TABLE 2-continued

| Cpd. No. | Structure | Name |
|---|---|---|
| 282 | 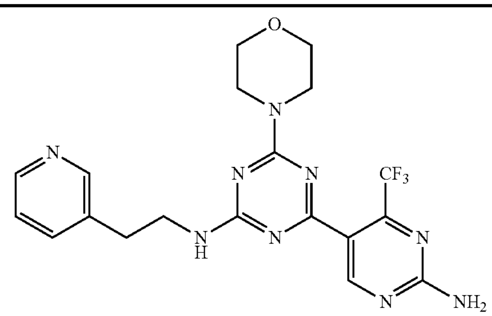 | 4-(2-amino-4-(trifluoromethyl)pyrimidin-5-yl)-6-morpholino-N-(2-(pyridin-3-yl)ethyl)-1,3,5-triazin-2-amine |
| 283 | 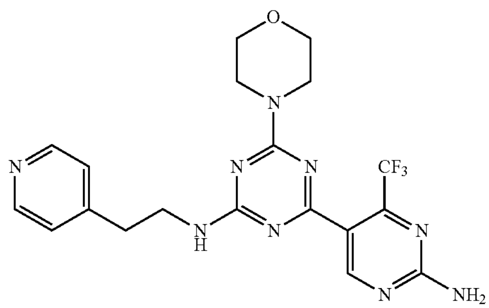 [SMILES: Nc1ncc(-c2nc(NCCc3ccncc3)nc(N3CCOCC3)n2)c(C(F)(F)F)n1] | 4-(2-amino-4-(trifluoromethyl)pyrimidin-5-yl)-6-morpholino-N-(2-(pyridin-4-yl)ethyl)-1,3,5-triazin-2-amine |
| 284 | 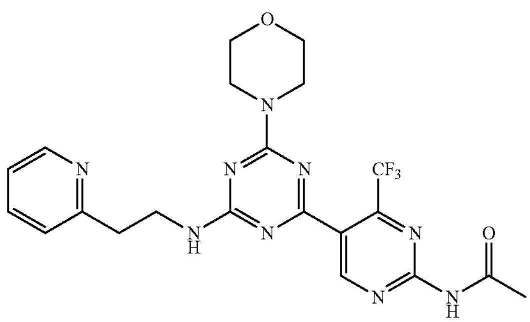 [SMILES: CC(=O)Nc1ncc(-c2nc(NCCc3ccccn3)nc(N3CCOCC3)n2)c(C(F)(F)F)n1] | N-(5-(4-morpholino-6-(2-(pyridin-2-yl)ethylamino)-1,3,5-triazin-2-yl)-4-(trifluoromethyl)pyrimidin-2-yl)acetamide |
| 285 | 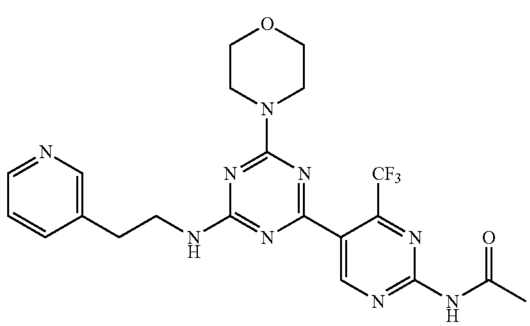 [SMILES: CC(=O)Nc1ncc(-c2nc(NCCc3cccnc3)nc(N3CCOCC3)n2)c(C(F)(F)F)n1] | N-(5-(4-morpholino-6-(2-(pyridin-3-yl)ethylamino)-1,3,5-triazin-2-yl)-4-(trifluoromethyl)pyrimidin-2-yl)acetamide |
| 286 | 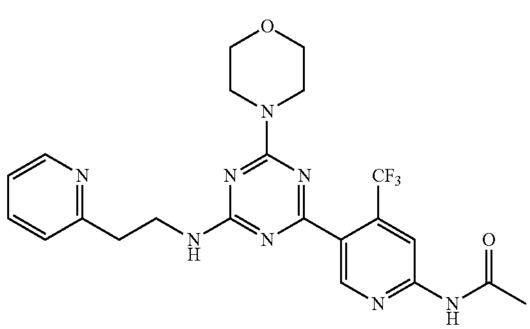 [SMILES: CC(=O)Nc1cc(C(F)(F)F)c(-c2nc(NCCc3ccccn3)nc(N3CCOCC3)n2)cn1] | N-(5-(4-morpholino-6-(2-(pyridin-2-yl)ethylamino)-1,3,5-triazin-2-yl)-4-(trifluoromethyl)pyridin-2-yl)acetamide |

TABLE 2-continued

| Cpd. No. | Structure | Name |
|---|---|---|
| 287 | 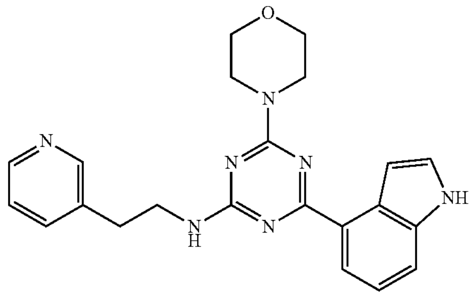 [SMILES: c1cncc(CCNc2nc(-c3cccc4[nH]ccc34)nc(N3CCOCC3)n2)c1] | 4-(1H-indol-4-yl)-6-morpholino-N-(2-(pyridin-3-yl)ethyl)-1,3,5-triazin-2-amine |
| 288 | 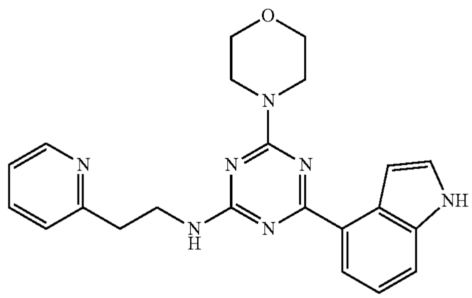 [SMILES: c1ccc(CCNc2nc(-c3cccc4[nH]ccc34)nc(N3CCOCC3)n2)nc1] | 4-(1H-indol-4-yl)-6-morpholino-N-(2-(pyridin-2-yl)ethyl)-1,3,5-triazin-2-amine |
| 289 | 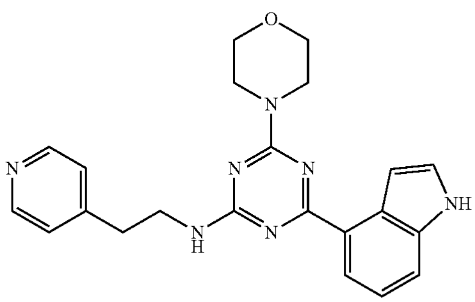 [SMILES: c1cc(-c2nc(NCCc3ccncc3)nc(N3CCOCC3)n2)c2cc[nH]c2c1] | 4-(1H-indol-4-yl)-6-morpholino-N-(2-(pyridin-4-yl)ethyl)-1,3,5-triazin-2-amine |
| 290 | 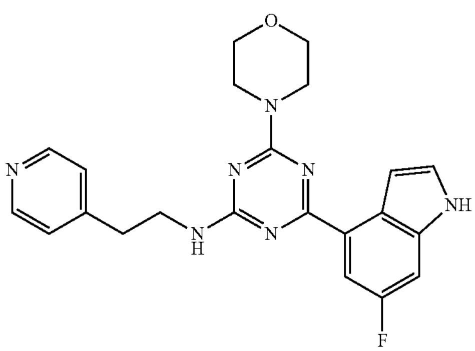 [SMILES: Fc1cc(-c2nc(NCCc3ccncc3)nc(N3CCOCC3)n2)c2cc[nH]c2c1] | 4-(6-fluoro-1H-indol-4-yl)-6-morpholino-N-(2-(pyridin-4-yl)ethyl)-1,3,5-triazin-2-amine |
| 291 | 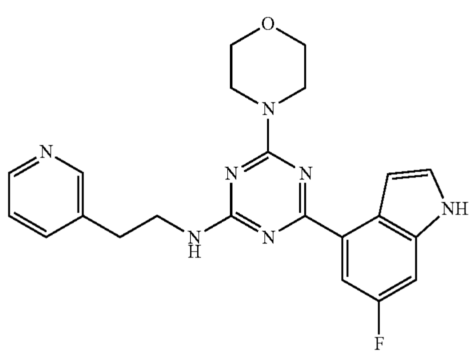 [SMILES: Fc1cc(-c2nc(NCCc3cccnc3)nc(N3CCOCC3)n2)c2cc[nH]c2c1] | 4-(6-fluoro-1H-indol-4-yl)-6-morpholino-N-(2-(pyridin-3-yl)ethyl)-1,3,5-triazin-2-amine |

TABLE 2-continued

| Cpd. No. | Structure | Name |
|---|---|---|
| 292 | 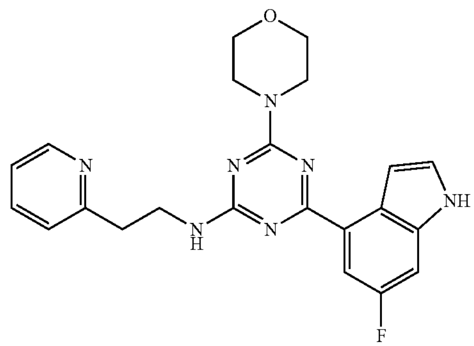 [SMILES: Fc1cc(-c2nc(NCCc3ccccn3)nc(N3CCOCC3)n2)c2cc[nH]c2c1] | 4-(6-fluoro-1H-indol-4-yl)-6-morpholino-N-(2-(pyridin-2-yl)ethyl)-1,3,5-triazin-2-amine |
| 293 | 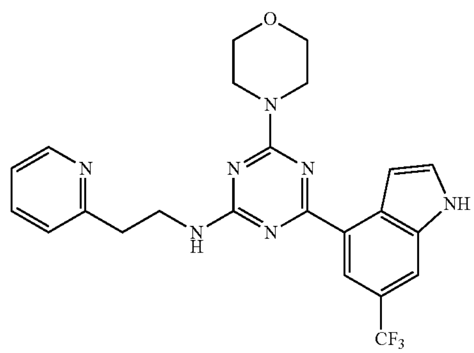 [SMILES: FC(F)(F)c1cc(-c2nc(NCCc3ccccn3)nc(N3CCOCC3)n2)c2cc[nH]c2c1] | 4-morpholino-N-(2-(pyridin-2-yl)ethyl)-6-(6-(trifluoromethyl)-1H-indol-4-yl)-1,3,5-triazin-2-amine |
| 294 | 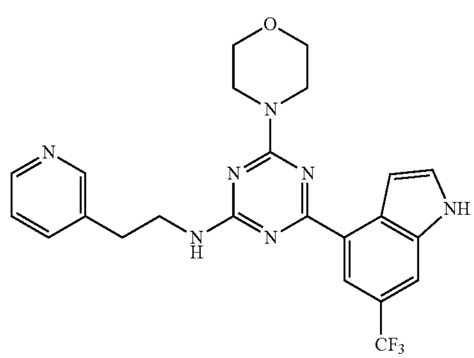 [SMILES: FC(F)(F)c1cc(-c2nc(NCCc3cccnc3)nc(N3CCOCC3)n2)c2cc[nH]c2c1] | 4-morpholino-N-(2-(pyridin-3-yl)ethyl)-6-(6-(trifluoromethyl)-1H-indol-4-yl)-1,3,5-triazin-2-amine |
| 295 | 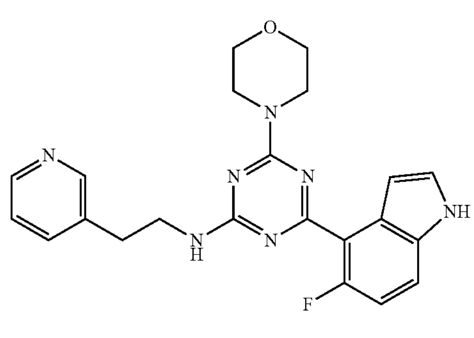 [SMILES: Fc1ccc2[nH]ccc2c1-c1nc(NCCc2cccnc2)nc(N2CCOCC2)n1] | 4-(5-fluoro-1H-indol-4-yl)-6-morpholino-N-(2-(pyridin-3-yl)ethyl)-1,3,5-triazin-2-amine |

TABLE 2-continued

| Cpd. No. | Structure | Name |
|---|---|---|
| 296 | 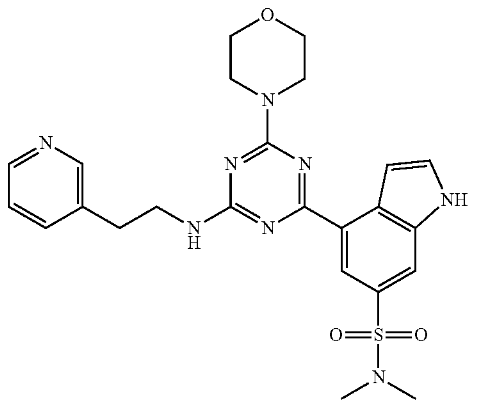 [SMILES: CN(C)S(=O)(=O)c1cc(-c2nc(NCCc3cccnc3)nc(N3CCOCC3)n2)c2cc[nH]c2c1] | N,N-dimethyl-4-(4-morpholino-6-(2-(pyridin-3-yl)ethylamino)-1,3,5-triazin-2-yl)-1H-indole-6-sulfonamide |
| 297 | 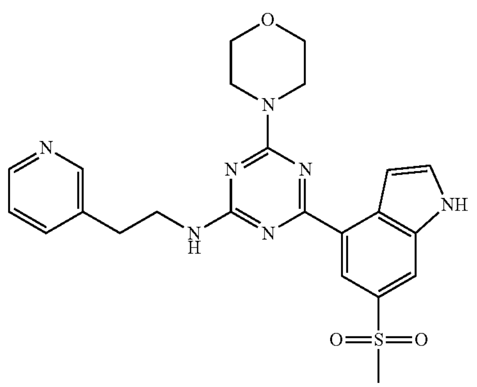 [SMILES: CS(=O)(=O)c1cc(-c2nc(NCCc3cccnc3)nc(N3CCOCC3)n2)c2cc[nH]c2c1] | 4-(6-(methylsulfonyl)-1H-indol-4-yl)-6-morpholino-N-(2-(pyridin-3-yl)ethyl)-1,3,5-triazin-2-amine |
| 298 | 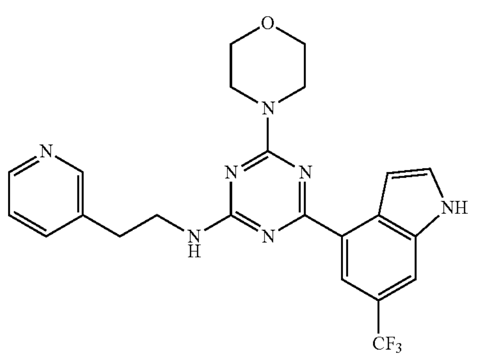 [SMILES: FC(F)(F)c1cc(-c2nc(NCCc3cccnc3)nc(N3CCOCC3)n2)c2cc[nH]c2c1] | 4-morpholino-N-(2-(pyridin-3-yl)ethyl)-6-(6-(trifluoromethyl)-1H-indol-4-yl)-1,3,5-triazin-2-amine |
| 299 | 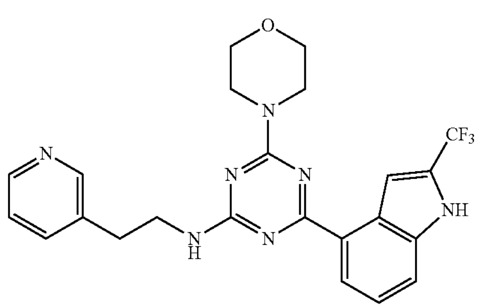 [SMILES: FC(F)(F)c1cc2c(-c3nc(NCCc4cccnc4)nc(N4CCOCC4)n3)cccc2[nH]1] | 4-morpholino-N-(2-(pyridin-3-yl)ethyl)-6-(2-(trifluoromethyl)-1H-indol-4-yl)-1,3,5-triazin-2-amine |

| Cpd. No. | Structure | Name |
|---|---|---|
| 300 | 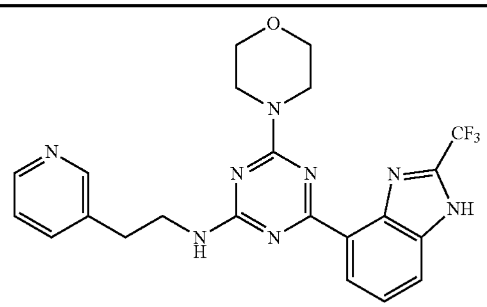 | 4-morpholino-N-(2-(pyridin-3-yl)ethyl)-6-(2-(trifluoromethyl)-1H-benzo[d]imidazol-4-yl)-1,3,5-triazin-2-amine |
| 301 | 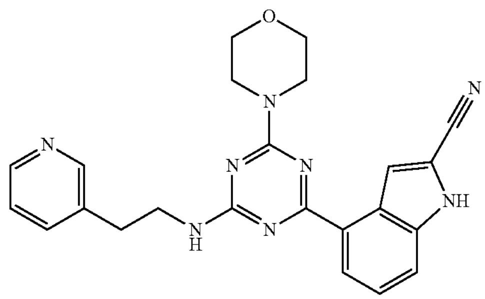 [SMILES: N#Cc1cc2c(-c3nc(NCCc4cccnc4)nc(N4CCOCC4)n3)cccc2[nH]1] | 4-(4-morpholino-6-(2-(pyridin-3-yl)ethylamino)-1,3,5-triazin-2-yl)-1H-indole-2-carbonitrile |
| 302 | 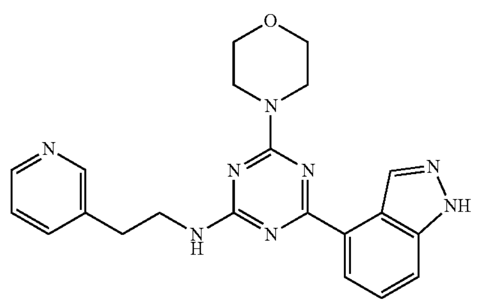 [SMILES: c1cncc(CCNc2nc(-c3cccc4[nH]ncc34)nc(N3CCOCC3)n2)c1] | 4-(1H-indazol-4-yl)-6-morpholino-N-(2-(pyridin-3-yl)ethyl)-1,3,5-triazin-2-amine |
| 303 | 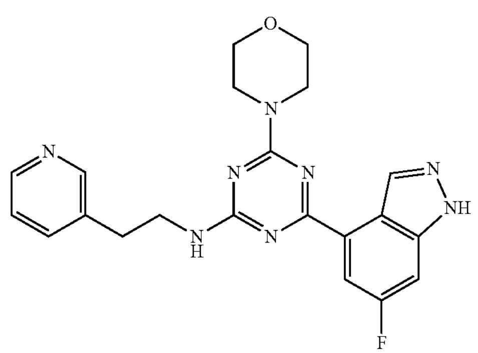 [SMILES: Fc1cc(-c2nc(NCCc3cccnc3)nc(N3CCOCC3)n2)c2cn[nH]c2c1] | 4-(6-fluoro-1H-indazol-4-yl)-6-morpholino-N-(2-(pyridin-3-yl)ethyl)-1,3,5-triazin-2-amine |
| 304 | 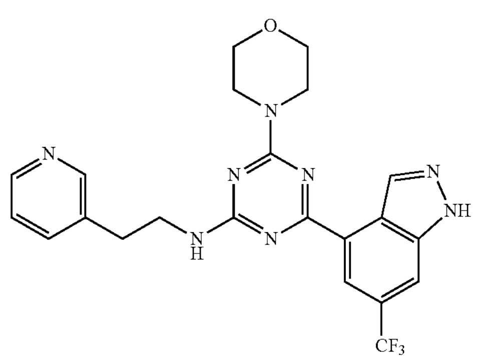 [SMILES: FC(F)(F)c1cc(-c2nc(NCCc3cccnc3)nc(N3CCOCC3)n2)c2cn[nH]c2c1] | 4-morpholino-N-(2-(pyridin-3-yl)ethyl)-6-(6-(trifluoromethyl)-1H-indazol-4-yl)-1,3,5-triazin-2-amine |

TABLE 2-continued

| Cpd. No. | Structure | Name |
|---|---|---|
| 305 | 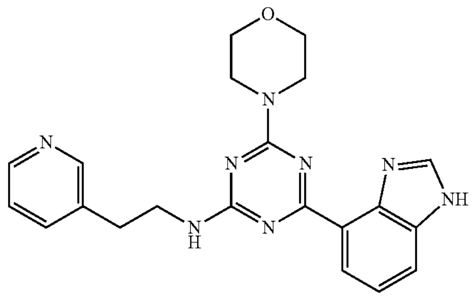 [SMILES: c1cncc(CCNc2nc(-c3cccc4[nH]cnc34)nc(N3CCOCC3)n2)c1] | 4-(1H-benzo[d]imidazol-4-yl)-6-morpholino-N-(2-(pyridin-3-yl)ethyl)-1,3,5-triazin-2-amine |
| 306 | 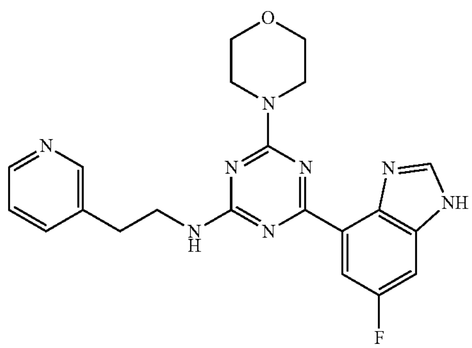 [SMILES: Fc1cc(-c2nc(NCCc3cccnc3)nc(N3CCOCC3)n2)c2nc[nH]c2c1] | 4-(6-fluoro-1H-benzo[d]imidazol-4-yl)-6-morpholino-N-(2-(pyridin-3-yl)ethyl)-1,3,5-triazin-2-amine |
| 307 | 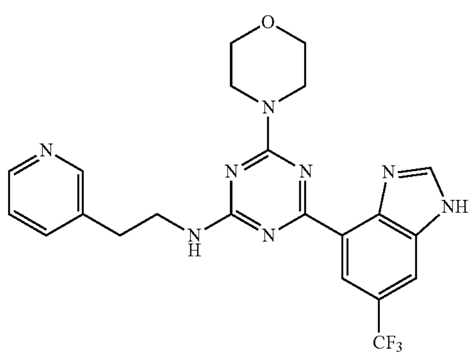 [SMILES: FC(F)(F)c1cc(-c2nc(NCCc3cccnc3)nc(N3CCOCC3)n2)c2nc[nH]c2c1] | 4-morpholino-N-(2-(pyridin-3-yl)ethyl)-6-(6-(trifluoromethyl)-1H-benzo[d]imidazol-4-yl)-1,3,5-triazin-2-amine |
| 308 | 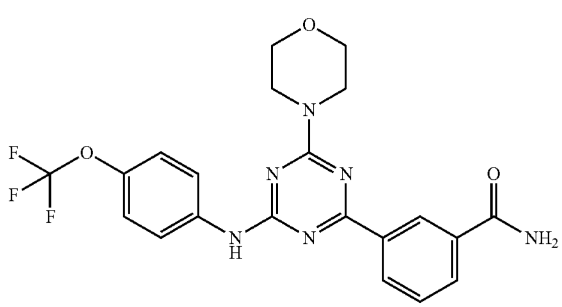 [SMILES: NC(=O)c1cccc(-c2nc(Nc3ccc(OC(F)(F)F)cc3)nc(N3CCOCC3)n2)c1] | 3-(4-morpholino-6-(4-(trifluoromethoxy)phenylamino)-1,3,5-triazin-2-yl)benzamide |

TABLE 2-continued
| Cpd. No. | Structure | Name |
|---|---|---|
| 309 | 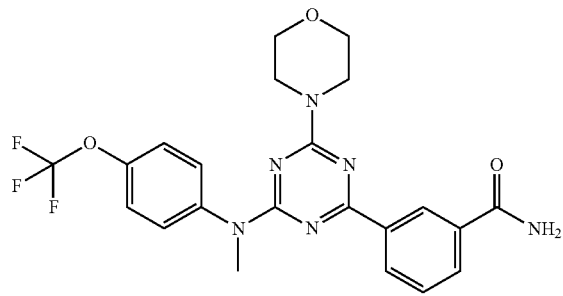 [SMILES: CN(c1ccc(OC(F)(F)F)cc1)c1nc(-c2cccc(C(N)=O)c2)nc(N2CCOCC2)n1] | 3-(4-(methyl(4-(trifluoromethoxy)phenyl)amino)-6-morpholino-1,3,5-triazin-2-yl)benzamide |
| 340 | 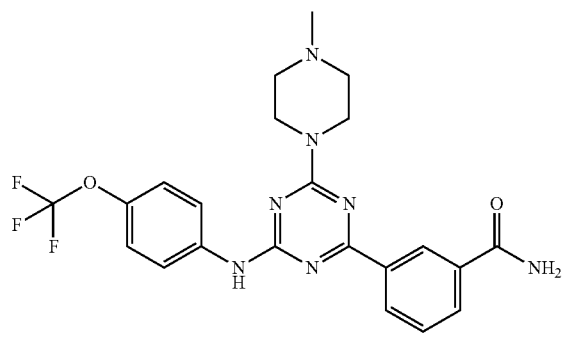 [SMILES: CN1CCN(c2nc(Nc3ccc(OC(F)(F)F)cc3)nc(-c3cccc(C(N)=O)c3)n2)CC1] | 3-(4-(4-methylpiperazin-1-yl)-6-(4-(trifluoromethoxy)phenylamino)-1,3,5-triazin-2-yl)benzamide |
| 341 | 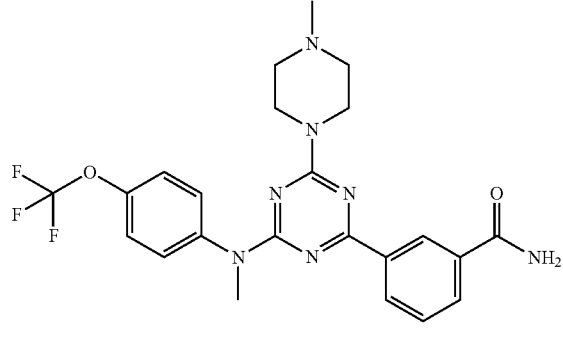 [SMILES: CN1CCN(c2nc(-c3cccc(C(N)=O)c3)nc(N(C)c3ccc(OC(F)(F)F)cc3)n2)CC1] | 3-(4-(methyl(4-(trifluoromethoxy)phenyl)amino)-6-(4-methylpiperazin-1-yl)-1,3,5-triazin-2-yl)benzamide |
| 342 | 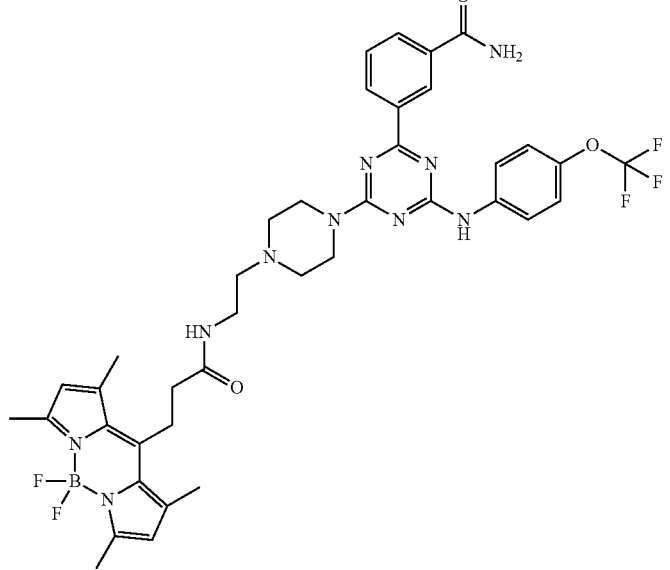 | |

TABLE 2-continued
| Cpd. No. | Structure | Name |
|---|---|---|
| 343 | 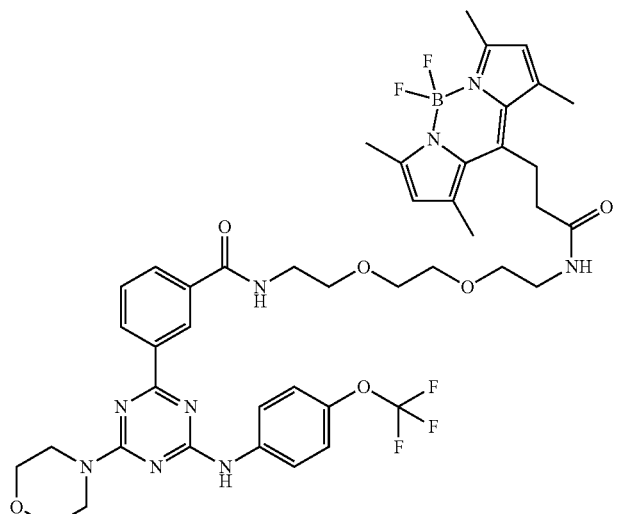 | |
| 344 | 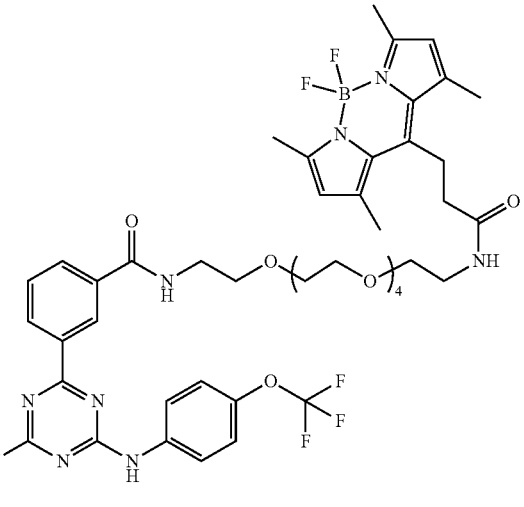 | |
| 345 | 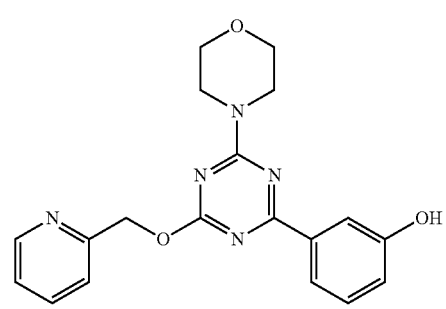 [SMILES: Oc1cccc(-c2nc(OCc3ccccn3)nc(N3CCOCC3)n2)c1] | 3-(4-morpholino-6-(pyridin-2-ylmethoxy)-1,3,5-triazin-2-yl)phenol |

TABLE 2-continued

| Cpd. No. | Structure | Name |
|---|---|---|
| 346 | 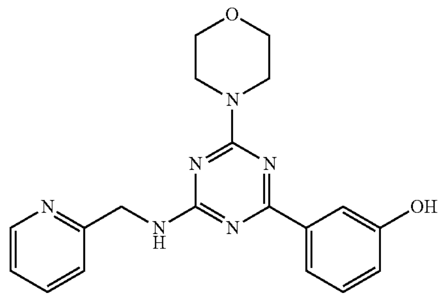 [SMILES: Oc1cccc(-c2nc(NCc3ccccn3)nc(N3CCOCC3)n2)c1] | 3-(4-morpholino-6-(pyridin-2-ylmethylamino)-1,3,5-triazin-2-yl)phenol |
| 347 | 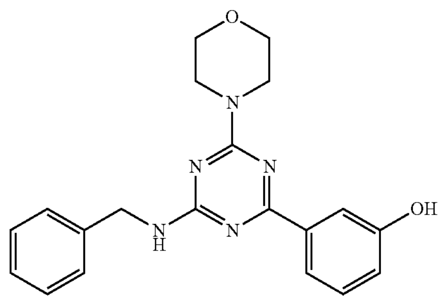 [SMILES: Oc1cccc(-c2nc(NCc3ccccc3)nc(N3CCOCC3)n2)c1] | 3-(4-(benzylamino)-6-morpholino-1,3,5-triazin-2-yl)phenol |
| 348 | 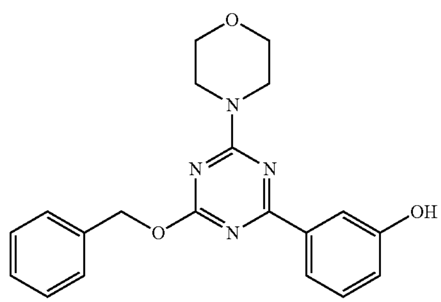 [SMILES: Oc1cccc(-c2nc(OCc3ccccc3)nc(N3CCOCC3)n2)c1] | 3-(4-(benzyloxy)-6-morpholino-1,3,5-triazin-2-yl)phenol |
| 349 | 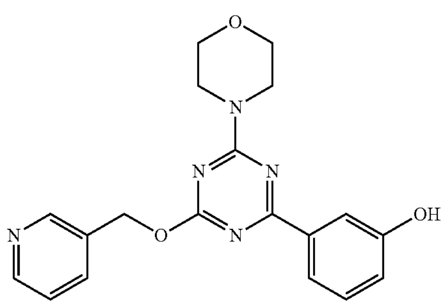 [SMILES: Oc1cccc(-c2nc(OCc3cccnc3)nc(N3CCOCC3)n2)c1] | 3-(4-morpholino-6-(pyridin-3-ylmethoxy)-1,3,5-triazin-2-yl)phenol |
| 350 | 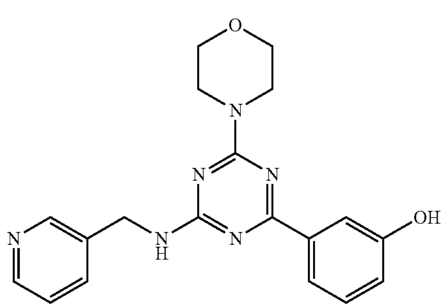 [SMILES: Oc1cccc(-c2nc(NCc3cccnc3)nc(N3CCOCC3)n2)c1] | 3-(4-morpholino-6-(pyridin-3-ylmethylamino)-1,3,5-triazin-2-yl)phenol |

TABLE 2-continued

| Cpd. No. | Structure | Name |
|---|---|---|
| 351 | 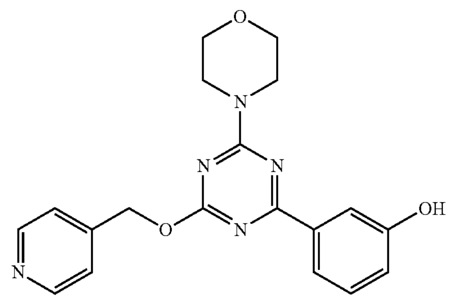 [SMILES: Oc1cccc(-c2nc(OCc3ccncc3)nc(N3CCOCC3)n2)c1] | 3-(4-morpholino-6-(pyridin-4-ylmethoxy)-1,3,5-triazin-2-yl)phenol |
| 352 | 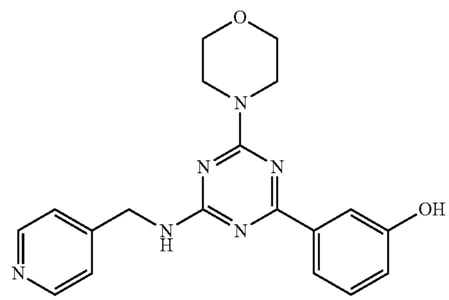 [SMILES: Oc1cccc(-c2nc(NCc3ccncc3)nc(N3CCOCC3)n2)c1] | 3-(4-morpholino-6-(pyridin-4-ylmethylamino)-1,3,5-triazin-2-yl)phenol |
| 353 | 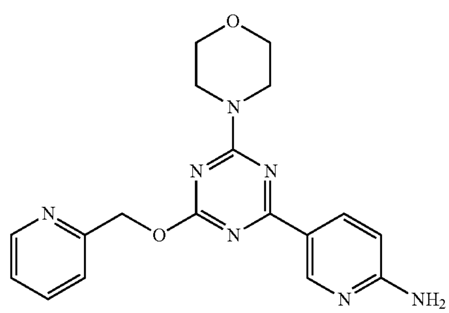 [SMILES: Nc1ccc(-c2nc(OCc3ccccn3)nc(N3CCOCC3)n2)cn1] | 5-(4-morpholino-6-(pyridin-2-ylmethoxy)-1,3,5-triazin-2-yl)pyridin-2-amine |
| 354 | 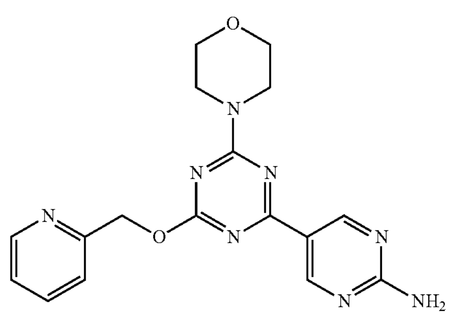 [SMILES: Nc1ncc(-c2nc(OCc3ccccn3)nc(N3CCOCC3)n2)cn1] | 5-(4-morpholino-6-(pyridin-2-ylmethoxy)-1,3,5-triazin-2-yl)pyrimidin-2-amine |
| 355 | 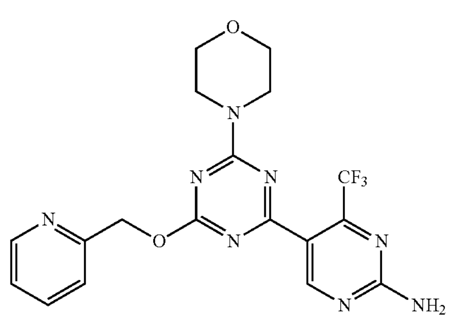 [SMILES: Nc1ncc(-c2nc(OCc3ccccn3)nc(N3CCOCC3)n2)c(C(F)(F)F)n1] | 5-(4-morpholino-6-(pyridin-2-ylmethoxy)-1,3,5-triazin-2-yl)-4-(trifluoromethyl)pyrimidin-2-amine |

| Cpd. No. | Structure | Name |
|---|---|---|
| 356 | 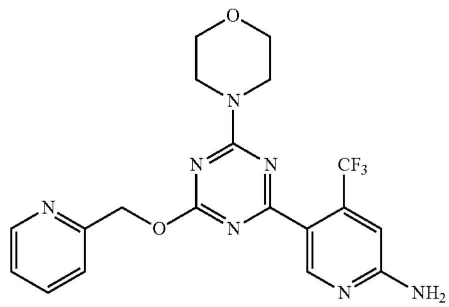 [SMILES: Nc1cc(C(F)(F)F)c(-c2nc(OCc3ccccn3)nc(N3CCOCC3)n2)cn1] | 5-(4-morpholino-6-(pyridin-2-ylmethoxy)-1,3,5-triazin-2-yl)-4-(trifluoromethyl)pyridin-2-amine |
| 357 | 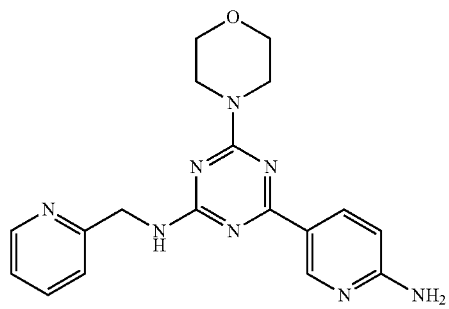 | 4-(6-aminopyridin-3-yl)-6-morpholino-N-(pyridin-2-ylmethyl)-1,3,5-triazin-2-amine |
| 358 | 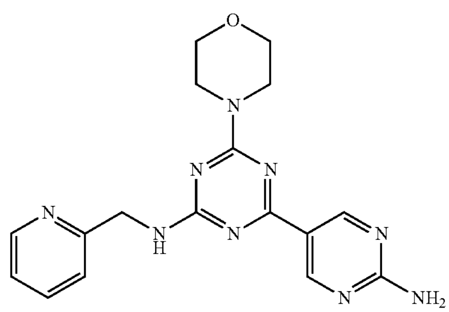 [SMILES: Nc1ncc(-c2nc(NCc3ccccn3)nc(N3CCOCC3)n2)cn1] | 4-(2-aminopyrimidin-5-yl)-6-morpholino-N-(pyridin-2-ylmethyl)-1,3,5-triazin-2-amine |
| 359 | 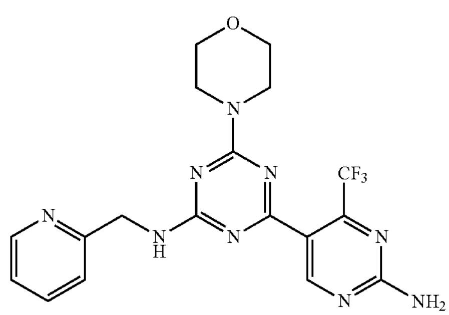 [SMILES: Nc1ncc(-c2nc(NCc3ccccn3)nc(N3CCOCC3)n2)c(C(F)(F)F)n1] | 4-(2-amino-4-(trifluoromethyl)pyrimidin-5-yl)-6-morpholino-N-(pyridin-2-ylmethyl)-1,3,5-triazin-2-amine |
| 360 | 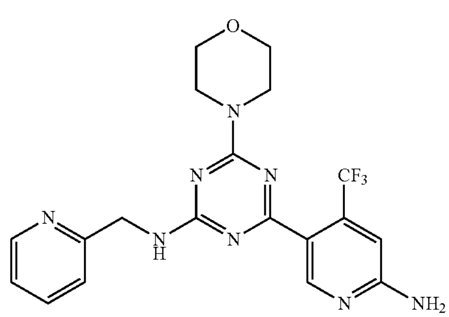 [SMILES: Nc1cc(C(F)(F)F)c(-c2nc(NCc3ccccn3)nc(N3CCOCC3)n2)cn1] | 4-(6-amino-4-(trifluoromethyl)pyridin-3-yl)-6-morpholino-N-(pyridin-2-ylmethyl)-1,3,5-triazin-2-amine |

TABLE 2-continued

| Cpd. No. | Structure | Name |
|---|---|---|
| 361 | 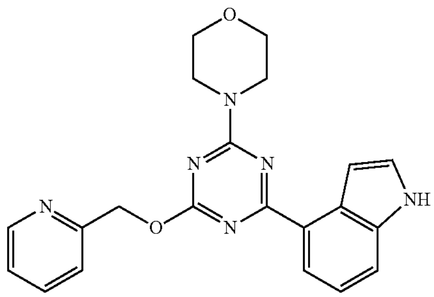 [SMILES: c1ccc(COc2nc(-c3cccc4[nH]ccc34)nc(N3CCOCC3)n2)nc1] | 4-(4-(1H-indol-4-yl)-6-(pyridin-2-ylmethoxy)-1,3,5-triazin-2-yl)morpholine |
| 361.1 | 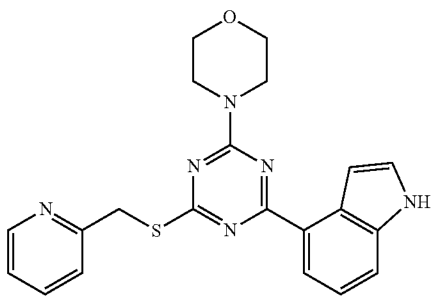 [SMILES: c1ccc(CSc2nc(-c3cccc4[nH]ccc34)nc(N3CCOCC3)n2)nc1] | 4-(4-(1H-indol-4-yl)-6-((pyridin-2-ylmethyl)thio)-1,3,5-triazin-2-yl)morpholine |
| 361.2 | 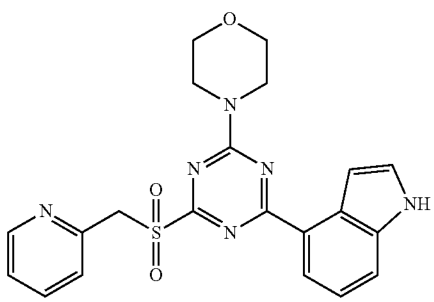 [SMILES: O=S(=O)(Cc1ccccn1)c1nc(-c2cccc3[nH]ccc23)nc(N2CCOCC2)n1] | 4-(4-(1H-indol-4-yl)-6-((pyridin-2-ylmethyl)sulfonyl)-1,3,5-triazin-2-yl)morpholine |
| 361.3 | 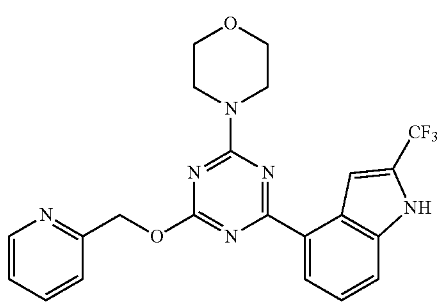 [SMILES: FC(F)(F)c1cc2c(-c3nc(OCc4ccccn4)nc(N4CCOCC4)n3)cccc2[nH]1] | 4-(4-(pyridin-2-ylmethoxy)-6-(2-(trifluoromethyl)-1H-indol-4-yl)-1,3,5-triazin-2-yl)morpholine |
| 362 | 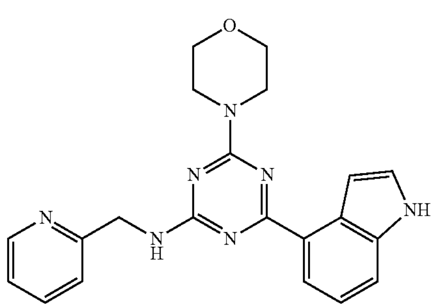 [SMILES: c1ccc(CNc2nc(-c3cccc4[nH]ccc34)nc(N3CCOCC3)n2)nc1] | 4-(1H-indol-4-yl)-6-morpholino-N-(pyridin-2-ylmethyl)-1,3,5-triazin-2-amine |

TABLE 2-continued

| Cpd. No. | Structure | Name |
|---|---|---|
| 363 | 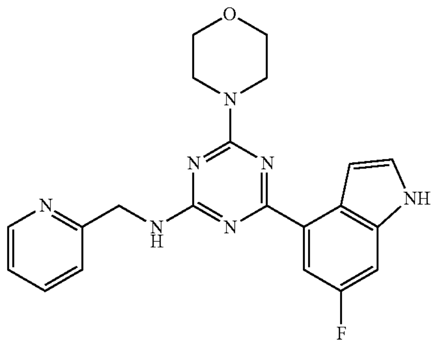 [SMILES: Fc1cc(-c2nc(NCc3ccccn3)nc(N3CCOCC3)n2)c2cc[nH]c2c1] | 4-(6-fluoro-1H-indol-4-yl)-6-morpholino-N-(pyridin-2-ylmethyl)-1,3,5-triazin-2-amine |
| 364 | 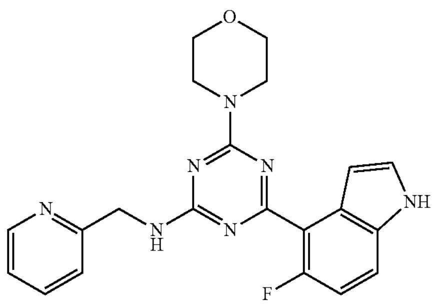 [SMILES: Fc1ccc2[nH]ccc2c1-c1nc(NCc2ccccn2)nc(N2CCOCC2)n1] | 4-(5-fluoro-1H-indol-4-yl)-6-morpholino-N-(pyridin-2-ylmethyl)-1,3,5-triazin-2-amine |
| 365 | 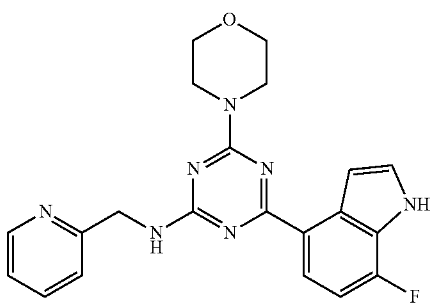 [SMILES: Fc1ccc(-c2nc(NCc3ccccn3)nc(N3CCOCC3)n2)c2cc[nH]c12] | 4-(7-fluoro-1H-indol-4-yl)-6-morpholino-N-(pyridin-2-ylmethyl)-1,3,5-triazin-2-amine |
| 366 | 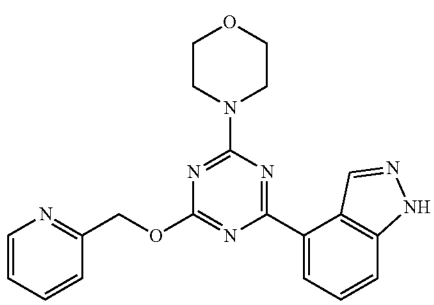 [SMILES: c1ccc(COc2nc(-c3cccc4[nH]ncc34)nc(N3CCOCC3)n2)nc1] | 4-(4-(1H-indazol-4-yl)-6-(pyridin-2-ylmethoxy)-1,3,5-triazin-2-yl)morpholine |
| 267 | 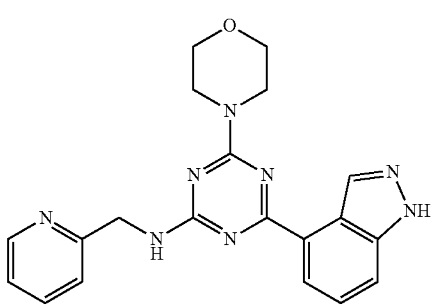 [SMILES: c1ccc(CNc2nc(-c3cccc4[nH]ncc34)nc(N3CCOCC3)n2)nc1] | 4-(1H-indazol-4-yl)-6-morpholino-N-(pyridin-2-ylmethyl)-1,3,5-triazin-2-amine |

TABLE 2-continued

| Cpd. No. | Structure | Name |
|---|---|---|
| 268 | 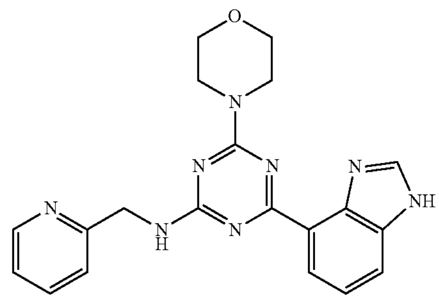 [SMILES: c1ccc(CNc2nc(-c3cccc4[nH]cnc34)nc(N3CCOCC3)n2)nc1] | 4-(1H-benzo[d]imidazol-4-yl)-6-morpholino-N-(pyridin-2-ylmethyl)-1,3,5-triazin-2-amine |
| 369 | 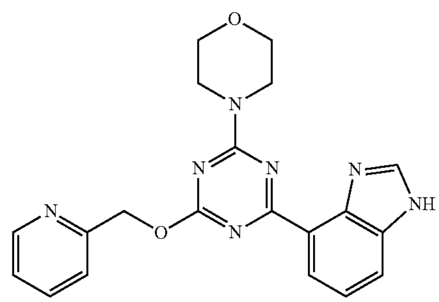 [SMILES: c1ccc(COc2nc(-c3cccc4[nH]cnc34)nc(N3CCOCC3)n2)nc1] | 4-(4-(1H-benzo[d]imidazol-4-yl)-6-(pyridin-2-ylmethoxy)-1,3,5-triazin-2-yl)morpholine |
| 370 | 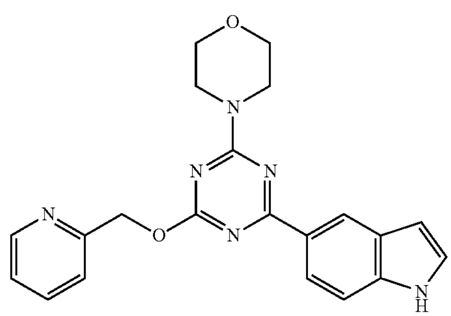 [SMILES: c1ccc(COc2nc(-c3ccc4[nH]ccc4c3)nc(N3CCOCC3)n2)nc1] | 4-(4-(1H-indol-5-yl)-6-(pyridin-2-ylmethoxy)-1,3,5-triazin-2-yl)morpholine |
| 371 | 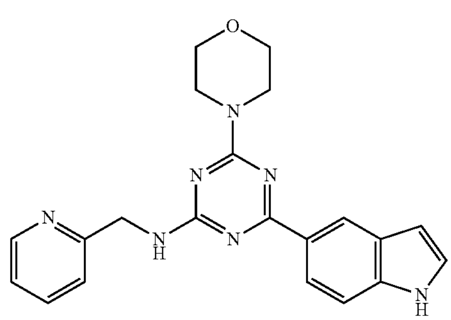 [SMILES: c1ccc(CNc2nc(-c3ccc4[nH]ccc4c3)nc(N3CCOCC3)n2)nc1] | 4-(1H-indol-5-yl)-6-morpholino-N-(pyridin-2-ylmethyl)-1,3,5-triazin-2-amine |
| 372 | 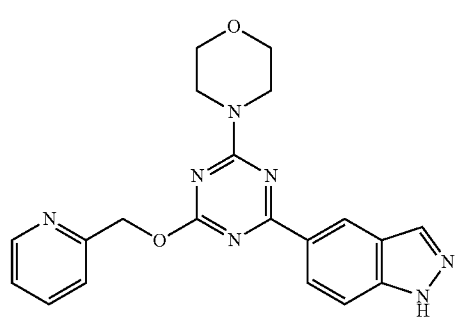 [SMILES: c1ccc(COc2nc(-c3ccc4[nH]ncc4c3)nc(N3CCOCC3)n2)nc1] | 4-(4-(1H-indazol-5-yl)-6-(pyridin-2-ylmethoxy)-1,3,5-triazin-2-yl)morpholine |

TABLE 2-continued

| Cpd. No. | Structure | Name |
|---|---|---|
| 373 | 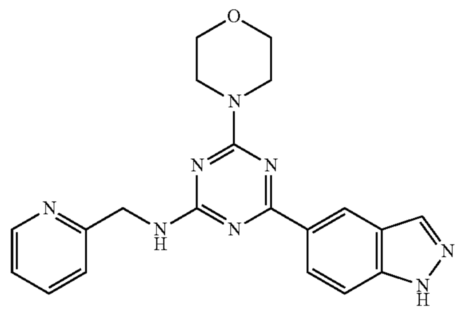 [SMILES: c1ccc(CNc2nc(-c3ccc4[nH]ncc4c3)nc(N3CCOCC3)n2)nc1] | 4-(1H-indazol-5-yl)-6-morpholino-N-(pyridin-2-ylmethyl)-1,3,5-triazin-2-amine |
| 374 | 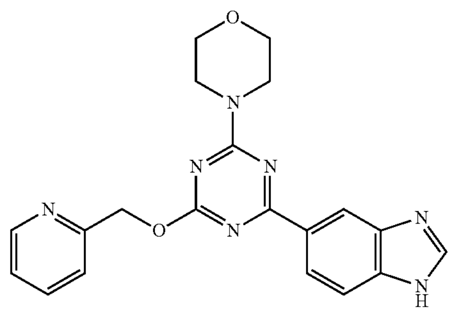 [SMILES: c1ccc(COc2nc(-c3ccc4[nH]cnc4c3)nc(N3CCOCC3)n2)nc1] | 4-(4-(1H-benzo[d]imidazol-5-yl)-6-(pyridin-2-ylmethoxy)-1,3,5-triazin-2-yl)morpholine |
| 375 | 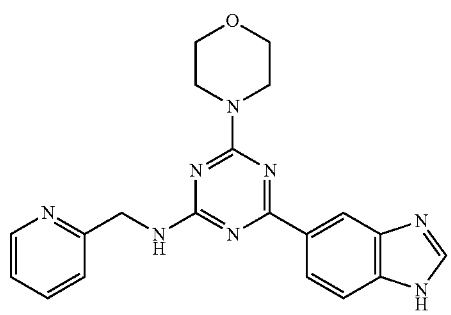 [SMILES: c1ccc(CNc2nc(-c3ccc4[nH]cnc4c3)nc(N3CCOCC3)n2)nc1] | 4-(1H-benzo[d]imidazol-5-yl)-6-morpholino-N-(pyridin-2-ylmethyl)-1,3,5-triazin-2-amine |
| 376 | 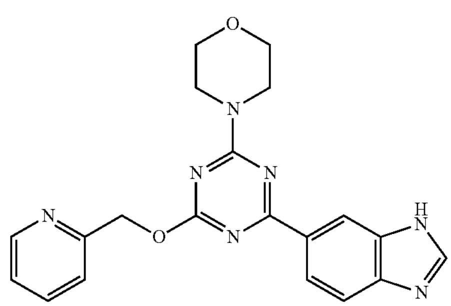 [SMILES: c1ccc(COc2nc(-c3ccc4nc[nH]c4c3)nc(N3CCOCC3)n2)nc1] | 4-(4-(1H-benzo[d]imidazol-6-yl)-6-(pyridin-2-ylmethoxy)-1,3,5-triazin-2-yl)morpholine |
| 377 | 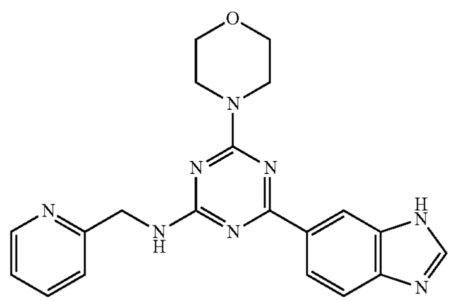 [SMILES: c1ccc(CNc2nc(-c3ccc4nc[nH]c4c3)nc(N3CCOCC3)n2)nc1] | 4-(1H-benzo[d]imidazol-6-yl)-6-morpholino-N-(pyridin-2-ylmethyl)-1,3,5-triazin-2-amine |

TABLE 2-continued

| Cpd. No. | Structure | Name |
|---|---|---|
| 378 | 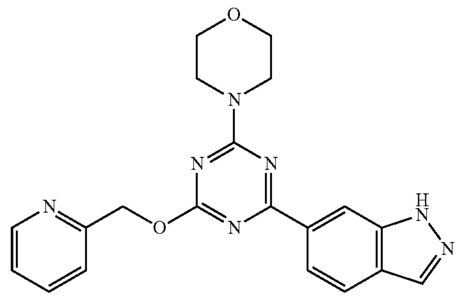 [SMILES: c1ccc(COc2nc(-c3ccc4cn[nH]c4c3)nc(N3CCOCC3)n2)nc1] | 4-(4-(1H-indazol-6-yl)-6-(pyridin-2-ylmethoxy)-1,3,5-triazin-2-yl)morpholine |
| 379 | 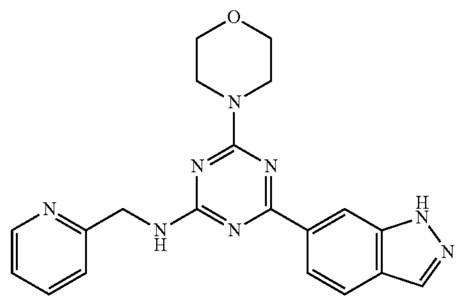 [SMILES: c1ccc(CNc2nc(-c3ccc4cn[nH]c4c3)nc(N3CCOCC3)n2)nc1] | 4-(1H-indazol-6-yl)-6-morpholino-N-(pyridin-2-ylmethyl)-1,3,5-triazin-2-amine |
| 380 | 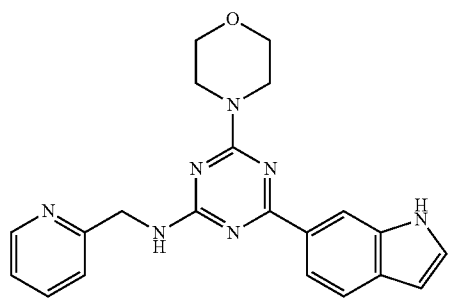 [SMILES: c1ccc(CNc2nc(-c3ccc4cc[nH]c4c3)nc(N3CCOCC3)n2)nc1] | 4-(1H-indol-6-yl)-6-morpholino-N-(pyridin-2-ylmethyl)-1,3,5-triazin-2-amine |
| 381 | 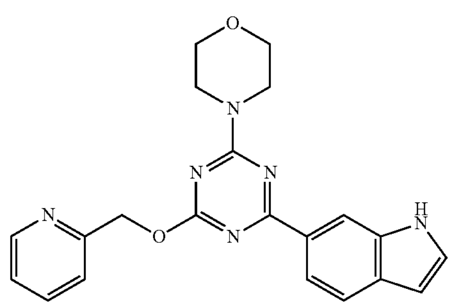 [SMILES: c1ccc(COc2nc(-c3ccc4cc[nH]c4c3)nc(N3CCOCC3)n2)nc1] | 4-(4-(1H-indol-6-yl)-6-(pyridin-2-ylmethoxy)-1,3,5-triazin-2-yl)morpholine |
| 382 | 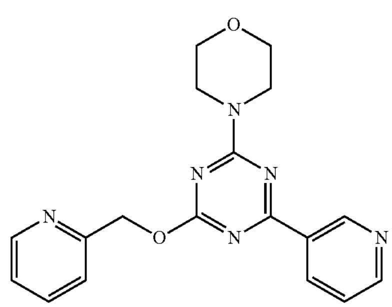 [SMILES: c1ccc(COc2nc(-c3cccnc3)nc(N3CCOCC3)n2)nc1] | 4-(4-(pyridin-2-ylmethoxy)-6-(pyridin-3-yl)-1,3,5-triazin-2-yl)morpholine |

TABLE 2-continued

| Cpd. No. | Structure | Name |
|---|---|---|
| 383 | 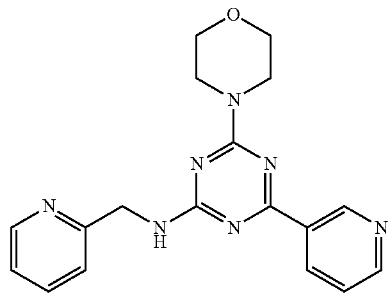 [SMILES: c1ccc(CNc2nc(-c3cccnc3)nc(N3CCOCC3)n2)nc1] | 4-morpholino-N-(pyridin-2-ylmethyl)-6-(pyridin-3-yl)-1,3,5-triazin-2-amine |
| 384 | 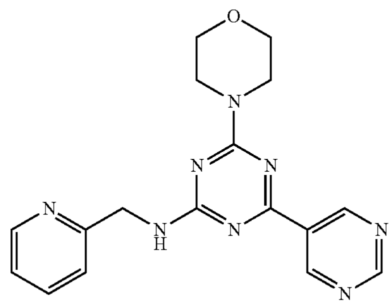 [SMILES: c1ccc(CNc2nc(-c3cncnc3)nc(N3CCOCC3)n2)nc1] | 4-morpholino-N-(pyridin-2-ylmethyl)-6-(pyrimidin-5-yl)-1,3,5-triazin-2-amine |
| 385 | 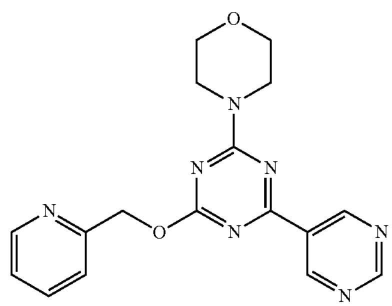 [SMILES: c1ccc(COc2nc(-c3cncnc3)nc(N3CCOCC3)n2)nc1] | 4-(4-(pyridin-2-ylmethoxy)-6-(pyrimidin-5-yl)-1,3,5-triazin-2-yl)morpholine |

Table 3 gives the structures and the corresponding IUPAC names (using ChemDraw Ultra, Version 11.0.1 as well as lower and upper software versions thereof, CambridgeSoft Corp., Cambridge Mass.) of exemplary compounds Nos. 386-473 of formula (If) or (Ig).

TABLE 3

| Cpd. No. | Structure | Name |
|---|---|---|
| 386 | 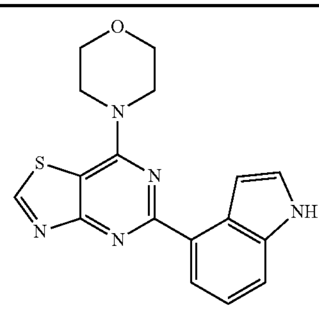 | 4-(5-(1H-indol-4-yl)thiazolo[4,5-d]pyrimidin-7-yl)morpholine |

TABLE 3-continued

| Cpd. No. | Structure | Name |
|---|---|---|
| 387 | 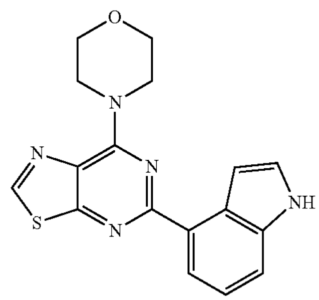 [SMILES: c1cc(-c2nc(N3CCOCC3)c3ncsc3n2)c2cc[nH]c2c1] | 4-(5-(1H-indol-4-yl)thiazolo[5,4-d]pyrimidin-7-yl)morpholine |
| 388 | 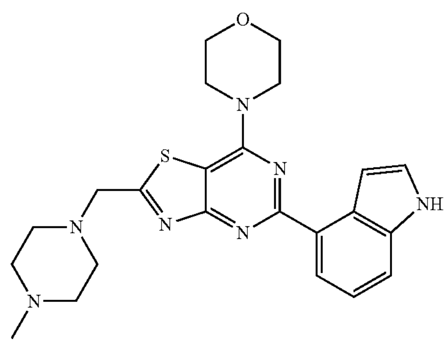 [SMILES: CN1CCN(Cc2nc3nc(-c4cccc5[nH]ccc45)nc(N4CCOCC4)c3s2)CC1] | 4-(5-(1H-indol-4-yl)-2-((4-methylpiperazin-1-yl)methyl)thiazolo[4,5-d]pyrimidin-7-yl)morpholine |
| 389 | 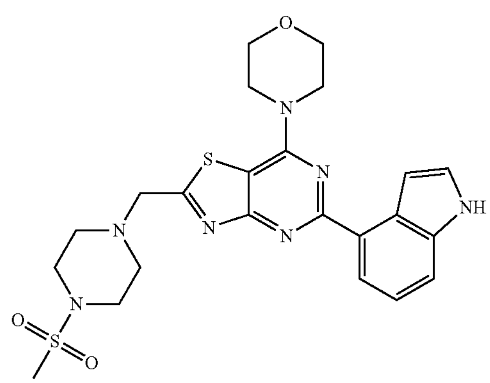 [SMILES: CS(=O)(=O)N1CCN(Cc2nc3nc(-c4cccc5[nH]ccc45)nc(N4CCOCC4)c3s2)CC1] | 4-(5-(1H-indol-4-yl)-2-((4-(methylsulfonyl)piperazin-1-yl)methyl)thiazolo[4,5-d]pyrimidin-7-yl)morpholine |
| 390 | 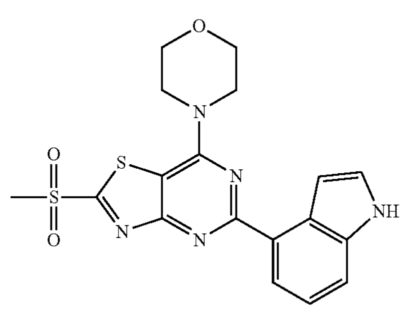 [SMILES: CS(=O)(=O)c1nc2nc(-c3cccc4[nH]ccc34)nc(N3CCOCC3)c2s1] | 4-(5-(1H-indol-4-yl)-2-(methylsulfonyl)thiazolo[4,5-d]pyrimidin-7-yl)morpholine |

TABLE 3-continued

| Cpd. No. | Structure | Name |
|---|---|---|
| 391 | 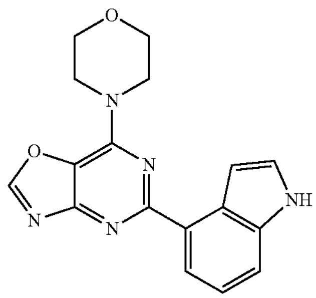 | 5-(1H-indol-4-yl)-7-morpholinooxazolo[4,5-d]pyrimidine |
| 392 | 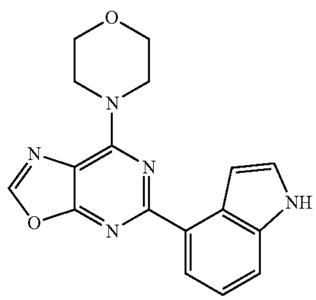 [SMILES: c1cc(-c2nc(N3CCOCC3)c3ncoc3n2)c2cc[nH]c2c1] | 5-(1H-indol-4-yl)-7-morpholinooxazolo[5,4-d]pyrimidine |
| 393 | 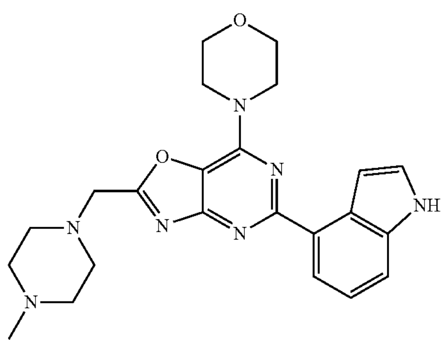 | 5-(1H-indol-4-yl)-2-((4-methylpiperazin-1-yl)methyl)-7-morpholinooxazolo[4,5-d]pyrimidine |
| 394 | 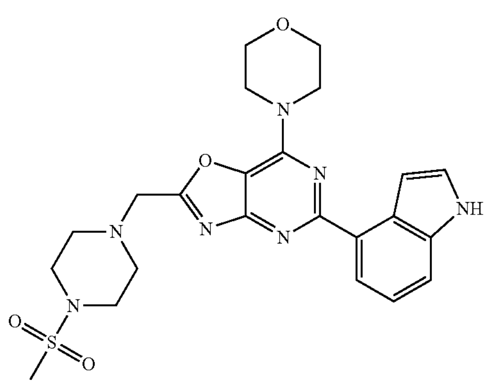 [SMILES: CS(=O)(=O)N1CCN(Cc2nc3nc(-c4cccc5[nH]ccc45)nc(N4CCOCC4)c3o2)CC1] | 5-(1H-indol-4-yl)-2-((4-(methylsulfonyl)piperazin-1-yl)methyl)-7-morpholinooxazolo[4,5-d]pyrimidine |

TABLE 3-continued

| Cpd. No. | Structure | Name |
|---|---|---|
| 395 | 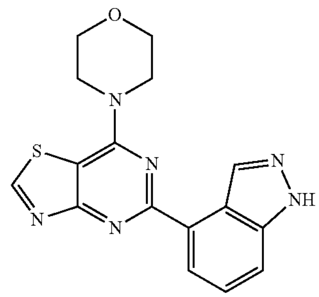 | 4-(5-(1H-indazol-4-yl)thiazolo[4,5-d]pyrimidin-7-yl)morpholine |
| 396 | 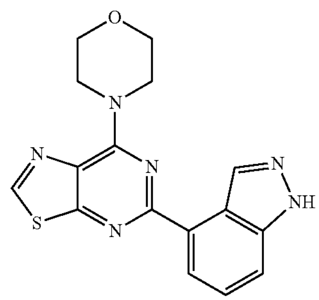 | 4-(5-(1H-indazol-4-yl)thiazolo[5,4-d]pyrimidin-7-yl)morpholine |
| 397 | 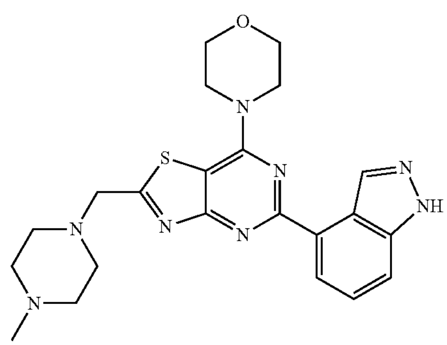 | 4-(5-(1H-indazol-4-yl)-2-((4-methylpiperazin-1-yl)methyl)thiazolo[4,5-d]pyrimidin-7-yl)morpholine |
| 398 | 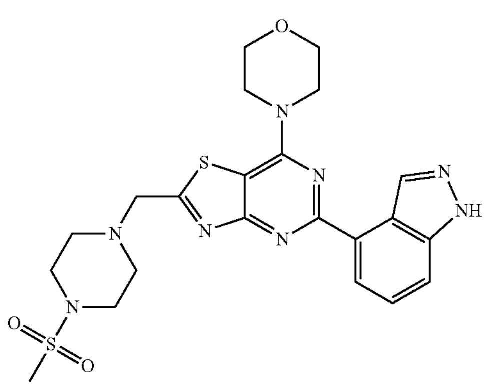 [SMILES: CS(=O)(=O)N1CCN(Cc2nc3nc(-c4cccc5[nH]ncc45)nc(N4CCOCC4)c3s2)CC1] | 4-(5-(1H-indazol-4-yl)-2-((4-(methylsulfonyl)piperazin-1-yl)methyl)thiazolo[4,5-d]pyrimidin-7-yl)morpholine |

TABLE 3-continued

| Cpd. No. | Structure | Name |
|---|---|---|
| 399 | 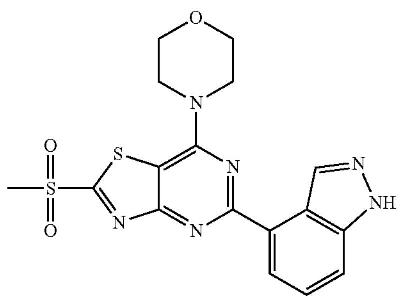 [SMILES: CS(=O)(=O)c1nc2nc(-c3cccc4[nH]ncc34)nc(N3CCOCC3)c2s1] | 4-(5-(1H-indazol-4-yl)-2-(methylsulfonyl)thiazolo[4,5-d]pyrimidin-7-yl)morpholine |
| 400 | 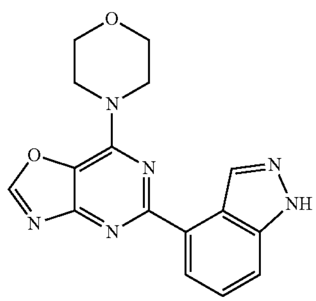 [SMILES: c1cc(-c2nc(N3CCOCC3)c3ocnc3n2)c2cn[nH]c2c1] | 5-(1H-indazol-4-yl)-7-morpholinooxazolo[4,5-d]pyrimidine |
| 401 | 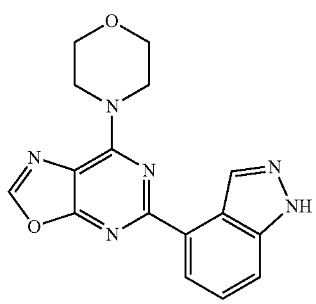 [SMILES: c1cc(-c2nc(N3CCOCC3)c3ncoc3n2)c2cn[nH]c2c1] | 5-(1H-indazol-4-yl)-7-morpholinooxazolo[5,4-d]pyrimidine |
| 402 | 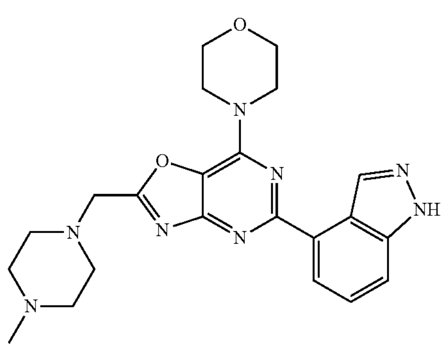 [SMILES: CN1CCN(Cc2nc3nc(-c4cccc5[nH]ncc45)nc(N4CCOCC4)c3o2)CC1] | 5-(1H-indazol-4-yl)-2-((4-methylpiperazin-1-yl)methyl)-7-morpholinooxazolo[4,5-d]pyrimidine |
| 403 | 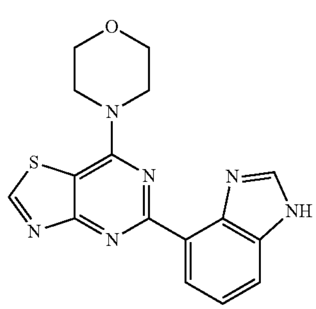 | 4-(5-(1H-benzo[d]imidazol-4-yl)thiazolo[4,5-d]pyrimidin-7-yl)morpholine |

TABLE 3-continued

| Cpd. No. | Structure | Name |
|---|---|---|
| 404 | 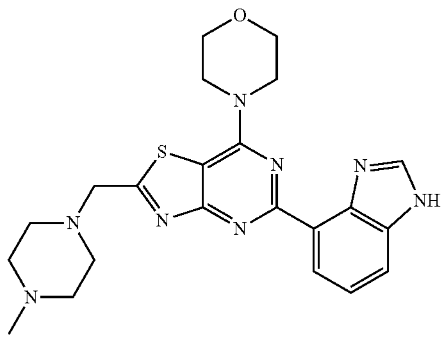 [SMILES: CN1CCN(Cc2nc3nc(-c4cccc5[nH]cnc45)nc(N4CCOCC4)c3s2)CC1] | 4-(5-(1H-benzo[d]imidazol-4-yl)-2-((4-methylpiperazin-1-yl)methyl)thiazolo[4,5-d]pyrimidin-7-yl)morpholine |
| 405 | 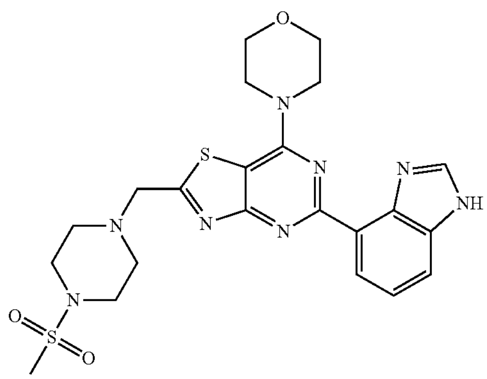 | 4-(5-(1H-benzo[d]imidazol-4-yl)-2-((4-(methylsulfonyl)piperazin-1-yl)methyl)thiazolo[4,5-d]pyrimidin-7-yl)morpholine |
| 406 | 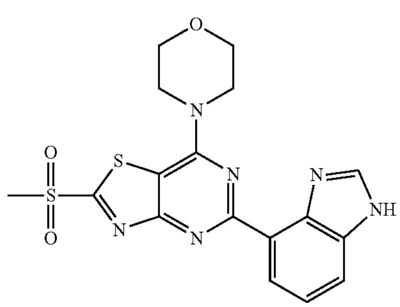 [SMILES: CS(=O)(=O)c1nc2nc(-c3cccc4[nH]cnc34)nc(N3CCOCC3)c2s1] | 4-(5-(1H-benzo[d]imidazol-4-yl)-2-(methylsulfonyl)thiazolo[4,5-d]pyrimidin-7-yl)morpholine |
| 407 | 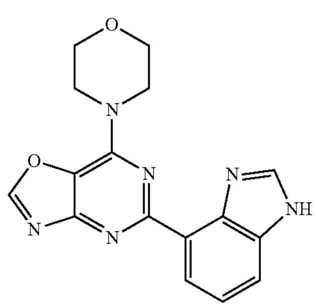 [SMILES: c1cc(-c2nc(N3CCOCC3)c3ocnc3n2)c2nc[nH]c2c1] | 5-(1H-benzo[d]imidazol-4-yl)-7-morpholinooxazolo[4,5-d]pyrimidine |

TABLE 3-continued

| Cpd. No. | Structure | Name |
|---|---|---|
| 408 | 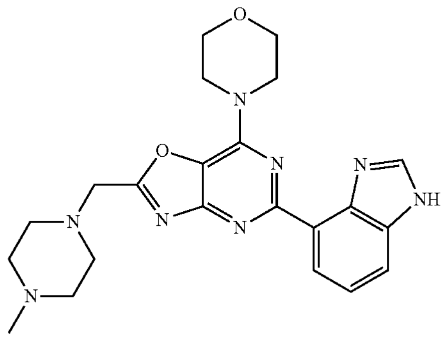 [SMILES: CN1CCN(Cc2nc3nc(-c4cccc5[nH]cnc45)nc(N4CCOCC4)c3o2)CC1] | 5-(1H-benzo[d]imidazol-4-yl)-2-((4-methylpiperazin-1-yl)methyl)-7-morpholinooxazolo[4,5-d]pyrimidine |
| 409 | 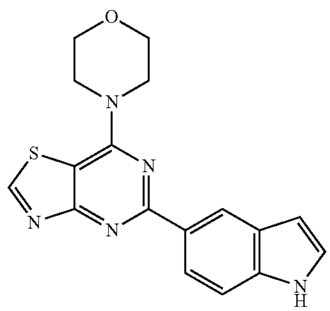 [SMILES: c1cc2cc(-c3nc(N4CCOCC4)c4scnc4n3)ccc2[nH]1] | 4-(5-(1H-indol-5-yl)thiazolo[4,5-d]pyrimidin-7-yl)morpholine |
| 410 | 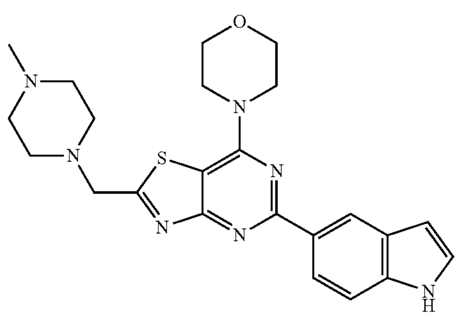 | 4-(5-(1H-indol-5-yl)-2-((4-methylpiperazin-1-yl)methyl)thiazolo[4,5-d]pyrimidin-7-yl)morpholine |
| 411 | 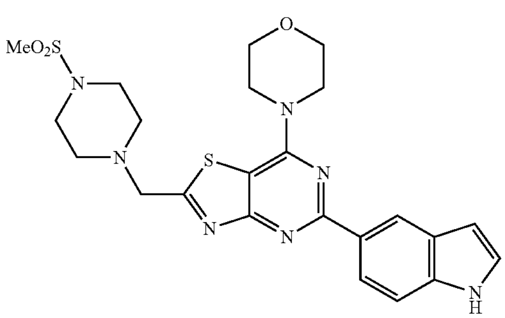 [SMILES: CS(=O)(=O)N1CCN(Cc2nc3nc(-c4ccc5[nH]ccc5c4)nc(N4CCOCC4)c3s2)CC1] | 4-(5-(1H-indol-5-yl)-2-((4-(methylsulfonyl)piperazin-1-yl)methyl)thiazolo[4,5-d]pyrimidin-7-yl)morpholine |
| 412 | 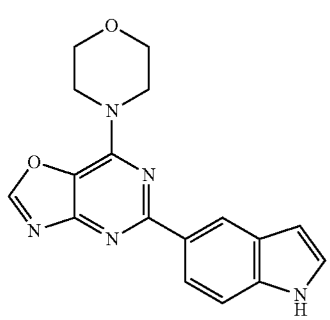 | 5-(1H-indol-5-yl)-7-morpholinooxazolo[4,5-d]pyrimidine |

TABLE 3-continued

| Cpd. No. | Structure | Name |
|---|---|---|
| 413 | 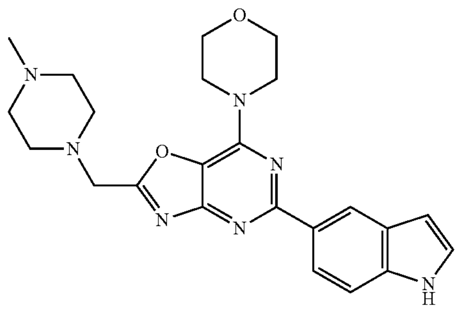 [SMILES: CN1CCN(Cc2nc3nc(-c4ccc5[nH]ccc5c4)nc(N4CCOCC4)c3o2)CC1] | 5-(1H-indol-5-yl)-2-((4-methylpiperazin-1-yl)methyl)-7-morpholinooxazolo[4,5-d]pyrimidine |
| 414 | 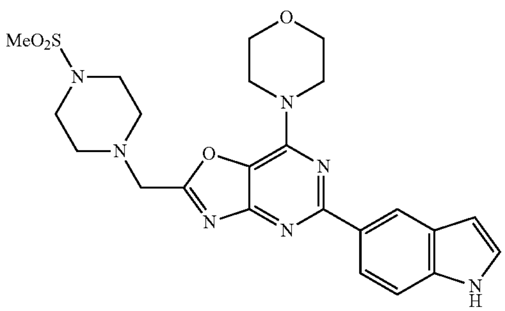 | 5-(1H-indol-5-yl)-2-((4-(methylsulfonyl)piperazin-1-yl)methyl)-7-morpholinooxazolo[4,5-d]pyrimidine |
| 415 | 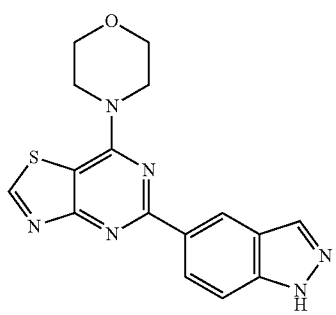 [SMILES: c1nc2nc(-c3ccc4[nH]ncc4c3)nc(N3CCOCC3)c2s1] | 4-(5-(1H-indazol-5-yl)thiazolo[4,5-d]pyrimidin-7-yl)morpholine |
| 416 | 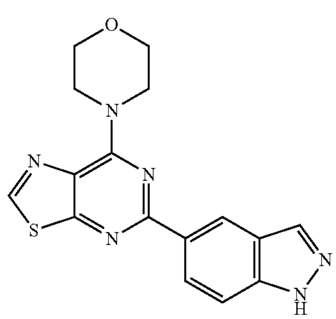 [SMILES: c1nc2c(N3CCOCC3)nc(-c3ccc4[nH]ncc4c3)nc2s1] | 4-(5-(1H-indazol-5-yl)thiazolo[5,4-d]pyrimidin-7-yl)morpholine |
| 417 | 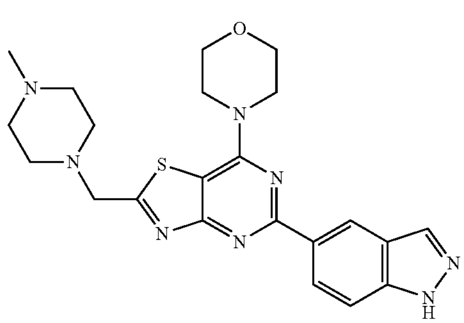 | 4-(5-(1H-indazol-5-yl)-2-((4-methylpiperazin-1-yl)methyl)thiazolo[4,5-d]pyrimidin-7-yl)morpholine |

TABLE 3-continued

| Cpd. No. | Structure | Name |
|---|---|---|
| 418 | 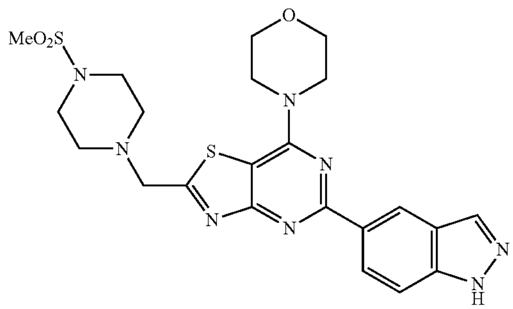 | 4-(5-(1H-indazol-5-yl)-2-((4-(methylsulfonyl)piperazin-1-yl)methyl)thiazolo[4,5-d]pyrimidin-7-yl)morpholine |
| 419 | 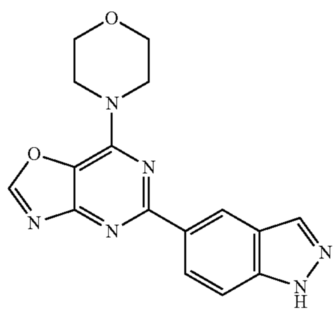 | 5-(1H-indazol-5-yl)-7-morpholinooxazolo[4,5-d]pyrimidine |
| 420 | 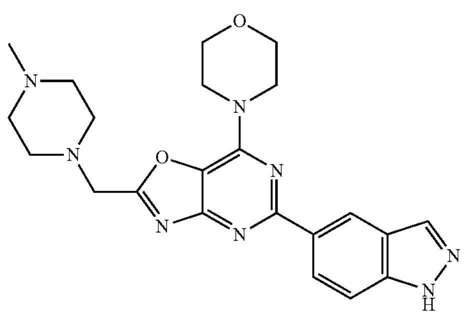 [SMILES: CN1CCN(Cc2nc3nc(-c4ccc5[nH]ncc5c4)nc(N4CCOCC4)c3s2)CC1] | 5-(1H-indazol-5-yl)-2-((4-methylpiperazin-1-yl)methyl)-7-morpholinooxazolo[4,5-d]pyrimidine |
| 421 | 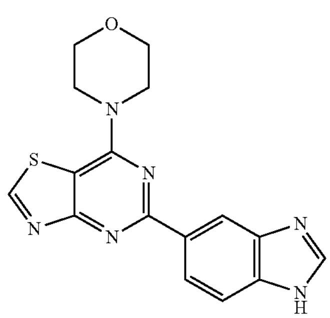 | 4-(5-(1H-benzo[d]imidazol-5-yl)thiazolo[4,5-d]pyrimidin-7-yl)morpholine |
| 422 | 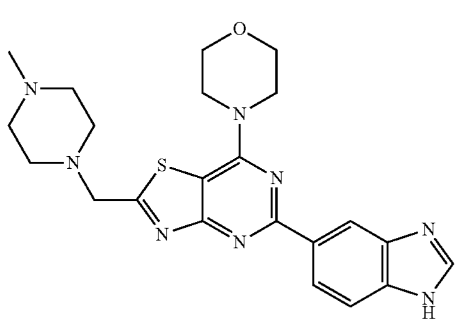 [SMILES: CN1CCN(Cc2nc3nc(-c4ccc5[nH]cnc5c4)nc(N4CCOCC4)c3s2)CC1] | 4-(5-(1H-benzo[d]imidazol-5-yl)-2-((4-methylpiperazin-1-yl)methyl)thiazolo[4,5-d]pyrimidin-7-yl)morpholine |

TABLE 3-continued

| Cpd. No. | Structure | Name |
|---|---|---|
| 423 | 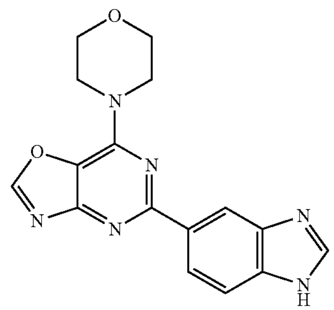 [SMILES: c1nc2cc(-c3nc(N4CCOCC4)c4ocnc4n3)ccc2[nH]1] | 5-(1H-benzo[d]imidazol-5-yl)-7-morpholinooxazolo[4,5-d]pyrimidine |
| 424 | 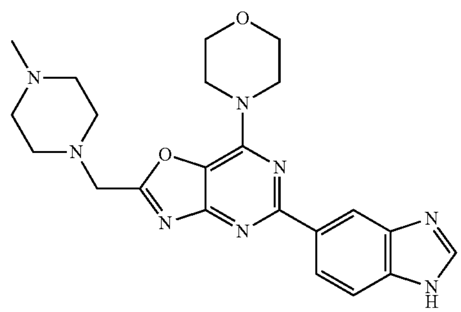 | 5-(1H-benzo[d]imidazol-5-yl)-2-((4-methylpiperazin-1-yl)methyl)-7-morpholinooxazolo[4,5-d]pyrimidine |
| 425 | 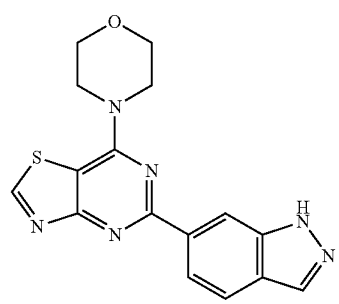 [SMILES: c1nc2nc(-c3ccc4cn[nH]c4c3)nc(N3CCOCC3)c2s1] | 4-(5-(1H-indazol-6-yl)thiazolo[4,5-d]pyrimidin-7-yl)morpholine |
| 426 | 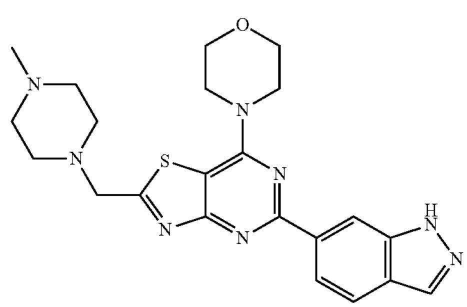 [SMILES: CN1CCN(Cc2nc3nc(-c4ccc5cn[nH]c5c4)nc(N4CCOCC4)c3s2)CC1] | 4-(5-(1H-indazol-6-yl)-2-((4-methylpiperazin-1-yl)methyl)thiazolo[4,5-d]pyrimidin-7-yl)morpholine |
| 427 | 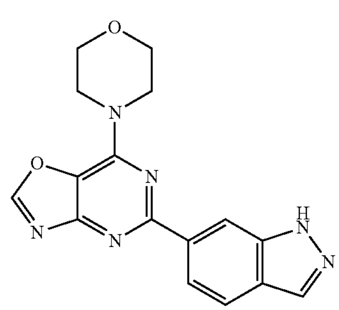 | 5-(1H-indazol-6-yl)-7-morpholinooxazolo[4,5-d]pyrimidine |

TABLE 3-continued

| Cpd. No. | Structure | Name |
|---|---|---|
| 428 | 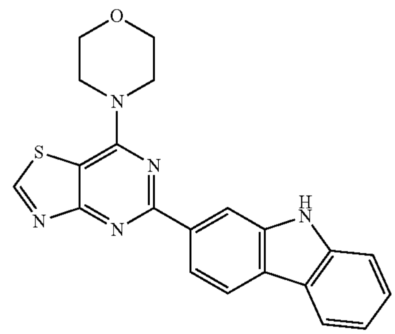 | 4-(5-(9H-carbazol-2-yl)thiazolo[4,5-d]pyrimidin-7-yl)morpholine |
| 429 | 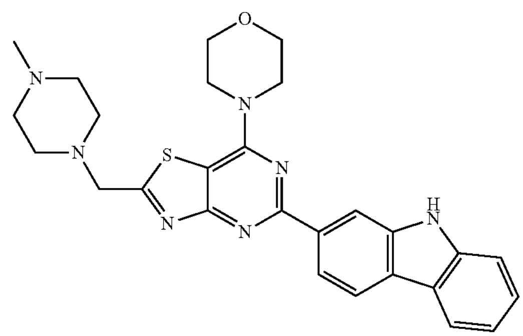 [SMILES: CN1CCN(Cc2nc3nc(-c4ccc5c(c4)[nH]c4ccccc45)nc(N4CCOCC4)c3s2)CC1] | 4-(5-(9H-carbazol-2-yl)-2-((4-methylpiperazin-1-yl)methyl)thiazolo[4,5-d]pyrimidin-7-yl)morpholine |
| 430 | 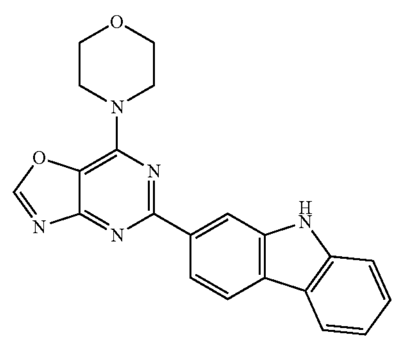 [SMILES: c1ccc2c(c1)[nH]c1cc(-c3nc(N4CCOCC4)c4ocnc4n3)ccc12] | 5-(9H-carbazol-2-yl)-7-morpholinooxazolo[4,5-d]pyrimidine |
| 431 | 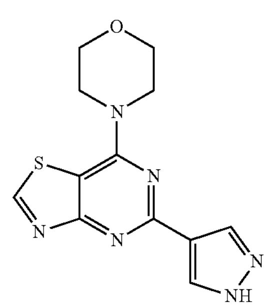 [SMILES: c1nc2nc(-c3cn[nH]c3)nc(N3CCOCC3)c2s1] | 4-(5-(1H-pyrazol-4-yl)thiazolo[4,5-d]pyrimidin-7-yl)morpholine |

TABLE 3-continued

| Cpd. No. | Structure | Name |
|---|---|---|
| 432 | 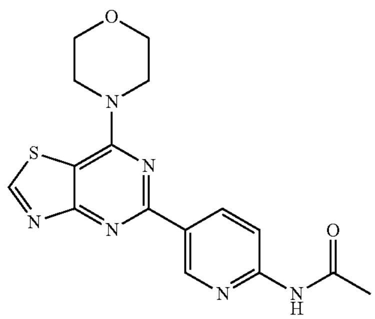 | N-(5-(7-morpholinothiazolo[4,5-d]pyrimidin-5-yl)pyridin-2-yl)acetamide |
| 433 | 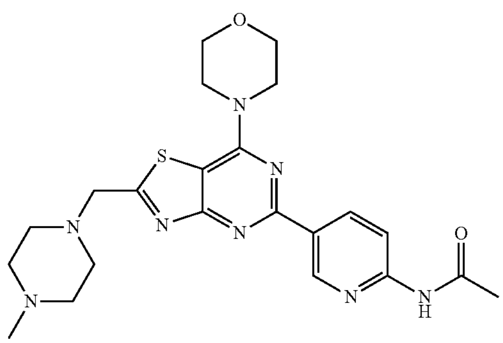 [SMILES: CC(=O)Nc1ccc(-c2nc(N3CCOCC3)c3sc(CN4CCN(C)CC4)nc3n2)cn1] | N-(5-(2-((4-methylpiperazin-1-yl)methyl)-7-morpholinothiazolo[4,5-d]pyrimidin-5-yl)pyridin-2-yl)acetamide |
| 434 | 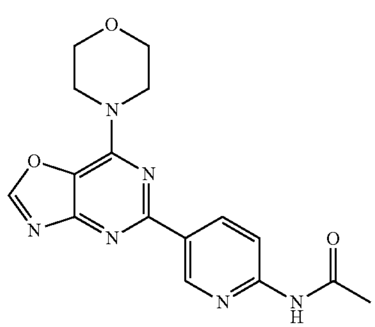 [SMILES: CC(=O)Nc1ccc(-c2nc(N3CCOCC3)c3ocnc3n2)cn1] | N-(5-(7-morpholinooxazolo[4,5-d]pyrimidin-5-yl)pyridin-2-yl)acetamide |
| 435 | 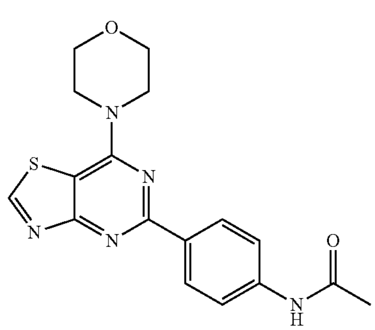 [SMILES: CC(=O)Nc1ccc(-c2nc(N3CCOCC3)c3scnc3n2)cc1] | N-(4-(7-morpholinothiazolo[4,5-d]pyrimidin-5-yl)phenyl)acetamide |

TABLE 3-continued

| Cpd. No. | Structure | Name |
| --- | --- | --- |
| 436 | 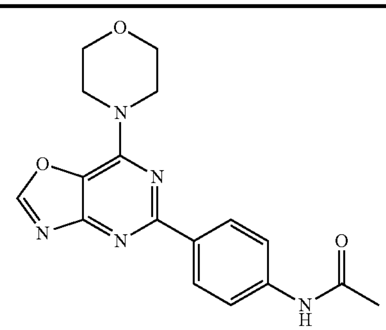 | N-(4-(7-morpholinooxazolo[4,5-d]pyrimidin-5-yl)phenyl)acetamide |
| 437 | 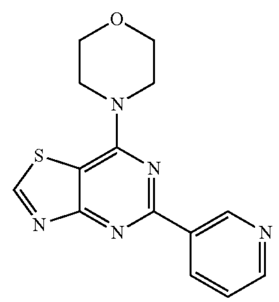 [SMILES: c1cncc(-c2nc(N3CCOCC3)c3scnc3n2)c1] | 4-(5-(pyridin-3-yl)thiazolo[4,5-d]pyrimidin-7-yl)morpholine |
| 438 | 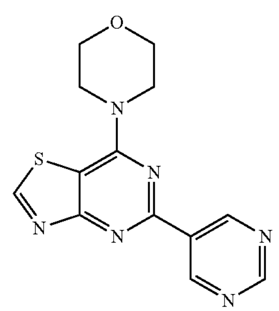 [SMILES: c1ncc(-c2nc(N3CCOCC3)c3scnc3n2)cn1] | 4-(5-(pyrimidin-5-yl)thiazolo[4,5-d]pyrimidin-7-yl)morpholine |
| 439 | 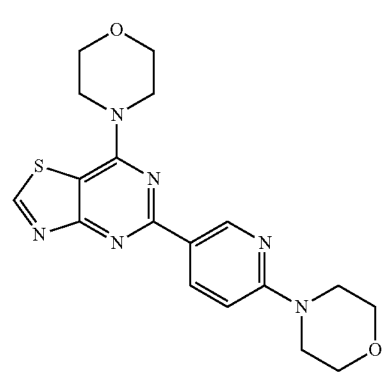 [SMILES: c1nc2nc(-c3ccc(N4CCOCC4)nc3)nc(N3CCOCC3)c2s1] | 4-(5-(6-morpholinopyridin-3-yl)thiazolo[4,5-d]pyrimidin-7-yl)morpholine |

TABLE 3-continued

| Cpd. No. | Structure | Name |
|---|---|---|
| 440 | 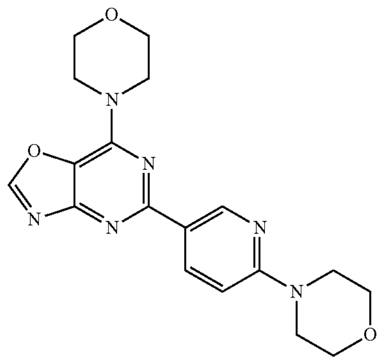 | 7-morpholino-5-(6-morpholinopyridin-3-yl)oxazolo[4,5-d]pyrimidine |
| 441 | 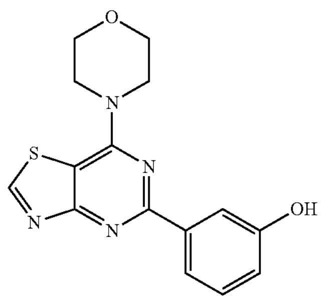 [SMILES: Oc1cccc(-c2nc(N3CCOCC3)c3scnc3n2)c1] | 3-(7-morpholinothiazolo[4,5-d]pyrimidin-5-yl)phenol |
| 441a | 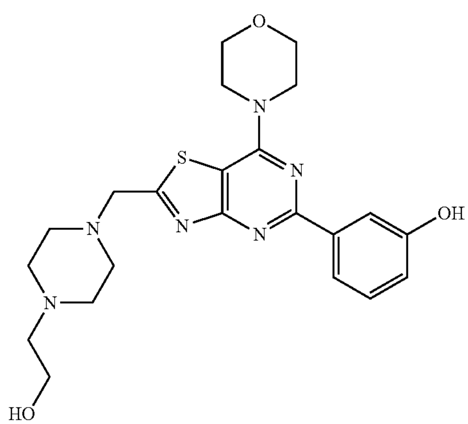 [SMILES: OCCN1CCN(Cc2nc3nc(-c4cccc(O)c4)nc(N4CCOCC4)c3s2)CC1] | 3-(2-((4-(2-hydroxyethyl)piperazin-1-yl)methyl)-7-morpholinothiazolo[4,5-d]pyrimidin-5-yl)phenol |
| 441b | 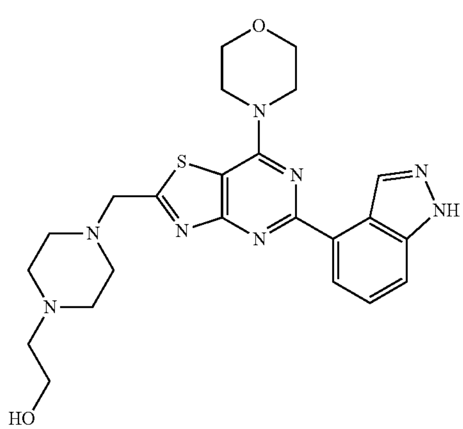 [SMILES: OCCN1CCN(Cc2nc3nc(-c4cccc5[nH]ncc45)nc(N4CCOCC4)c3s2)CC1] | 2-(4-((5-(1H-indazol-4-yl)-7-morpholinothiazolo[4,5-d]pyrimidin-2-yl)methyl)piperazin-1-yl)ethanol |

TABLE 3-continued

| Cpd. No. | Structure | Name |
| --- | --- | --- |
| 441c | 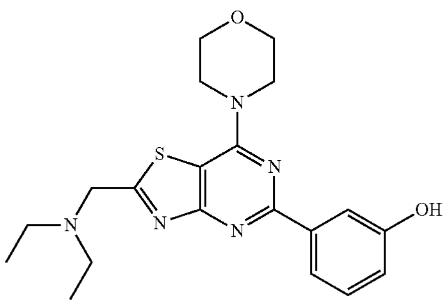 [SMILES: CCN(CC)Cc1nc2nc(-c3cccc(O)c3)nc(N3CCOCC3)c2s1] | 3-(2-((diethylamino)methyl)-7-morpholinothiazolo[4,5-d]pyrimidin-5-yl)phenol |
| 441d | 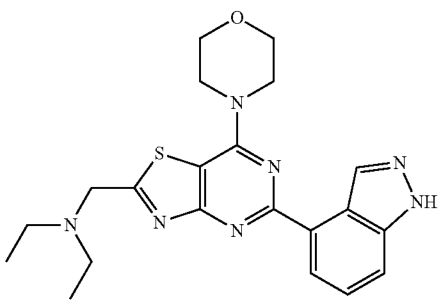 [SMILES: CCN(CC)Cc1nc2nc(-c3cccc4[nH]ncc34)nc(N3CCOCC3)c2s1] | N-((5-(1H-indazol-4-yl)-7-morpholinothiazolo[4,5-d]pyrimidin-2-yl)methyl)-N-ethylethanamine |
| 441e | 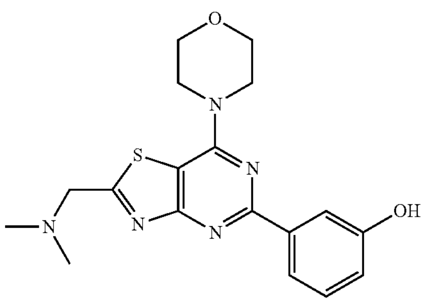 [SMILES: CN(C)Cc1nc2nc(-c3cccc(O)c3)nc(N3CCOCC3)c2s1] | 3-(2-((dimethylamino)methyl)-7-morpholinothiazolo[4,5-d]pyrimidin-5-yl)phenol |
| 441f | 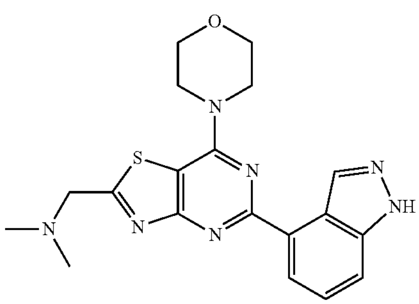 [SMILES: CN(C)Cc1nc2nc(-c3cccc4[nH]ncc34)nc(N3CCOCC3)c2s1] | 1-(5-(1H-indazol-4-yl)-7-morpholinothiazolo[4,5-d]pyrimidin-2-yl)-N,N-dimethylmethanamine |
| 442 | 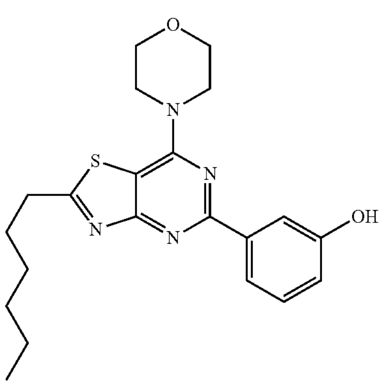 [SMILES: CCCCCCc1nc2nc(-c3cccc(O)c3)nc(N3CCOCC3)c2s1] | 3-(2-hexyl-7-morpholinothiazolo[4,5-d]pyrimidin-5-yl)phenol |

TABLE 3-continued
| Cpd. No. | Structure | Name |
|---|---|---|
| 443 | 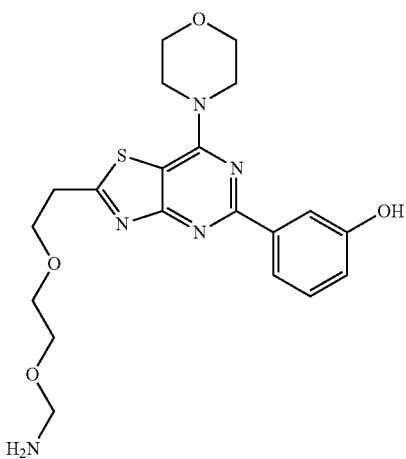 [SMILES: NCOCCOCCc1nc2nc(-c3cccc(O)c3)nc(N3CCOCC3)c2s1] | 3-(2-(2-(2-(aminomethoxy)ethoxy)ethyl)-7-morpholinothiazolo[4,5-d]pyrimidin-5-yl)phenol |
| 443.1 | 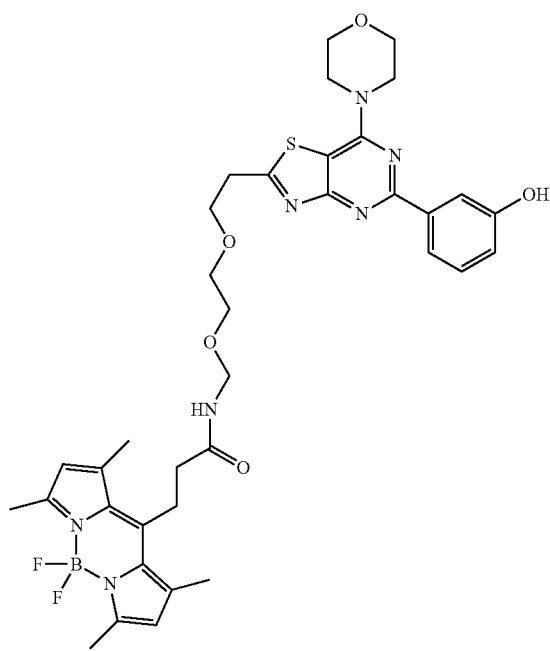 | |

TABLE 3-continued
| Cpd. No. | Structure | Name |
|---|---|---|
444
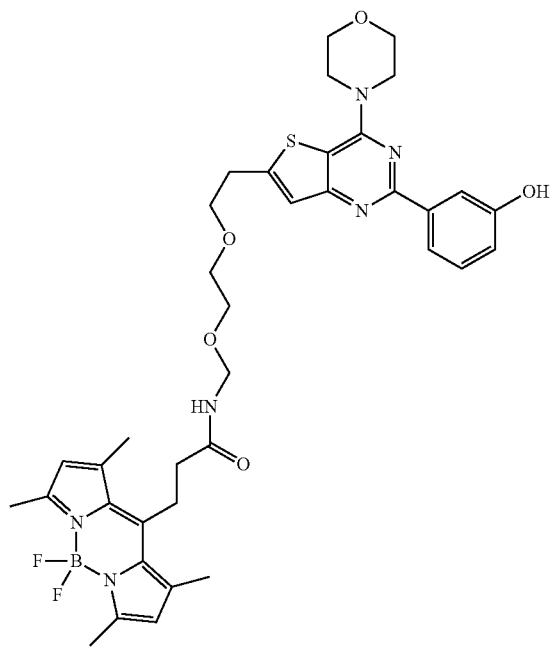
445
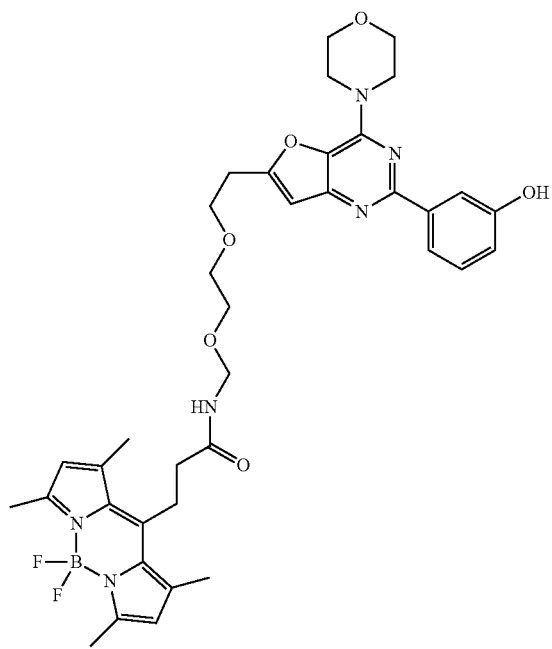

TABLE 3-continued
| Cpd. No. | Structure | Name |
|---|---|---|
446 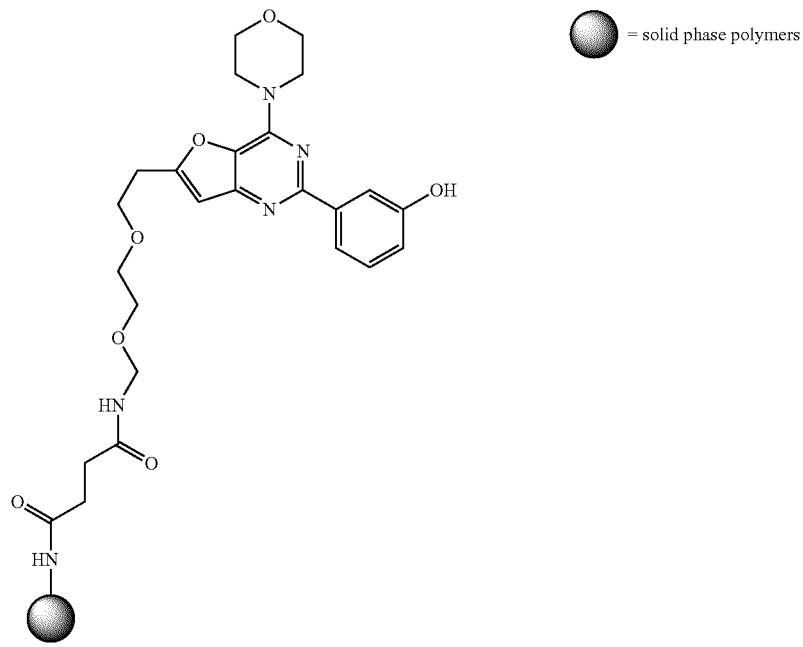 ◉ = solid phase polymers
445 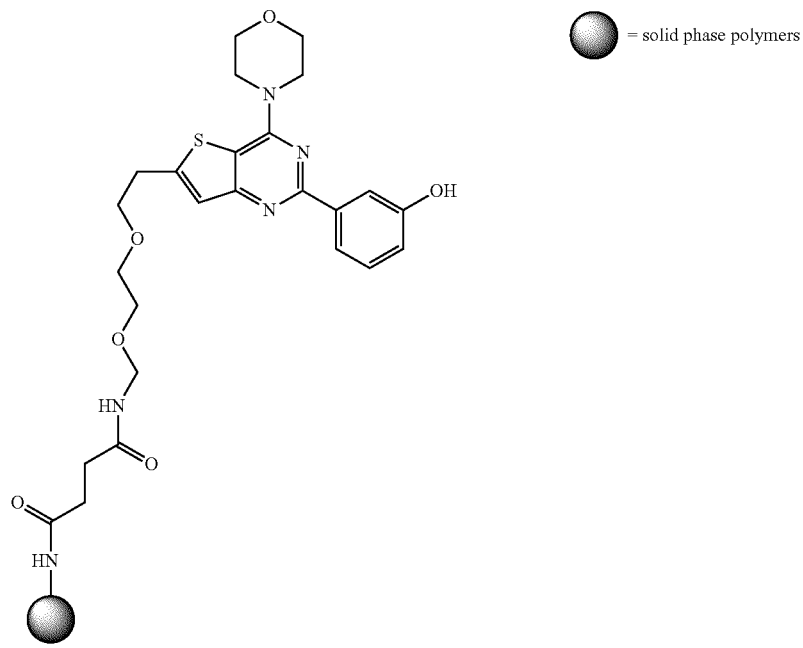 ◉ = solid phase polymers TABLE 3-continued

| Cpd. No. | Structure | Name |
|---|---|---|
| 446 | 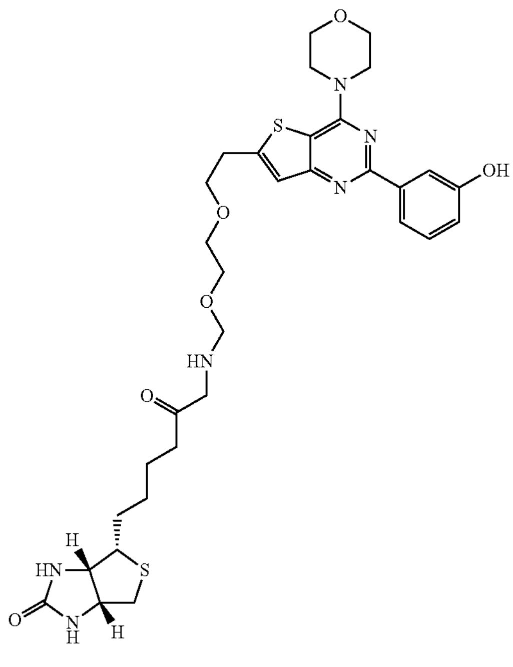 [SMILES: O=C(CCCC[C@@H]1SC[C@@H]2NC(=O)N[C@@H]21)CNCOCCOCCc1cc2nc(-c3cccc(O)c3)nc(N3CCOCC3)c2s1] | (3aS,4S,6aR)-4-(6-((2-(2-(2-(3-hydroxyphenyl)-4-morpholinothieno[3,2-d]pyrimidin-6-yl)ethoxy)ethoxy)methylamino)-5-oxohexyl)tetrahydro-1H-thieno[3,4-d]imidazol-2(3H)-one |
| 447 | 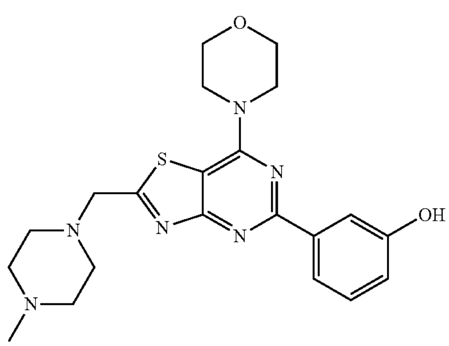 [SMILES: CN1CCN(Cc2nc3nc(-c4cccc(O)c4)nc(N4CCOCC4)c3s2)CC1] | 3-(2-((4-methylpiperazin-1-yl)methyl)-7-morpholinothiazolo[4,5-d]pyrimidin-5-yl)phenol |
| 447a | 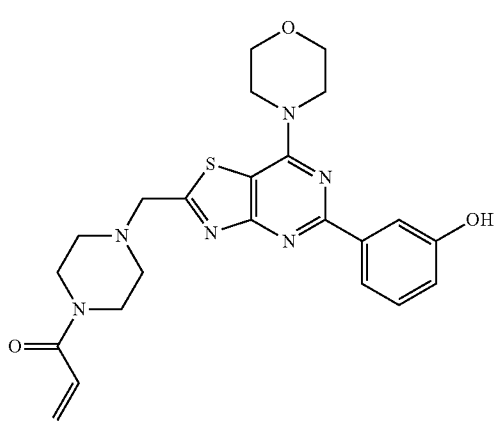 [SMILES: C=CC(=O)N1CCN(Cc2nc3nc(-c4cccc(O)c4)nc(N4CCOCC4)c3s2)CC1] | 1-(4-((5-(3-hydroxyphenyl)-7-morpholinothiazolo[4,5-d]pyrimidin-2-yl)methyl)piperazin-1-yl)prop-2-en-1-one |

TABLE 3-continued

| Cpd. No. | Structure | Name |
|---|---|---|
| 447aa | 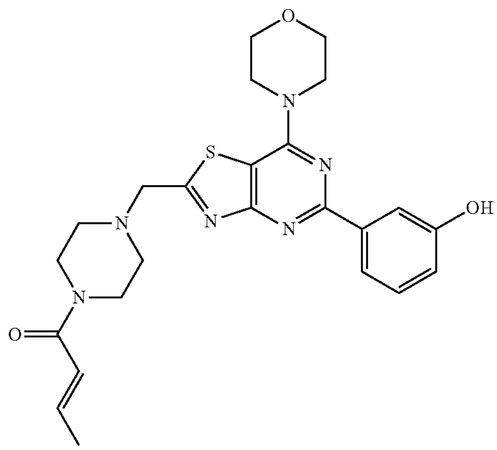 [SMILES: C/C=C/C(=O)N1CCN(Cc2nc3nc(-c4cccc(O)c4)nc(N4CCOCC4)c3s2)CC1] | (E)-1-(4-((5-(3-hydroxyphenyl)-7-morpholinothiazolo[4,5-d]pyrimidin-2-yl)methyl)piperazin-1-yl)but-2-en-1-one |
| 447b | 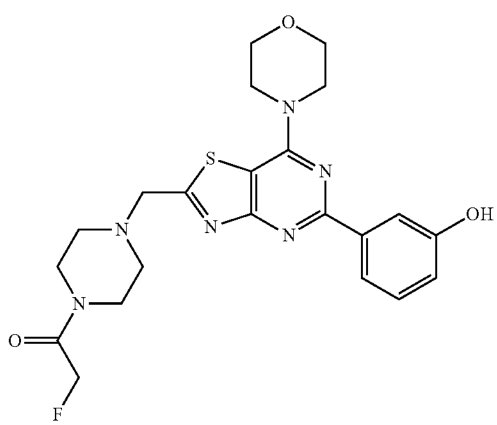 [SMILES: O=C(CF)N1CCN(Cc2nc3nc(-c4cccc(O)c4)nc(N4CCOCC4)c3s2)CC1] | 2-fluoro-1-(4-((5-(3-hydroxyphenyl)-7-morpholinothiazolo[4,5-d]pyrimidin-2-yl)methyl)piperazin-1-yl)ethanone |
| 447c | 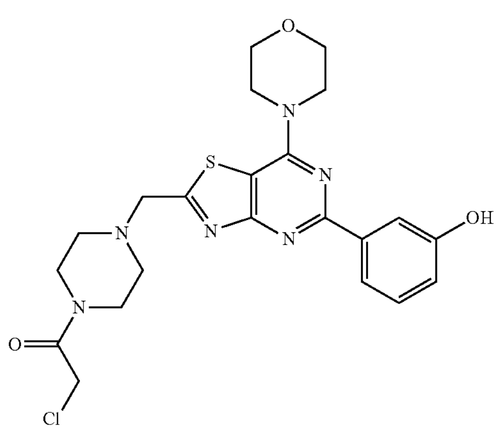 | 2-chloro-1-(4-((5-(3-hydroxyphenyl)-7-morpholinothiazolo[4,5-d]pyrimidin-2-yl)methyl)piperazin-1-yl)ethanone |

TABLE 3-continued
| Cpd. No. | Structure | Name |
|---|---|---|
| 447d | 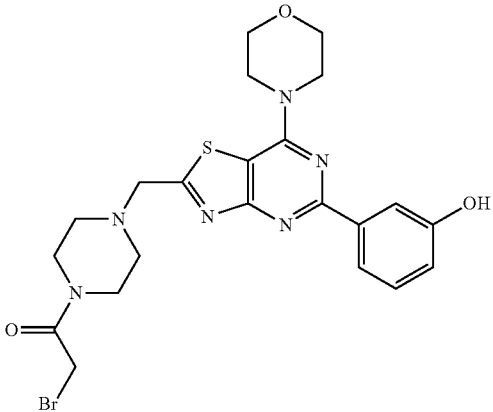 [SMILES: O=C(CCl)N1CCN(Cc2nc3nc(-c4cccc(O)c4)nc(N4CCOCC4)c3s2)CC1] | 2-bromo-1-(4-((5-(3-hydroxyphenyl)-7-morpholinothiazolo[4,5-d]pyrimidin-2-yl)methyl)piperazin-1-yl)ethanone |
| 447e | 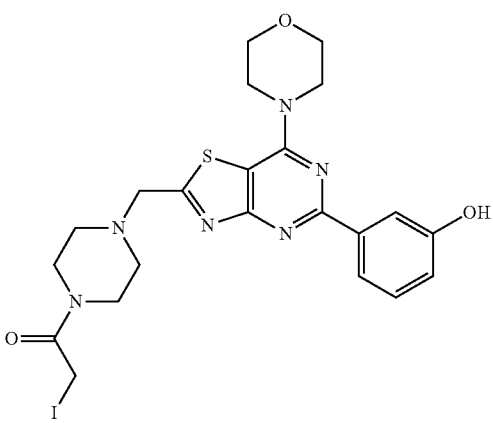 | 1-(4-((5-(3-hydroxyphenyl)-7-morpholinothiazolo[4,5-d]pyrimidin-2-yl)methyl)piperazin-1-yl)-2-iodoethanone |
| 447f | 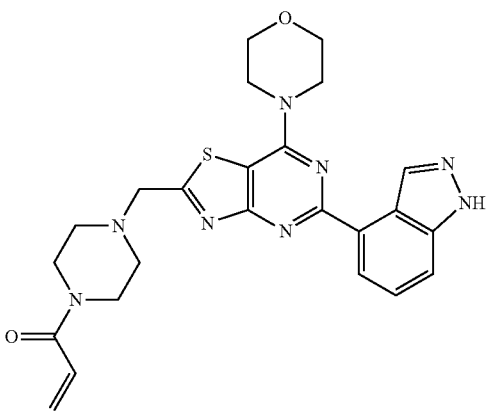 [SMILES: C=CC(=O)N1CCN(Cc2nc3nc(-c4cccc5[nH]ncc45)nc(N4CCOCC4)c3s2)CC1] | 1-(4-((5-(1H-indazol-4-yl)-7-morpholinothiazolo[4,5-d]pyrimidin-2-yl)methyl)piperazin-1-yl)prop-2-en-1-one |

TABLE 3-continued
| Cpd. No. | Structure | Name |
|---|---|---|
| 447g | 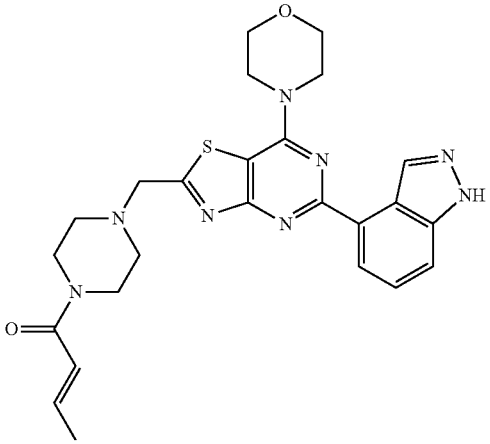 [SMILES: C/C=C/C(=O)N1CCN(Cc2nc3nc(-c4cccc5[nH]ncc45)nc(N4CCOCC4)c3s2)CC1] | (E)-1-(4-((5-(1H-indazol-4-yl)-7-morpholinothiazolo[4,5-d]pyrimidin-2-yl)methyl)piperazin-1-yl)but-2-en-1-one |
| 447h | 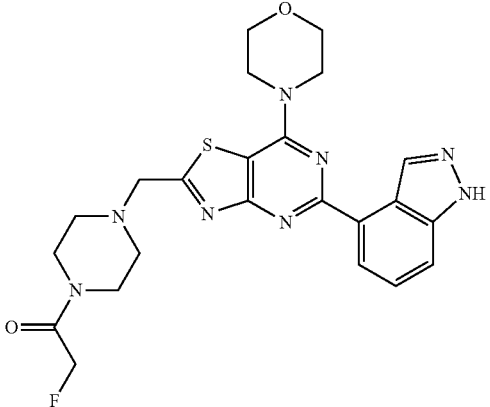 | 1-(4-((5-(1H-indazol-4-yl)-7-morpholinothiazolo[4,5-d]pyrimidin-2-yl)methyl)piperazin-1-yl)-2-fluoroethanone |
| 447i | 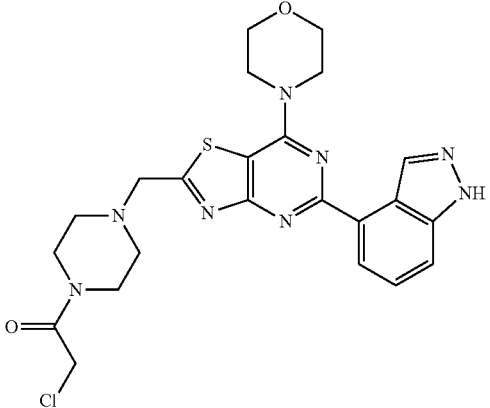 | 1-(4-((5-(1H-indazol-4-yl)-7-morpholinothiazolo[4,5-d]pyrimidin-2-yl)methyl)piperazin-1-yl)-2-chloroethanone |

TABLE 3-continued

| Cpd. No. | Structure | Name |
|---|---|---|
| 447j | 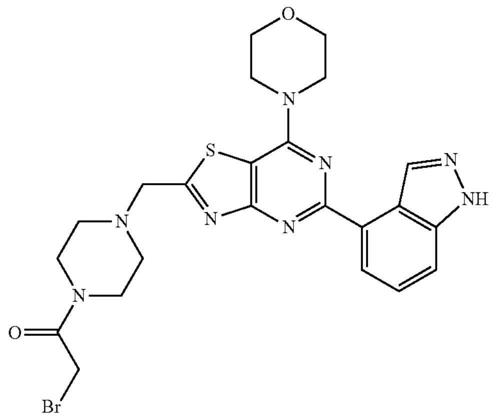 [SMILES: O=C(CCl)N1CCN(Cc2nc3nc(-c4cccc5[nH]ncc45)nc(N4CCOCC4)c3s2)CC1] | 1-(4-((5-(1H-indazol-4-yl)-7-morpholinothiazolo[4,5-d]pyrimidin-2-yl)methyl)piperazin-1-yl)-2-bromoethanone |
| 447k | 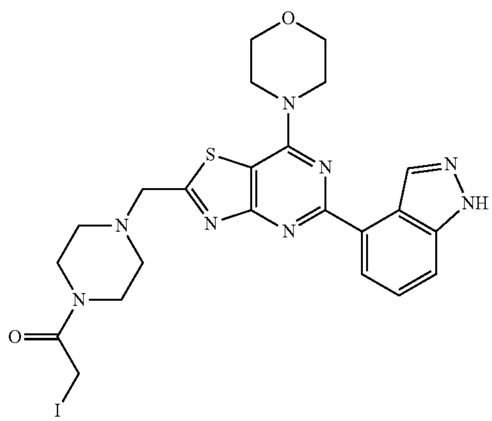 [SMILES: O=C(CI)N1CCN(Cc2nc3nc(-c4cccc5[nH]ncc45)nc(N4CCOCC4)c3s2)CC1] | 1-(4-((5-(1H-indazol-4-yl)-7-morpholinothiazolo[4,5-d]pyrimidin-2-yl)methyl)piperazin-1-yl)-2-iodoethanone |
| 448 | 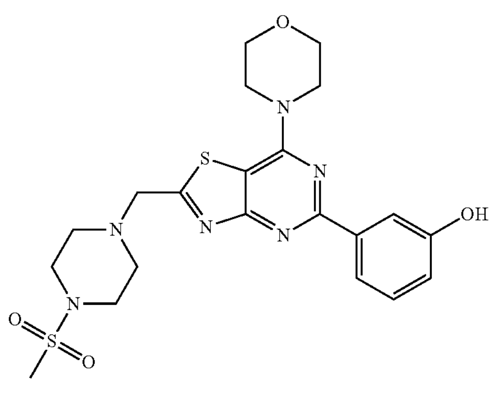 [SMILES: CS(=O)(=O)N1CCN(Cc2nc3nc(-c4cccc(O)c4)nc(N4CCOCC4)c3s2)CC1] | 3-(2-((4-(methylsulfonyl)piperazin-1-yl)methyl)-7-morpholinothiazolo[4,5-d]pyrimidin-5-yl)phenol |
| 449 | 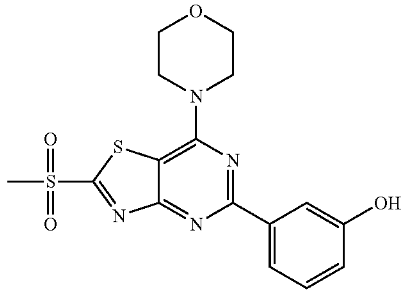 [SMILES: CS(=O)(=O)c1nc2nc(-c3cccc(O)c3)nc(N3CCOCC3)c2s1] | 3-(2-(methylsulfonyl)-7-morpholinothiazolo[4,5-d]pyrimidin-5-yl)phenol |

TABLE 3-continued

| Cpd. No. | Structure | Name |
|---|---|---|
| 450 | 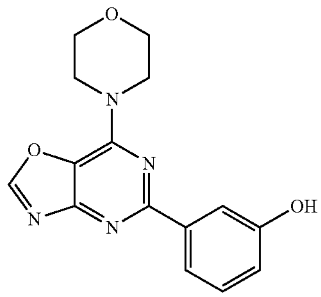 [SMILES: Oc1cccc(-c2nc(N3CCOCC3)c3ocnc3n2)c1] | 3-(7-morpholinooxazolo[4,5-d]pyrimidin-5-yl)phenol |
| 451 | 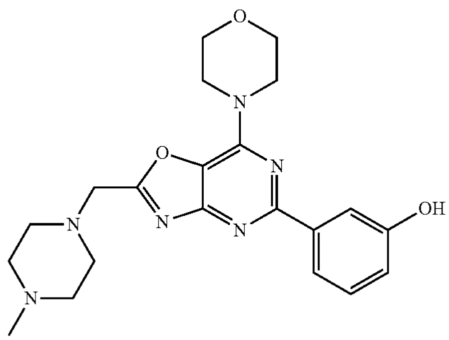 [SMILES: CN1CCN(Cc2nc3nc(-c4cccc(O)c4)nc(N4CCOCC4)c3o2)CC1] | 3-(2-((4-methylpiperazin-1-yl)methyl)-7-morpholinooxazolo[4,5-d]pyrimidin-5-yl)phenol |
| 452 | 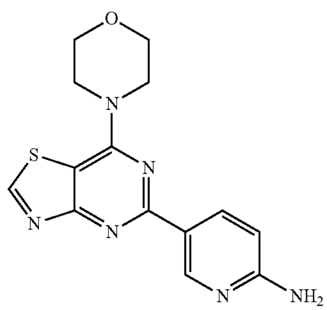 | 5-(7-morpholinothiazolo[4,5-d]pyrimidin-5-yl)pyridin-2-amine |
| 453 | 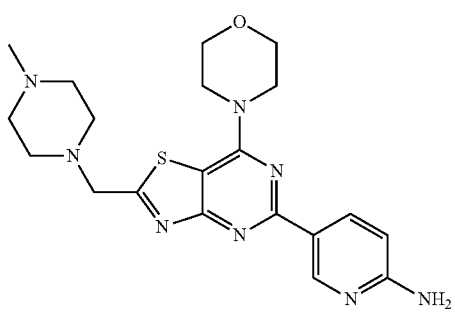 | 5-(2-((4-methylpiperazin-1-yl)methyl)-7-morpholinothiazolo[4,5-d]pyrimidin-5-yl)pyridin-2-amine |
| 454 | 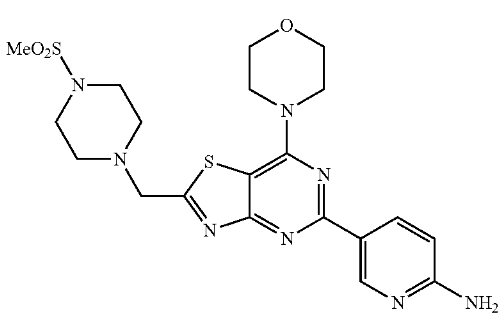 [SMILES: CS(=O)(=O)N1CCN(Cc2nc3nc(-c4ccc(N)nc4)nc(N4CCOCC4)c3s2)CC1] | 5-(2-((4-(methylsulfonyl)piperazin-1-yl)methyl)-7-morpholinothiazolo[4,5-d]pyrimidin-5-yl)pyridin-2-amine |

TABLE 3-continued

| Cpd. No. | Structure | Name |
|---|---|---|
| 455 | 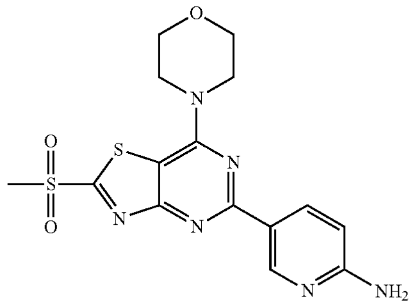 [SMILES: CS(=O)(=O)c1nc2nc(-c3ccc(N)nc3)nc(N3CCOCC3)c2s1] | 5-(2-(methylsulfonyl)-7-morpholinothiazolo[4,5-d]pyrimidion-5-yl)pyridin-2-amine |
| 456 | 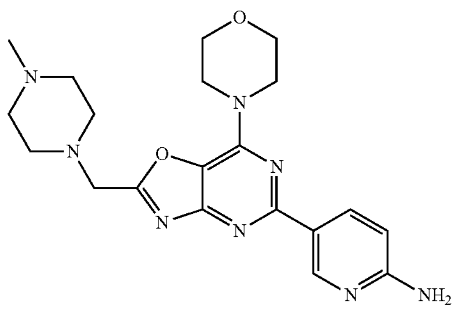 [SMILES: CN1CCN(Cc2nc3nc(-c4ccc(N)nc4)nc(N4CCOCC4)c3o2)CC1] | 5-(7-morpholinooxazolo[4,5-d]pyrimidin-5-yl)pyridin-2-amine |
| 457 | 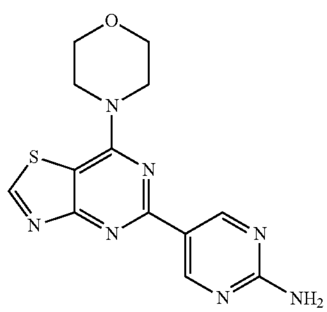 [SMILES: Nc1ncc(-c2nc(N3CCOCC3)c3scnc3n2)cn1] | 5-(7-morpholinothiazolo[4,5-d]pyrimidin-5-yl)pyrimidin-2-amine |
| 458 | 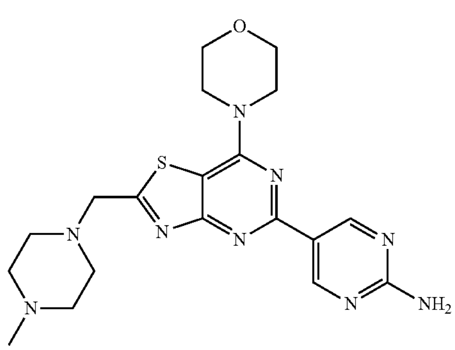 [SMILES: CN1CCN(Cc2nc3nc(-c4cnc(N)nc4)nc(N4CCOCC4)c3s2)CC1] | 5-(2-((4-methylpiperazin-1-yl)methyl)-7-morpholinothiazolo[4,5-d]pyrimidin-5-yl)pyrimidin-2-amine |

TABLE 3-continued

| Cpd. No. | Structure | Name |
|---|---|---|
| 459 | 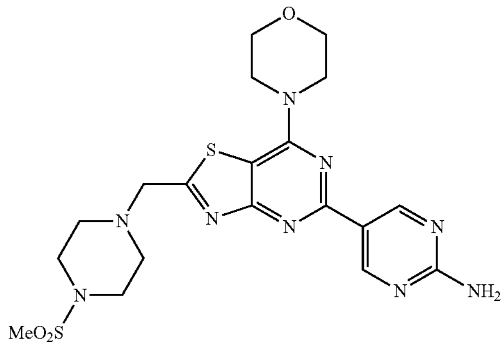 [SMILES: CS(=O)(=O)N1CCN(Cc2nc3nc(-c4cnc(N)nc4)nc(N4CCOCC4)c3s2)CC1] | 5-(2-((4-(methylsulfonyl)piperazin-1-yl)methyl)-7-morpholinothiazolo[4,5-d]pyrimidin-5-yl)pyrimidin-2-amine |
| 460 | 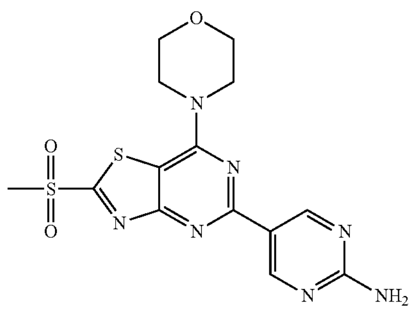 [SMILES: CS(=O)(=O)c1nc2nc(-c3cnc(N)nc3)nc(N3CCOCC3)c2s1] | 5-(2-(methylsulfonyl)-7-morpholinothiazolo[4,5-d]pyrimidin-5-yl)pyrimidin-2-amine |
| 461 | 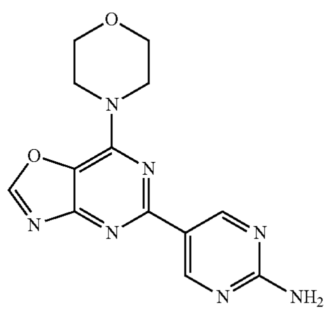 | 5-(7-morpholinooxazolo[4,5-d]pyrimidin-5-yl)pyrimidin-2-amine |
| 462 | 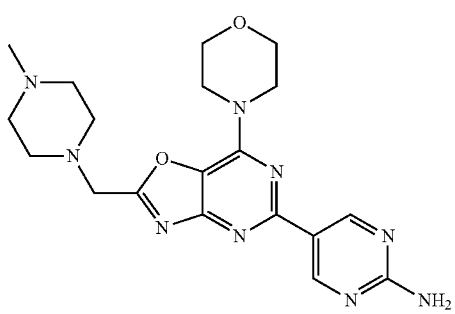 | 5-(2-((4-methylpiperazin-1-yl)methyl)-7-morpholinooxazolo[4,5-d]pyrimidin-5-yl)pyrimidin-2-amine |
| 463 | 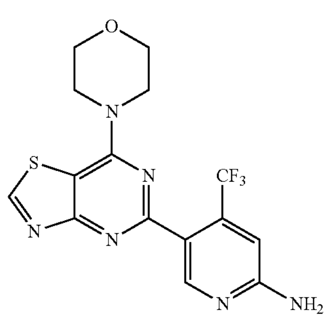 [SMILES: Nc1cc(C(F)(F)F)c(-c2nc(N3CCOCC3)c3scnc3n2)cn1] | 5-(7-morpholinothiazolo[4,5-d]pyrimidin-5-yl)-4-(trifluoromethyl)pyridin-2-amine |

TABLE 3-continued

| Cpd. No. | Structure | Name |
|---|---|---|
| 464 | 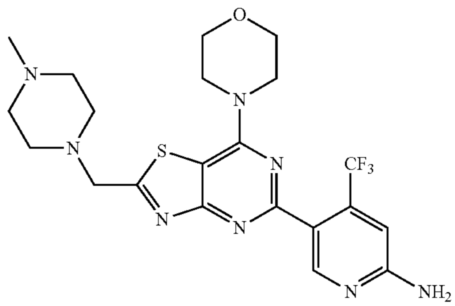 [SMILES: CN1CCN(Cc2nc3nc(-c4cnc(N)cc4C(F)(F)F)nc(N4CCOCC4)c3s2)CC1] | 5-(2-((4-methylpiperazin-1-yl)methyl)-7-morpholinothiazolo[4,5-d]pyrimidin-5-yl)-4-(trifluoromethyl)pyridin-2-amine |
| 465 | 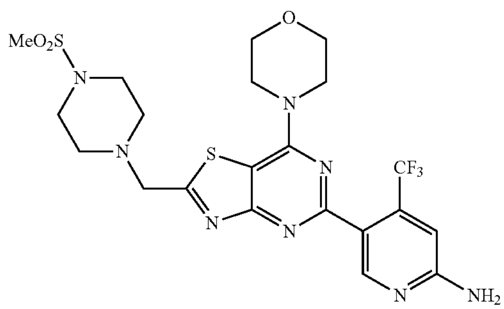 [SMILES: CS(=O)(=O)N1CCN(Cc2nc3nc(-c4cnc(N)cc4C(F)(F)F)nc(N4CCOCC4)c3s2)CC1] | 5-(2-((4-(methylsulfonyl)piperazin-1-yl)methyl)-7-morpholinothiazolo[4,5-d]pyrimidin-5-yl)-4-(trifluoromethyl)pyridin-2-amine |
| 466 | 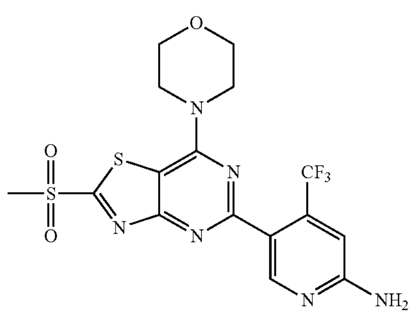 [SMILES: CS(=O)(=O)c1nc2nc(-c3cnc(N)cc3C(F)(F)F)nc(N3CCOCC3)c2s1] | 5-(2-(methylsulfonyl)-7-morpholinothiazolo[4,5-d]pyrimidin-5-yl)-4-(trifluoromethyl)pyridin-2-amine |
| 467 | 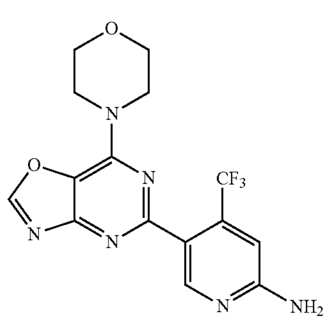 | 5-(7-morpholinooxazolo[4,5-d]pyrimidin-5-yl)-4-(trifluoromethyl)pyridin-2-amine |

TABLE 3-continued

| Cpd. No. | Structure | Name |
|---|---|---|
| 468 | 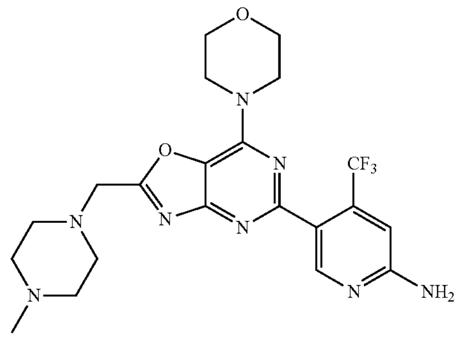 [SMILES: CN1CCN(Cc2nc3nc(-c4cnc(N)cc4C(F)(F)F)nc(N4CCOCC4)c3o2)CC1] | 5-(2-((4-methylpiperazin-1-yl)methyl)-7-morpholinooxazolo[4,5-d]pyrimidin-5-yl)-4-(trifluoromethyl)pyridin-2-amine |
| 469 | 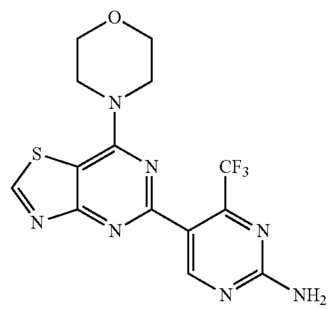 [SMILES: Nc1ncc(-c2nc(N3CCOCC3)c3scnc3n2)c(C(F)(F)F)n1] | 5-(7-morpholinothiazolo[4,5-d]pyrimidin-5-yl)-4-(trifluoromethyl)pyrimidin-2-amine |
| 470 | 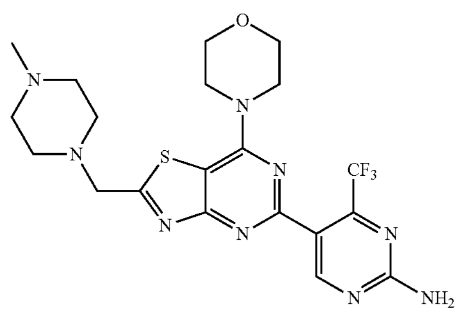 [SMILES: CN1CCN(Cc2nc3nc(-c4cnc(N)nc4C(F)(F)F)nc(N4CCOCC4)c3s2)CC1] | 5-(2-((4-methylpiperazin-1-yl)methyl)-7-morpholinothiazolo[4,5-d]pyrimidin-5-yl)-4-(trifluoromethyl)pyrimidin-2-amine |
| 471 | 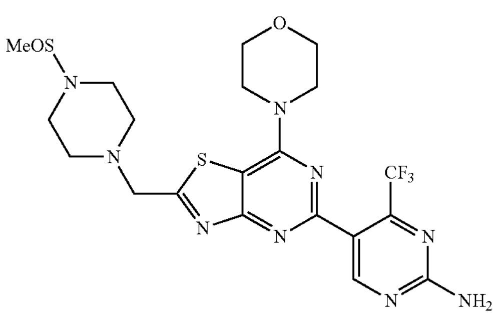 | 5-(2-((4-(methylsulfinyl)piperazin-1-yl)methyl)-7-morpholinothiazolo[4,5-d]pyrimidin-5-yl)-4-(trifluoromethyl)pyrimidin-2-amine |
| 472 | 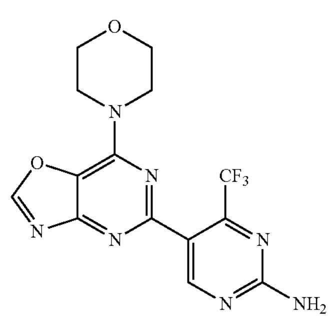 | 5-(7-morpholinooxazolo[4,5-d]pyrimidin-5-yl)-4-(trifluoromethyl)pyrimidin-2-amine |

TABLE 3-continued

| Cpd. No. | Structure | Name |
|---|---|---|
| 473 | 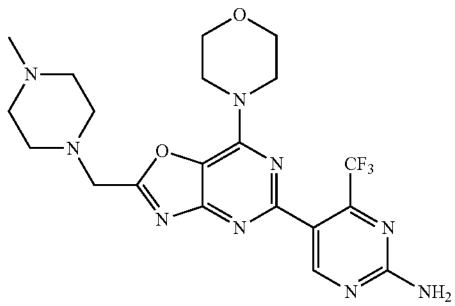 [SMILES: CN1CCN(Cc2nc3nc(-c4cnc(N)nc4C(F)(F)F)nc(N4CCOCC4)c3o2)CC1] | 5-(2-((4-methylpiperazin-1-yl)methyl)-7-morpholinooxazolo[4,5-d]pyrimidin-5-yl)-4-(trifluoromethyl)pyrimidin-2-amine |

Table 4 gives the structures and the corresponding IUPAC names (using ChemDraw Ultra, Version 11.0.1 as well as lower and upper software versions thereof, CambridgeSoft Corp., Cambridge Mass.) of exemplary compounds Nos. 474-537 of formula (Ih) or (Ii).

TABLE 4

| Cpd. No. | Structure | Name |
|---|---|---|
| 474 | 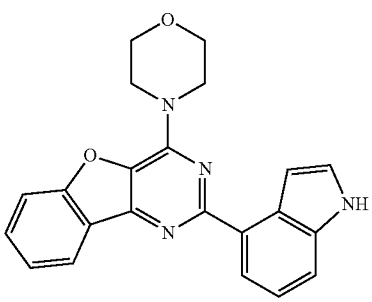 [SMILES: c1cc(-c2nc(N3CCOCC3)c3oc4ccccc4c3n2)c2cc[nH]c2c1] | 2-(1H-indol-4-yl)-4-morpholinobenzofuro[3,2-d]pyrimidine |
| 475 | 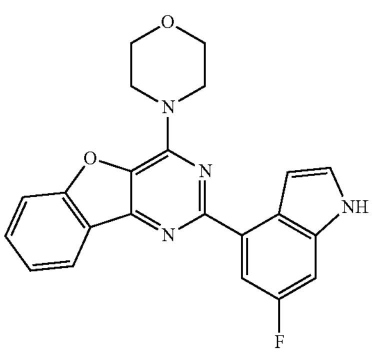 [SMILES: Fc1cc(-c2nc(N3CCOCC3)c3oc4ccccc4c3n2)c2cc[nH]c2c1] | 2-(6-fluoro-1H-indol-4-yl)-4-morpholinobenzofuro[3,2-d]pyrimidine |
| 476 | 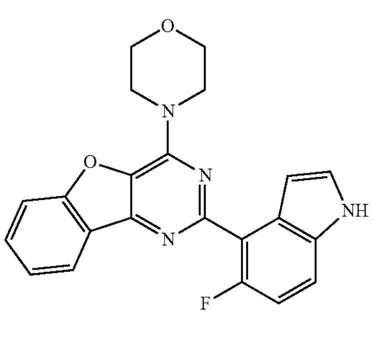 [SMILES: Fc1ccc2[nH]ccc2c1-c1nc(N2CCOCC2)c2oc3ccccc3c2n1] | 2-(5-fluoro-1H-indol-4-yl)-4-morpholinobenzofuro[3,2-d]pyrimidine |

TABLE 4-continued

| Cpd. No. | Structure | Name |
|---|---|---|
| 477 | 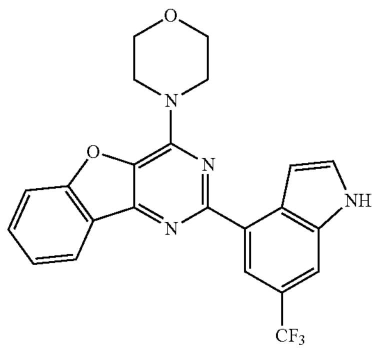 [SMILES: FC(F)(F)c1cc(-c2nc(N3CCOCC3)c3oc4ccccc4c3n2)c2cc[nH]c2c1] | 4-morpholino-2-(6-(trifluoromethyl)-1H-indol-4-yl)benzofuro[3,2-d]pyrimidine |
| 478 | 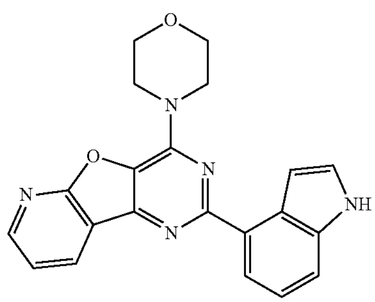 [SMILES: c1cc(-c2nc(N3CCOCC3)c3oc4ncccc4c3n2)c2cc[nH]c2c1] | 6-(1H-Indol-4-yl)-8-morpholin-4-yl-9-oxa-1,5,7-triaza-fluorene |
| 479 | 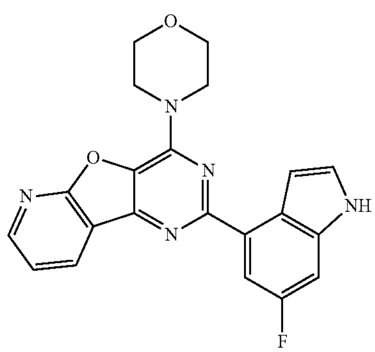 [SMILES: Fc1cc(-c2nc(N3CCOCC3)c3oc4ncccc4c3n2)c2cc[nH]c2c1] | 6-(6-Fluoro-1H-indol-4-yl)-8-morpholin-4-yl-9-oxa-1,5,7-triaza-fluorene |
| 480 | 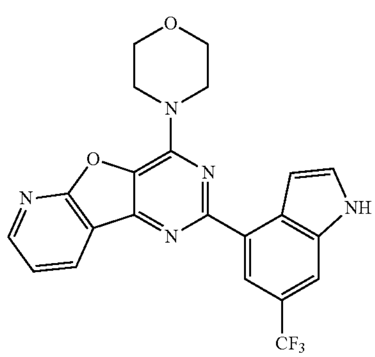 [SMILES: FC(F)(F)c1cc(-c2nc(N3CCOCC3)c3oc4ncccc4c3n2)c2cc[nH]c2c1] | 8-Morpholin-4-yl-6-(6-trifluoromethyl-1H-indol-4-yl)-9-oxa-1,5,7-triaza-fluorene |

TABLE 4-continued

| Cpd. No. | Structure | Name |
|---|---|---|
| 481 | 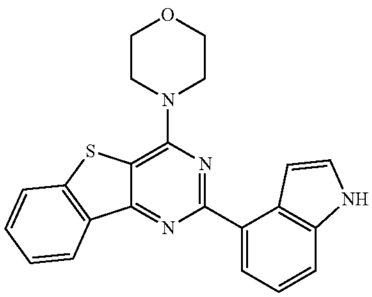 [SMILES: c1cc(-c2nc(N3CCOCC3)c3sc4ccccc4c3n2)c2cc[nH]c2c1] | 2-(1H-Indol-4-yl)-4-morpholin-4-yl-benzo[4,5]thieno[3,2-d]pyrimidine |
| 482 | 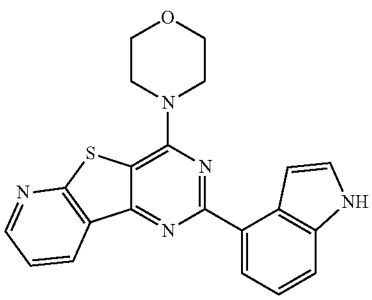 | 6-(1H-Indol-4-yl)-8-morpholin-4-yl-9-thia-1,5,7-triaza-fluorene |
| 483 | 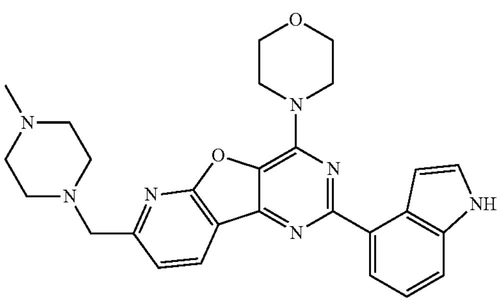 [SMILES: CN1CCN(Cc2ccc3c(n2)oc2c(N4CCOCC4)nc(-c4cccc5[nH]ccc45)nc23)CC1] | 6-(1H-Indol-4-yl)-2-(4-methyl-piperazin-1-ylmethyl)-8-morpholin-4-yl-9-oxa-1,5,7-triaza-fluorene |
| 484 | 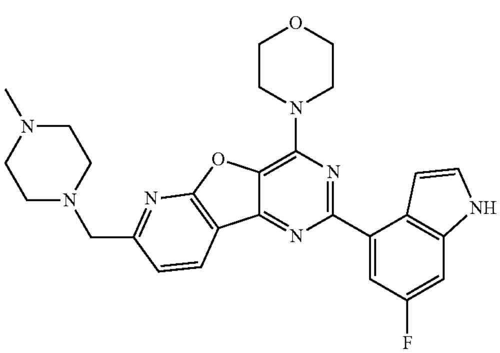 [SMILES: CN1CCN(Cc2ccc3c(n2)oc2c(N4CCOCC4)nc(-c4cc(F)cc5[nH]ccc45)nc23)CC1] | 6-(6-Fluoro-1H-indol-4-yl)-2-(4-methyl-piperazin-1-ylmethyl)-8-morpholin-4-yl-9-oxa-1,5,7-triaza-fluorene |
| 485 | 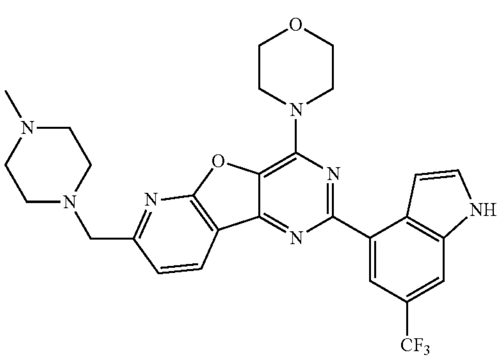 [SMILES: CN1CCN(Cc2ccc3c(n2)oc2c(N4CCOCC4)nc(-c4cc(C(F)(F)F)cc5[nH]ccc45)nc23)CC1] | 2-(4-Methyl-piperazin-1-ylmethyl)-8-morpholin-4-yl-6-(6-trifluoromethyl-1H-indol-4-yl)-9-oxa-1,5,7-triaza-fluorene |

TABLE 4-continued

| Cpd. No. | Structure | Name |
| --- | --- | --- |
| 486 | 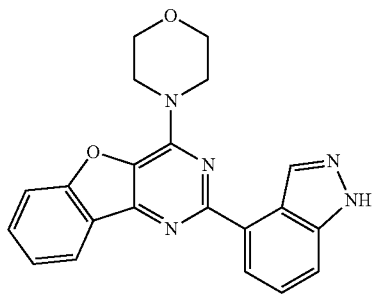 | 2-(1H-indazol-4-yl)-4-morpholinobenzofuro[3,2-d]pyrimidine |
| 486a | 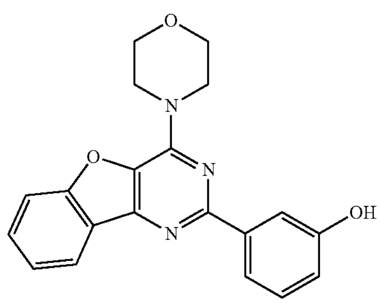 [SMILES: Oc1cccc(-c2nc(N3CCOCC3)c3oc4ccccc4c3n2)c1] | 3-(4-morpholinobenzofuro[3,2-d]pyrimidin-2-yl)phenol |
| 486b | 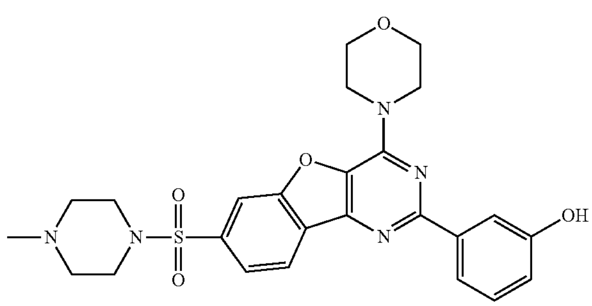 [SMILES: CN1CCN(S(=O)(=O)c2ccc3c(c2)oc2c(N4CCOCC4)nc(-c4cccc(O)c4)nc23)CC1] | 3-(7-(4-methylpiperazin-1-ylsulfonyl)-4-morpholinobenzofuro[3,2-d]pyrimidin-2-yl)phenol |
| 487 | 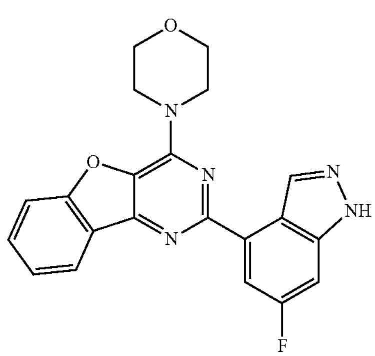 [SMILES: Fc1cc(-c2nc(N3CCOCC3)c3oc4ccccc4c3n2)c2cn[nH]c2c1] | 2-(6-fluoro-1H-indazol-4-yl)-4-morpholinobenzofuro[3,2-d]pyrimidine |

TABLE 4-continued

| Cpd. No. | Structure | Name |
|---|---|---|
| 488 | 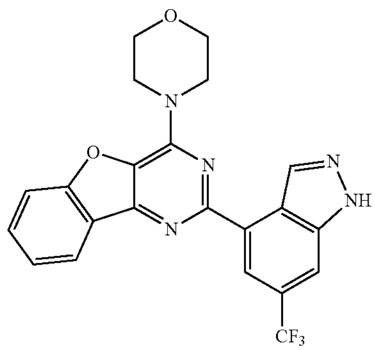 | 4-morpholino-2-(6-(trifluoromethyl)-1H-indazol-4-yl)benzofuro[3,2-d]pyrimidine |
| 489 | 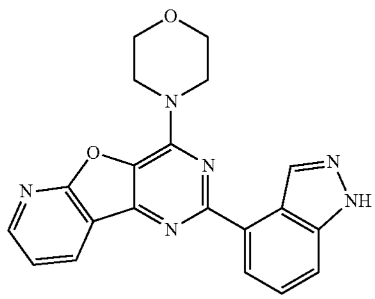 [SMILES: c1cc(-c2nc(N3CCOCC3)c3oc4ncccc4c3n2)c2cn[nH]c2c1] | 6-(1H-Indazol-4-yl)-8-morpholin-4-yl-9-oxa-1,5,7-triaza-fluorene |
| 490 | 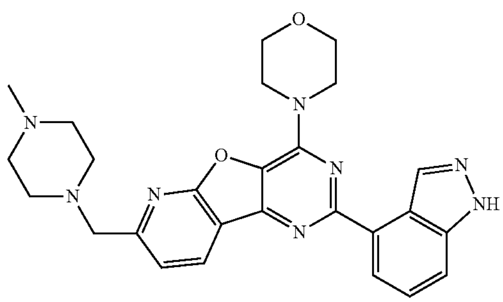 [SMILES: CN1CCN(Cc2ccc3c(n2)oc2c(N4CCOCC4)nc(-c4cccc5[nH]ncc45)nc23)CC1] | 6-(1H-Indazol-4-yl)-2-(4-methyl-piperazin-1-ylmethyl)-8-morpholin-4-yl-9-oxa-1,5,7-triaza-fluorene |
| 491 | 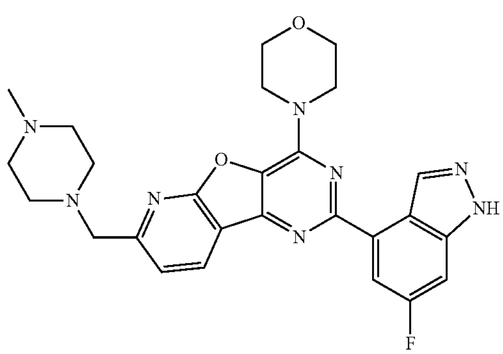 | 6-(6-Fluoro-1H-indazol-4-yl)-2-(4-methyl-piperazin-1-ylmethyl)-8-morpholin-4-yl-9-oxa-1,5,7-triaza-fluorene |
| 492 | 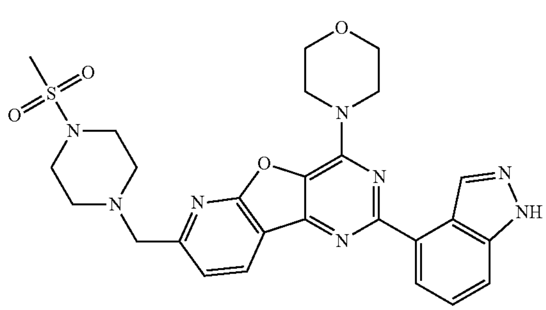 [SMILES: CS(=O)(=O)N1CCN(Cc2ccc3c(n2)oc2c(N4CCOCC4)nc(-c4cccc5[nH]ncc45)nc23)CC1] | 6-(1H-Indazol-4-yl)-2-(4-methanesulfonyl-piperazin-1-ylmethyl)-8-morpholin-4-yl-9-oxa-1,5,7-triaza-fluorene |

TABLE 4-continued
| Cpd. No. | Structure | Name |
|---|---|---|
| 493 | 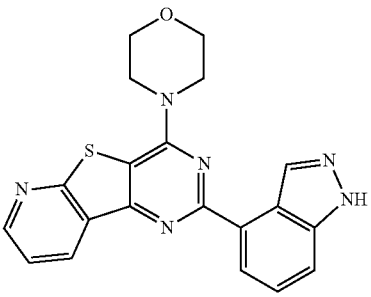 | 6-(1H-Indazol-4-yl)-8-morpholin-4-yl-9-thia-1,5,7-triaza-fluorene |
| 494 | 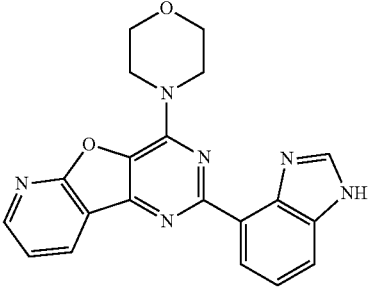 [SMILES: c1cc(-c2nc(N3CCOCC3)c3oc4ccccc4c3n2)c2nc[nH]c2c1] | 6-(1H-Benzoimidazol-4-yl)-8-morpholin-4-yl-9-oxa-1,5,7-triaza-fluorene |
| 495 | 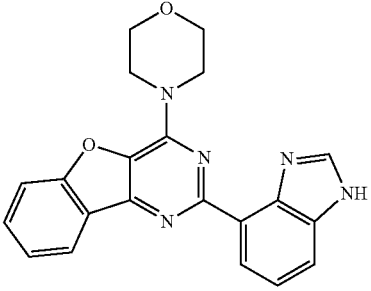 | 2-(1H-benzo[d]imidazol-4-yl)-4-morpholinobenzofuro[3,2-d]pyrimidine |
| 496 | 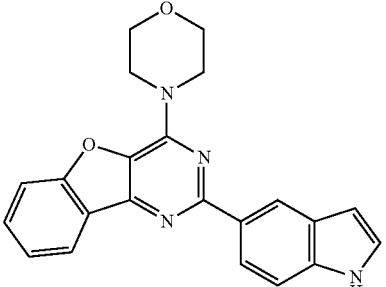 | 2-(1H-indol-5-yl)-4-morpholinobenzofuro[3,2-d]pyrimidine |
| 497 | 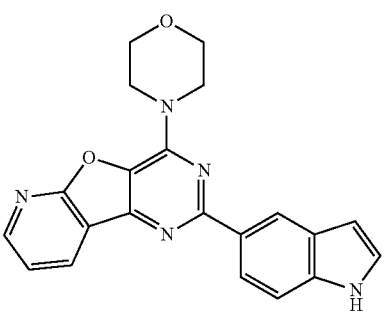 [SMILES: c1cnc2oc3c(N4CCOCC4)nc(-c4ccc5[nH]ccc5c4)nc3c2c1] | 6-(1H-Indol-5-yl)-8-morpholin-4-yl-9-oxa-1,5,7-triaza-fluorene |

TABLE 4-continued

| Cpd. No. | Structure | Name |
|---|---|---|
| 498 | 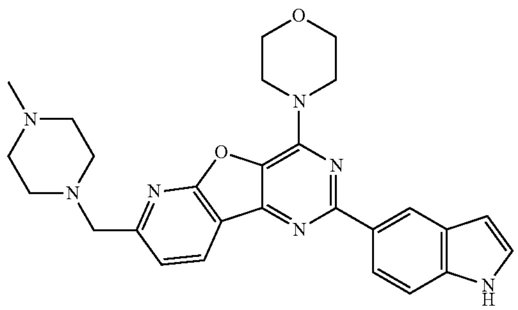 [SMILES: CN1CCN(Cc2ccc3c(n2)oc2c(N4CCOCC4)nc(-c4ccc5[nH]ccc5c4)nc23)CC1] | 6-(1H-Indol-5-yl)-2-(4-methyl-piperazin-1-ylmethyl)-8-morpholin-4-yl-9-oxa-1,5,7-triaza-fluorene |
| 499 | 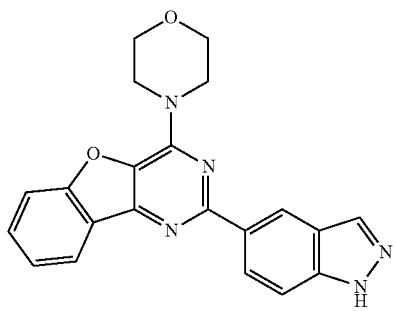 [SMILES: c1ccc2c(c1)oc1c(N3CCOCC3)nc(-c3ccc4[nH]ncc4c3)nc12] | 2-(1H-indazol-5-yl)-4-morpholinobenzofuro[3,2-d]pyrimidine |
| 500 | 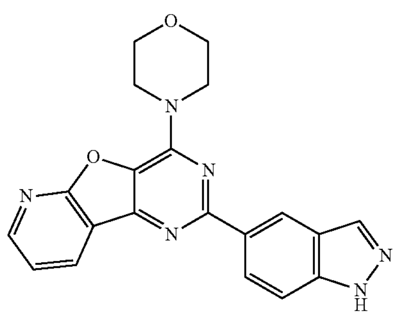 [SMILES: c1cnc2oc3c(N4CCOCC4)nc(-c4ccc5[nH]ncc5c4)nc3c2c1] | 6-(1H-Indazol-5-yl)-8-morpholin-4-yl-9-oxa-1,5,7-triaza-fluorene |
| 501 | 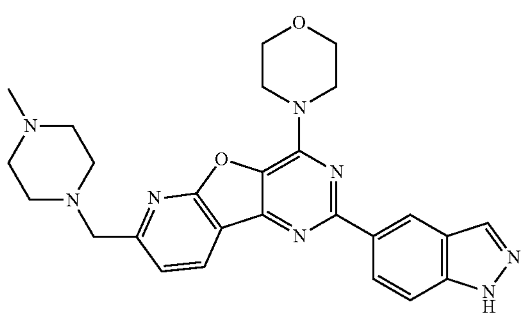 [SMILES: CN1CCN(Cc2ccc3c(n2)oc2c(N4CCOCC4)nc(-c4ccc5[nH]ncc5c4)nc23)CC1] | 6-(1H-Indazol-5-yl)-2-(4-methyl-piperazin-1-ylmethyl)-8-morpholin-4-yl-9-oxa-1,5,7-triaza-fluorene |
| 502 | 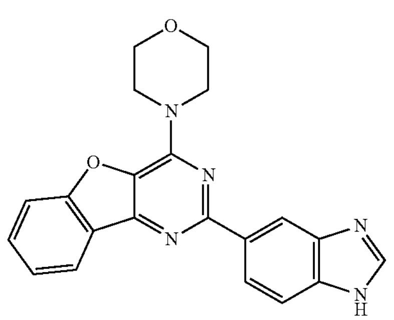 [SMILES: c1ccc2c(c1)oc1c(N3CCOCC3)nc(-c3ccc4[nH]cnc4c3)nc12] | 2-(1H-benzo[d]imidazol-5-yl)-4-morpholinobenzofuro[3,2-d]pyrimidine |

TABLE 4-continued

| Cpd. No. | Structure | Name |
|---|---|---|
| 503 | 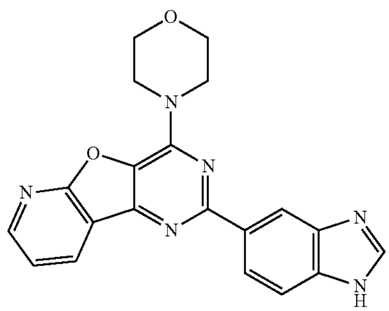 [SMILES: c1cnc2oc3c(N4CCOCC4)nc(-c4ccc5[nH]cnc5c4)nc3c2c1] | 6-(1H-Benzoimidazol-5-yl)-8-morpholin-4-yl-9-oxa-1,5,7-triaza-fluorene |
| 504 | 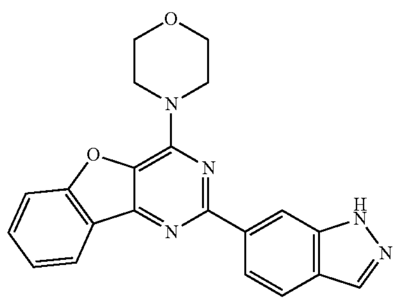 [SMILES: c1ccc2c(c1)oc1c(N3CCOCC3)nc(-c3ccc4cn[nH]c4c3)nc12] | 2-(1H-indazol-6-yl)-4-morpholinobenzofuro[3,2-d]pyrimidine |
| 505 | 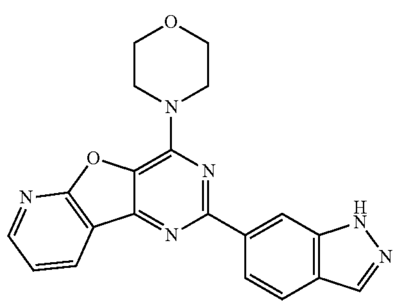 [SMILES: c1cnc2oc3c(N4CCOCC4)nc(-c4ccc5cn[nH]c5c4)nc3c2c1] | 6-(1H-Indazol-6-yl)-8-morpholin-4-yl-9-oxa-1,5,7-triaza-fluorene |
| 506 | 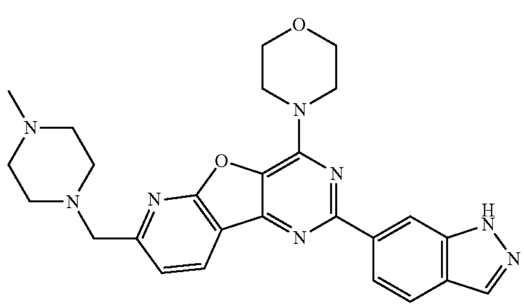 [SMILES: CN1CCN(Cc2ccc3c(n2)oc2c(N4CCOCC4)nc(-c4ccc5cn[nH]c5c4)nc23)CC1] | 6-(1H-Indazol-6-yl)-2-(4-methyl-piperazin-1-ylmethyl)-8-morpholin-4-yl-9-oxa-1,5,7-triaza-fluorene |
| 507 | 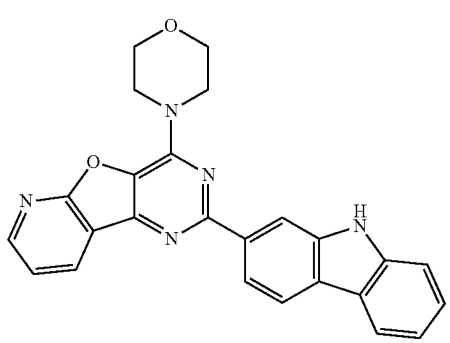 [SMILES: c1ccc2c(c1)[nH]c1cc(-c3nc(N4CCOCC4)c4oc5ncccc5c4n3)ccc12] | 6-(9H-Carbazol-2-yl)-8-morpholin-4-yl-9-oxa-1,5,7-triaza-fluorene |

TABLE 4-continued

| Cpd. No. | Structure | Name |
|---|---|---|
| 508 | 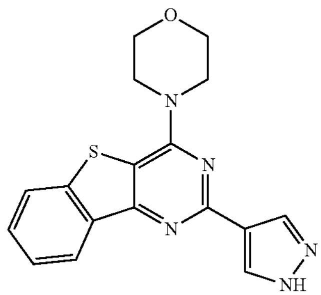 | 4-Morpholin-4-yl-2-(1H-pyrazol-4-yl)-benzo[4,5]thieno[3,2-d]pyrimidine |
| 509 | 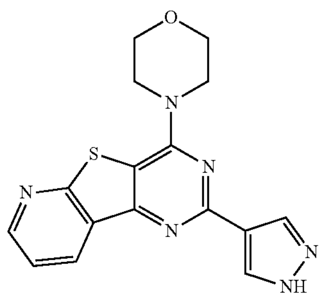 [SMILES: c1cnc2sc3c(N4CCOCC4)nc(-c4cn[nH]c4)nc3c2c1] | 8-Morpholin-4-yl-6-(1H-pyrazol-4-yl)-9-thia-1,5,7-triaza-fluorene |
| 510 | 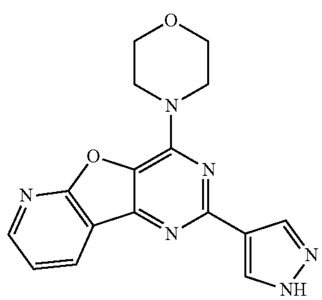 [SMILES: c1cnc2oc3c(N4CCOCC4)nc(-c4cn[nH]c4)nc3c2c1] | 8-Morpholin-4-yl-6-(1H-pyrazol-4-yl)-9-oxa-1,5,7-triaza-fluorene |
| 511 | 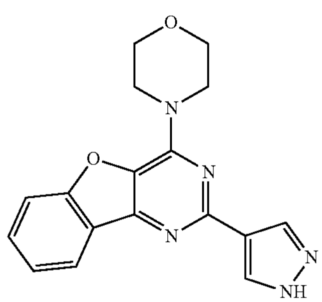 [SMILES: c1ccc2c(c1)oc1c(N3CCOCC3)nc(-c3cn[nH]c3)nc12] | 4-morpholino-2-(1H-pyrazol-4-yl)benzofuro[3,2-d]pyrimidine |
| 511.1 | 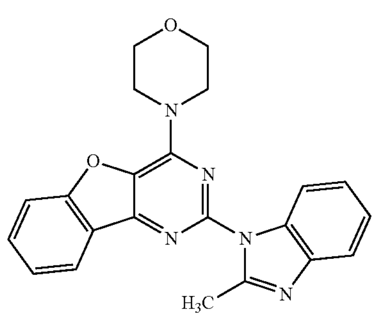 [SMILES: Cc1nc2ccccc2n1-c1nc(N2CCOCC2)c2oc3ccccc3c2n1] | 2-(2-methyl-1H-benzo[d]imidazol-1-yl)-4-morpholinobenzofuro[3,2-d]pyrimidine |

TABLE 4-continued

| Cpd. No. | Structure | Name |
|---|---|---|
| 511.2 | 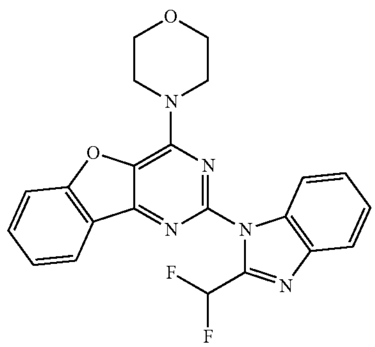 [SMILES: FC(F)c1nc2ccccc2n1-c1nc(N2CCOCC2)c2oc3ccccc3c2n1] | 2-(2-(difluoromethyl)-1H-benzo[d]imidazol-1-yl)-4-morpholinobenzofuro[3,2-d]pyrimidine |
| 511.3 | 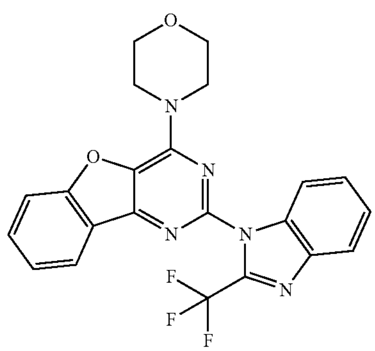 [SMILES: FC(F)(F)c1nc2ccccc2n1-c1nc(N2CCOCC2)c2oc3ccccc3c2n1] | 4-morpholino-2-(2-(trifluoromethyl)-1H-benzo[d]imidazol-1-yl)benzofuro[3,2-d]pyrimidine |
| 512 | 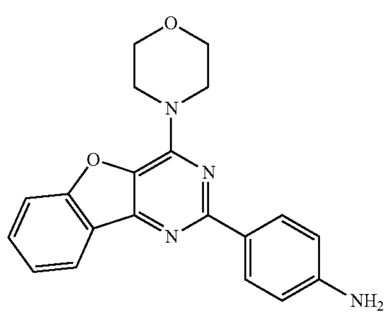 [SMILES: Nc1ccc(-c2nc(N3CCOCC3)c3oc4ccccc4c3n2)cc1] | 4-(4-morpholinobenzofuro[3,2-d]pyrimidin-2-yl)aniline |
| 513 | 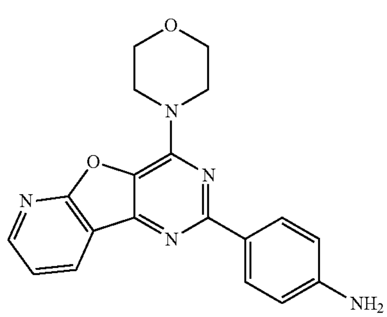 | 4-(8-Morpholin-4-yl-9-oxa-1,5,7-triaza-fluoren-6-yl)-phenylamine |

TABLE 4-continued
| Cpd. No. | Structure | Name |
|---|---|---|
| 514 | 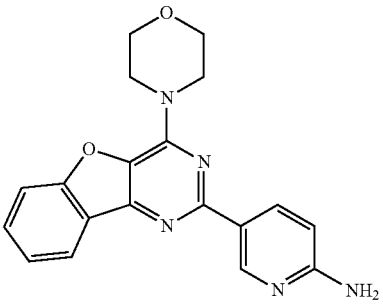 [SMILES: Nc1ccc(-c2nc(N3CCOCC3)c3oc4ccccc4c3n2)cn1] | 5-(4-morpholinobenzofuro[3,2-d]pyrimidin-2-yl)pyridin-2-amine |
| 515 | 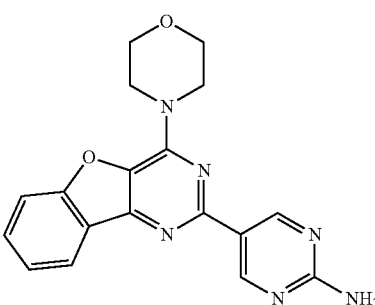 | 5-(4-morpholinobenzofuro[3,2-d]pyrimidin-2-yl)pyrimidin-2-amine |
| 516 | 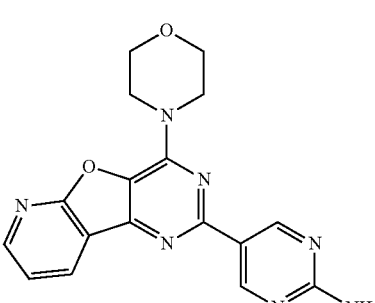 | 5-(8-Morpholin-4-yl-9-oxa-1,5,7-triaza-fluoren-6-yl)-pyrimidin-2-ylamine |
| 517 | 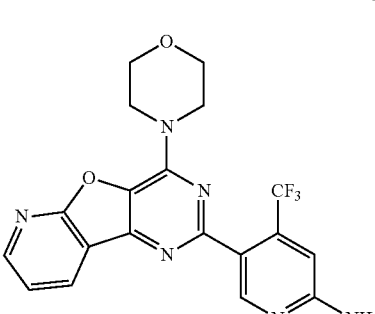 | 5-(8-Morpholin-4-yl-9-oxa-1,5,7-triaza-fluoren-6-yl)-4-trifluoromethyl-pyridin-2-ylamine |
| 517.1 | 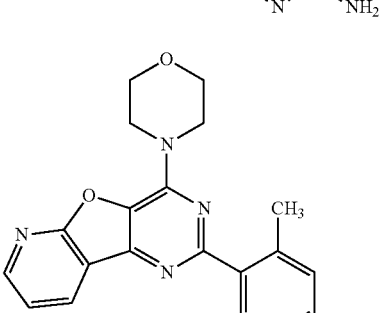 | 4-methyl-5-(4-morpholinopyrido[3',2':4,5]furo[3,2-d]pyrimidin-2-yl)pyridin-2-amine |

TABLE 4-continued

| Cpd. No. | Structure | Name |
|---|---|---|
| 518 | 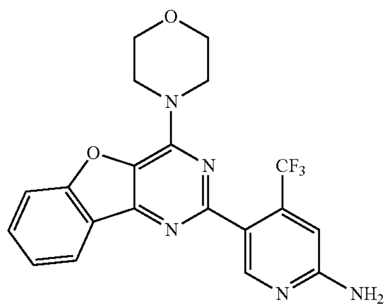 | 5-(4-morpholinobenzofuro[3,2-d]pyrimidin-2-yl)-4-(trifluoromethyl)pyridin-2-amine |
| 518.1 | 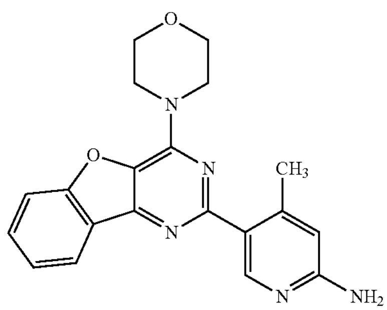 [SMILES: Cc1cc(N)ncc1-c1nc(N2CCOCC2)c2oc3ncccc3c2n1] | 4-methyl-5-(4-morpholinobenzofuro[3,2-d]pyrimidin-2-yl)pyridin-2-amine |
| 519 | 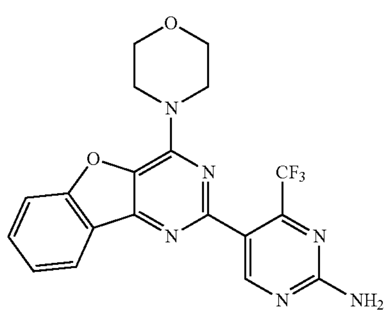 [SMILES: Nc1ncc(-c2nc(N3CCOCC3)c3oc4ccccc4c3n2)c(C(F)(F)F)n1] | 5-(4-morpholinobenzofuro[3,2-d]pyrimidin-2-yl)-4-(trifluoromethyl)pyrimidin-2-amine |
| 520 | 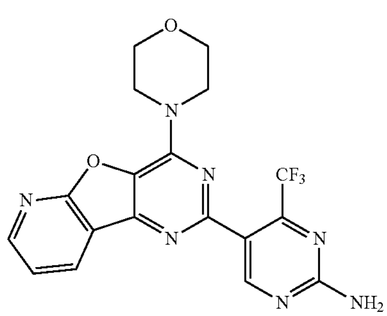 [SMILES: Nc1ncc(-c2nc(N3CCOCC3)c3oc4ncccc4c3n2)c(C(F)(F)F)n1] | 5-(8-Morpholin-4-yl-9-oxa-1,5,7-triaza-fluoren-6-yl)-4-trifluoromethyl-pyrimidin-2-ylamine |
| 521 | 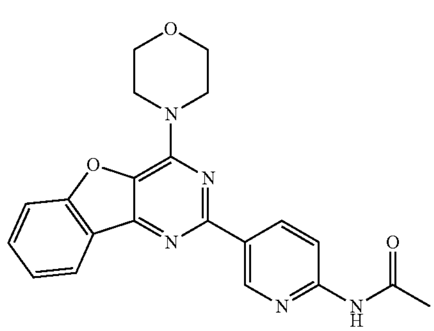 [SMILES: CC(=O)Nc1ccc(-c2nc(N3CCOCC3)c3oc4ccccc4c3n2)cn1] | N-(5-(4-morpholinobenzofuro[3,2-d]pyrimidin-2-yl)pyridin-2-yl)acetamide |

TABLE 4-continued
| Cpd. No. | Structure | Name |
|---|---|---|
| 522 | 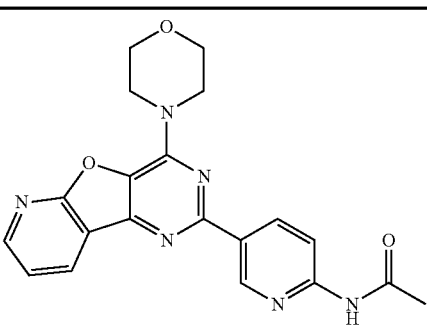 | N-[5-(8-Morpholin-4-yl-9-oxa-1,5,7-triaza-fluoren-6-yl)-pyridin-2-yl]-acetamide |
| 523 | 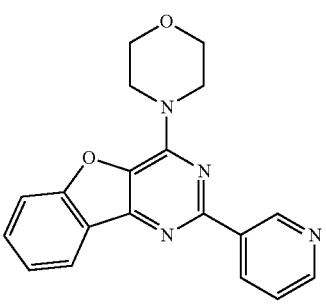 [SMILES: c1cncc(-c2nc(N3CCOCC3)c3oc4ccccc4c3n2)c1] | 4-morpholino-2-(pyridin-3-yl)benzofuro[3,2-d]pyrimidine |
| 524 | 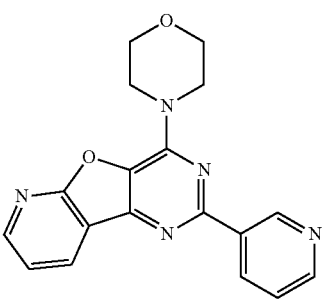 [SMILES: c1cncc(-c2nc(N3CCOCC3)c3oc4ncccc4c3n2)c1] | 8-Morpholin-4-yl-6-pyridin-3-yl-9-oxa-1,5,7-triaza-fluorene |
| 525 | 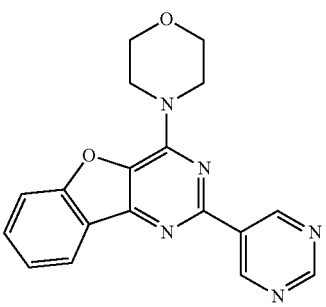 [SMILES: c1ccc2c(c1)oc1c(N3CCOCC3)nc(-c3cncnc3)nc12] | 4-morpholino-2-(pyrimidin-5-yl)benzofuro[3,2-d]pyrimidine |
| 526 | 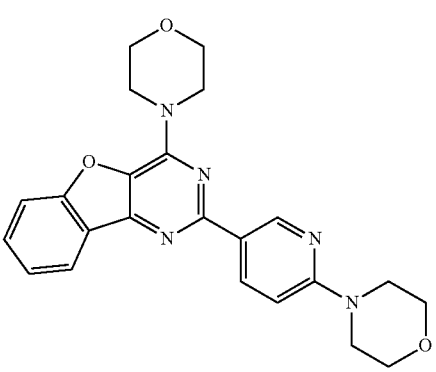 [SMILES: c1ccc2c(c1)oc1c(N3CCOCC3)nc(-c3ccc(N4CCOCC4)nc3)nc12] | 4-morpholino-2-(6-morpholinopyridin-3-yl)benzofuro[3,2-d]pyrimidine |

TABLE 4-continued

| Cpd. No. | Structure | Name |
|---|---|---|
| 526.1 | 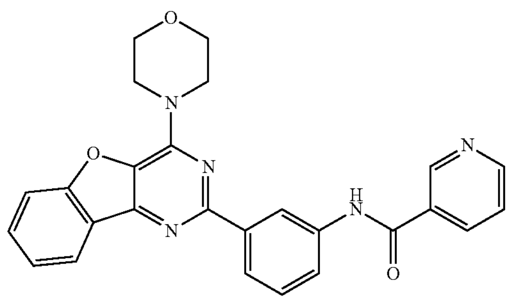 [SMILES: O=C(Nc1cccc(-c2nc(N3CCOCC3)c3oc4ccccc4c3n2)c1)c1cccnc1] | N-(3-(4-morpholinobenzofuro[3,2-d]pyrimidin-2-yl)phenyl)nicotinamide |
| 526.2 | 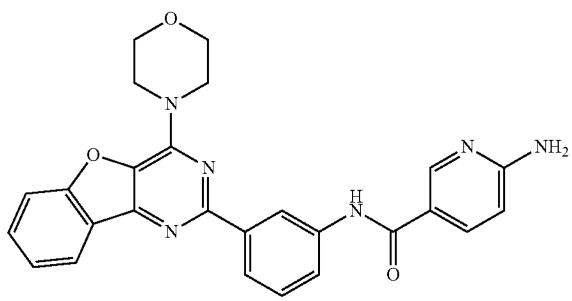 [SMILES: Nc1ccc(C(=O)Nc2cccc(-c3nc(N4CCOCC4)c4oc5ccccc5c4n3)c2)cn1] | 6-amino-N-(3-(4-morpholinobenzofuro[3,2-d]pyrimidin-2-yl)phenyl)nicotinamide |
| 526.3 | 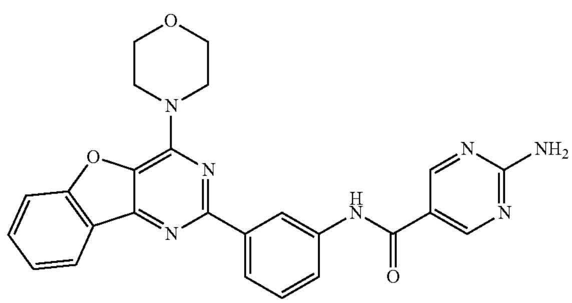 [SMILES: Nc1ncc(C(=O)Nc2cccc(-c3nc(N4CCOCC4)c4oc5ccccc5c4n3)c2)cn1] | 2-amino-N-(3-(4-morpholinobenzofuro[3,2-d]pyrimidin-2-yl)phenyl)pyrimidine-5-carboxamide |
| 526.4 | 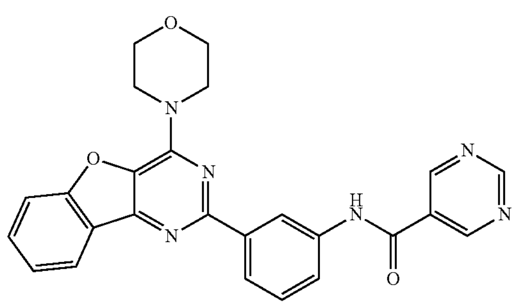 [SMILES: O=C(Nc1cccc(-c2nc(N3CCOCC3)c3oc4ccccc4c3n2)c1)c1cncnc1] | N-(3-(4-morpholinobenzofuro[3,2-d]pyrimidin-2-yl)phenyl)pyrimidine-5-carboxamide |
| 527 | 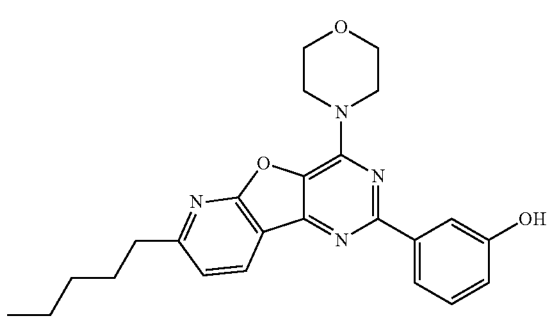 [SMILES: CCCCCc1ccc2c(n1)oc1c(N3CCOCC3)nc(-c3cccc(O)c3)nc12] | 3-(8-Morpholin-4-yl-2-pentyl-9-oxa-1,5,7-triaza-fluoren-6-yl)-phenol |

TABLE 4-continued

| Cpd. No. | Structure | Name |
|---|---|---|
| 528 | 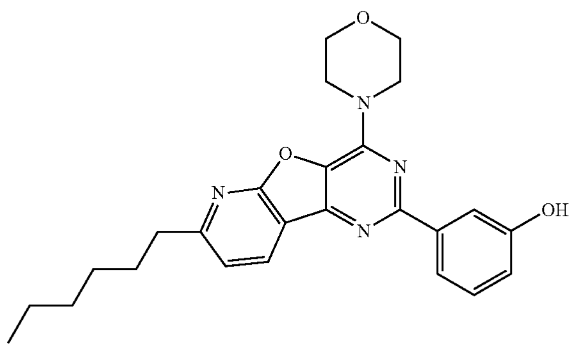 [SMILES: CCCCCCc1ccc2c(n1)oc1c(N3CCOCC3)nc(-c3cccc(O)c3)nc12] | 3-(2-Hexyl-8-morpholin-4-yl)-9-oxa-1,5,7-triaza-fluoren-6-yl)-phenol |
| 529 | 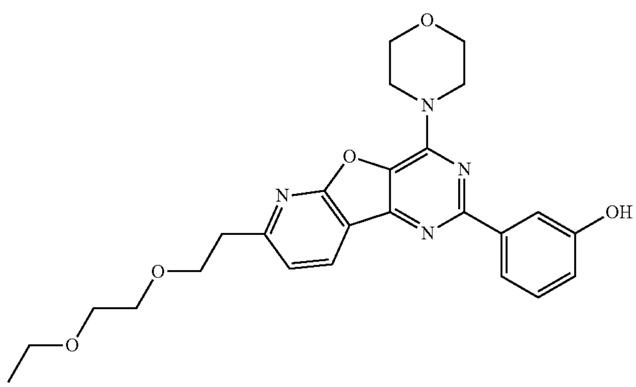 [SMILES: CCOCCOCCc1ccc2c(n1)oc1c(N3CCOCC3)nc(-c3cccc(O)c3)nc12] | 3-{2-[2-(2-Ethoxy-ethoxy)-ethyl]-8-morpholin-4-yl-9-oxa-1,5,7-triaza-fluoren-6-yl}-phenol |
| 530 | 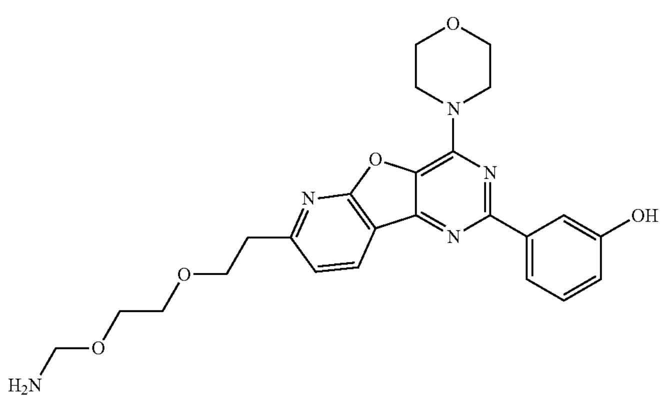 [SMILES: NCOCCOCCc1ccc2c(n1)oc1c(N3CCOCC3)nc(-c3cccc(O)c3)nc12] | 3-{2-[2-(2-Aminomethoxy-ethoxy)-ethyl]-8-morpholin-4-yl-9-oxa-1,5,7-triaza-fluoren-6-yl}-phenol |
| 531 | 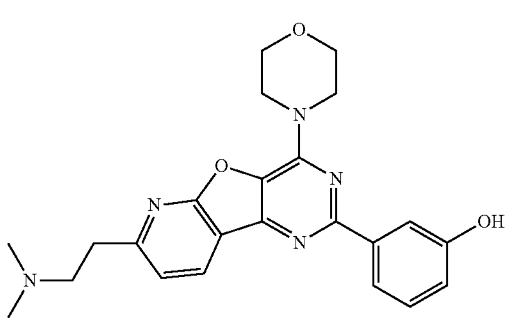 [SMILES: CN(C)CCc1ccc2c(n1)oc1c(N3CCOCC3)nc(-c3cccc(O)c3)nc12] | 3-[2-(2-Dimethylamino-ethyl)-8-morpholin-4-yl-9-oxa-1,5,7-triaza-fluoren-6-yl]-phenol |

TABLE 4-continued

| Cpd. No. | Structure | Name |
|---|---|---|
| 532 | 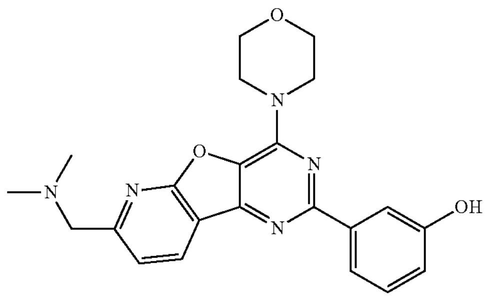 [SMILES: CN(C)Cc1ccc2c(n1)oc1c(N3CCOCC3)nc(-c3cccc(O)c3)nc12] | 3-(2-Dimethylaminomethyl-8-morpholin-4-yl-9-oxa-1,5,7-triaza-fluoren-6-yl)-phenol |
| 533 | 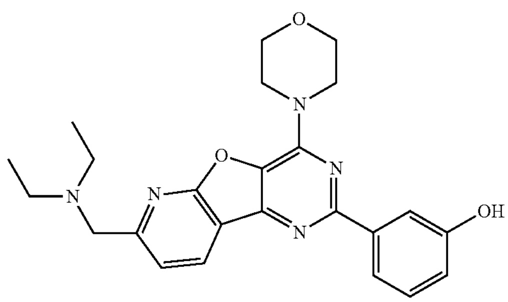 [SMILES: CCN(CC)Cc1ccc2c(n1)oc1c(N3CCOCC3)nc(-c3cccc(O)c3)nc12] | 3-(2-Diethylaminomethyl-8-morpholin-4-yl-9-oxa-1,5,7-triaza-fluoren-6-yl)-phenol |
| 534 | 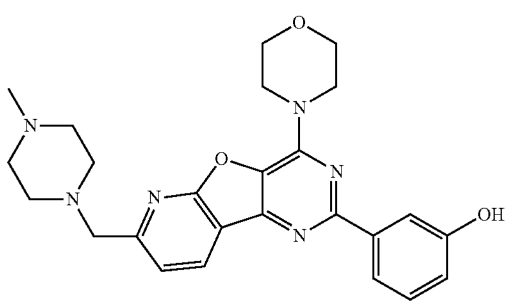 [SMILES: CN1CCN(Cc2ccc3c(n2)oc2c(N4CCOCC4)nc(-c4cccc(O)c4)nc23)CC1] | 3-[2-(4-Methyl-piperazin-1-ylmethyl)-8-morpholin-4-yl-9-oxa-1,5,7-triaza-fluoren-6-yl]-phenol |
| 535 | 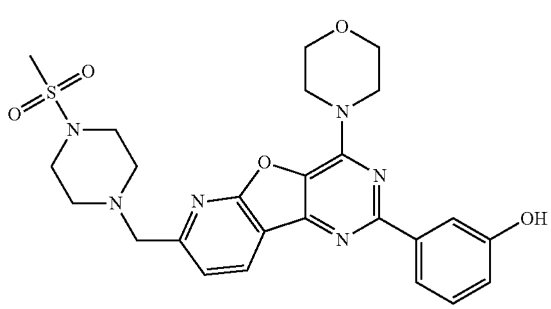 [SMILES: CS(=O)(=O)N1CCN(Cc2ccc3c(n2)oc2c(N4CCOCC4)nc(-c4cccc(O)c4)nc23)CC1] | 3-[2-(4-Methanesulfonyl-piperazin-1-ylmethyl)-8-morpholin-4-yl-9-oxa-1,5,7-triaza-fluoren-6-yl]-phenol |

TABLE 4-continued
| Cpd. No. | Structure | Name |
|---|---|---|
| 536 | 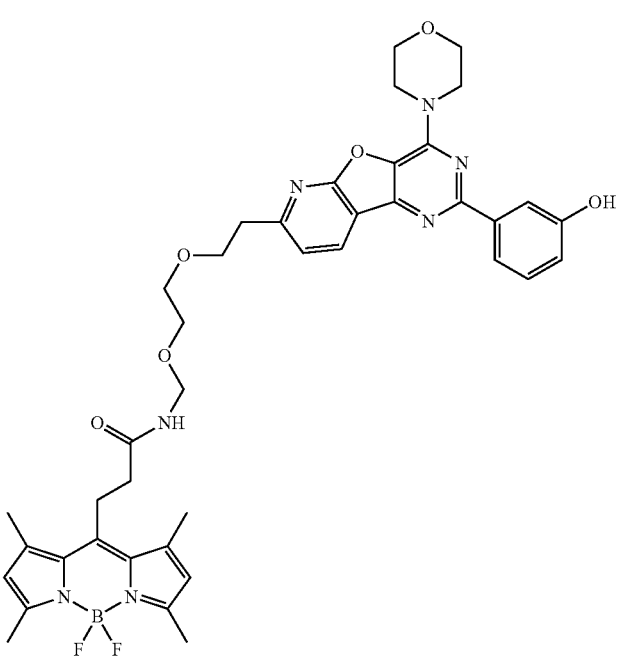 | |
| 537 | 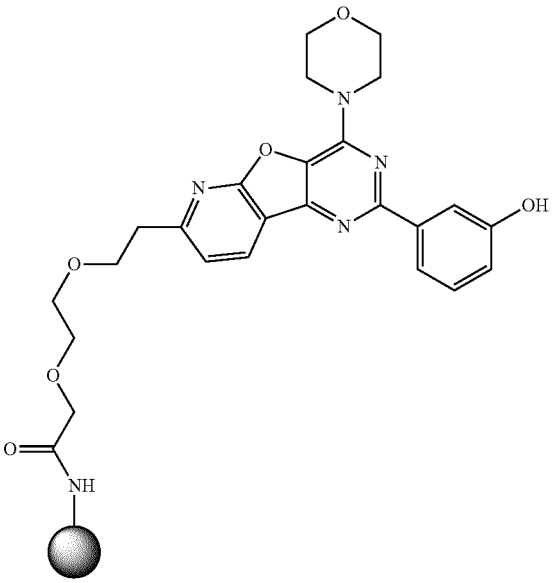 [SMILES: CNC(=O)COCCOCCc1ccc2c(n1)oc1c(N3CCOCC3)nc(-c3cccc(O)c3)nc12] |  = solid phase polymers |
Table 5 gives the structures and the corresponding IUPAC names (using ChemDraw Ultra, Version 11.0.1 as well as lower and upper software versions thereof, CambridgeSoft Corp., Cambridge Mass.) of exemplary compounds Nos. 538-590 of formula (Ie).

TABLE 5

| Cpd. No. | Structure | Name |
|---|---|---|
| 538 | 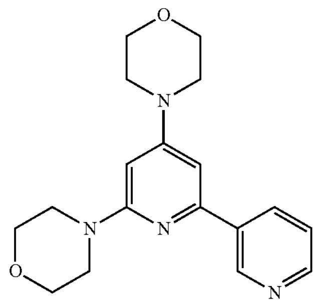 [SMILES: c1cncc(-c2cc(N3CCOCC3)cc(N3CCOCC3)n2)c1] | 4,4'-(2,3'-bipyridine-4,6-diyl)dimorpholine |
| 539 | 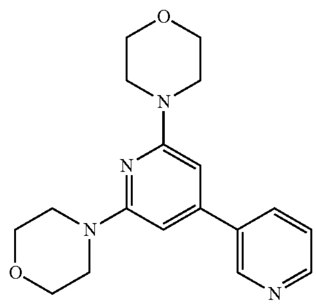 [SMILES: c1cncc(-c2cc(N3CCOCC3)nc(N3CCOCC3)c2)c1] | 2',6'-dimorpholino-3,4'-bipyridine |
| 540 | 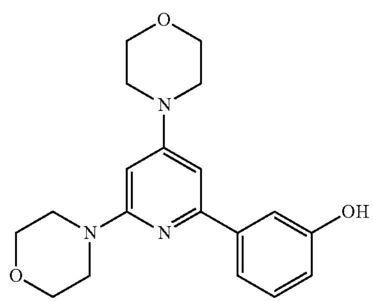 [SMILES: Oc1cccc(-c2cc(N3CCOCC3)cc(N3CCOCC3)n2)c1] | 3-(4,6-dimorpholinopyridin-2-yl)phenol |
| 541 | 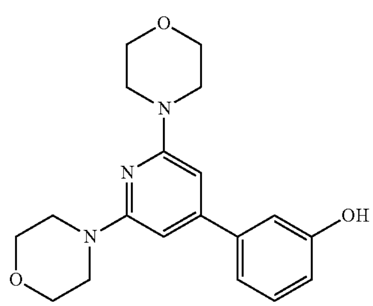 [SMILES: Oc1cccc(-c2cc(N3CCOCC3)nc(N3CCOCC3)c2)c1] | 3-(2,6-dimorpholinopyridin-4-yl)phenol |
| 542 | 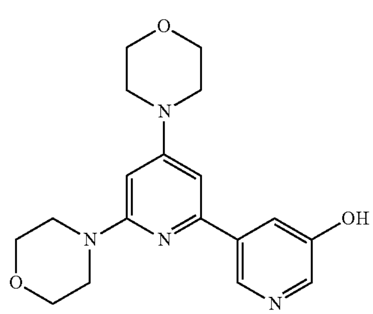 [SMILES: Oc1cncc(-c2cc(N3CCOCC3)cc(N3CCOCC3)n2)c1] | 4,6-dimorpholino-2,3'-bipyridin-5'-ol |

TABLE 5-continued

| Cpd. No. | Structure | Name |
|---|---|---|
| 543 | 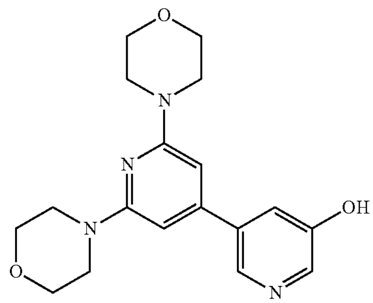 [SMILES: Oc1cncc(-c2cc(N3CCOCC3)nc(N3CCOCC3)c2)c1] | 2',6'-dimorpholino-3,4'-bipyridin-5-ol |
| 544 | 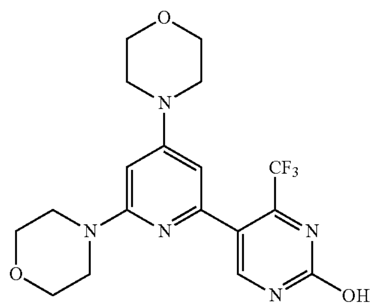 [SMILES: Oc1ncc(-c2cc(N3CCOCC3)cc(N3CCOCC3)n2)c(C(F)(F)F)n1] | 5-(4,6-dimorpholinopyridin-2-yl)-4-(trifluoromethyl)pyrimidin-2-ol |
| 545 | 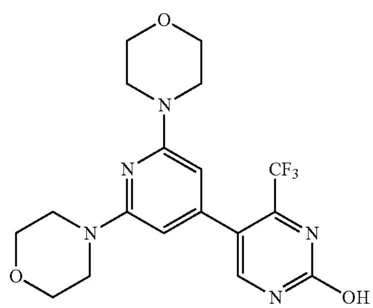 [SMILES: Oc1ncc(-c2cc(N3CCOCC3)nc(N3CCOCC3)c2)c(C(F)(F)F)n1] | 5-(2,6-dimorpholinopyridin-4-yl)-4-(trifluoromethyl)pyrimidin-2-ol |
| 546 | 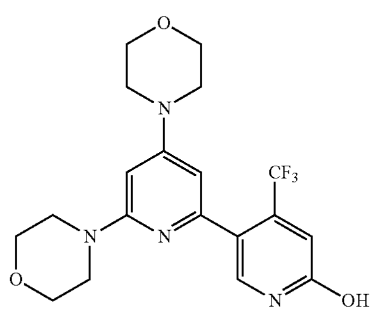 [SMILES: Oc1cc(C(F)(F)F)c(-c2cc(N3CCOCC3)cc(N3CCOCC3)n2)cn1] | 4,6-dimorpholino-4'-(trifluoromethyl)-2,3'-bipyridin-6'-ol |
| 547 | 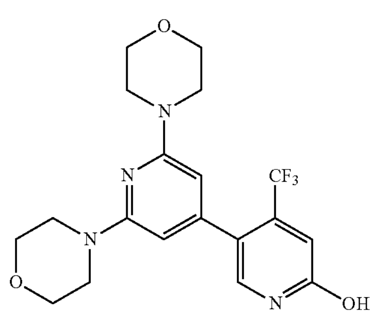 [SMILES: Oc1cc(C(F)(F)F)c(-c2cc(N3CCOCC3)nc(N3CCOCC3)c2)cn1] | 2',6'-dimorpholino-4-(trifluoromethyl)-3,4'-bipyridin-6-ol |

TABLE 5-continued

| Cpd. No. | Structure | Name |
|---|---|---|
| 548 | 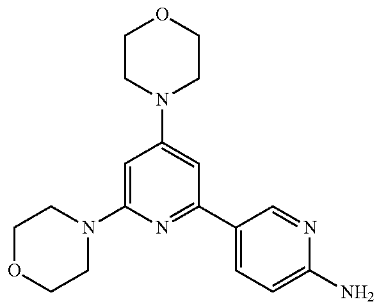 [SMILES: Nc1ccc(-c2cc(N3CCOCC3)cc(N3CCOCC3)n2)cn1] | 4,6-dimorpholino-2,3'-bipyridin-6'-amine |
| 549 | 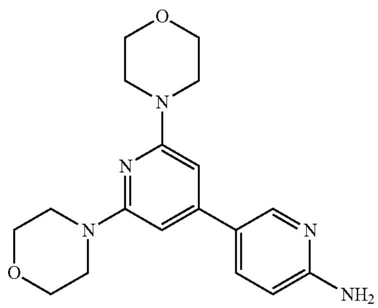 [SMILES: Nc1ccc(-c2cc(N3CCOCC3)nc(N3CCOCC3)c2)cn1] | 2',6'-dimorpholino-3,4'-bipyridin-6-amine |
| 550 | 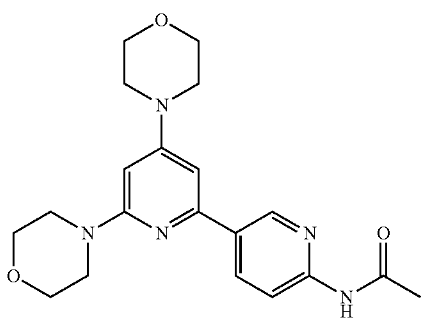 [SMILES: CC(=O)Nc1ccc(-c2cc(N3CCOCC3)cc(N3CCOCC3)n2)cn1] | N-(4,6-dimorpholino-2,3'-bipyridin-6'-yl)acetamide |
| 551 | 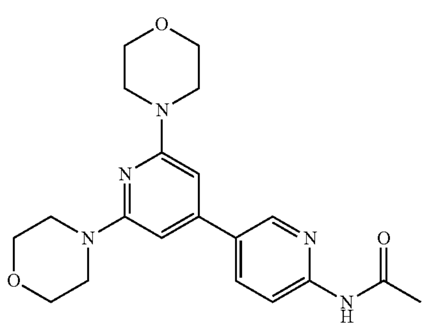 [SMILES: CC(=O)Nc1ccc(-c2cc(N3CCOCC3)nc(N3CCOCC3)c2)cn1] | N-(2',6'-dimorpholino-3,4'-bipyridin-6-yl)acetamide |
| 552 | 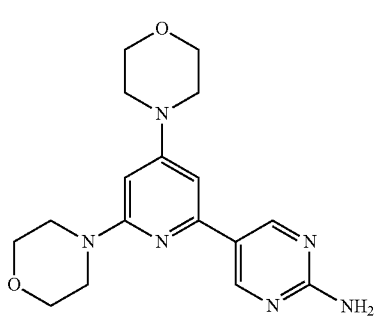 [SMILES: Nc1ncc(-c2cc(N3CCOCC3)cc(N3CCOCC3)n2)cn1] | 5-(4,6-dimorpholinopyridin-2-yl)pyrimidin-2-amine |

TABLE 5-continued

| Cpd. No. | Structure | Name |
|---|---|---|
| 553 | 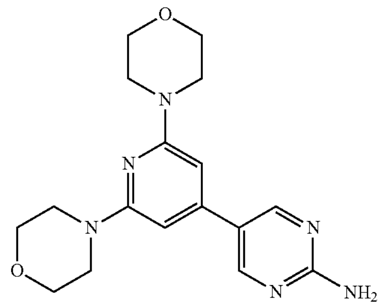 [SMILES: Nc1ncc(-c2cc(N3CCOCC3)nc(N3CCOCC3)c2)cn1] | 5-(2,6-dimorpholinopyridin-4-yl)pyrimidin-2-amine |
| 554 | 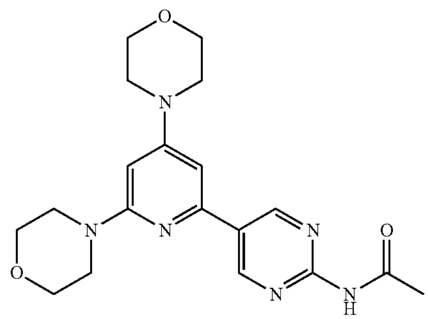 [SMILES: CC(=O)Nc1ncc(-c2cc(N3CCOCC3)cc(N3CCOCC3)n2)cn1] | N-(5-(4,6-dimorpholinopyridin-2-yl)pyrimidin-2-yl)acetamide |
| 555 | 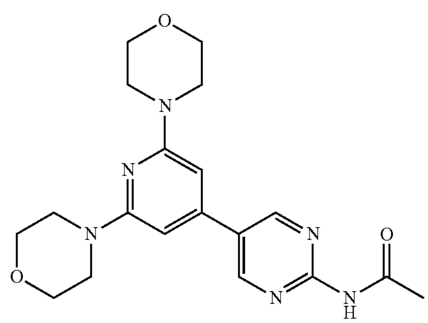 [SMILES: CC(=O)Nc1ncc(-c2cc(N3CCOCC3)nc(N3CCOCC3)c2)cn1] | N-(5-(2,6-dimorpholinopyridin-4-yl)pyrimidin-2-yl)acetamide |
| 556 | 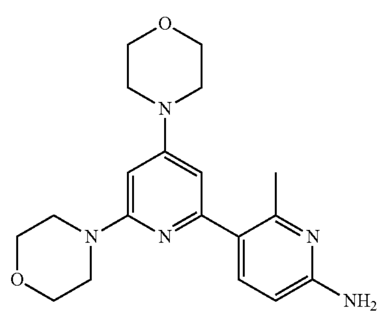 [SMILES: Cc1nc(N)ccc1-c1cc(N2CCOCC2)cc(N2CCOCC2)n1] | 2'-methyl-4,6-dimorpholino-2,3'-bipyridin-6'-amine |
| 557 | 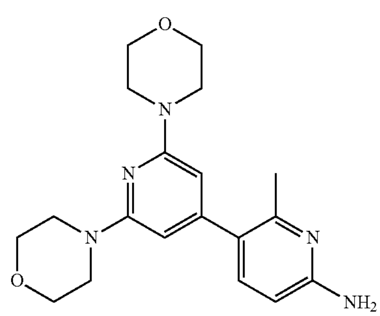 [SMILES: Cc1nc(N)ccc1-c1cc(N2CCOCC2)nc(N2CCOCC2)c1] | 2-methyl-2',6'-dimorpholino-3,4'-bipyridin-6-amine |

TABLE 5-continued

| Cpd. No. | Structure | Name |
|---|---|---|
| 558 | 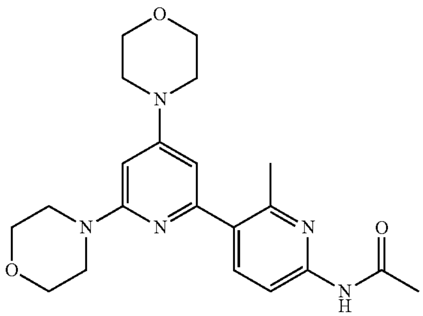 [SMILES: CC(=O)Nc1ccc(-c2cc(N3CCOCC3)cc(N3CCOCC3)n2)c(C)n1] | N-(2'-methyl-4,6-dimorpholino-2-3'-bipyridin-6'-yl)acetamide |
| 559 | 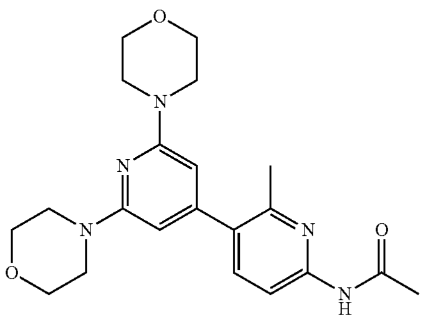 [SMILES: CC(=O)Nc1ccc(-c2cc(N3CCOCC3)nc(N3CCOCC3)c2)c(C)n1] | N-(2-methyl-2',6'-dimorpholino-3,4'-bipyridin-6-yl)acetamide |
| 560 | 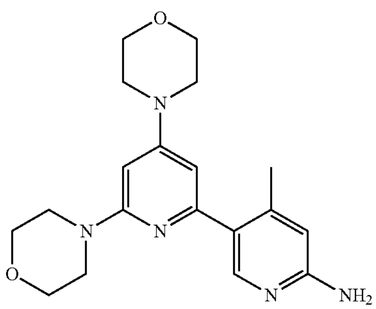 | 4'-methyl-4,6-dimorpholino-2,3'-bipyridin-6'-amine |
| 561 | 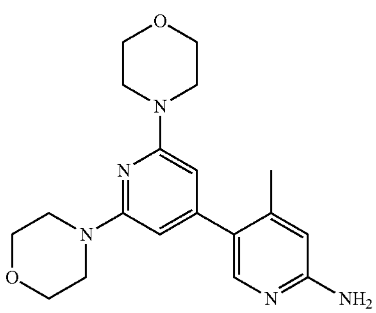 [SMILES: Cc1cc(N)ncc1-c1cc(N2CCOCC2)nc(N2CCOCC2)c1] | 4-methyl-2',6'-dimorpholino-3,4'-bipyridin-6-amine |
| 562 | 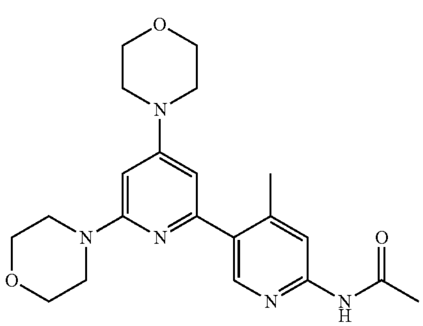 [SMILES: CC(=O)Nc1cc(C)c(-c2cc(N3CCOCC3)cc(N3CCOCC3)n2)cn1] | N-(4'-methyl-4,6-dimorpholino-2,3'-bipyridin-6'-yl)acetamide |

TABLE 5-continued

| Cpd. No. | Structure | Name |
|---|---|---|
| 563 | 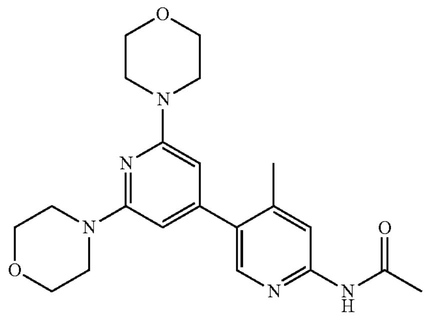 [SMILES: CC(=O)Nc1cc(C)c(-c2cc(N3CCOCC3)nc(N3CCOCC3)c2)cn1] | N-(4-methyl-2',6'-dimorpholino-3,4'-bipyridin-6-yl)acetamide |
| 564 | 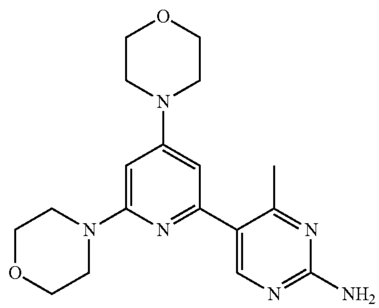 [SMILES: Cc1nc(N)ncc1-c1cc(N2CCOCC2)cc(N2CCOCC2)n1] | 5-(4,6-dimorpholinopyridin-2-yl)-4-methylpyrimidin-2-amine |
| 565 | 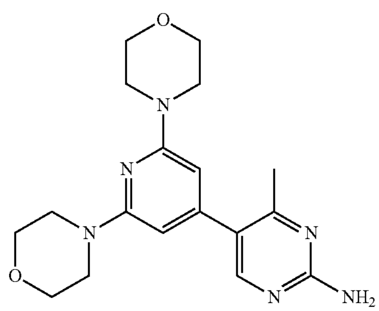 [SMILES: Cc1nc(N)ncc1-c1cc(N2CCOCC2)nc(N2CCOCC2)c1] | 5-(2,6-dimorpholinopyridin-4-yl)-4-methylpyrimidin-2-amine |
| 566 | 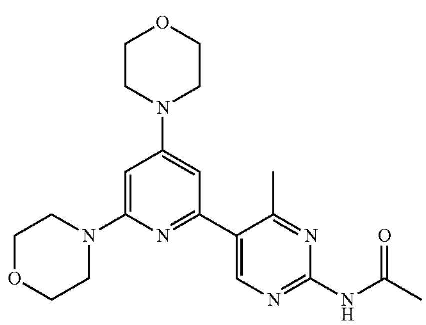 [SMILES: CC(=O)Nc1ncc(-c2cc(N3CCOCC3)cc(N3CCOCC3)n2)c(C)n1] | N-(5-(4,6-dimorpholinopyridin-2-yl)-4-methylpyrimidin-2-yl)acetamide |
| 567 | 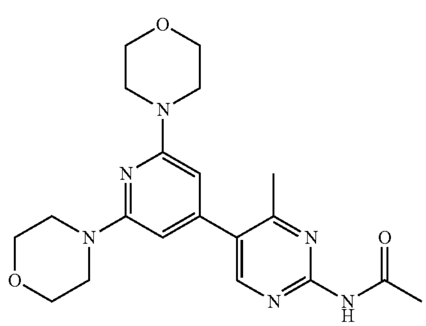 [SMILES: CC(=O)Nc1ncc(-c2cc(N3CCOCC3)nc(N3CCOCC3)c2)c(C)n1] | N-(5-(2,6-dimorpholinopyridin-4-yl)-4-methylpyrimidin-2-yl)acetamide |

TABLE 5-continued

| Cpd. No. | Structure | Name |
|---|---|---|
| 568 | 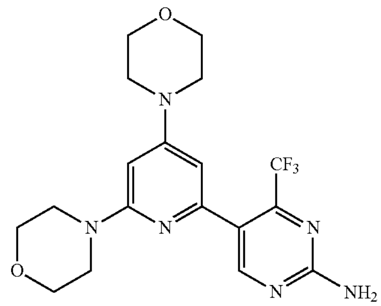 [SMILES: Nc1ncc(-c2cc(N3CCOCC3)cc(N3CCOCC3)n2)c(C(F)(F)F)n1] | 5-(4,6-dimorpholinopyridin-2-yl)-4-(trifluoromethyl)pyrimidin-2-amine |
| 569 | 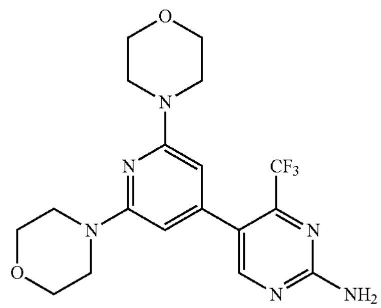 [SMILES: Nc1ncc(-c2cc(N3CCOCC3)nc(N3CCOCC3)c2)c(C(F)(F)F)n1] | 5-(2,6-dimorpholinopyridin-4-yl)-4-(trifluoromethyl)pyrimidin-2-amine |
| 570 | 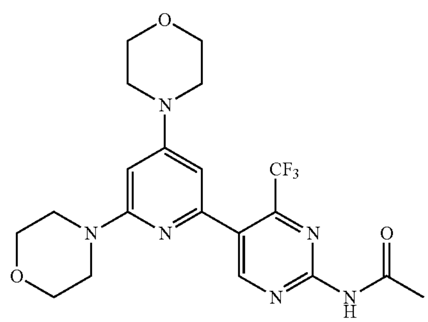 [SMILES: CC(=O)Nc1ncc(-c2cc(N3CCOCC3)cc(N3CCOCC3)n2)c(C(F)(F)F)n1] | N-(5-(4,6-dimorpholinopyridin-2-yl)-4-(trifluoromethyl)pyrimidin-2-yl)acetamide |
| 571 | 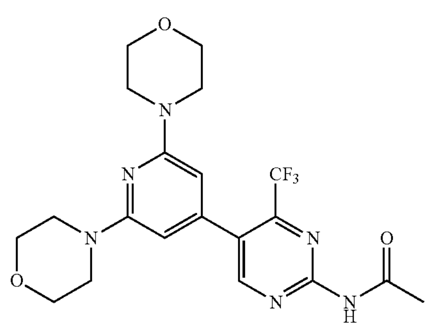 [SMILES: CC(=O)Nc1ncc(-c2cc(N3CCOCC3)nc(N3CCOCC3)c2)c(C(F)(F)F)n1] | N-(5-(2,6-dimorpholinopyridin-4-yl)-4-(trifluoromethyl)pyrimidin-2-yl)acetamide |
| 572 | 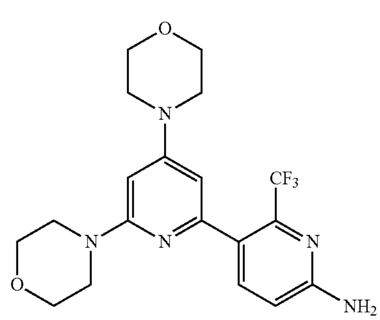 | 4,6-dimorpholino-2'-(trifluoromethyl)-2,3'-bipyridin-6'-amine |

TABLE 5-continued

| Cpd. No. | Structure | Name |
|---|---|---|
| 573 | 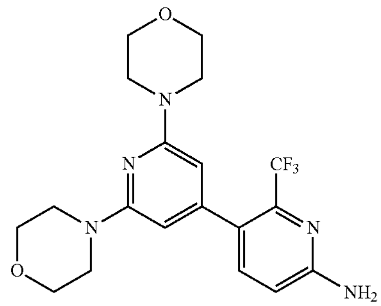 | 2',6'-dimorpholino-2-(trifluoromethyl)-3,4'-bipyridin-6-amine |
| 574 | 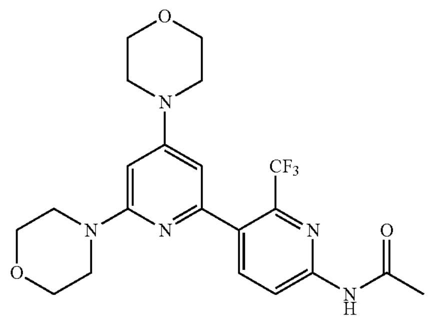 [SMILES: CC(=O)Nc1ccc(-c2cc(N3CCOCC3)cc(N3CCOCC3)n2)c(C(F)(F)F)n1] | N-(4,6-dimorpholino-2'-(trifluoromethyl)-2,3'-bipyridin-6'-yl)acetamide |
| 575 | 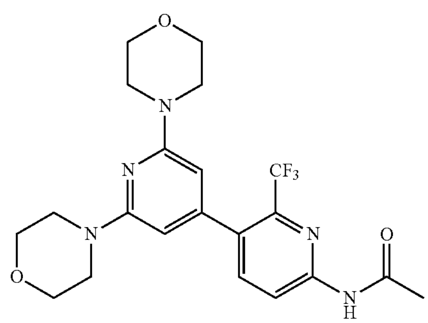 [SMILES: CC(=O)Nc1ccc(-c2cc(N3CCOCC3)nc(N3CCOCC3)c2)c(C(F)(F)F)n1] | N-(2',6'-dimorpholino-2-(trifluoromethyl)-3,4'-bipyridin-6-yl)acetamide |
| 576 | 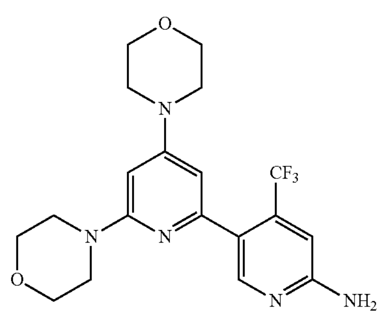 | 4,6-dimorpholino-4'-(trifluoromethyl)-2,3'-bipyridin-6'-amine |
| 477 | 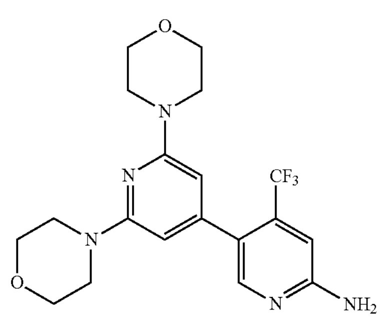 | 2,'6'-dimorpholino-4-(trifluoromethyl)-3,4'-bipyridin-6-amine |

TABLE 5-continued

| Cpd. No. | Structure | Name |
|---|---|---|
| 578 | 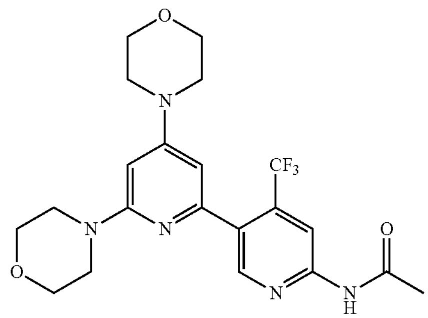 [SMILES: CC(=O)Nc1cc(C(F)(F)F)c(-c2cc(N3CCOCC3)cc(N3CCOCC3)n2)cn1] | N-(4,6-dimorpholino-4'-(trifluoromethyl)-2,3'-bipyridin-6'-yl)acetamide |
| 579 | 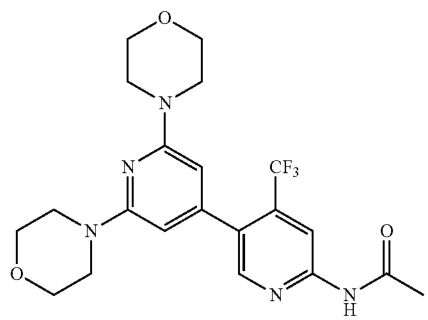 [SMILES: CC(=O)Nc1cc(C(F)(F)F)c(-c2cc(N3CCOCC3)nc(N3CCOCC3)c2)cn1] | N-(2',6'-dimorpholino-4-(trifluoromethyl)-3,4'-bipyridin-6-yl)acetamfde |
| 580 | 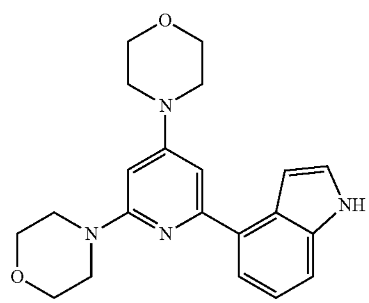 [SMILES: c1cc(-c2cc(N3CCOCC3)cc(N3CCOCC3)n2)c2cc[nH]c2c1] | 4,4'-(6-(1H-indol-4-yl)pyridine-2,4-diyl)dimorpholine |
| 581 | 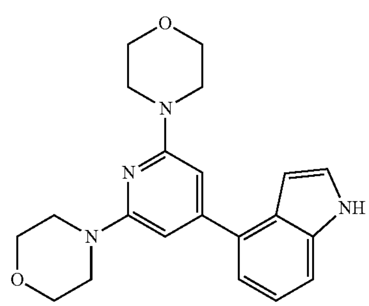 [SMILES: c1cc(-c2cc(N3CCOCC3)nc(N3CCOCC3)c2)c2cc[nH]c2c1] | 4,4'-(4-(1H-indol-4-yl)pyridine-2,6-diyl)dimorpholine |
| 582 | 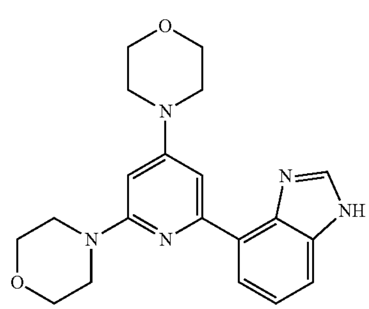 [SMILES: c1cc(-c2cc(N3CCOCC3)cc(N3CCOCC3)n2)c2nc[nH]c2c1] | 4,4'-(6-(1H-benzo[d]imidazol-4-yl)pyridine-2,4-diyl)dimorpholine |

TABLE 5-continued
| Cpd. No. | Structure | Name |
|---|---|---|
| 583 | 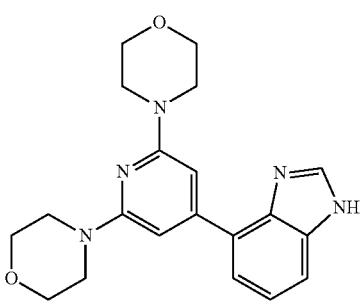 | 4,4'-(4-(1H-benzo[d]imidazol-4-yl)pyridine-2,6-diyl)dimorpholine |
| 584 | 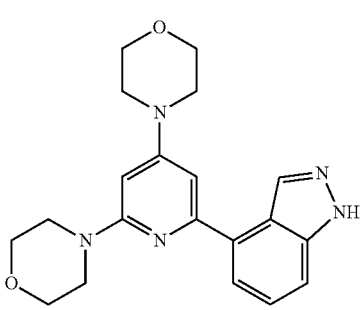 [SMILES: c1cc(-c2cc(N3CCOCC3)cc(N3CCOCC3)n2)c2cn[nH]c2c1] | 4,4'-(6-(1H-indazol-4-yl)pyridine-2,4-diyl)dimorpholine |
| 585 | 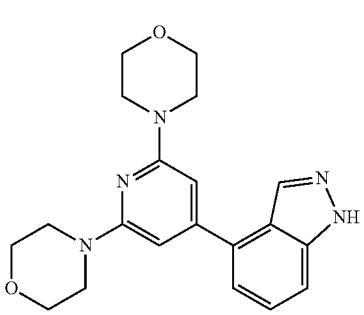 [SMILES: c1cc(-c2cc(N3CCOCC3)nc(N3CCOCC3)c2)c2cn[nH]c2c1] | 4,4'-(4-(1H-indazol-4-yl)pyridine-2,6-diyl)dimorpholine |
| 586 | 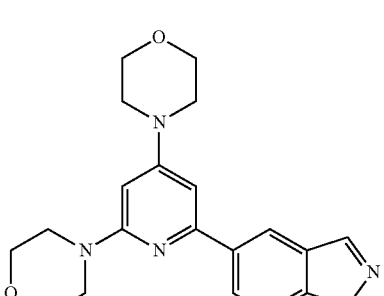 | 4,4'-(6-(1H-indazol-5-yl)pyridine-2,4-diyl)dimorpholine |
| 586 | 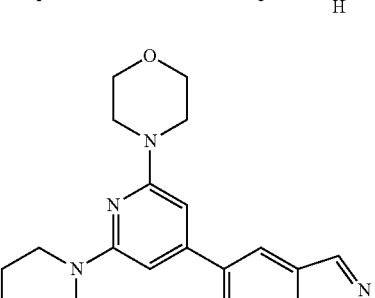 | 4,4'-(4-(1H-indazol-5-yl)pyridine-2,6-diyl)dimorpholine |

TABLE 5-continued

| Cpd. No. | Structure | Name |
|---|---|---|
| 587 | 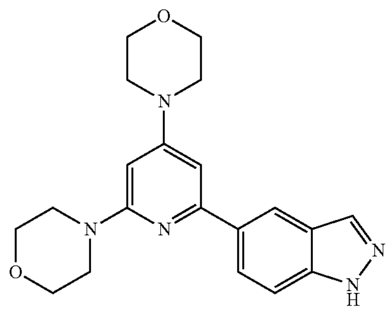 [SMILES: c1cc2[nH]ncc2cc1-c1cc(N2CCOCC2)cc(N2CCOCC2)n1] | 4,4'-(6-(1H-benzo[d]imidazol-5-yl)pyridine-2,4-diyl)dimorpholine |
| 588 | 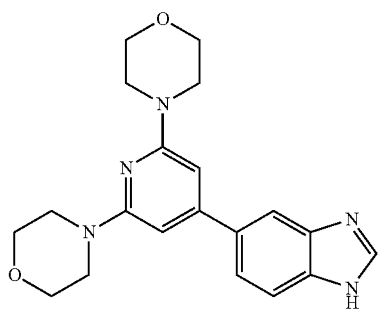 [SMILES: c1nc2cc(-c3cc(N4CCOCC4)nc(N4CCOCC4)c3)ccc2[nH]1] | 4,4'-(4-(1H-benzo[d]imidazol-5-yl)pyridine-2,6-diyl)dimorpholine |
| 589 | 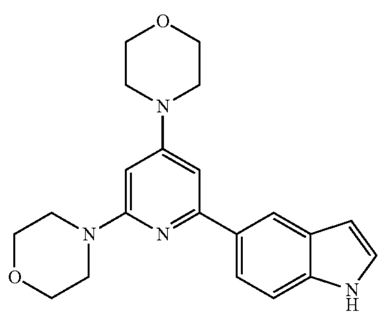 [SMILES: c1cc2cc(-c3cc(N4CCOCC4)cc(N4CCOCC4)n3)ccc2[nH]1] | 4,4'-(6-(1H-indol-5-yl)pyridine-2,4-diyl)dimorpholine |
| 590 | 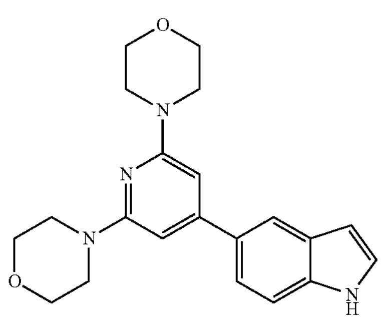 [SMILES: c1cc2cc(-c3cc(N4CCOCC4)nc(N4CCOCC4)c3)ccc2[nH]1] | 4,4'-(4-(1H-indol-5-yl)pyridine-2,6-diyl)dimorpholine |
| 591 | 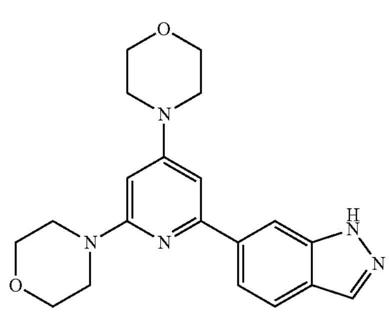 [SMILES: c1cc2cn[nH]c2cc1-c1cc(N2CCOCC2)cc(N2CCOCC2)n1] | 4,4'-(6-(1H-indazol-6-yl)pyridine-2,4-diyl)dimorpholine |

TABLE 5-continued

| Cpd. No. | Structure | Name |
|---|---|---|
| 592 | 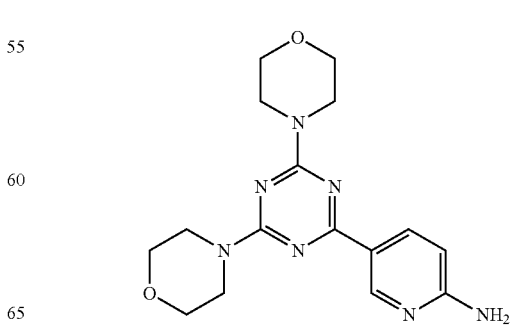 | 4,4'-(4-(1H-indazol-6-yl)pyridine-2,6-diyl)dimorpholine |

Examples of Preparation of Compounds of the Invention

The chemical reactions described in the Examples may be readily adapted to prepare a number of other lipid kinase inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Aldrich Chemical Company, Fluorochem, Acros, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted by using Merck silica gel. $^1$H NMR spectra were recorded on a Bruker instrument operating at 400 MHz, 500 MHz and 600 MHz. $^1$H NMR spectra were obtained in deuterated CDCl$_3$, Cl$_6$-DMSO, CH$_3$OD or d$_6$-acetone solutions (reported in ppm), using chloroform as the reference standard (7.25 ppm) or TMS (o ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example P1

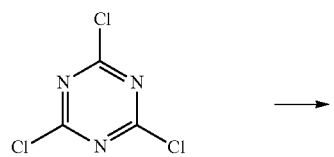

-continued

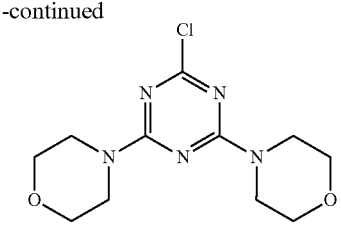

4,4'-(6-chloro-1,3,5-triazine-2,4-diyl)dimorpholine

Cyanuric chloride (1.00 g, 5.42 mmol, 1.0 eq.) was dissolved in DMF (5 ml) and morpholine (2.11 ml, 24.4 mmol, 4.5 eq.) was slowly added into reaction mixture at 0° C., stirred for 20 minutes at the same temperature, poured to water and colorless precipitate was filtered, washed with hexane and diethyl ether and dried to provide the title compound as a colorless solid (860 mg, 56%).

Analytical Data:

$^1$H-NMR (400 MHz, CDCl$_3$): δ 3.78-3.69 (16H, m).

$^{13}$C-NMR (100 MHz, CDCl$_3$): δ 170.10, 164.88, 67.28, 66.98, 44.23.

ESI-MS (70 eV, m/z): calcd. for C$_{11}$H$_{16}$ClN$_5$O$_2$ [M+H]$^+$: 286. found 360.

X-Ray analysis: the structure of 4,4'-(6-chloro-1,3,5-triazine-2,4-diyl)dimorpholine was confirmed by x-ray analysis.

Example P2

5-(4,6-dimorpholino-1,3,5-triazin-2-yl)pyridin-2-amine

Following the general procedure A, 4,4'-(6-chloro-1,3,5-triazine-2,4-diyl)dimorpholine was coupled with 2-aminopyridine-5-boronic acid pinacol ester with the reaction time of 15 h. Chromatography (methylene chloride/methanol 97:3) gave 69% of the title compound as a light yellow solid.
Analytical Data:
$^1$H NMR (400 MHz, CDCl$_3$): δ 9.06 (s, 1H), 8.36 (dd, J=2.28, 8.59 Hz, 1H), 6.50 (d, J=8.59 Hz, 1H), 4.82 (s, 2H), 3.87-3.73 (m, 16H), 2.22 (s, 1H), 1.23 (s, 1H).
$^{13}$C NMR (100 MHz, CDCl$_3$): δ 169.42, 165.37, 160.56, 150.02, 138.31, 123.91, 107.89, 67.27, 44.01, 25.27.
ESI-MS (70 eV, m/z): calcd. for C$_{16}$H$_{21}$N$_7$O$_2$ [M+H]$^+$: 344.38. found 344.30.

Example P3

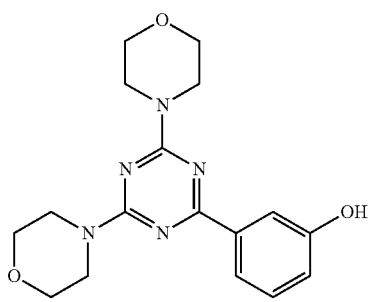

3-(4,6-dimorpholino-1,3,5-triazin-2-yl)phenol

Following the general procedure A, 4,4'-(6-chloro-1,3,5-triazine-2,4-diyl)dimorpholine was coupled with 3-hydroxyphenylboronic acid pinacol ester with reaction time of 15 h. Chromatography (hexane/ethyl acetate 1:1) gave the title compound as a colorless solid.
Analytical Data:
$^1$H NMR (400 MHz, DMSO): δ 9.51 (s, 1H), 7.77-7.74 (m, 2H), 7.23 (t, J=8.08 Hz, 1H), 6.90-6.88 (m, 1H), 3.81-3.55 (m, 16H), 1.25 (s, 1H).
$^{13}$C NMR (100 MHz, DMSO): δ 170.27, 165.60, 165.47, 158.12, 138.99, 130.01, 119.73, 119.36, 115.56, 66.86, 44.01.
ESI-MS (70 eV, m/z): calcd. for C$_{17}$H$_{21}$N$_5$O$_3$[2M]$^+$: 685.32. found 685.8.

Example P4

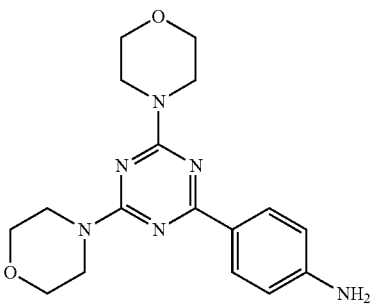 [SMILES: Nc1ccc(-c2nc(N3CCOCC3)nc(N3CCOCC3)n2)cc1]

4-(4,6-dimorpholino-1,3,5-triazin-2-yl)aniline

Following the general procedure A, 4,4'-(6-chloro-1,3,5-triazine-2,4-diyl)dimorpholine was coupled with 4-aminophenylboronic acid pinacol ester with reaction time of 24 h. Chromatography (hexane/ethyl acetate 6:4) gave the title compound as a yellow solid.
Analytical Data:
$^1$H NMR (400 MHz, CDCl$_3$): δ 8.21 (d, J=8.59, 2H), 6.68 (d, J=8.84, 2H), 3.93-3.73 (m, 19H), 3.71-3.68 (m, 2H).
$^{13}$C NMR (100 MHz, CDCl$_3$): δ 170.59, 165.62, 149.97, 130.45, 127.82, 114.54, 67.32, 67.29, 44.04, 44.01.
ESI-MS (70 eV, m/z): calcd. for C$_{17}$H$_{22}$N$_6$O$_2$ [M+H]$^+$: 343.18. found 343.40.

Example P5

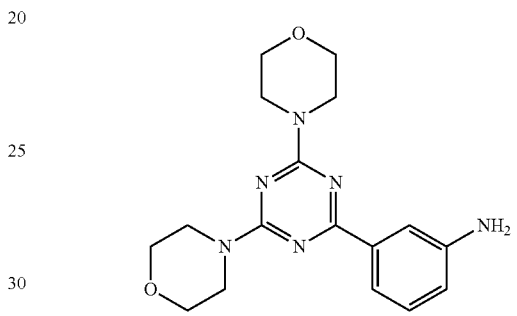

3-(4,6-dimorpholino-1,3,5-triazin-2-yl)aniline

Following the general procedure A, 4,4'-(6-chloro-1,3,5-triazine-2,4-diyl)dimorpholine was coupled with 3-aminophenylboronic acid pinacol ester with reaction time of 15 h. Column chromatography (hexane/ethyl acetate 1:1) gave the title compound as an colorless solid.
Analytical Data:
$^1$H NMR (400 MHz, CDCl$_3$): δ 7.80-7.77 (m, 1H), 7.72-7.71 (m, 1H), 7.22 (t, J=7.83 Hz, 1H), 6.82-6.79 (m, 1H), 3.90-3.74 (m, 18H).
$^{13}$C NMR (100 MHz, CDCl$_3$): δ 170.91, 165.64, 146.68, 138.86, 129.47, 119.26, 118.53, 115.21, 67.29, 44.03.
ESI-MS (70 eV, m/z): calcd. for C$_{17}$H$_{22}$N$_8$O$_2$ [M+H]$^+$: 343.18. found 343.30.

Example P6

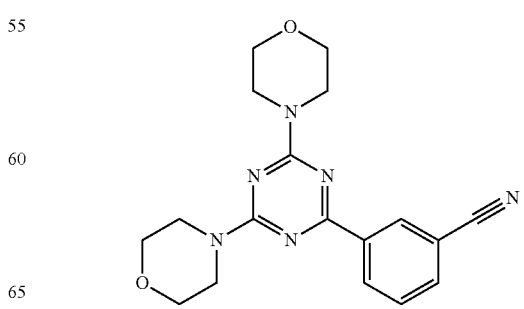

3-(4,6-dimorpholino-1,3,5-triazin-2-yl)benzonitrile

Following the general procedure A, 4,4'-(6-chloro-1,3,5-triazine-2,4-diyl)dimorpholine was coupled with 3-cyanophenylboronic acid pinacol ester with reaction time of 15 h. Column chromatography (hexane/ethyl acetate 1:1) gave 57% of the title compound as an colorless solid.
Analytical Data:
$^{1}$H NMR (400 MHz, CDCl$_{3}$): δ 8.68-8.67 (m, 1H), 8.61-8.59 (m, 1H), 7.76-7.74 (m, 1H), 7.57 (t, J=7.83 Hz, 1H), 3.95-3.76 (m, 17H).
$^{13}$C NMR (100 MHz, CDCl$_{3}$): δ 168.79, 165.47, 139.09, 134.64, 132.83, 132.64, 129.36, 119.30, 112.73, 67.23, 44.06.
ESI-MS (70 eV, m/z): calcd. for C$_{18}$H$_{20}$N$_{6}$O$_{2}$[M+H]$^{+}$: 353.16. found 353.50.

Example P7

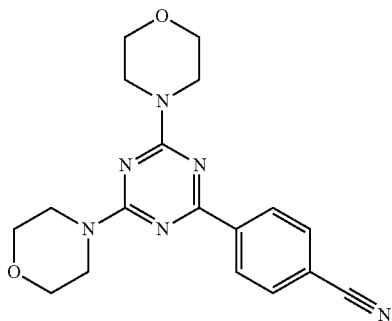

4-(4,6-dimorpholino-1,3,5-triazin-2-yl)benzonitrile

Following the general procedure A, 4,4'-(6-chloro-1,3,5-triazine-2,4-diyl)dimorpholine was coupled with 4-cyanophenylboronic acid pinacol ester with reaction time of 15 h. Chromatography (hexane/ethyl acetate 1:1) gave the 40% of the title compound as a colorless solid.
Analytical Data:
$^{1}$H NMR (400 MHz, CDCl$_{3}$): δ 8.47 (d, J=8.34, 2H), 7.71 (d, J=8.08, 2H), 3.93-3.75 (m, 16H), 1.35 (s, 1H).
$^{13}$C NMR (100 MHz, CDCl$_{3}$): δ 169.14, 165.50, 142.09, 132.33, 129.20, 123.67, 119.23, 114.79, 67.22, 44.13, 44.08, 25.27.
ESI-MS (70 eV, m/z): calcd. for C$_{18}$H$_{20}$N$_{6}$O$_{2}$ [M+H]$^{+}$: 353.16, desired mass was not found.

Example P8

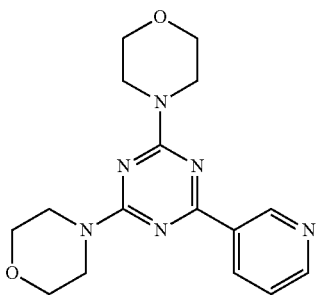 [SMILES: c1cncc(-c2nc(N3CCOCC3)nc(N3CCOCC3)n2)c1]

4,4'-(6-(pyridin-3-yl)-1,3,5-triazine-2,4-diyl)dimorpholine

Following the general procedure A, 4,4'-(6-chloro-1,3,5-triazine-2,4-diyl)dimorpholine was coupled with 3-pyridineboronic acid pinacol ester with reaction time of 15 h. Chromatography (hexane/ethyl acetate 1:1) gave the title compound as a colorless solid.
Analytical Data:
$^{1}$H NMR (400 MHz, CDCl$_{3}$): δ 9.53 (s, 1H), 8.70-8.68 (m, 1H), 8.61-8.57 (m, 1H), 7.36-7.32 (m, 1H), 3.92-3.75 (m, 1H), 1.92 (s, 1H).
$^{13}$C NMR (100 MHz, CDCl$_{3}$): δ 169.24, 165.40, 152.25, 150.54, 136.04, 133.24, 123.40, 67.23, 44.06.
ESI-MS (70 eV, m/z): calcd. for C$_{16}$H$_{20}$N$_{6}$O$_{2}$[M+H]$^{+}$: 329.16. found 329.20.

Example P9

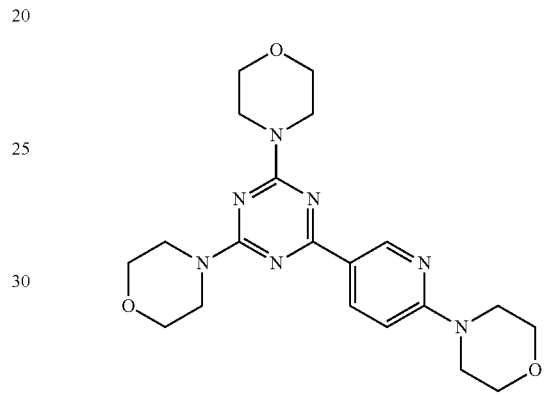

4,4'-(6-(6-morpholinopyridin-3-yl)-1,3,5-triazine-2,4-diyl)dimorpholine

Following the general procedure A, 4,4'-(6-chloro-1,3,5-triazine-2,4-diyl)dimorpholine was coupled with 6-(morpholin-4-yl)pyridine-3-boronic acid pinacol ester acid pinacol ester with reaction time of 15 h. Chromatography (hexane/ethyl acetate 1:1) gave the title compound as a colorless solid.
Analytical Data:
$^{1}$H NMR (400 MHz, CDCl$_{3}$): δ 9.19-9.18 (m, 1H), 8.39 (dd, J=2.40, 8.97 Hz, 1H), 6.61 (d, J=8.71 Hz, 1H), 3.87-3.81 (m, 12H), 3.74 (t, J=4.8 Hz, 8H), 3.62 (t, J=4.92, 4H), 1.66 (s, 1H).
$^{13}$C NMR (100 MHz, CDCl$_{3}$): δ 169.49, 165.40, 161.08, 149.99, 137.78, 123.05, 105.67, 67.27, 67.08, 45.68, 44.02.
ESI-MS (70 eV, m/z): calcd. for C$_{20}$H$_{27}$N$_{7}$O$_{3}$ [M+H]$^{+}$: 414.22. found 414.40.

Example P10

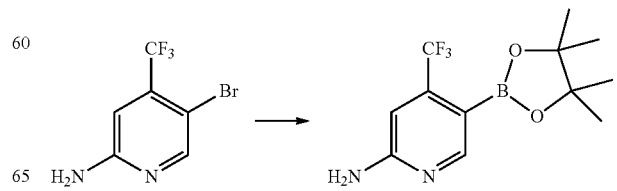

5-(4,4,5,5-tetramethyl-1,3,2-dioxaborolan-2-yl)-4-(trifluoromethyl)pyridin-2-amine To a dry 25 ml flask was added 5-bromo-4-(trifluoromethyl)pyridin-2-amine (300 mg, 1.24 mmol, 1.0 eq.), potassium acetate (366 mg, 3.73 mmol, 3.0 eq.), bis(pinacolato)diboran (348 mg, 1.37 mmol, 1.1 eq.) and dioxane (8 ml). Argon was bubbled through the solution for 15 minutes, at which time 1,1-bis(diphenylphosphino)ferrocene-palladium (II)dichloride dichloromethane complex (50.8 mg, 60 µmol, 0.05 eq.) was added. The reaction was refluxed in a 115° C. oil bath for 8 hours under argon. After cooling to room temperature, the dioxane was removed in vacuo. Ethyl acetate was added and the resulting slurry was sonicated and filtered. Additional ethyl acetate was used to wash the solid. The combined organic extracts were concentrated and the crude material was partially purified by silica gel chromatography (hexane/ethyl acetate 6:4). Upon removal of solvent, hexane was added, decantation was done and resulting colorless solid was dried on a high vacuum for three days.

Analytical Data:

$^1$H NMR (400 MHz, CDCl$_3$): δ 8.49 (s, 1H), 6.71 (s, 1H), 4.86 (s, 2H), 1.33 (s, 12H), 1.27 (s, 2H), 1.24 (s, 2H).

$^{19}$F (400 MHz, CDCl$_3$): 8-64.24.

ESI-MS (70 eV, m/z): calcd. for C$_{12}$H$_{16}$BF$_3$N$_2$O$_2$[M+H]$^+$: 289.13. found 289.10.

Example P11

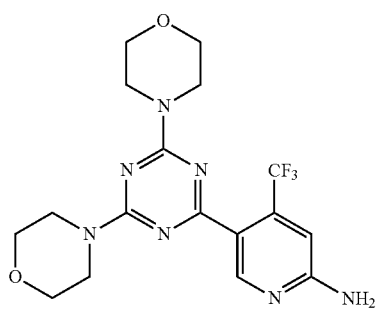 [SMILES: Nc1cc(C(F)(F)F)c(-c2nc(N3CCOCC3)nc(N3CCOCC3)n2)cn1]

5-(4,6-dimorpholino-1,3,5-triazin-2-yl)-4-(trifluoromethyl)pyridin-2-amine

Following the general procedure A, 4,4'-(6-chloro-1,3,5-triazine-2,4-diyl)dimorpholine was coupled with 5-(4,4,5,5-tetramethyl-1,3,2-dioxaborolan-2-yl)-4-(trifluoromethyl)pyridin-2-amine with reaction time of 15 h. Chromatography (dichlormethane/methanol 97:3) gave the title compound as an colorless oil.

Analytical Data:

$^1$H NMR (400 MHz, CDCl$_3$): δ 8.71 (s, 1H), 6.78 (s, 1H), 4.93 (s, 2H), 3.85-3.73 (m, 16H), 1.73 (s, 1H), 1.24 (s, 1H).

$^{13}$C NMR (125 MHz, CDCl$_3$): δ 169.90, 164.71, 159.49, 152.65, 138.30, 122.34, 105.40, 105.35, 66.81, 43.59, 24.87.

$^{19}$F (400 MHz, CDCl$_3$): 3-60.95.

ESI-MS (70 eV, m/z): calcd. for C$_{17}$H$_{20}$F$_3$N$_7$O$_2$[M+H]$^+$: 412.16. found 412.20.

Example P12

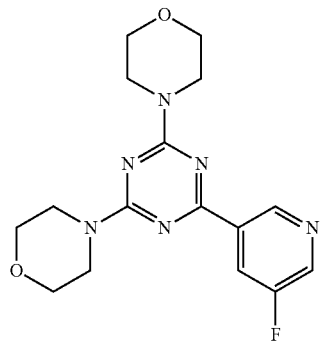 [SMILES: Fc1cncc(-c2nc(N3CCOCC3)nc(N3CCOCC3)n2)c1]

4,4'-(6-(5-fluoropyridin-3-yl)-1,3,5-triazine-2,4-diyl)dimorpholine

Following the general procedure A, 4,4'-(6-chloro-1,3,5-triazine-2,4-diyl)dimorpholine was coupled with 3-fluoropyridine-5-boronic acid pinacol ester with reaction time of 15 h. Chromatography (hexane/ethyl acetate 1:1) gave the 31% of the title compound.

Analytical Data:

$^1$H NMR (400 MHz, CDCl$_3$): δ 9.36-9.35 (m, 1H), 8.55 (d, J=3.03 Hz, 1H), 8.31-8.28 (m, 1H), 3.94-3.75 (m, 16H).

$^{13}$C NMR (100 MHz, CDCl$_3$): δ 165.30, 146.30, 142.65, 140.68, 140.45, 122.69, 122.50, 67.29, 67.20, 44.04.

$^{19}$F (400 MHz, CDCl$_3$): δ −128.86, −128.88.

ESI-MS (70 eV, m/z): calcd. for C$_{16}$H$_{19}$FN$_6$O$_2$[M+H]$^+$: 347.16. found 347.50.

Example P13

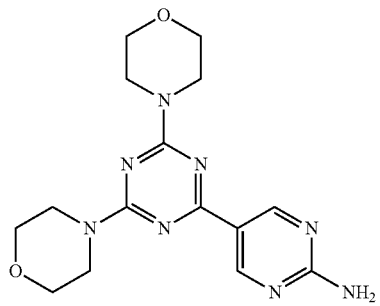 [SMILES: Nc1ncc(-c2nc(N3CCOCC3)nc(N3CCOCC3)n2)cn1]

5-(4,6-dimorpholino-1,3,5-triazin-2-yl)pyrimidin-2-amine

Following the general procedure A, 4,4'-(6-chloro-1,3,5-triazine-2,4-diyl)dimorpholine was coupled with 2-aminopyrimidine-5-boronic acid pinacol ester with reaction time of 17 h. Chromatography (hexane/ethyl acetate 1:1) gave the title compound as a colorless solid.

Analytical Data:

$^1$H NMR (400 MHz, CDCl$_3$): δ 9.17 (s, 2H), 5.37 (s, 2H), 3.87-3.74 (m, 17H), 1.63 (s, 3H).

ESI-MS (70 eV, m/z): calcd. for $C_{15}H_{20}N_8O_2[M+H]^+$: 345.17. found 345.80.

Example P14

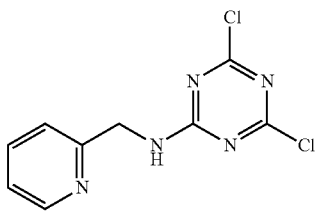 [SMILES: Clc1nc(Cl)nc(NCc2ccccn2)n1]

4,6-dichloro-N-(pyridin-2-ylmethyl)-1,3,5-triazin-2-amine

Following the general procedure A, 2,4,6-trichloro-1,3,5-triazine was coupled with 2-aminomethylpyridine with reaction time of 2 h. Purification by column chromatography gave the title compound.
Analytical Data:
ESI-MS (70 eV, m/z): calcd. for $C_9H_8Cl_2N_5[M+H]^+$: 256.01. found 256.

Example P15

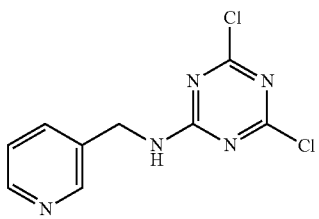 [SMILES: Clc1nc(Cl)nc(NCc2cccnc2)n1]

4,6-dichloro-N-(pyridin-3-ylmethyl)-1,3,5-triazin-2-amine

Following the general procedure A, 2,4,6-trichloro-1,3,5-triazine was coupled with 3-aminomethylpyridine with reaction time of 2 h. Purification by column chromatography gave the title compound.
Analytical Data:
ESI-MS (70 eV, m/z): calcd. for $C_9H_8Cl_2N_5[M+H]^+$: 256.01. found 256.

Example P16

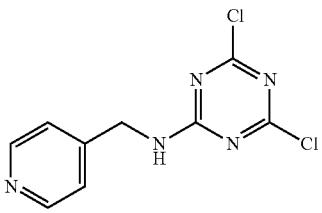 [SMILES: Clc1nc(Cl)nc(NCc2ccncc2)n1]

4,6-dichloro-N-(pyridin-4-ylmethyl)-1,3,5-triazin-2-amine

Following the general procedure A, 2,4,6-trichloro-1,3,5-triazine was coupled with 4-aminomethylpyridine with reaction time of 2 h. Purification by column chromatography gave the title compound.
Analytical Data:
ESI-MS (70 eV, m/z): calcd. for $C_9H_8Cl_2N_5[M++1]^+$: 256.01. found 256.

Example P17

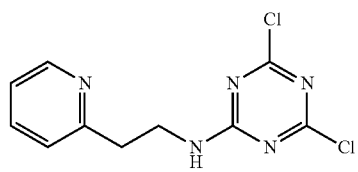 [SMILES: Clc1nc(Cl)nc(NCCc2ccccn2)n1]

4,6-dichloro-N-(2-(pyridin-2-yl)ethyl)-1,3,5-triazin-2-amine

Following the general procedure A, 2,4,6-trichloro-1,3,5-triazine was coupled with 2-(2-aminoethyl)pyridine with reaction time of 2 h. Purification by column chromatography gave the title compound.
Analytical Data:
ESI-MS (70 eV, m/z): calcd. for $C_{10}H_{19}Cl_2N_5[M+H]^+$: 270.02. found 270.

Example P18

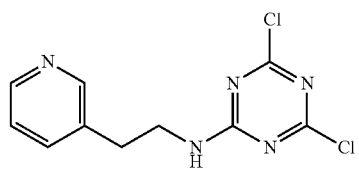 [SMILES: Clc1nc(Cl)nc(NCCc2cccnc2)n1]

4,6-dichloro-N-(2-(pyridin-3-yl)ethyl)-1,3,5-triazin-2-amine

Following the general procedure A, 2,4,6-trichloro-1,3,5-triazine was coupled with 3-(2-aminoethyl)pyridine with reaction time of 2 h. Purification by column chromatography gave the title compound.
Analytical Data:
ESI-MS (70 eV, m/z): calcd. for $C_{10}H_{10}Cl_2N_5[M+H]^+$: 270.02. found 270.

Example P19

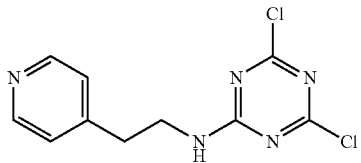 [SMILES: Clc1nc(Cl)nc(NCCc2ccncc2)n1]

4,6-dichloro-N-(2-(pyridin-4-yl)ethyl)-1,3,5-triazin-2-amine

Following the general procedure A 2,4,6-trichloro-1,3,5-triazine was coupled with 4-(2-Aminoethyl)pyridine with reaction time of 2 h. Purification by column chromatography gave the title compound.
Analytical Data:
ESI-MS (70 eV, m/z): calcd. for $C_{10}H_{10}Cl_2N_5[M+H]^+$: 270.02, found 270.

Example P20

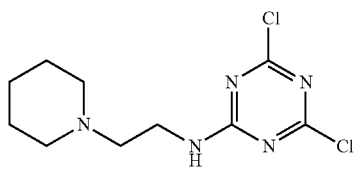 [SMILES: Clc1nc(Cl)nc(NCCN2CCCCC2)n1]

4,6-dichloro-N-(2-(piperidin-1-yl)ethyl)-1,3,5-triazin-2-amine

Following the general procedure A, 2,4,6-trichloro-1,3,5-triazine was coupled with 1-(2-Aminoethyl)piperidine with reaction time of 2 h. Purification by column chromatography gave the title compound.
Analytical Data:
ESI-MS (70 eV, m/z): calcd. for $C_{10}H_{16}Cl_2N_5 [M+H]^+$: 276.07. found 276.

Example P21

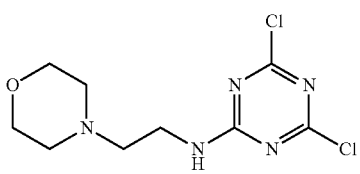 [SMILES: Clc1nc(Cl)nc(NCCN2CCOCC2)n1]

4,6-dichloro-N-(2-morpholinoethyl)-1,3,5-triazin-2-amine

Following the general procedure A, 2,4,6-trichloro-1,3,5-triazine was coupled with N-(2-aminoethyl)morpholine with reaction time of 2 h. Purification by column chromatography gave the title compound.
Analytical Data:
ESI-MS (70 eV, m/z): calcd. for $C_9H_{14}Cl_2N_5O [M+H]^+$: 278.05. found 278.

Example P22

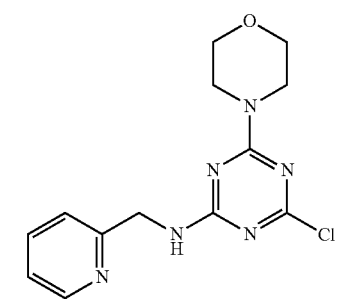 [SMILES: Clc1nc(NCc2ccccn2)nc(N2CCOCC2)n1]

4-chloro-6-morpholino-N-(pyridin-2-ylmethyl)-1,3,5-triazin-2-amine

Following the general procedure, the desired compound was obtained. Purification by column chromatography gave the title compound.
Analytical Data:
ESI-MS (70 eV, m/z): calcd. for $C_9H_{14}Cl_2N_5O [M+H]^+$: 278.05. found 278.

Example P23

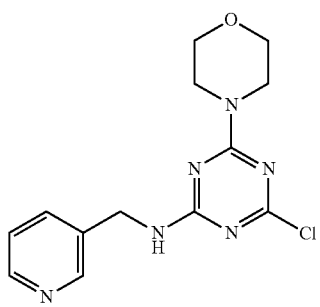 [SMILES: Clc1nc(NCc2cccnc2)nc(N2CCOCC2)n1]

4-chloro-6-morpholino-N-(pyridin-3-ylmethyl)-1,3,5-triazin-2-amine

Following the general procedure A-1, the desired compound was obtained. Purification by column chromatography gave the title compound.
Analytical Data:
ESI-MS (70 eV, m/z): calcd. for $C_{13}H_{16}ClN_6O [M+H]^+$: 307.10. found 307.

Example P24

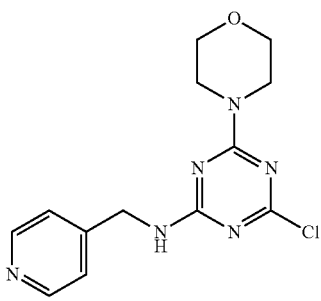 [SMILES: Clc1nc(NCc2ccncc2)nc(N2CCOCC2)n1]

4-chloro-6-morpholino-N-(pyridin-4-ylmethyl)-1,3,5-triazin-2-amine

Following the general procedure A-1, the desired compound was obtained. Purification by column chromatography gave the title compound.
Analytical Data:
ESI-MS (70 eV, m/z): calcd. for $C_{13}H_{16}ClN_6O [M+H]^+$: 307.10. found 307.

Example P25

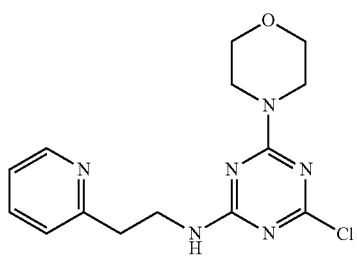 [SMILES: Clc1nc(NCCc2ccccn2)nc(N2CCOCC2)n1]

4-chloro-6-morpholino-N-(2-(pyridin-2-yl)ethyl)-1,3,5-triazin-2-amine

Following the general procedure A-1, the desired compound was obtained. Purification by column chromatography gave the title compound.
Analytical Data:
ESI-MS (70 eV, m/z): calcd. for $C_{14}H_{18}ClN_6O$ [M+1-1]$^+$: 321.12. found 321.

Example P26

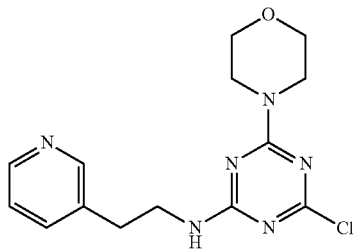 [SMILES: Clc1nc(NCCc2cccnc2)nc(N2CCOCC2)n1]

4-chloro-6-morpholino-N-(2-(pyridin-3-yl)ethyl)-1,3,5-triazin-2-amine

Following the general procedure A-1, the desired compound was obtained. Purification by column chromatography gave the title compound.
Analytical Data:
ESI-MS (70 eV, m/z): calcd. for $C_{14}H_{18}ClN_6O$ [M+H]$^+$: 321.12. found 321.

Example P27

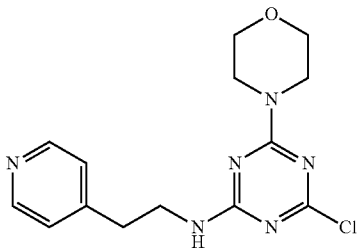 [SMILES: Clc1nc(NCCc2ccncc2)nc(N2CCOCC2)n1]

4-chloro-6-morpholino-N-(2-(pyridin-4-yl)ethyl)-1,3,5-triazin-2-amine

Following the general procedure A-1, the desired compound was obtained. Purification by column chromatography gave the title compound.
Analytical Data:
ESI-MS (70 eV, m/z): calcd. for $C_{14}H_{18}ClN_6O$ [M+H]$^+$: 321.12. found 321.

Example P28

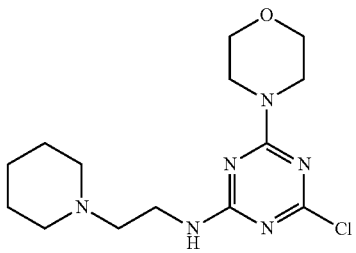 [SMILES: Clc1nc(NCCN2CCCCC2)nc(N2CCOCC2)n1]

4-chloro-6-morpholino-N-(2-(piperidin-1-yl)ethyl)-1,3,5-triazin-2-amine

Following the general procedure A-1, the desired compound was obtained. Purification by column chromatography gave the title compound.
Analytical Data:
ESI-MS (70 eV, m/z): calcd. for $C_{14}H_{24}ClN_6O$ [M+H]$^+$: 327.17. found 327.

Example P29

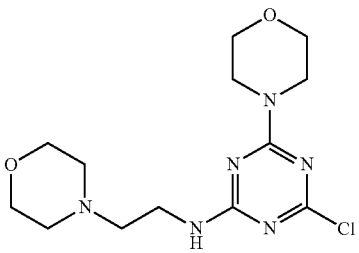 [SMILES: Clc1nc(NCCN2CCOCC2)nc(N2CCOCC2)n1]

4-chloro-6-morpholino-N-(2-morpholinoethyl)-1,3,5-triazin-2-amine

Following the general procedure A-1, the desired compound was obtained. Purification by column chromatography gave the title compound.
Analytical Data:
ESI-MS (70 eV, m/z): calcd. for $C_{13}H_{22}ClN_6O_2$ [M+H]$^+$: 329.14. found 329.

Example P30

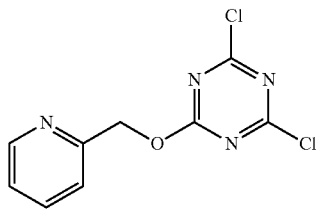 [SMILES: Clc1nc(Cl)nc(OCc2ccccn2)n1]

2,4-dichloro-6-(pyridin-2-ylmethoxy)-1,3,5-triazine

Following the general procedure A-2, 4,6-dichloro-N-(2-(piperidin-1-yl)ethyl)-1,3,5-triazin-2-amine was coupled with 2-pyridinemethanol with reaction time of 3 h. Purification by column chromatography gave the title compound.

Analytical Data:

ESI-MS (70 eV, m/z): calcd. for $C_9H_7Cl_2N_4O$ $[M+H]^+$: 256.99. found 257.

Example P31

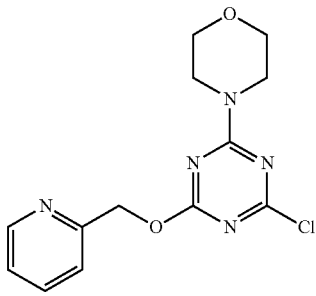 [SMILES: Clc1nc(OCc2ccccn2)nc(N2CCOCC2)n1]

4-(4-chloro-6-(pyridin-2-ylmethoxy)-1,3,5-triazin-2-yl)morpholine

Following the general procedure A-1, the desired compound was obtained. Purification by column chromatography gave the title compound.

Analytical Data:

ESI-MS (70 eV, m/z): calcd. for $C_{13}R_{15}ClN_5O_2$ $[M+H]^+$: 256.99. found 257.

Example P32

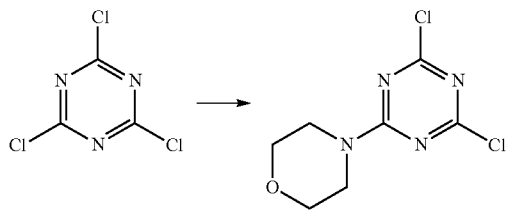 [SMILES: Clc1nc(Cl)nc(Cl)n1 ; Clc1nc(Cl)nc(N2CCOCC2)n1]

4-(4,6-dichloro-1,3,5-triazin-2-yl)morpholine

Cyanuric chloride (10.0 g, 54.2 mmol, 1.0 eq.) was dissolved in methylene chloride (60 ml) and morpholine (4.70 ml, 54.2 mmol, 1.0 eq.) was slowly added (drop by drop) to the reaction mixture at −50° C., stirred for 20 minutes at the same temperature and poured into water. After extraction with methylene chloride and ethyl acetate (2×), the organic layers were dried over MgSO$_4$ and concentrated. Further purification was done by flash chromatography (1:1 hexane/ethyl acetate) to yield the title compound as a colorless solid (3.56 g, 28%).

Analytical Data:

$^1$H-NMR (400 MHz, CDCl$_3$): δ 3.76-3.74 (8H, m).

ESI-MS (70 eV, m/z): calcd. for $C_7H_8Cl_2N_4O$ $[M+Na]^+$ (258). found 258.

X-Ray analysis: the structure of the title compound was confirmed by x-ray analysis.

Alternatively Method 1 for the Synthesis of 4-(4,6-dichloro-1,3,5-triazin-2-yl)morpholin According to EP1020462B1:

Cyanuric chloride (10.0 g, 54.0 mmol) dissolved in acetone (100 ml) was cooled to −5° C., slowly added with triethylamine (4.70 ml, 49.0 mmol) dropwise and further, slowly added with morpholine (7.50 g, 54.0 mmol) dropwise. The reaction mixture was stirred at the same temperature for one hour and then stirred at room temperature for one hour. The reaction solution was poured into water (500 ml). The precipitated crystals were collected by filtration, washed with trace amount of acetone and dried to obtain 9.70 g (yield: 69%) of 2,4-dichloro-6-morpholino-1,3,5-triazine as colorless crystals with melting point of 155° C.-157° C.

Alternatively Method 2 for the Synthesis of 4-(4,6-dichloro-1,3,5-triazin-2-yl)morpholin According to EP1020462B1:

An aqueous solution of morpholine (120 mmol, 2.0 eq.) was slowly added dropwise to a solution of cyanuric chloride (60.2 mmol, 1.0 eq.) in ethyleneglycol dimethyl ether (130 ml) at −15° C. to −5° C. The reaction mixture was stirred at −15° C. for 2 h and then at room temperature for 20 h. After removal of the solvent, the residue was extracted with CH$_2$Cl$_2$. The extract was washed with brine, dried over MgSO$_4$ and concentrated to give the title compound as colorless crystals (Yield: 63%).

Analytical Data:

$^1$H-NMR (400 MHz, CDCl$_3$): δ 3.60-3.80 (8H, m).

ESI-MS (70 eV, m/z): calcd. for $C_7H_8Cl_2N_4O$ $[M^+]$ (234). found 234.

X-Ray analysis: the structure of the title compound was confirmed by x-ray analysis.

Example P33

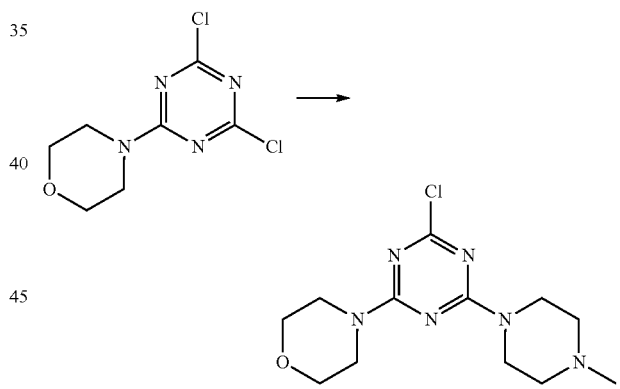

4-(4-chloro-6-(4-methylpiperazin-1-yl)-1,3,5-triazin-2-yl)morpholine 4-(4,6-dichloro-1,3,5-triazin-2-yl)morpholine (1.40 g, 5.96 mmol, 1.0 eq.) was dissolved in dichloromethane (21 ml). N-Methylpiperazine (727 μl, 6.56 mmol, 1.1 eq.) was added to the reaction mixture at 0° C. and stirred for 30 minutes at the same temperature. The solvent was evaporated under reduced pressure and purification by flash chromatography yielded the title compound as a white solid (690 mg, 39%).

Analytical Data:

$^1$H-NMR (400 MHz, CDCl$_3$): δ 3.78-3.68 (17H, m), 2.42 (4H, t, J=5.3, J=5.05), 2.32 (3H, s), 0.87-0.72 (1H, m).

$^{13}$C-NMR (100 MHz, CDCl$_3$): δ 170.05, 164.92, 164.69, 46.51, 44.24, 43.75, 43.68.

ESI-MS (70 eV, m/z): calcd for $C_{12}H_{19}ClN_6O$ $[M+H]^+$ (299). found 299.

Example P34

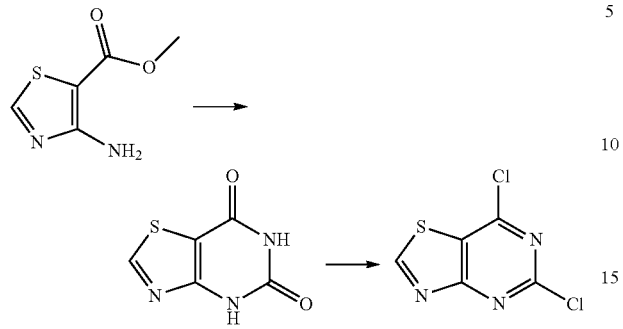

A mixture of methyl 4-aminothiazole-5-carboxylate (1.0 eq.) and urea (5 eq.) was heated at 190° C. for 2 hours. The hot reaction mixture was poured onto sodium hydroxide solution and any insoluble material was removed by filtration. The mixture was then acidified (HCl, 2N) to yield thiazolo[4,5-d]pyrimidine-5,7(4H,6H)-dione as a white precipitate, which was collected by filtration and air dried.

Analytical Data:
ESI-MS (70 eV, m/z): calcd for $C_5H_4N_3O_2S$ $[M+H]^+$ (170). found 170.

A mixture of thiazolo[4,5-d]pyrimidine-5,7(4H,6H)-dione 2 (9.49 g, 56.5 mmol) and phosphorous oxychloride (150 mL) was heated at reflux for 6 h. The reaction mixture was then cooled and $POCl_3$ was evaporated under reduced pressure. The crude product was washed with diethyl ether and $NaHCO_3$. The mixture was then filtered to yield 5,7-dichlorothiazolo[4,5-d]pyrimidine as a white solid.

Analytical Data:
ESI-MS (70 eV, m/z): calcd for $C_5H_2Cl_2N_3S$ $[M+H]^+$ (206). found 206.

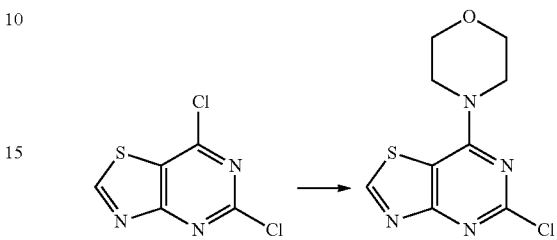

A mixture of 5,7-dichlorothiazolo[4,5-d]pyrimidine (1.0 eq.), morpholine (2.2 eq.) and MeOH was stirred at room temperature for 1 h. The reaction mixture was then filtered, washed with water and MeOH, to yield 4-(5-chlorothiazolo[4,5-d]pyrimidin-7-yl)morpholine as a white solid (100%).

Analytical Data:
ESI-MS (70 eV, m/z): calcd for $C_9H_{10}ClN_4OS$ $[M+H]^+$ (257). found 257.

An alternative formed schema for the synthesis of

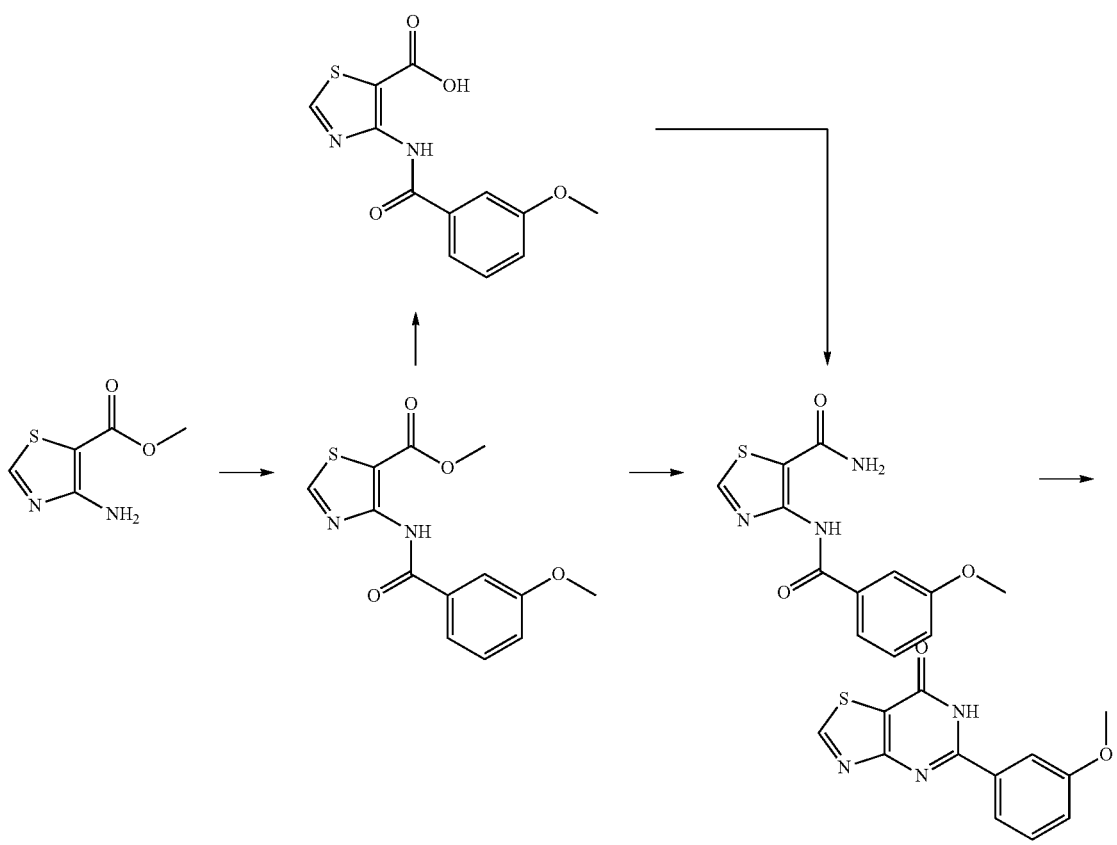

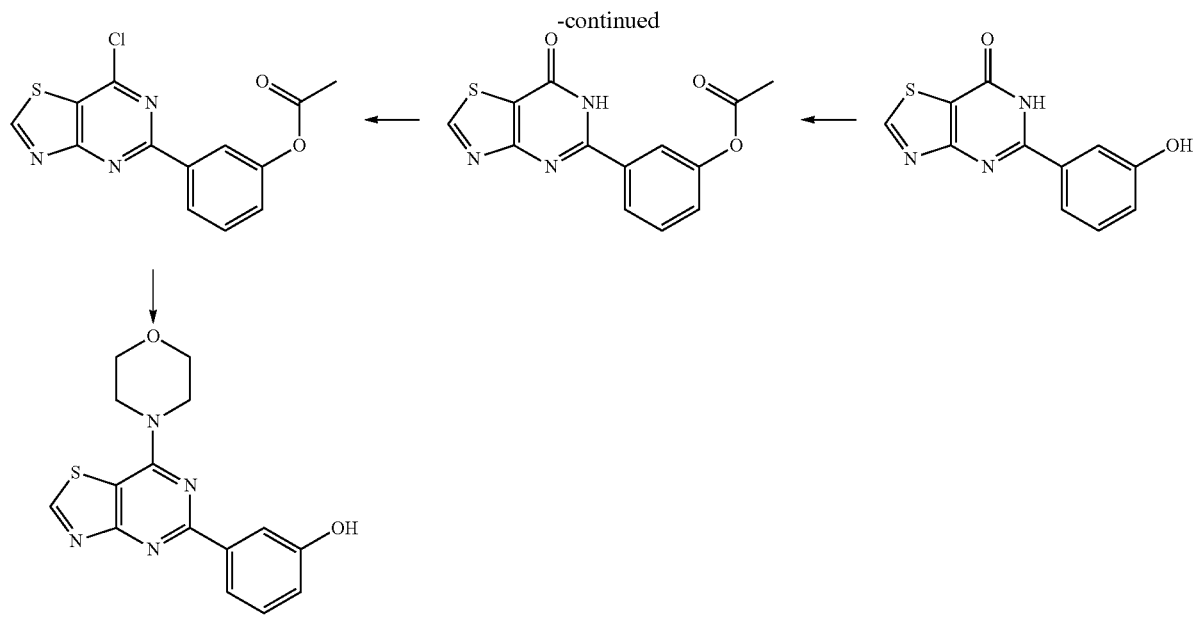

Example P35

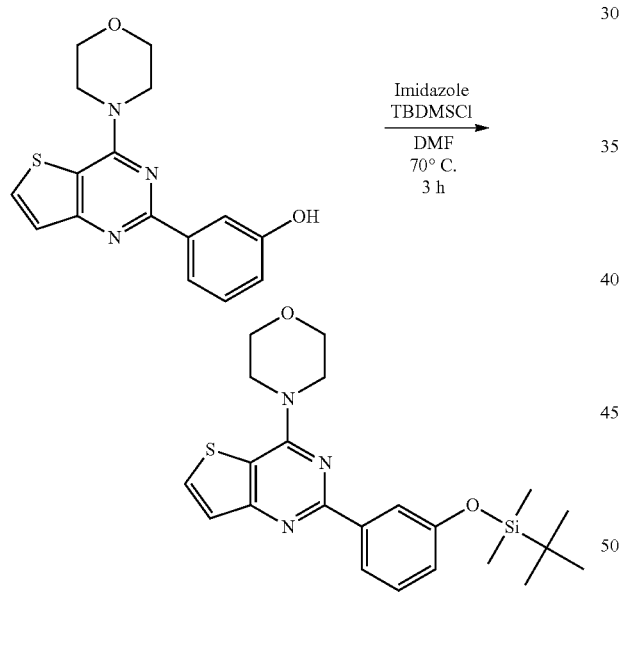

4-(2-(3-(tert-butyldimethylsilyloxy)phenyl)thieno[3,2-d]pyrimidin-4-yl)morpholine 3-(4-morpholinothieno[3,2-d]pyrimidin-2-yl)phenol [synthesized according to Hayakawa et al., Bioorganic & Med. Chem. 14:6847-6858 (2006)] (540 mg, 1.72 mmol, 1.0 eq.) was dissolved in DMF (5 ml). To this imidazole (936 mg, 13.8 mmol, 8.0 eq.) and TBDMSCl (909 mg, 6.02 mmol, 3.5 eq.) were added and the mixture was heated at 70° C. for 3 h. DMF was evaporated under reduced pressure and purification by flash chromatography (hexane:ethyl acetate, gradient from 100%-50% hexane in EtOAc) yielded the title compound as a white solid.

Analytical Data:
ESI-MS (70 eV, m/z): calcd for $C_{22}H_{30}N_3O_2SSi$ [M+H]$^+$ (428). found 428

Example P36

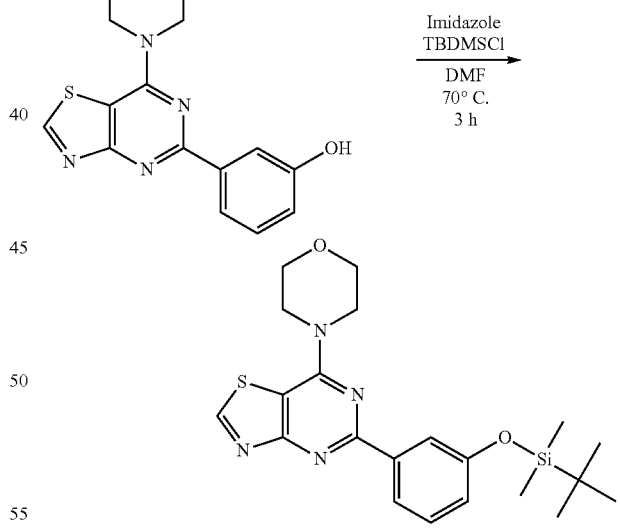

4-(5-(3-(tert-butyldimethylsilyloxy)phenyl)thiazolo[4,5-d]pyrimidin-7-yl)morpholine 3-(7-morpholinothiazolo[4,5-d]pyrimidin-5-yl)phenol (1.0 eq.) was dissolved in DMF (5 ml). To this imidazole (8.0 eq.) and TBDMSCl (3.5 eq.) were added and the mixture was heated at 70° C. for 5 h. DMF was evaporated under reduced pressure and purification by flash chromatography (hexane: ethyl acetate, gradient from 100%-50% hexane in EtOAc) yielded the title compound as a white solid.

Analytical Data:

ESI-MS (70 eV, m/z): calcd for $C_{21}H_{29}N_4O_2SSi$ $[M+H]^+$ (428). found 428.

Example P37

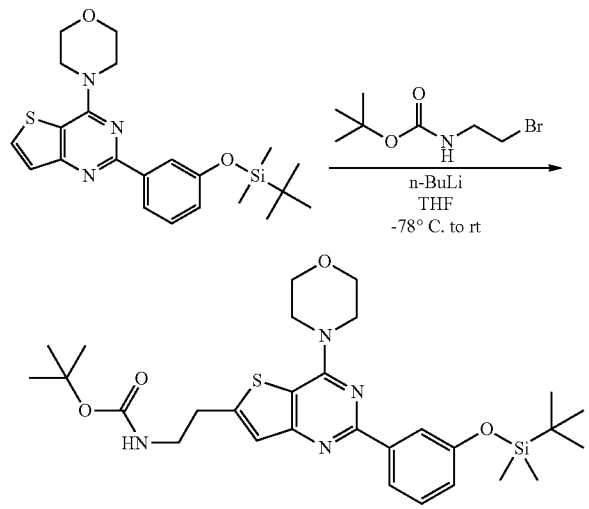

tert-butyl 2-(2-(3-(tert-butyldimethylsilyloxy)phenyl)-4-morpholinothieno[3,2-d]pyrimidin-6-yl)ethylcarbamate 4-(2-(3-(tert-butyldimethylsilyloxy)phenyl)thieno[3,2-d]pyrimidin-4-yl)morpholine (166 mg, 388 µmol, 1.0 eq.) was solved with dry THF (3 ml) under room temperature and added to a round-two-neck flask that was heated under vacuum and flushed with nitrogen. The solution was then cooled to −78° C. and n-BuLi (315 µl, 1.6 M solution in hexanes, 1.3 eq.) was added dropwise. After stirring for 20 min., 2-(boc-amino)ethyl bromide (130 mg, 582 µmol, 1.5 eq.) was added to the reaction mixture and the reaction mixture was stirred at −78° C. for 20 min. and then warmed to room temperature. The reaction mixture was further stirred at room temperature overnight.

Analytical Data:

ESI-MS (70 eV, m/z): calcd for $C_{29}H_{43}N_4O_4SSi$ $[M+H]^+$ (571.27). found 571.

Example P38

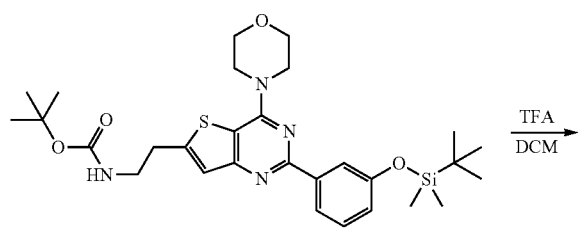

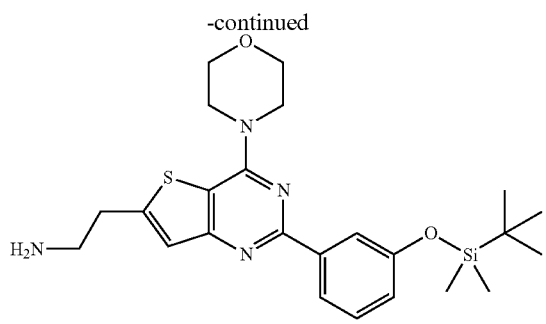

2-(2-(3-(tert-butyldimethylsilyloxy)phenyl)-4-morpholinothieno[3,2-d]pyrimidin-6-yl)ethanamine tert-butyl 2-(2-(3-(tert-butyldimethylsilyloxy)phenyl)-4-morpholinothieno[3,2-d]pyrimidin-6-yl)ethylcarbamate (10.0 mg, 1.0 eq.) was solved in 3 ml of TFA:DCM (1:1). The reaction mixture was stirred at room temperature for 2 h. The silica column chromatography (DCM:MeOH/95:5) gave the title compound.

Analytical Data:

ESI-MS (70 eV, m/z): calcd for $C_{24}H_{35}N_4O_2SSi$ $[M+H]^+$ (471.22). found 471.

Example P39

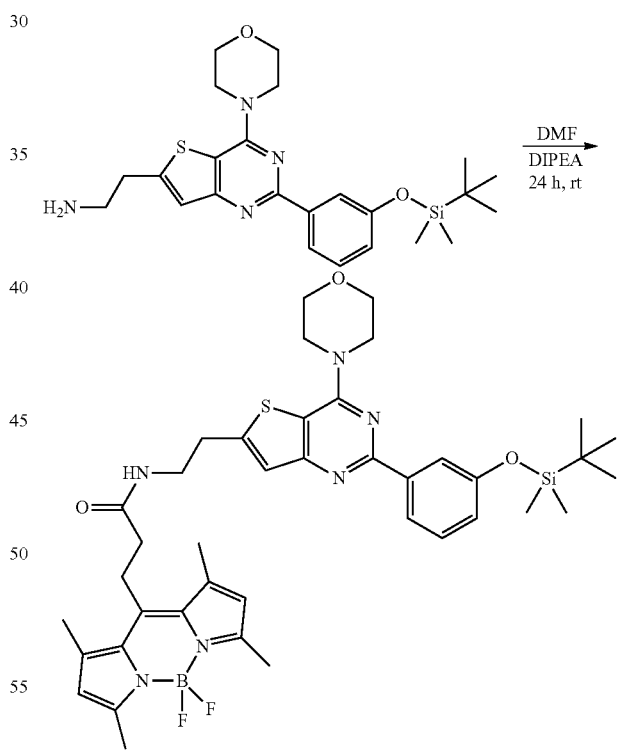

10-(3-(2-(2-(3-(tert-butyldimethylsilyloxy)phenyl)-4-morpholinothieno[3,2-d]pyrimidin-6-yl)ethylamino)-3-oxopropyl)-5,5-difluoro-1,3,7,9-tetramethyl-5H-dipyrrolo[1,2-c:1',2'-f][1,3,2]diazaborinin-4-ium-5-uide To a solution of 2-(2-(3-(tert-butyldimethylsilyloxy)phenyl)-4-morpholinothieno[3,2-d]pyrimidin-6-yl)ethanamine (0.010895 mmol, 1.0 eq.) in DMF (200 µl) at room temperature was added Bodipy-NHS (0.011984 mmol, 1.1 eq.), followed by DIPEA (0.02179 mmol, 2.0 eq.). After 24 h stirring at room temperature in dark, the solvents were removed at high vacuum and the mixture was purified by flash chromatography (DCM:MeOH/35:1). Further purification by preparative TLC yielded the title compound.

Analytical Data:
ESI-MS (70 eV, m/z): calcd for $C_{40}H_{52}BF_2N_6O_3SSi$ [M+H]$^+$ (773). found 773.

Example P40

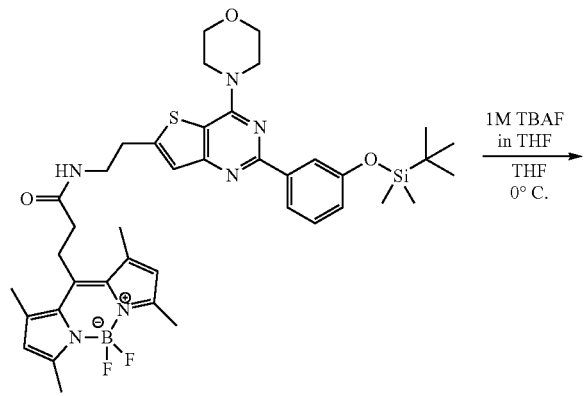

5,5-difluoro-10-(3-(2-(2-(3-hydroxyphenyl)-4-morpholinothieno[3,2-d]pyrimidin-6-yl)ethylamino)-3-oxopropyl)-1,3,7,9-tetramethyl-5H-dipyrrolo[1,2-c:1',2'-f][1,3,2]diazaborinin-4-ium-5-uide To a solution of TBDMS protected phenol derivative (0.060269 mmol, 1.0 eq.) in 3 ml abs. THF cooled to 0° C. was added a 1M solution of tetrabutyl ammonium fluoride (TBAF) in THF (0.120538 mmol, 2.0 eq.). After 40 min. stirring at 0° C., the solvent was removed in vacuo and the residue purified by flash chromatography (gradient, hexane:ethyl acetate) and then the residue was triturated with EtOAc/MeOH mixture to yield the title compound as a colorless solid.

Analytical Data:
ESI-MS (70 eV, m/z): calcd for $C_{34}H_{38}BF_2N_6O_3S$ [M+H]$^+$ (659). found 659.

Example P41

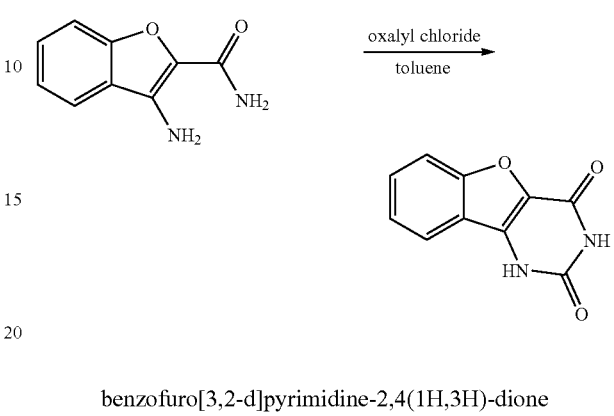

benzofuro[3,2-d]pyrimidine-2,4(1H,3H)-dione

To a stirred solution of 3-amino-2,3-dihydrobenzofuran-2-carboxamide (82.2 mg, 0.461 mmol, 1.0 eq.) in anhydrous toluene (8 mL) under an inert atmosphere was added oxalyl chloride (70.2 mg, 553 µmol, 1.2 eq.) in a dropwise manner. The resulting mixture was heated to reflux (115° C.) for 4 hours whereupon it was cooled and stirred for a further 16 hours. The crude reaction mixture was concentrated to half of its volume and filtered to give a colorless solid (41.5 mg, 45%).

Analytical Data:
$^1$H-NMR (400 MHz, DMSO): δ 11.80 (s, 1H), 8.50-7.20 (m, 4H).
$^{13}$C-NMR (125 MHz, DMSO): δ 162.2, 157.0, 152.7, 134.6, 128.4, 125.9, 125.1, 123.5, 121.1, 112.2.

Example P42

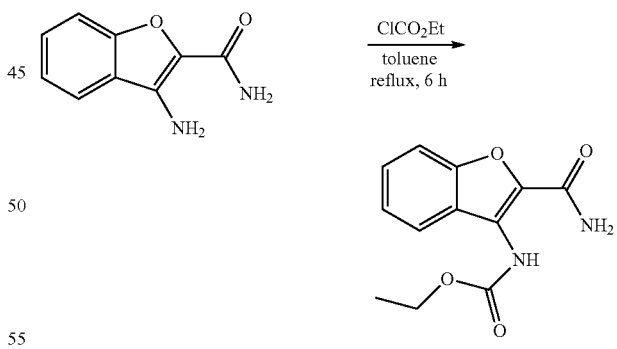

ethyl 2-carbamoyl benzofuran-3-ylcarbamate 3-amino-2,3-dihydrobenzofuran-2-carboxamide (200 mg, 1.14 mmol, 1.0 eq.) and ethyl chloroformate (109 ml, 1.14 mmol, 1.0 eq.) in anhydrous toluene (10 mL) under an inert atmosphere was heated to reflux (115° C.) for 6 hours and then stirred at room temperature overnight. The solvent was removed and the residue was purified by chromatography (gradient from 100% hexan in EtOAc to 50%) to yield a white solid (130 mg, 46%).

Analytical Data:

¹H-NMR (400 MHz, CDCl₃): δ 9.19 (s, 1H), 8.45 (d, ³J$_{HH}$=8.1 Hz, 1H), 7.45-7.41 (m, 2H), 7.28-7.26 (m, 1H), 6.34 (s, br, 1H), 5.8 (s, br, 1H), 4.28 (q, ³J$_{HH}$=7.1 Hz, 2H), 1.35 (t, ³J$_{HH}$=7.1 Hz, 3H).

¹³C-NMR (100 MHz, CDCl₃): δ 163.4, 154.0, 153.9, 129.6, 128.7, 126.7, 123.6, 122.0, 112.1.

ESI-MS (MeOH, 70 eV): calculated for C₁₂H₁₂N₂O₄ [M+Na]⁺ (271). found 271.

Example P43

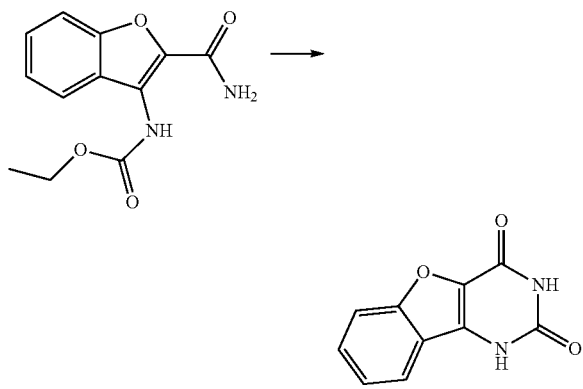

benzofuro[3,2-d]pyrimidine-2,4(1H,3H)-dione

Ethyl 2-carbamoylbenzofuran-3-ylcarbamate (114 mg, 0.460 mmol, 1.0 eq) in a 5% NaOH solution (3.7 mL, 4.60 mmol, 10.0 eq) and EtOH (2.2 mL) was heated to reflux for 1 h. After the mixture was cooled to room temperature, the product was precipitated by adding HCl (conc., 37%) and a solid was collected by filtration and washed with water and Et₂O. This compound (40 mg, 43%) was used for the next step without further purification.

Analytical Data:

¹H-NMR (500 MHz, DMSO): δ 12.03 (s, 1H), 11.43 (s, 1H), 8.00 (d, ³J$_{HH}$=7.3 Hz, 1H), 7.75 (d, ³J$_{HH}$=8.5 Hz, 1H), 7.64 (t, ³J$_{HH}$=7.3 Hz, 1H), 7.45 (t, ³J$_{HH}$=7.3 Hz, 1H)

¹³C-NMR (100 MHz, DMSO): δ 155.5, 154.9, 151.3, 133.3, 130.6, 129.8, 123.9, 121.6, 117.6, 112.9.

Example P44

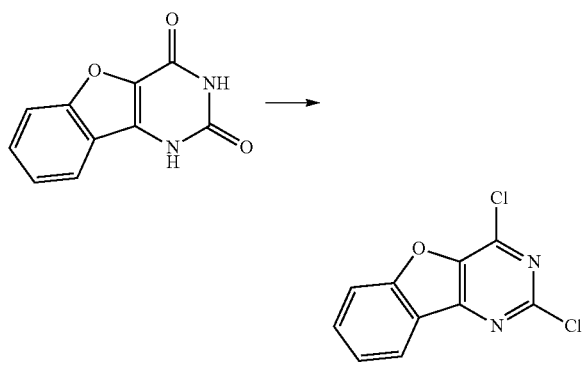

2,4-dichlorobenzofuro[3,2-d]pyrimidine

Benzofuro[3,2-d]pyrimidine-2,4(1H,3H)-dione (100 mg, 495 μmol, 1.0 eq) in toluen (810 μL), under an inert atmosphere, was added N,N-diisopropylethylamin (427 mL, 2.48 mmol, 5.0 eq). Phosphorus oxychloride (227 mL, 2.48 mmol, 5.0 eq) was then added to the mixture dropwise before the reaction was heated to 100° C. for 22 hours. The mixture was then concentrated in vacuo and water was added (20 mL) and the mixture was extracted with DCM and washed with sat. NaHCO₃. Solvents were removed by HV and the compound was purified by chromatography (gradient from 100% hexane in EtOAc to 50% hexan) to yield a colorless solid (68.3 mg, 58%).

Analytical Data:

¹H-NMR (500 MHz, DMSO): δ 8.28 (d, ³J$_{HH}$=7.3 Hz, 1H), 8.01 (d, ³J$_{HH}$=8.5 Hz, 1H), 7.93 (t, ³J$_{HH}$=7.9 Hz, 1H), 7.65 (t, ³J$_{HH}$=7.3 Hz, 1H).

¹³C-NMR (125 MHz, DMSO): δ 158.4, 153.3, 151.8, 143.6, 142.4, 133.9, 125.5, 122.8, 120.1, 113.5.

TLC (SiO₂, hexane/EtOAc (1:1), R$_f$=0.88

Example P45

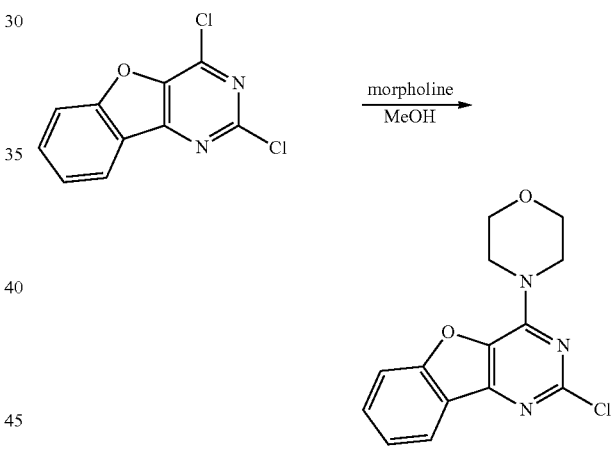

2-chloro-4-morpholinobenzofuro[3,2-d]pyrimidine 2,4-dichlorobenzofuro[3,2-d]pyrimidine (61 mg, 0.255 mmol, 1.0 eq) was dissolved in MeOH (2 mL) and morpholine (49.1 mL, 562 μmol, 2.2 eq) was added. The reaction mixture was hated to reflux for 30 minutes and then cooled to room temperature. Solvents were removed in vacuo and the residue was purified by silica gel chromatography (gradient from 100% hexane in EtOAc to 50% hexane) and a colorless solid was obtained (59.4 mg, 80%).

Analytical Data:

¹H-NMR (400 MHz, DMSO): δ 8.06 (d, ³J$_{HH}$=7.3 Hz, 1H), 7.82 (d, ³J$_{HH}$=8.3 Hz, 1H), 7.71 (t, ³J$_{HH}$=7.8 Hz, 1H), 7.50 (t, ³J$_{HH}$=7.6 Hz, 1H), 4.00-3.99 (m, 4H), 3.77 (t, ³J$_{HH}$=5.1 Hz, 4H).

MS-ESI (MeOH, 70 eV): calculated for C₁₄H₁₃ClN₃O₂ [M+H]⁺ (290). found 290.

Example P46

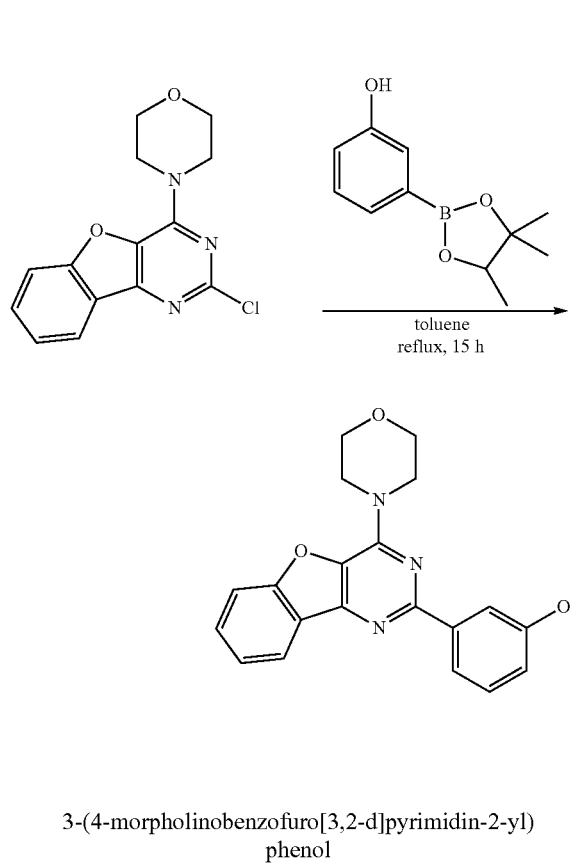

3-(4-morpholinobenzofuro[3,2-d]pyrimidin-2-yl) phenol

Argon gas was bubbled through a mixture of 2-chloro-4-morpholinobenzofuro[3,2-d]pyrimidine (ASA66) (48.7 mg, 168 µmol, 1.0 eq) and 3-Hydroxyphenylboronic acid pinacol ester (MW 220) (148 mg, 672 µmol, 4.0 eq) in 1,2 dimethoxyethan and 2 M $Na_2CO_3$ (3:1) (4 mL) for 5 min. Dichloro 1,1'-bis(diphenylphosphino)ferrocene-palladium (II) dichloromethane complex (MW 732) (3.07 mg, 4.20 µmol, 0.025 eq) was added and the reaction mixture was heated to reflux (90° C.) for 15.5 h. The red solution was cooled and diluted with EtOAc (6.5 mL). The organic solution was washed with a mixture of $H_2O:Na_2CO_3:NH_4OH$ (conc. 32% in water)=5:4:1 (6.5 mL), then $NH_4Cl$ (sat.) and brine (2×), dried over $Na_2CO_3$, filtered and concentrated. Purification by silica gel chromatography gave a colorless solid (49 mg, 85%).

Analytical Data:

$^1$H-NMR (400 MHz, DMSO): δ 9.52 (s, 1H), 8.14-8.12 (d, $^3J_{HH}$=7.0 Hz, 1H), 7.88-7.86 (m, 2H), 7.80-7.78 (d, $^3J_{HH}$=8.3 Hz, 1H), 7.68 (t, $^3J_{HH}$=7.7 Hz, 1H), 7.49 (t, $^3J_{HH}$=7.3 Hz, 1H), 7.27 (t, $^3J_{HH}$=7.6 Hz, 1H), 6.87-6.84 (m, 1H), 4.08 (t, $^3J_{HH}$=4.6 Hz, 4H), 3.81 ($^3J_{HH}$=4.8 Hz, 4H).

$^{13}$C-NMR (100 MHz, DMSO): δ 158.9, 158.3, 156.7, 149.2, 148.9, 140.1, 134.8, 131.3, 130.2, 124.9, 122.8, 122.2, 119.6, 117.8, 115.4, 113.6, 66.9, 46.1.

MS-ESI (MeOH, 70 eV): calculated for $C_{20}H_{17}N_3O_3$ [M+H]$^+$ (348). found 349.

Example P47

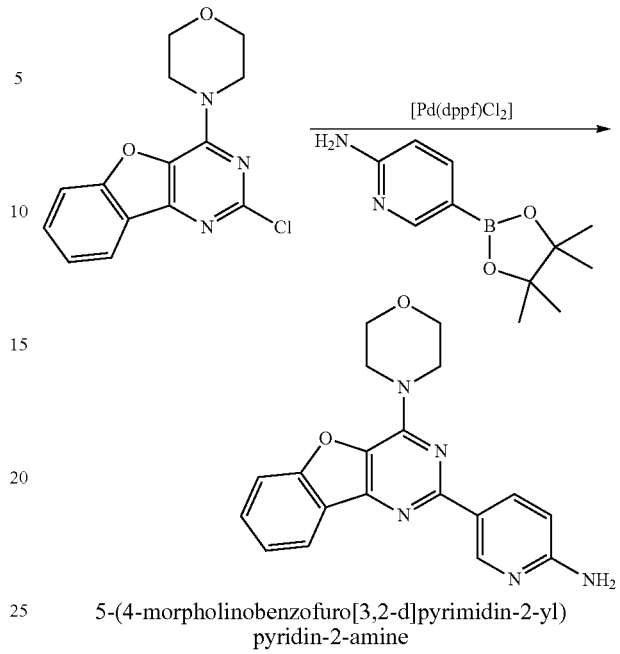

5-(4-morpholinobenzofuro[3,2-d]pyrimidin-2-yl) pyridin-2-amine

Argon gas was bubbled through a mixture of 2-chloro-4-morpholinobenzofuro[3,2-d]pyrimidine (ASA75) (80 mg, 0.276 mmol, 1.0 eq) and 2-Aminopyridine-5-boronic acid pinacol ester (MW 220) (243 mg, 1.10 mmol, 4.0 eq) in 1,2 dimethoxyethan and 2 M $Na_2CO_3$ (3:1) (6 mL) for 5 min. dichioro 1,1-bis(diphenylphosphino)ferrocene-palladium(II) dichloromethane complex (MW 732) (5.05 mg, 0.00690 mmol, 0.025 eq) was added and the reaction mixture was heated to reflux (90° C.) for 14 h 45 min, cooled and diluted with EtOAc (9 mL). The organic solution was washed with a mixture of $H_2O:Na_2CO_3:NH_4OH$ (conc. 32% in water)=5:4:1 (9 mL), then $NH_4Cl$ (sat.) and brine (2×), dried over $Na_2CO_3$, filtered and concentrated. Purification by silica gel chromatography (gradient from=% MeOH in DCM to 5% MeOH in DCM) gave a colorless solid (4.40 mg, 5%).

Analytical Data:

$^1$H-NMR (400 MHz, DMSO): δ 8.96 (d, $J_{HH}$=1.8 Hz, 1H), 8.37 (dd, $^3J_{HH}$=8.4 Hz, $^4J_{HH}$=2.5 Hz, 1H), 8.12 (d, $^3J_{HH}$=7.6 Hz, 1H), 7.78 (d, $^3J_{HH}$=8.4 Hz, 1H), 7.67 (dt, $^3J_{HH}$=7.1 Hz, $^4J_{HH}$=1.3 Hz, 1H), 7.48 (t, $^3J_{HH}$=7.1 Hz, 1H), 6.58 (s, 1H), 6.56 (s, 2H), 4.06-4.05 (m, 4H), 3.81-3.80 (m, 4H).

MS-ESI (MeOH, 70 eV): calculated for $C_{19}H_{17}N_5O_2$ [M+H]$^+$ (348). found 348.

Example P48

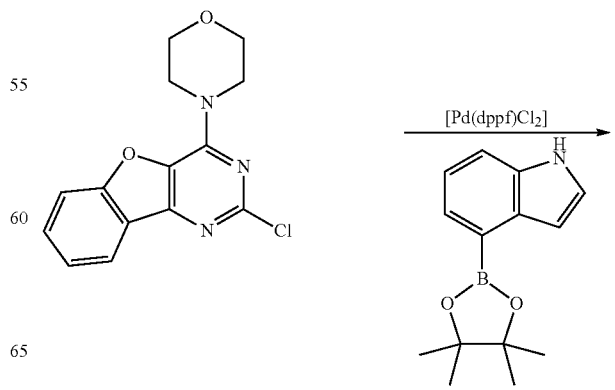

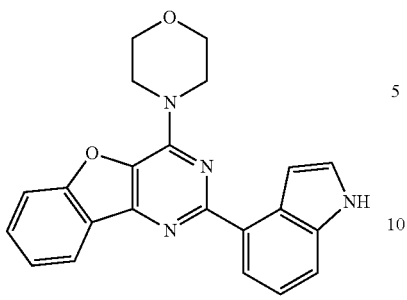

2-(1H-indol-4-yl)-4-morpholinobenzofuro[3,2-d]pyrimidine

Argon gas was bubbled through a mixture of 2-chloro-4-morpholinobenzofuro[3,2-d]pyrimidine (ASA75) (80 mg, 0.276 mmol, 1.0 eq) and Indole-4-boronic acid pinacol ester (MW 243) (267 mg, 1.10 mmol, 4.0 eq) in 1,2 dimethoxyethane and 2 M $Na_2CO_3$ (3:1) (6 mL) for 5 min. dichloro 1,1'-bis(diphenylphosphino)ferrocene-palladium(II) dichloromethane complex (MW 732) (5.05 mg, 0.00690 mmol, 0.025 eq) was added and the reaction mixture was heated to reflux (90° C.) for 15 h 30 min, cooled and diluted with EtOAc (20 mL). The organic solution was washed with a mixture of $H_2O:Na_2CO_3:NH_4OH$ (conc. 32% in water)=5:4:1 (9 mL), then $NH_4Cl$ (sat.) and brine (2×), dried over $Na_2CO_3$, filtered and concentrated. Purification by silica gel chromatography (gradient from 100% hexane in EtOAc to 50% hexane) gave a yellowish solid (89.0 mg, 87%).

Analytical Data:

$^1$H-NMR (400 MHz, DMSO): δ 11.26 (s, 1H), 8.20-8.17 (m, 2H), 7.76 (d, $^3J_{HH}$=8.4 Hz, 1H), 7.66 (dt, $^3J_{HH}$=6.0 Hz, $^4J_{HH}$=1.3 Hz, 1H), 7.55-7.53 (m, 2H), 7.50-7.47 (m, 2H), 7.22 (t, $^3J_{HH}$=7.8 Hz, 1H), 4.08 (t, $^3J_{HH}$=5.1 Hz, 4H), 3.81 (t, $^3J_{HH}$=5.0 Hz, 4H).

$^{13}$C-NMR (100 MHz, DMSO): δ 161.2, 156.6, 149.3, 148.9, 138.0, 134.3, 131.1, 130.5, 127.2, 126.9, 124.8, 123.0, 122.2, 121.5, 121.3, 114.2, 113.5, 104.4, 66.9, 46.3.

MS-ESI (MeOH, 70 eV): calculated for $C_{22}H_{18}N_4O_2$ [M+H]$^+$ (371). found 372.

Example P49

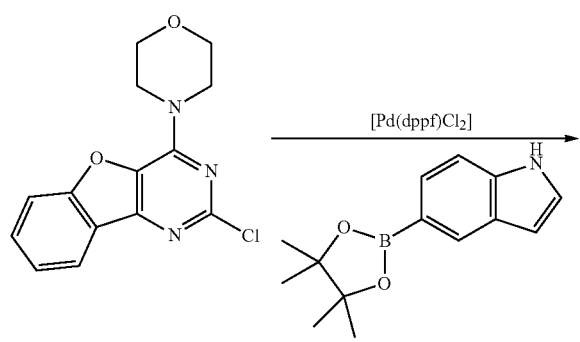

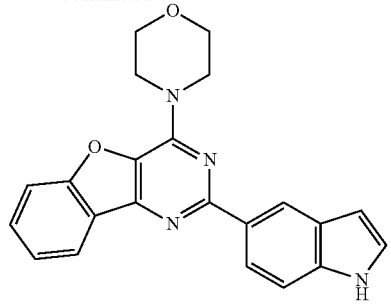

2-(1H-indol-5-yl)-4-morpholinobenzofuro[3,2-d]pyrimidine

Argon gas was bubbled through a mixture of 2-chloro-4-morpholinobenzofuro[3,2-d]pyrimidine (ASA75) (80 mg, 0.276 mmol, 1.0 eq) and Indole-5-boronic acid pinacol ester (MW 243) (267 mg, 1.10 mmol, 4.0 eq) in 1,2 dimethoxyethane and 2 M $Na_2CO_3$ (3:1) (6 mL) for 5 min. dichloro 1,1'-bis(diphenylphosphino)ferrocene-palladium(II) dichloromethane complex (MW 732) (5.05 mg, 0.00690 mmol, 0.025 eq) was added and the reaction mixture was heated to reflux (90° C.) for 15 h, cooled and diluted with EtOAc (20 mL). The organic solution was washed with a mixture of $H_2O:Na_2CO_3:NH_4OH$ (conc. 32 (% in water)=5:4:1 (9 mL), then $NH_4Cl$ (sat.) and brine (2×), dried over $Na_2CO_3$, filtered and concentrated. Purification by silica gel chromatography (gradient from 100% hexane in EtOAc to 70% hexane) gave a colorless solid (35 mg, 34%).

Analytical Data:

$^1$H-NMR (400 MHz, DMSO): δ 11.23 (s, 1H), 8.71 (s, 1H), 8.29 (dd, $^3J_{HH}$=8.6 Hz, $^4J_{HH}$=1.5 Hz, 1H), 8.17 (d, $^3J_{HH}$=7.6 Hz, 1H), 7.75 (d, 8.3 Hz, 1H), 7.65 (dt, $^3J_{HH}$=7.8 Hz, $^4J_{HH}$=1.0 Hz, 1H), 7.50-7.46 (m, 2H), 7.39 (t, $J_{HH}$=2.8 Hz, 1H), 6.57 (s, 1H), 4.09-4.06 (m, 4H), 3.82.3.80 (m, 4H).

Example P50

In Cell Western-Inhibition Assay (Protocol for Phospho-PKB/PKB Detection on A2058 Melanoma Inhibitor efficacy of formula I compounds were measured by a cell assay employing the following protocol:

Cells were plated in black 96 well view plates (Packard) 24 hours prior to the experiment. Inhibitor or DMSO as control were added to the medium (each sample as duplicates) and incubated for 3 hours. 4% para-formaldehyde was applied for 20 minutes at room temperature to fix the cells. After washing with PBS/0.1% Triton/X-100, blocking with 10% goat serum in PBS was done for 1 hour. On a shaker, antibodies diluted in PBS against pPKB Ser473 (Cell Signalling) and PKB (gift from E. Hirsch) or pS6 Ser 235/236 (Cell Signalling) were incubated overnight at 4° C. After washing with PBS, secondary antibodies (LI-COR) diluted in PBS were applied at room temperature in the dark. Plates were washed with PBS prior to scanning on an Odyssey reader.

Day 0
1. Plate 80,000 cells/well in a black Packard 96 well ViewPlate.
2. Pipette with the multi channel pipette 200 μl of cell suspension per well.
3. Check under the microscope the homogeneity of the plating.
4. Incubate cells 24 hours.

Day 1
1. Carefully throw away the medium and refill the wells with 100 µl of medium. Check under the microscope for cell loss.
2. Add 1 µl of 100× concentrated DMSO or Inhibitor.
3. Incubate for 3 hours at 37°.
4. Add 60 µl para-formaldehyde 10% (final 4%) and incubate at room temperature for 20 minutes.
5. Wash 3×5 minutes with (200 µl) PBS/0.1% Triton/X-100.
6. Block 60 minutes with (100 µl) of 10% FCS in PBS at room temperature.
7. Incubate over night with 50 µl pPKB Ser473 (1:500) and PKB (1:500) or pS6 Ser 235/236 (1:500) in PBS at 4° C. on a shaker.

Day 2
1. Wash 3×5 minutes with PBS.
2. Incubate 60 minutes with 50 µl secondary antibody anti-rabbit IRDye800 (1:800) and anti-mouse IRDye680 (1:500) in PBS at room temperature in the dark on a shaker.
3. Wash 3×5 minutes with PBS.
4. Read the plate on an Odyssey reader.

Reagents:
Packard ViewPlate (black) #6005225
Anti-Phospho PKB Ser 473 (Cell Signaling cat. 4058)
Anti-PKB (gift from E. Hirsch, Torino)
Anti-pS6 Ser235/236 (Cell Signaling cat. 4856)
Goat anti-Rabbit—IRDye 800 CW (LI-COR cat. 926-32211)
Goat anti Mouse—IRDye 680 (LI-COR cat. 926-32220)
Examples of in Cell Western Inhibition Assay:

The more phosphorylated PKB was measured on the Odyssey scan, the higher the pPKB/PKB values were i.e. the less strong was inhibition of signalling. A summary of the results obtained for some exemplary compounds is depicted in table 7.

Assessment of compound permeability was indirectly intepretated by using this assay. The compounds were applied to the apical surface of cell monolayers and compound permeation into the cellular compartment could be interpretated by measuring the inhibition of PI3Ks.

TABLE 6

Some of biologically active PI3K inhibitors:

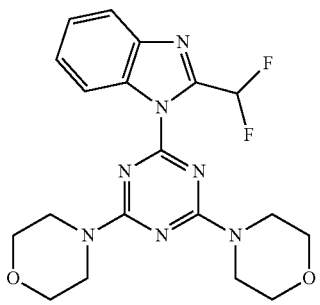

(ZSTK474) was a reference triazine compound for our experiments (IP of Zenyaku)

4,4'-(6-(2-difluoromethyl)-1H-benzo[d]imidazol-1-yl)-1,3,5-triazine-2,4-diyl)dimorpholine TABLE 6-continued Some of biologically active PI3K inhibitors:

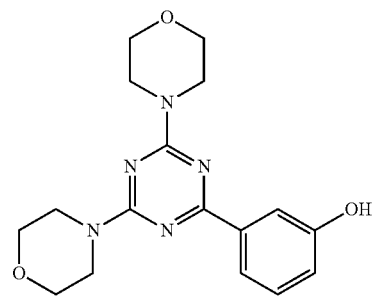

Example P3

3-(4,6-dimorpholino-1,3,5-triazin-2-yl)phenol

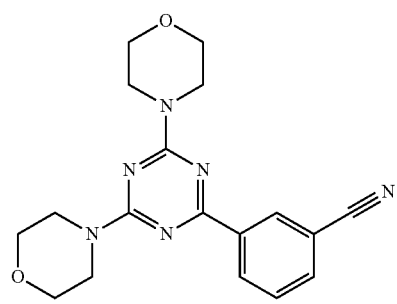

Example P6

3-(4,6-dimorpholino-1,3,5-triazin-2-yl)benzonitrile

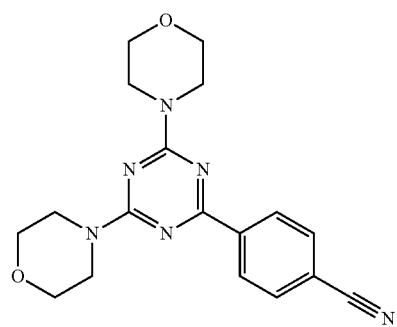

Example P7

4-(4,6-dimorpholino-1,3,5-triazin-2-yl)benzonitrile

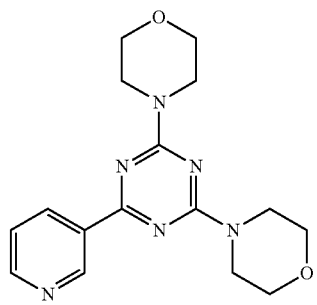

Example P8

4,4'-(6-(pyridin-3-yl)-1,3,5-triazine-2,4-diyl)dimorpholine

TABLE 6-continued

Some of biologically active PI3K inhibitors:

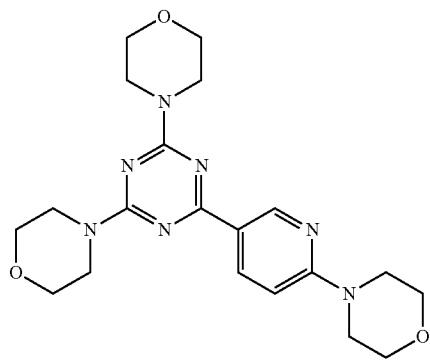

Example P9

4,4'-(6-(6-morpholinopyridin-3-yl)-
1,3,5-triazine-2,4-diyl)dimorpholine

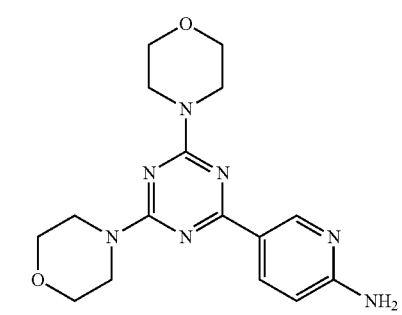

Example P2

5-(4,6-dimorpholino-1,3,5-
triazin-2-yl)pyridin-2-amine

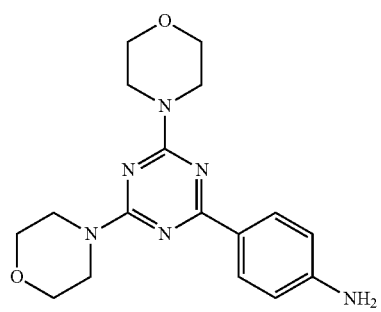

Example P4

4-(4,6-dimorpholino-1,3,5-
triazin-2-yl)analine

TABLE 6-continued

Some of biologically active PI3K inhibitors:

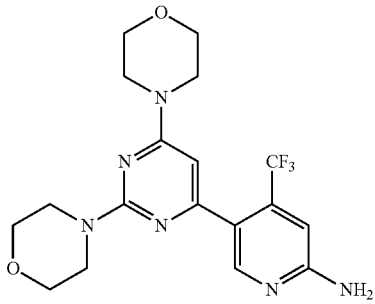

NCA235 or 5-(2,6-
dimorpholinopyrimidin-4-yl)-4-
(trifluoromethyl)pyridin-2-amine was a
reference pyrimidine compound for our
experiments (IP of Novartis)

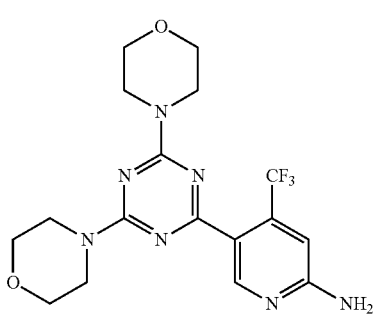

Example P11

5-(4,6-dimorpholino-1,3,5-triazin-2-yl)-
4-(trifluoromethyl)pyridin-2-amine

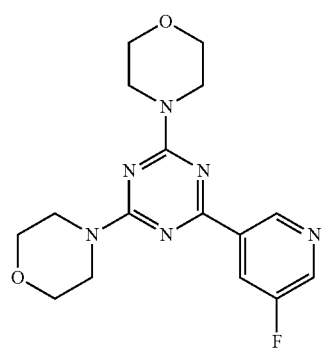

Example P12

4,4'-(6-(5-fluoropyridin-3-yl)-1,3,5-
triazine-2,4-diyl)dimorpholine

TABLE 7

| Example | A2058 pPKB/PKB 1 uM | A2058 pPKB/PKB 10 uM | A2058 pS6 1 uM | A2058 pS6 10 uM | 1205lu pS6 1 uM | 1205lu pS6 10 uM |
|---|---|---|---|---|---|---|
| ZSTK474 | ++++ | ++++ | +++ | +++ | ++(+) | +++ |
| P2 | − | ++++ | | | | |
| P3 | ++ | ++++ | +++ | | +++ | |
| P4 | − | +++ | | | | |
| P6 | − | − | | | | |
| P7 | − | − | | | | |
| P8 | + | ++++ | +(+) | | | |
| P9 | − | − | | | | |
| NCA235 | +++(+) | ++++ | + | ++ | | |
| P11 | ++++ | ++++ | +++(+) | +++(+) | | |
| P12 | − | +(+) | − | (+) | | |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:

1. A compound of formula (Ib):

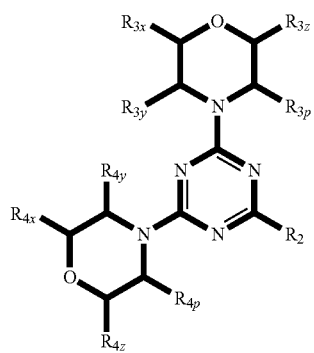

(Ib)

and stereoisomers, geometric isomers, tautomers, solvates, and pharmaceutically acceptable salts thereof, wherein $R_2$ is selected from a monocyclic heteroaryl group of the structure

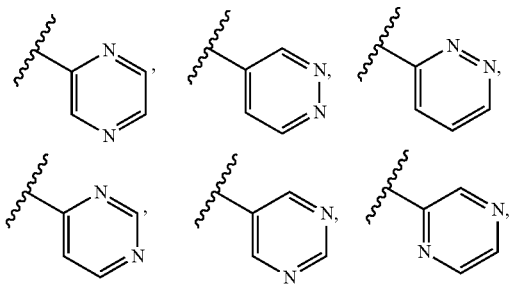

-continued

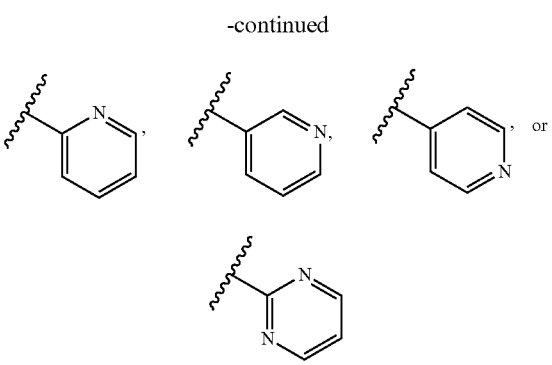

wherein the wavy line indicates the attachment to the 4-position of the triazine ring, and wherein the monocyclic heteroaryl group is optionally substituted with one or more groups selected from F, Cl, Br, I, $-NR_{10}R_{11}$, $-OR_{10}$, $-C(O)R_{10}$, $-NR_{10}C(O)R_{11}$, $-N(C(O)R_{11})_2$, $-NR_{10}C(O)NR_{10}R_{11}$, $-C(=O)OR_{10}$, $-C(=O)NR_{10}R_{11}$, and $C_1$-$C_{12}$ alkyl, or from a monocyclic or bicyclic heteroaryl group of the structure

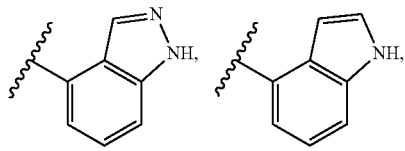

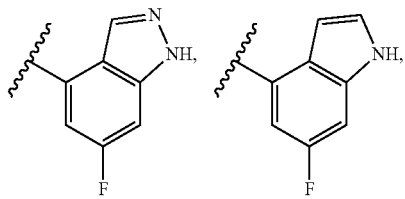

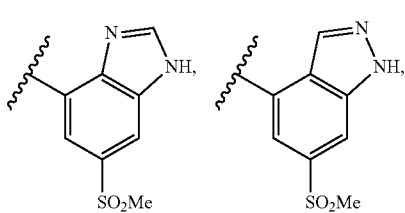

411
-continued
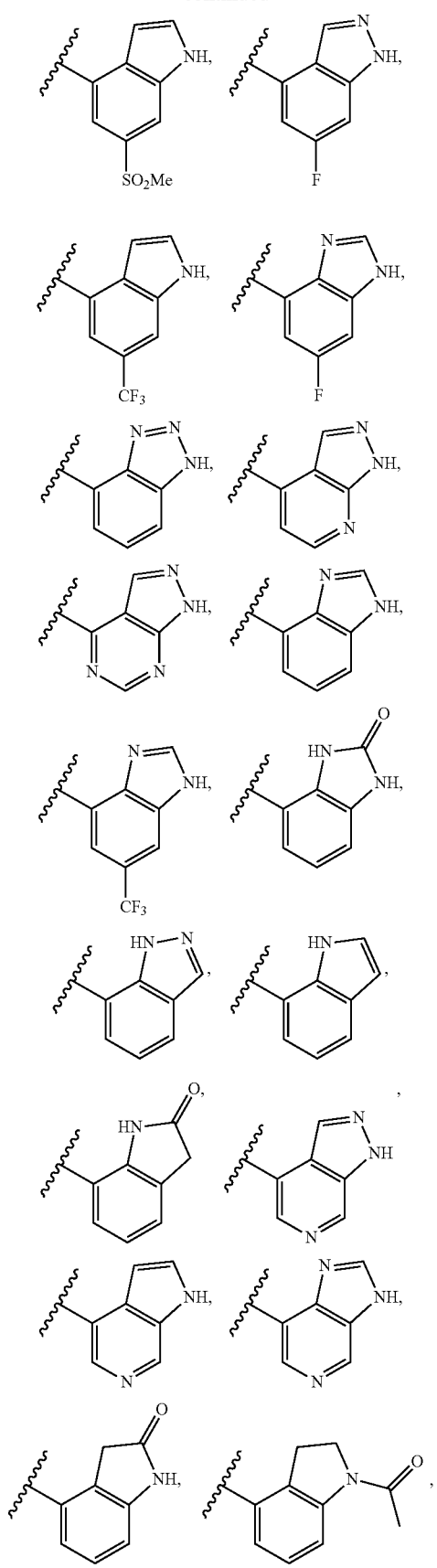
412
-continued
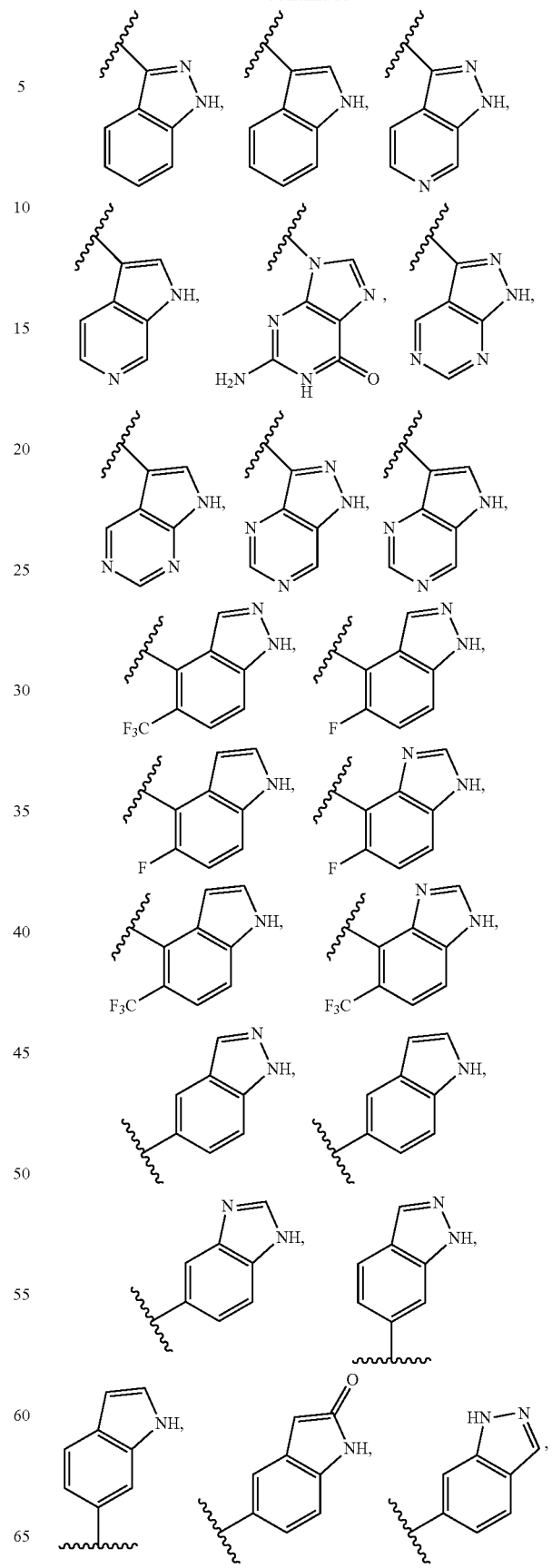

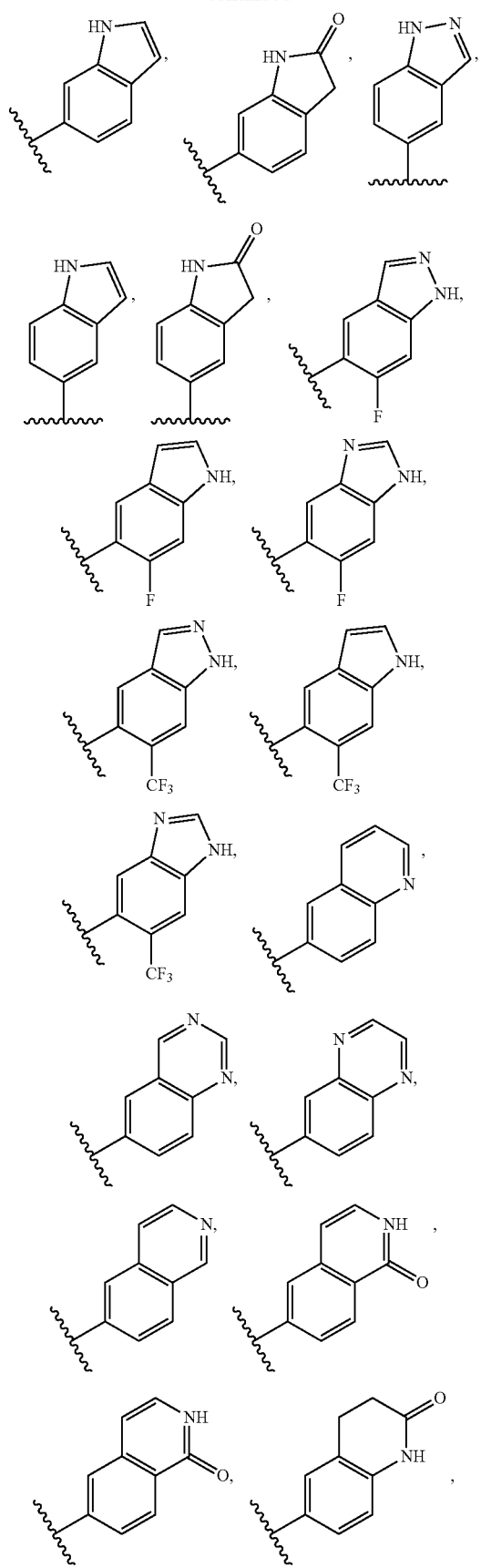
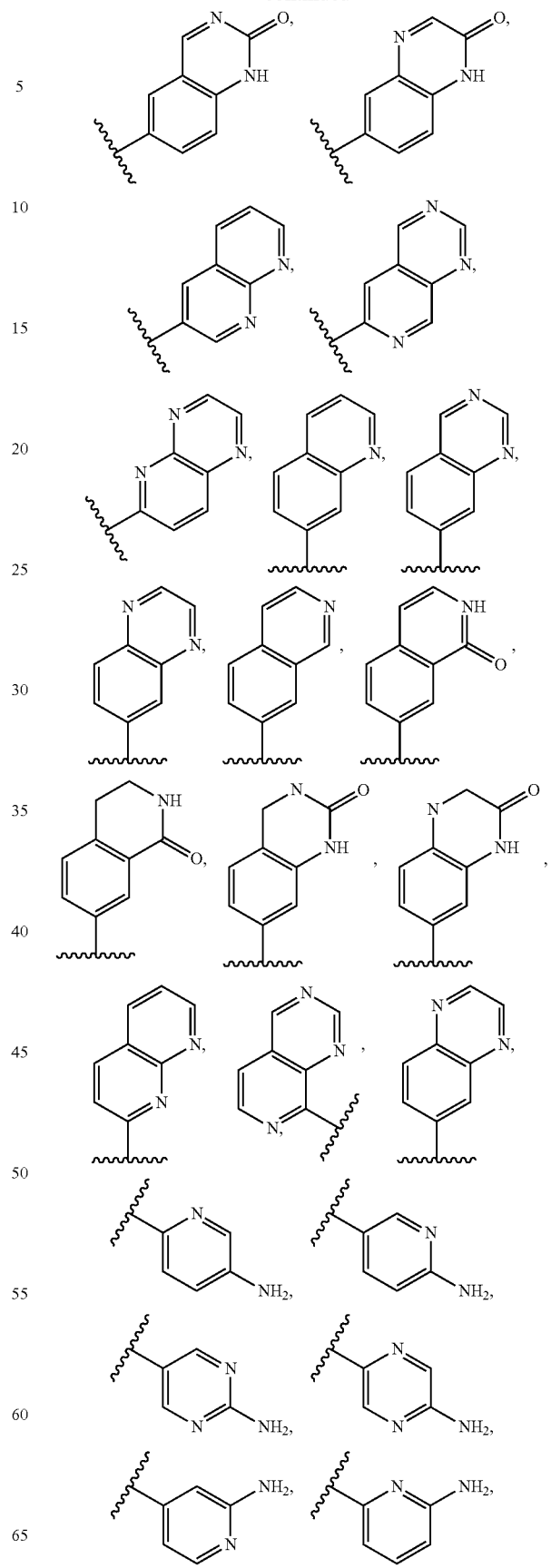

415
-continued

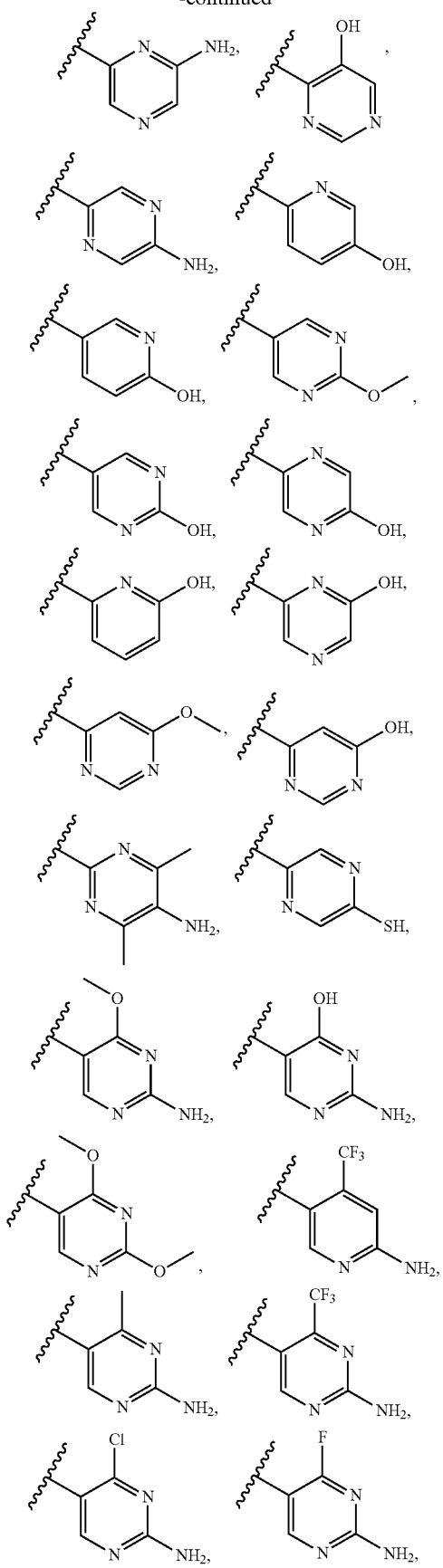

416
-continued

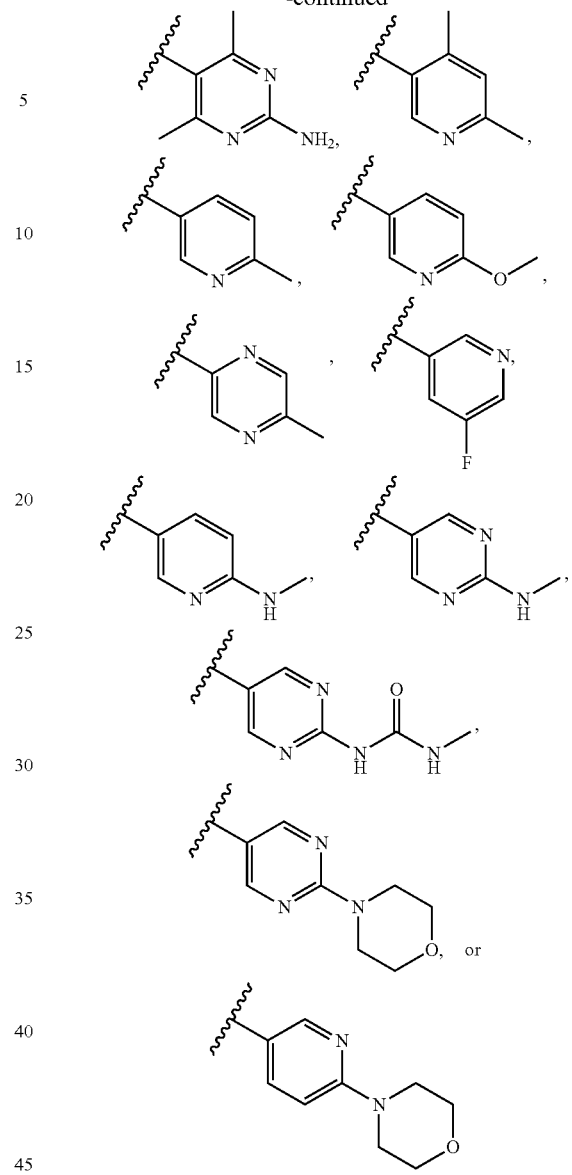

wherein the wavy line indicates the attachment to the 4-position of the triazine ring, and wherein the monocyclic or bicyclic heteroaryl group is optionally substituted with one or more groups selected from F, —$NH_2$, —$NHCH_3$, —$N(CH_3)_2$, —OH, —$OCH_3$, —$C(O)CH_3$, —$NHC(O)CH_3$, —$N(C(O)CH_3)_2$, —$NHC(O)NH_2$, —$CO_2H$, —CHO, —$CH_2OH$, —$C(=O)NHCH_3$, —$C(=O)NH_2$, and —$CH_3$;

$R_3$, $R_{3y}$, $R_{3z}$ and $R_{3p}$ are independently from each other selected from the group consisting of:

hydrogen, F, Cl, Br, I, —$C(C_1\text{-}C_6 \text{ alkyl})_2NR_{10}R_{11}$, —$(CR_{14}R_{15})_tNR_{10}R_{11}$, —$C(R_{14}R_{15})_nNR_{12}C(=Y)R_{10}$, —$(CR_{14}R_{15})_nNR_{12}S(O)_2R_{10}$, —$CH(OR_{10})R_{10}$, —$(CR_{14}R_{15})_nOR_{10}$, —$(CR_{14}R_{15})_nS(O)_2R_{10}$, —$(CR_{14}R_{15})_nS(O)_2NR_{10}R_{11}$, —$C(=Y)R_{10}$, —$C(=Y)OR_{10}$, —$C(=Y)NR_{10}R_{11}$, —$C(=Y)NR_{12}OR_{10}$, —$C(=O)NR_{12}S(O)_2R_{10}$, —$C(=O)NR_{12}(CR_{14}R_{15})_mNR_{10}R_{11}$, —$NO_2$, —$NHR_{12}$, —$NR_{12}C(=Y)R_{11}$, —$NR_{12}C(=Y)OR_{11}$, —$NR_{12}C(=Y)NR_{10}R_{11}$, —$NR_{12}S(O)_2R_{10}$, —$NR_{12}SO_2NR_{10}R_{11}$, —$S(O)_2R_{10}$, —$S(O)_2NR_{10}R_{11}$, —$SC(=Y)R_{10}$, —$SC(=Y)OR_{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl; or where the $C_3$-$C_{12}$ carbocyclyl, $C_2$-$C_{20}$ heterocyclyl, $C_6$-$C_{20}$ aryl, or $C_1$-$C_{20}$ heteroaryl is substituted at vicinal carbon atoms of the morpholine and forms a fused bicyclic morpholinyl;

wherein said alkyl, alkenyl, alkynyl, carbocyclyl, heterocyclyl, aryl and heteroaryl are optionally substituted with one or more groups independently selected from F, Cl, Br, I, —CN, $CF_3$, —$NO_2$, oxo, —C(=Y)$R_{10}$, —C(=Y)O$R_{10}$, —C(=Y)N$R_{10}R_{11}$, —(C$R_{14}R_{15}$)$_n$N$R_{10}R_{11}$, —(C$R_{14}R_{15}$)$_n$C(=Y)N$R_{10}R_{11}$, —(C$R_{14}R_{15}$)$_n$ C(=Y)O$R_{10}$, (C$R_{14}R_{15}$)$_n$N$R_{12}SO_2R_{10}$, —(C$R_{14}R_{15}$)$_n$O$R_{10}$, —(C$R_{14}R_{15}$)$_n$R$_{10}$, —(C$R_{14}R_{15}$)$_n$SO$_2R_{10}$, —N$R_{10}R_{11}$, —N$R_{12}$C(=Y)$R_{10}$, —N$R_{12}$C(=Y)O$R_{11}$, —N$R_{12}$C(=Y)N$R_{10}R_{11}$, —N$R_{12}$SO$_2R_{10}$, =N$R_{12}$, O$R_{10}$, —OC(=Y)$R_{10}$, —OC(=Y)O$R_{10}$, —OC(=Y)N$R_{10}R_{11}$, —OS(O)$_2$(O$R_{10}$), —OP(=Y)(O$R_{10}$)(O$R_{11}$), —OP(O$R_{10}$)(O$R_{11}$), S$R_{10}$, —S(O)$R_{10}$, —S(O)$_2R_{10}$, —S(O)$_2$N$R_{10}R_{11}$, —S(O)(O$R_{10}$), —S(O)$_2$ (O$R_{10}$), —SC(=Y)$R_{10}$, —SC(=Y)O$R_{10}$, —SC(=Y)N$R_{10}R_{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

$R_{4x}$, $R_{4y}$, $R_{4z}$ and $R_{4p}$ are independently from each other selected from the group consisting of: hydrogen, F, Cl, Br, I, —C($C_1$-$C_6$ alkyl)$_2$N$R_{10}R_{11}$, —(C$R_{14}R_{15}$)$_n$N$R_{10}R_{11}$, —C(C$R_{14}R_{15}$)$_n$N$R_{12}$C(=Y)$R_{10}$, —(C$R_{14}R_{15}$)$_n$N$R_{12}$S(O)$_2R_{10}$, —CH(O$R_{10}$)$R_{10}$, —(C$R_{14}R_{15}$)$_n$O$R_{10}$, —(C$R_{14}R_{15}$)$_n$S(O)$_2R_{10}$, —(C$R_{14}R_{15}$)$_n$S(O)$_2$N$R_{10}R_{11}$, —C(=Y)$R_{10}$, —C(=Y)O$R_{10}$, —C(=Y)N$R_{10}R_{11}$, —C(=Y)N$R_{12}$O$R_{10}$, —C(=O)N$R_{12}$S(O)$_2R_{10}$, —C(=O)N$R_{12}$(C$R_{14}R_{15}$)$_m$N$R_{10}R_{11}$, —$NO_2$, —NH$R_{12}$, —N$R_{12}$C(=Y)$R_{11}$, —N$R_{12}$C(=Y)O$R_{11}$, —N$R_{12}$C(=Y)N$R_{10}R_{11}$, —N$R_{12}$S(O)$_2R_{10}$, —N$R_{12}$SO$_2$N$R_{10}R_{11}$, —S(O)$_2R_{10}$, —S(O)$_2$N$R_{10}R_{11}$, —SC(=Y)$R_{10}$, —SC(=Y)O$R_{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl; or where the $C_3$-$C_{12}$ carbocyclyl, $C_2$-$C_{20}$ heterocyclyl, $C_6$-$C_{20}$ aryl, or $C_1$-$C_{20}$ heteroaryl is substituted at vicinal carbon atoms of the morpholine and forms a fused bicyclic morpholinyl;

wherein said alkyl, alkenyl, alkynyl, carbocyclyl, heterocyclyl, aryl and heteroaryl are optionally substituted with one or more groups independently selected from F, Cl, Br, I, —CN, $CF_3$, —$NO_2$, oxo, —C(=Y)$R_{10}$, —C(=Y)O$R_{10}$, —C(=Y)N$R_{10}R_{11}$, —C$R_{14}R_{15}$)$_n$N$R_{10}R_{11}$, —(C$R_{14}R_{15}$)$_n$C(=Y)N$R_{10}R_{11}$, —(C$R_{14}R_{15}$)$_n$ C(=Y)O$R_{10}$, (C$R_{14}R_{15}$)$_n$N$R_{12}SO_2R_{10}$, —C$R_{14}R_{15}$)$_n$O$R_{10}$, —(C$R_{14}R_{15}$)$_n$R$_{10}$, —(C$R_{14}R_{15}$)$_n$SO$_2R_{10}$, —N$R_{10}R_{11}$, —N$R_{12}$C(=Y)$R_{10}$, —$R_{12}$C(=Y)O$R_{11}$, —N$R_{12}$C(=Y)N$R_{10}R_{11}$, —N$R_{12}$SO$_2R_{10}$, =N$R_{12}$, O$R_{10}$, —OC(=Y)$R_{10}$, —C(=Y)O$R_{10}$, —OC(=Y)N$R_{10}R_{11}$, —OS(O)$_2$(O$R_{10}$), —OP(=Y)(O$R_{10}$)(O$R_{11}$), —OP(O$R_{10}$)(O$R_{11}$), S$R_{10}$, —S(O)$R_{10}$, —S(O)$_2$ $R_{10}$, —S(O)$_2$N$R_{10}R_{11}$, —S(O)(O$R_{10}$), —S(O)$_2$ (O$R_{10}$), —SC(=Y)$R_{10}$, —C(=Y)O$R_{10}$, —SC(=Y)N$R_{10}R_{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

wherein $R_{10}$, $R_{11}$ and $R_{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R_{10}$, $R_{11}$ together with the nitrogen to which they are attached optionally form a $C_3$-$C_{20}$ heterocyclic ring optionally containing one or more additional ring atoms selected from N, O or S, wherein said heterocyclic ring is optionally substituted with one or more groups independently selected from oxo, $CF_3$, F, Cl, Br, I, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl; and wherein $R_{14}$ and $R_{15}$ are independently selected from H, $C_1$-$C_{12}$ alkyl, or —(CH$_2$)$_n$-aryl, or $R_{14}$ and $R_{15}$ together with the atoms to which they are attached form a saturated or partially unsaturated $C_3$-$C_{12}$ carbocyclic ring.

2. A compound of claim 1, wherein $R_{3x}$, $R_{3y}$, $R_{3z}$, $R_{3p}$ are independently selected from the structures:

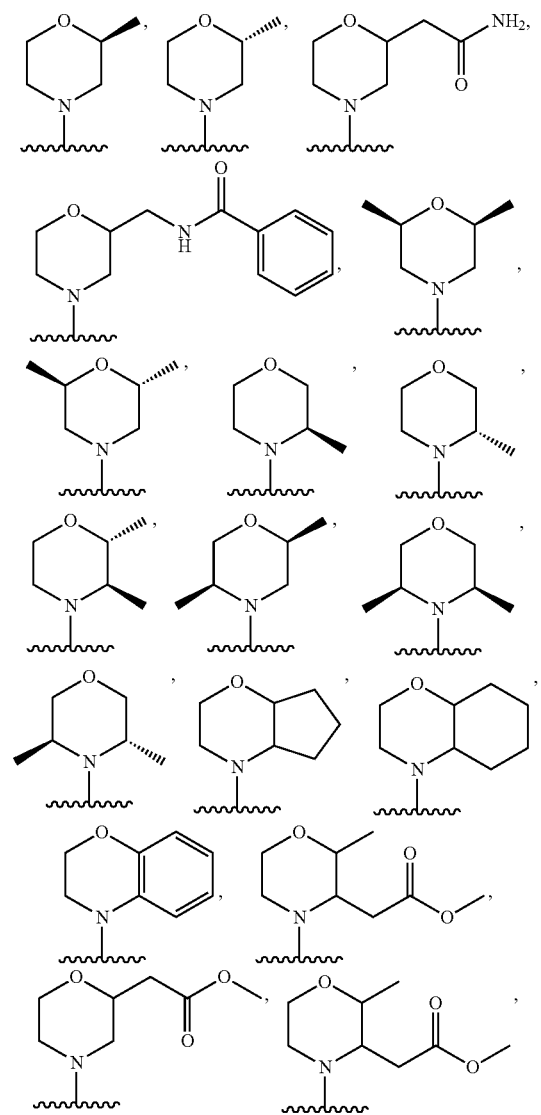

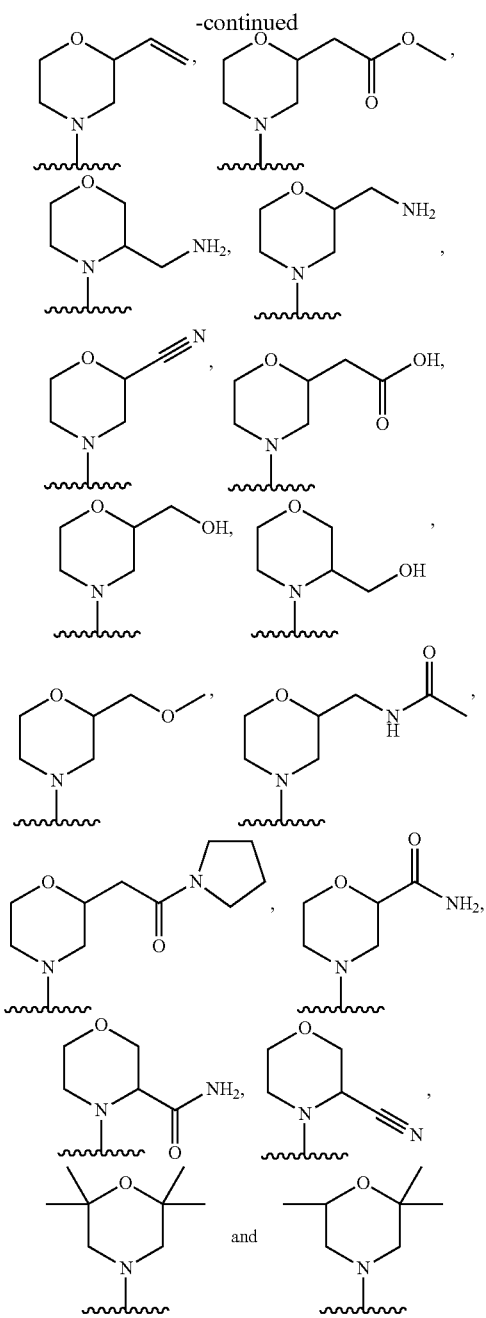

wherein the wavy line indicates the attachment to the 6-position of the triazine ring.

3. A compound, wherein the compound is
4,4'-(6-(pyridin-3-yl)-1,3,5-triazine-2,4-diyl)dimorpholine,
3-(4,6-dimorpholino-1,3,5-triazin-2-yl)phenol,
5-(4,6-dimorpholino-1,3,5-triazin-2-yl)pyridin-3-ol,
5-(4,6-dimorpholino-1,3,5-triazin-2-yl)pyridin-2-amine,
5-(4,6-dimorpholino-1,3,5-triazin-2-yl)pyrimidin-2-amine,
5-(4,6-dimorpholino-1,3,5-triazin-2-yl)-4-(trifluoromethyl)pyridin-2-amine,
5-(4,6-dimorpholino-1,3,5-triazin-2-yl)-4-(trifluoromethyl)pyrimidin-2-amine,
N-(5-(4,6-dimorpholino-1,3,5-triazin-2-yl)pyridin-2-yl)acetamide,
N-(5-(4,6-dimorpholino-1,3,5-triazin-2-yl)pyrimidin-2-yl)acetamide,
N-(5-(4,6-dimorpholino-1,3,5-triazin-2-yl)-4-(trifluoromethyl)pyrimidin-2-yl)acetamide,
N-(5-(4,6-dimorpholino-1,3,5-triazin-2-yl)-4-(trifluoromethyl)pyridin-2-yl)acetamide,
5-(4,6-dimorpholino-1,3,5-triazin-2-yl)-6-(trifluoromethyl)pyridin-2-amine,
4,4'-(6-(1H-indazol-5-yl)-1,3,5-triazine-2,4-diyl)dimorpholine,
4,4'-(6-(1H-indol-5-yl)-1,3,5-triazine-2,4-diyl)dimorpholine,
4,4'-(6-(1H-benzo[d]imidazol-5-yl)-1,3,5-triazine-2,4-diyl)dimorpholine,
4,4'-(6-(1H-benzo[d]imidazol-4-yl)-1,3,5-triazine-2,4-diyl)dimorpholine,
4,4'-(6-(1H-indol-4-yl)-1,3,5-triazine-2,4-diyl)dimorpholine,
4,4'-(6-(1H-indazol-4-yl)-1,3,5-triazine-2,4-diyl)dimorpholine,
4,4'-(6-(1H-indazol-6-yl)-1,3,5-triazine-2,4-diyl)dimorpholine,
5-(4-morpholino-6-(pyridin-2-ylmethoxy)-1,3,5-triazin-2-yl)pyridin-2-amine,
5-(4-morpholino-6-(pyridin-2-ylmethoxy)-1,3,5-triazin-2-yl)pyrimidin-2-amine,
4-(4-(1H-indol-4-yl)-6-(pyridin-2-ylmethoxy)-1,3,5-triazin-2-yl)morpholine,
4-(4-(1H-indazol-4-yl)-6-(pyridin-2-ylmethoxy)-1,3,5-triazin-2-yl)morpholine,
4-(4-(1H-benzo[d]imidazol-4-yl)-6-(pyridin-2-ylmethoxy)-1,3,5-triazin-2-yl)morpholine,
4-(4-(1H-benzo[d]imidazol-5-yl)-6-(pyridin-2-ylmethoxy)-1,3,5-triazin-2-yl)morpholine,
4-(4-(1H-indazol-5-yl)-6-(pyridin-2-ylmethoxy)-1,3,5-triazin-2-yl)morpholine,
4-(4-(1H-indol-5-yl)-6-(pyridin-2-ylmethoxy)-1,3,5-triazin-2-yl)morpholine,
3-(4-morpholino-6-(pyridin-2-ylmethylamino)-1,3,5-triazin-2-yl)phenol,
4-(6-aminopyridin-3-yl)-6-morpholino-N-(pyridin-2-ylmethyl)-1,3,5-triazin-2-amine,
4-(2-aminopyrimidin-5-yl)-6-morpholino-N-(pyridin-2-ylmethyl)-1,3,5-triazin-2-amine,
4-(1H-indol-5-yl)-6-morpholino-N-(pyridin-2-ylmethyl)-1,3,5-triazin-2-amine,
4-(1H-indazol-5-yl)-6-morpholino-N-(pyridin-2-ylmethyl)-1,3,5-triazin-2-amine,
4-(1H-benzo[d]imidazol-5-yl)-6-morpholino-N-(pyridin-2-ylmethyl)-1,3,5-triazin-2-amine,
4-(1H-benzo[d]imidazol-4-yl)-6-morpholino-N-(pyridin-2-ylmethyl)-1,3,5-triazin-2-amine,
4-(1H-indol-4-yl)-6-morpholino-N-(pyridin-2-ylmethyl)-1,3,5-triazin-2-amine,
4-(1H-indazol-4-yl)-6-morpholino-N-(pyridin-2-ylmethyl)-1,3,5-triazin-2-amine,
3-(7-morpholinothiazolo[4,5-d]pyrimidin-5-yl)phenol,
3-(7-morpholinooxazolo[4,5-d]pyrimidin-5-yl)phenol,
3-(2-((4-methylpiperazin-1-yl)methyl)-7-morpholinooxazolo[4,5-d]pyrimidin-5-yl)phenol,
3-(2-((4-methylpiperazin-1-yl)methyl)-7-morpholinothiazolo[4,5-d]pyrimidin-5-yl)phenol,
3-(2-((4-(methylsulfonyl)piperazin-1-yl)methyl)-7-morpholinothiazolo[4,5-d]pyrimidin-5-yl)phenol,
5-(7-morpholinothiazolo[4,5-d]pyrimidin-5-yl)pyrimidin-2-amine, 5-(7-morpholinothiazolo[4,5-d]pyrimidin-5-yl)pyridin-2-amine,
5-(2-((4-methylpiperazin-1-yl)methyl)-7-morpholinothiazolo[4,5-d]pyrimidin-5-yl)pyrimidin-2-amine,
5-(2-((4-methylpiperazin-1-yl)methyl)-7-morpholinooxazolo[4,5-d]pyrimidin-5-yl)pyrimidin-2-amine,
4-(5-(1H-indazol-4-yl)thiazolo[4,5-d]pyrimidin-7-yl)morpholine,
4-(5-(1H-indazol-4-yl)-2-((4-methylpiperazin-1-yl)methyl)thiazolo[4,5-d]pyrimidin-7-yl)morpholine,
4-(5-(1H-indazol-4-yl)-2-((4-(methylsulfonyl)piperazin-1-yl)methyl)thiazolo[4,5-d]pyrimidin-7-yl)morpholine,
4-(5-(1H-indol-4-yl)thiazolo[4,5-d]pyrimidin-7-yl)morpholine,
4-(5-(1H-benzo[d]imidazol-4-yl)thiazolo[4,5-d]pyrimidin-7-yl)morpholine,
4-(5-(1H-benzo[d]imidazol-5-yl)thiazolo[4,5-d]pyrimidin-7-yl)morpholine,
4-(5-(1H-indol-5-yl)thiazolo[4,5-d]pyrimidin-7-yl)morpholine,
4-(5-(1H-indol-5-yl)-2-((4-methylpiperazin-1-yl)methyl)thiazolo[4,5-d]pyrimidin-7-yl)morpholine,
4-(5-(1H-indazol-5-yl)thiazolo[4,5-d]pyrimidin-7-yl)morpholine,
2-(1H-benzo[d]imidazol-5-yl)-4-morpholinobenzofuro[3,2-d]pyrimidine,
2-(1H-indol-5-yl)-4-morpholinobenzofuro[3,2-d]pyrimidine,
2-(1H-indazol-5-yl)-4-morpholinobenzofuro[3,2-d]pyrimidine,
6-(1H-Indazol-5-yl)-8-morpholin-4-yl-9-oxa-1,5,7-triaza-fluorene,
6-(1H-Benzoimidazol-5-yl)-8-morpholin-4-yl-9-oxa-1,5,7-triaza-fluorene,
6-(1H-Indol-5-yl)-8-morpholin-4-yl-9-oxa-1,5,7-triaza-fluorene,
2-(1H-indol-4-yl)-4-morpholinobenzofuro[3,2-d]pyrimidine,
2-(1H-indazol-4-yl)-4-morpholinobenzofuro[3,2-d]pyrimidine,
2-(1H-benzo[d]imidazol-4-yl)-4-morpholinobenzofuro[3,2-d]pyrimidine,
6-(1H-Indazol-4-yl)-8-morpholin-4-yl-9-oxa-1,5,7-triaza-fluorene,
6-(1H-Indazol-4-yl)-2-(4-methyl-piperazin-1-ylmethyl)-8-morpholin-4-yl-9-oxa-1,5,7-triaza-fluorene,
6-(1H-Benzoimidazol-4-yl)-8-morpholin-4-yl-9-oxa-1,5,7-triaza-fluorene,
6-(1H-Indol-4-yl)-8-morpholin-4-yl-9-oxa-1,5,7-triaza-fluorene,
5-(8-Morpholin-4-yl-9-oxa-1,5,7-triaza-fluoren-6-yl)-pyrimidin-2-ylamine,
3-[2-(4-Methyl-piperazin-1-ylmethyl)-8-morpholin-4-yl-9-oxa-1,5,7-triaza-fluoren-6-yl]-phenol,
5-(8-Morpholin-4-yl-9-oxa-1,5,7-triaza-fluoren-6-yl)-pyridin-2-ylamine,
5-(4-morpholinobenzofuro[3,2-d]pyrimidin-2-yl)pyridin-2-amine,
5-(4-morpholinobenzofuro[3,2-d]pyrimidin-2-yl)pyrimidin-2-amine, or
3-(4-morpholinobenzofuro[3,2-d]pyrimidin-2-yl)phenol.

4. A compound of claim 3, wherein the compound is 5-(4,6-dimorpholino-1,3,5-triazin-2-yl)-4-(trifluoromethyl)pyridin-2-amine or 5-(4,6-dimorpholino-1,3,5-triazin-2-yl)-4-(trifluoromethyl)pyrimidin-2-amine.

5. A pharmaceutical composition, comprising a pharmaceutically acceptable carrier and a compound of claim 1.

6. The composition of claim 5 further comprising an anti-hyperproliferative therapeutic agent.

7. The composition of claim 6, wherein the therapeutic agent is vatalanib, imatinib or gefitinib.

8. A kit, comprising a compound of claim 1 and a package insert or other labelling including directions for administering said compound.

9. A pharmaceutical composition comprising a compound of claim 3 and a pharmaceutically acceptable carrier.

10. The composition of claim 9 further comprising a second anti-hyperproliferative therapeutic agent.

11. The composition of claim 10, wherein the therapeutic agent is vatalanib, imatinib or gefitinib.

12. A pharmaceutical composition, comprising a pharmaceutically acceptable carrier and an amount of a compound of claim 3 effective to inhibit mTOR activity in a human or animal subject when administered thereto.

13. The composition of claim 12, effective to inhibit PI3K alpha activity in a human or animal subject when administered thereto.

14. A kit, comprising a compound of claim 3 and a package insert or other labelling including directions for administering said compound.

15. A method for therapeutically treating melanoma in a human or animal subject, comprising administering to a human or animal subject an effective amount of a compound of claim 1.

16. A method for therapeutically treating melanoma in a human or animal subject, comprising administering to a human or animal subject an effective amount of a compound of claim 3.

* * * * *

UNITED STATES PATENT AND TRADEMARK OFFICE
CERTIFICATE OF CORRECTION

| | | |
|---|---|---|
| PATENT NO. | : 8,921,361 B2 | Page 1 of 1 |
| APPLICATION NO. | : 13/128436 | |
| DATED | : December 30, 2014 | |
| INVENTOR(S) | : Vladimir Cmiljanovic et al. | |

It is certified that error appears in the above-identified patent and that said Letters Patent is hereby corrected as shown below:

In the Claims

Column 422, lines Approximately 27-28, Claim 10 should read,

-- The composition of claim 9 further comprising an anti-hyperproliferative therapeutic agent. --

Signed and Sealed this
Fourteenth Day of July, 2015

Michelle K. Lee
*Director of the United States Patent and Trademark Office*